US012338265B2

(12) United States Patent
Sawamoto et al.

(10) Patent No.: US 12,338,265 B2
(45) Date of Patent: Jun. 24, 2025

(54) CROSSLINKED ARTIFICIAL NUCLEIC ACID ALNA

(71) Applicants: MITSUBISHI TANABE PHARMA CORPORATION, Osaka (JP); OSAKA UNIVERSITY, Suita (JP)

(72) Inventors: Hiroaki Sawamoto, Osaka (JP); Shinji Kumagai, Osaka (JP); Hiroyuki Furukawa, Osaka (JP); Tomo Araki, Osaka (JP); Masayuki Utsugi, Osaka (JP); Satoshi Obika, Suita (JP)

(73) Assignee: MITSUBISHI TANABE PHARMA CORPORATION, Osaka (JP)

(*) Notice: Subject to any disclaimer, the term of this patent is extended or adjusted under 35 U.S.C. 154(b) by 1024 days.

(21) Appl. No.: 17/292,963

(22) PCT Filed: Nov. 11, 2019

(86) PCT No.: PCT/JP2019/044182
§ 371 (c)(1),
(2) Date: May 11, 2021

(87) PCT Pub. No.: WO2020/100826
PCT Pub. Date: May 22, 2020

(65) Prior Publication Data

US 2022/0002336 A1 Jan. 6, 2022

(30) Foreign Application Priority Data

Nov. 12, 2018 (JP) ................................ 2018-212424

(51) Int. Cl.
*C07H 19/20* (2006.01)
*C07H 19/10* (2006.01)
*C07H 21/04* (2006.01)

(52) U.S. Cl.
CPC ............ *C07H 19/20* (2013.01); *C07H 19/10* (2013.01); *C07H 21/04* (2013.01)

(58) Field of Classification Search
None
See application file for complete search history.

(56) References Cited

U.S. PATENT DOCUMENTS

2015/0266917 A1 9/2015 Obika et al.
2018/0251488 A1 9/2018 Obika et al.

FOREIGN PATENT DOCUMENTS

EP 3 950 006 A1 2/2022
WO WO 99/14228 A2 8/1999
WO WO 2007/145593 A1 12/2007
WO WO 2011/156202 A1 12/2011
WO WO 2012/142085 A1 10/2012
WO WO 2013/013068 A2 1/2013
WO WO 2014/046212 A1 3/2014
WO WO 2014-124952 A1 8/2014
WO WO 2016/128583 A2 8/2016
WO WO 2017/047816 A1 8/2017

OTHER PUBLICATIONS

Astakhova, I. K., Samokhina, E., Babu, B. R., & Wengel, J. (2012). Novel (phenylethynyl) pyrene—LNA constructs for fluorescence SNP sensing in polymorphic nucleic acid targets. ChemBioChem, 13(10), 1509-1519. (Year: 2012).*
Astakhova et al., "Scaffolding along Nucleic Acid Duplexes Using 2'-Amino-Locked Nucleic Acids," Accounts of Chemical Research, vol. 47, 2014 (Published Apr. 21, 2014), pp. 1768-1777.
Babu et al., "Optimized DNA Targeting Using N,N-bis(2-pyridylmethyl)-β-alanyl 2'-amino-LNA," Chem. Commun., vol. 12, 2005 (Published on Feb. 3, 2005), pp. 1706-1707.

(Continued)

*Primary Examiner* — Dale R Miller
(74) *Attorney, Agent, or Firm* — Birch, Stewart, Kolasch & Birch, LLP

(57) ABSTRACT

The present invention provides a novel bridged artificial nucleic acid and an oligomer containing the same as a monomer. The present invention provides specifically a compound represented by general formula (I) (wherein each symbol is the same as defined in the specification) or salts thereof; as well as an oligonucleotide compound represented by general formula (I') (wherein each symbol is the same as defined in the specification) or salts thereof.

(I)

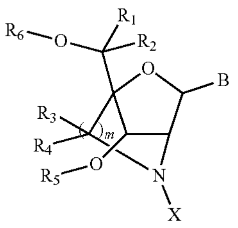

(I')

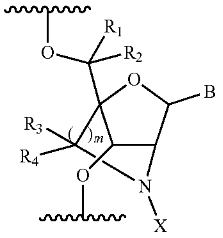

36 Claims, No Drawings

Specification includes a Sequence Listing.

(56) References Cited

OTHER PUBLICATIONS

Bryld et al., "Allachment of Cholesterol to Amino-LNA: Synthesis and Hybridization Properties," Nucleosides, Nucleotides and Nucleic Acids, vol. 26, No. 10-12, 2007 (Published online Dec. 5, 2007), pp. 1645-1647 (total 4 pages).
English translation of the International Search Report, dated Jan. 21, 2020, for International Application No. PCT/JP2019/044182.
Fluiter et al., "On the in vitro and in vivo Properties of Four Locked Nucleic Acid Nucleotides Incorporated into an Anti-H-Ras Antisense Oligonucleotide," ChemBioChem, vol. 6, 2005 (Published online on Apr. 28, 2005), pp. 1104-1109.
International Preliminary Report on Patentability and Written Opinion of the International Searching Authority, with an English translation, dated May 11, 2021, for International Application No. PCT/JP2019/044182.
Johannsen et al., "Amino Acids Attached to 2'-amino-LNA: Synthesis and Excellent Duplex Stabilily." Org. Biomol. Chem., vol. 9, 2011 (Published on Nov. 3, 20210), pp. 243-252.
Jørgensen et al., "Clickable' LNA/DNA Probes for Fluorescence Sensing of Nucleic Acids and Autoimmune Antibodies," Chem. Commun., vol. 49, 2013 (Published on Sep. 27, 2013), pp. 10751-10753.
Kalek et al., "Effective Modulation of DNA Duplex Stability by Reversible Transition Metal Complex Formation in the Minor Groove," J. Am. Chem. Soc., vol. 129, No. 30, 2007 (Published on Web Jul. 7, 2007), pp. 8392-9400.
Kumar et al., "Functionalized 2'-Amino-α-L-LNA: Directed Positioning of Intercalalors for DNA Targeting," J. Org. Chem., vol. 74, No. 3, 2009 (Published on Web Dec. 24, 2008), pp. 1070-1061.
Lou et al., "Oligonucleotides Containing a Piperazinomodified 2'-amino-LNA Monomer Exhibit Very High Duplex Stability and Remarkable Nuclease Resistance," Chem. Commun., vol. 51, 2015. (Published on Feb. 3, 2015). pp. 4024-4027.
Ries et al., "Synthesis and Biophysical Investigations of Oligonucleotides Containing Galactose-Modified DNA, LNA, and 2'-Amino-LNA Monomers," J. Org. Chem., vol. 81, 2016 (Published Oct. 13, 2016), pp. 10845-10858.
Sawamoto et al., "Synthetic Method for 2'-Amino-LNA Bearing Any of the Four Nucleobases via a Transglycosylation Reaction," Org. Lett., vol. 20, 2018 (Published Mar. 12, 2018), pp. 1928-1931.
Shrestha et al., "Guanidine Bridged Nucleic acid (GuNA): An Effect of a Cationic Bridged Nucleic Acid on DNA Binding Affinity," Chem. Commun., vol. 50, No. 5, 2014. (Published on Nov. 6, 2103), pp. 576-577.
Singh et al., "Synthesis of Novel Bicyclo[2.2.1] Ribonucleosides: 2'-Amino-and 2'-Thio-LNA Monomeric Nucleosides," J. Org. Chem., vol. 63, No. 18, Jul 21, 1998, pp. 6078-6079 (total 9 pages).
Sørensen et al., "Functionalized LNA (Locked Nucleic Acid): High-affinity Hybridization of Oligonucleotides Containing N-acylated and N-alkylated 2'-amino-LNA Monomers," Chem. Commun., 2003 (First published as an Advance Article on the web Jul. 28, 2003), pp. 2130-2131.
Umemoto et al., "Functionalization 2'-amino-LNA with Additional Nucleobases," Org. Biomol. Chem., vol. 7, 2009 (First published as an Advance Article on the web Mar. 19, 2009), pp. 1793-1797.
Van Calenbergh et al., "62, Synthesis and Conformational Analysis of 2'-Deoxy-2'-(3-methoxybenzamido)adenosine, a Rational-Designed Inhibitor of Trypanosomal Glyceraldehyde Phosphate Dehydrogenase (GAPDH)," Helvetica Chimica Acta. vol. 77, No. 3, 1994, pp. 631-644.
Wolfrom et al., "Anomeric Purine Nucleosides of the Furanose Form of 2-Amino-2-deoxy-o-ribose," Journal of Organic Chemistry, vol. 32, No. 6, Jun. 1967, 1823-1825.
Extended European Search Report for European Application No. 23191048.0, dated Oct. 23, 2023.
Extended European Search Report for European Application No. 23191049.8, dated Oct. 23, 2023.
Barman et al., "2'-N-Guanidino,4'-C-ethylene bridged thymidine (GENA-T) modified with oligonucleotide exhibits triplex formation with excellent enzymatic stability," RCS Advances (2015), vol. 5, pp. 12257-12260.
Partial Supplementary European Search Report issued Sep. 20, 2022, in European Patent Application No. 19885739.3.
Duechler et al., "Nucleoside Modifications in the Regulation of Gene Expression: Focus on tRNA", Cellular and Molecular Life Sciences, vol. 73, 2016, pp. 3075-3095.
Knorre et al., "Biological Chemistry: Student's Book for Chemistry, Biol. and Med. of Spec. Universities", Moscow: Higher School, The Third, Revised Edition, 2000, 479 p. pp. 49-50 (3 pages total), with an English translation.
Russian Office Action for Russian Application No. 2021116558, dated May 17, 2023, with an English translation.

* cited by examiner

CROSSLINKED ARTIFICIAL NUCLEIC ACID ALNA

TECHNICAL FIELD

The present invention relates to a monomer of amino LNA, and an oligomer containing the same.

BACKGROUND ART

A therapeutic method for diseases with nucleic acid medicine include an antisense method, an antigen method, a method with aptamer, and a method with siRNA, and so on. Among them, the antisense method is a method in which a disease is treated or prevented by introducing with an oligonucleotide (antisense strand) complementary to disease-related mRNA or non-coding RNA from the outside to form a double strain, and accordingly, by adjusting the function of RNA involved in the disease to treat or prevent the disease.

Though various artificial nucleic acids have been developed as materials for the nucleic acid medicine, problems such as avoiding toxicity in organs where nucleic acid medicines are likely to accumulate, such as the liver and kidneys after systemic administration, and developing sufficient medicinal efficacy remain, there is still no molecule that should be a trump card. A 2'-amino LNA which was developed by Wengel et al., in 1998 (hereinafter, described as "ALNA") (Patent document 1, and Non-Patent Document 1) can synthesize various artificial nucleic acids by modifying the substituent at 2' position and so on, and many ALNA derivatives have been synthesized so far, mainly including alkyl or acyl derivatives (Patent documents 2 to 4, and Non-Patent Documents 2 to 11), and a characteristic tissue distribution after systemic administration has been reported (Non-Patent Document 12), however, it is insufficient in terms of pharmacological activity and accordingly, the derivatives have not been applied to pharmaceuticals so far.

We apply the efficient synthesis method of GuNA previously found (Patent Document 5 and Non-Patent Document 13) to synthesize a wide variety of novel ALNA derivatives, and perform screening specialized in pharmacological activity evaluation, and accordingly, have found out a novel artificial nucleic acid having excellent in vitro and in vivo pharmacological activity as compared with the existing ALNA, and completed the invention of the present application.

CITATION LIST

Patent Document

Patent Document 1: WO 99/014226 pamphlet

Patent Document 2: WO 2013/013068 pamphlet

Patent Document 3: WO 2014/124952 pamphlet

Patent Document 4: WO 2016/128583 pamphlet

Patent Document 5: WO 2017/047816 pamphlet

Non-Patent Document

Non-Patent Document 1: S. K. Singh et al., J. Org. Chem. 1998, 63, 6078-6079

Non-Patent Document 2: M. D. Sorensen et al., Chem. Commun. 2003, 2130

Non-Patent Document 3: B. R. Babu et al., Chem. Commun. 2005, 13, 1705-1707

Non-Patent Document 4: T. Bryld et al., Nucleosides, Nucleotides & Nucleic Acids 2007, 26, 1645-1647

Non-Patent Document 5: M. Kalek et al., J. Am. Chem. Soc. 2007, 129, 9392-9400

Non-Patent Document 6: T. Umemoto et al., Org. Biomol. Chem. 2009, 7, 1793-1797

Non-Patent Document 7: M. W. Johannsen et al., Org. Biomol. Chem. 2011, 9, 243-252

Non-Patent Document 8: A. S. Jφrgensen et al., Chem. Commun. 2013, 49, 10751-10753

Non-Patent Document 9: I. K. Astakhova et al., Acc. Chem. Res. 2014, 47, 1768-1777

Non-Patent Document 10: C. Lou et al., Chem. Commun. 2015, 51, 4024-4027

Non-Patent Document 11: A. Ries et al., J. Org. Chem. 2016, 81, 10845-10856

Non-Patent Document 12: K. Fluiter et al., Chem. Bio. Chem. 2005, 6, 1104-1109

Non-Patent Document 13: K. Sawamoto et al., Org. Lett. 2018, 20, 1928-1931

SUMMARY OF INVENTION

Problems to be Solved by Invention

The present invention relates to a novel bridged artificial nucleic acid, as well as monomer containing the same as a monomer.

Means to Solve Problems

In order to solve the above-mentioned problems to be solved, the inventors have intensively studied to find our a novel 2'-amino LNA and salts thereof, as well as oligomer containing the same as a monomer, thereby completed the present invention.

That is, the present invention includes the following Items [1] to [33], which should not be limited thereto.

Item [1] A compound represented by general formula I:

(I)

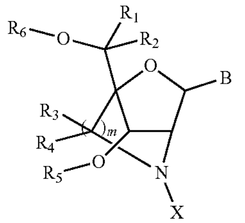

[wherein

B represents a base moiety of nucleic acid wherein the base moiety may be optionally substituted with one or more substituents;

$R_1$, $R_2$, $R_3$ and $R_4$ represent independently of each ether a hydrogen atom, or a $C_{1-6}$ alkyl group which may be optionally substituted with one or more substituents;

$R_5$ and $R_6$ represent independently of each other a hydrogen atom, a protecting group for hydroxy group, or a phosphate group which may be optionally substituted with substituents;

m is an integer of 1 or 2;

X represents a group represented by the following formula (II-1), (II-2) or (II-3):

(II-1)

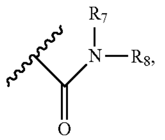

(II-2)

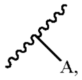

(II-3)

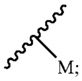

the symbols:

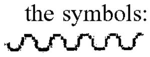

which is described in the formula (II-1), (II-2) or (II-3) represents a binding point to 2'-amino group;

$R_7$ and $R_8$ represent independently of each other a hydrogen atom, a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, or an aromatic group which may be optionally substituted with one or mere substituents;

A represents an aromatic group;

M represents a sulfonyl group which is substituted with one substituent selected from the group consisting of a $C_{1-6}$ alkyl group which may be optionally substituted with one or mere substituents and an aromatic group which may be optionally substituted with one or more substituents.]

or salts thereof (hereinafter, the compound represented by formula (I) or salts thereof is referred to as "Present compound" or "Compound of the present invention").

[2] The compound according to [1] or salt thereof wherein B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents, or an uracilyl group which may be optionally substituted with one or more substituents.

[3] The compound according to [1] or [2] or salts thereof wherein $R_1$, $R_2$, $R_3$ and $R_4$ represent independently of each other a hydrogen atom; and m is an integer of 1.

[4] The compound according to any one of [1] to [3] or salts thereof wherein

X represents a group represented by formula (II-1); and $R_7$ and $R_8$ represent independently of each other a hydrogen atom, a $C_{1-6}$ alkyl group which may be optionally substituted with one or more substituents, or an aromatic group which may be optionally substituted with one or more substituents.

[5] The compound according to [4] or salts thereof wherein $R_7$ and $R_8$ represent independently of each other a hydrogen atom, or a $C_{1-3}$ alkyl group which may be optionally substituted with one or more substituents.

[6] The compound according to [5] or salts thereof wherein one of $R_7$ and $R_8$ represents a hydrogen atom, and the other thereof represents a methyl group.

[7] The compound according to [5] or salts thereof wherein one of $R_7$ and $R_8$ represents a hydrogen atom, and the other thereof represents an isopropyl group.

[8] The compound according to any one of [1] to [3] or salts thereof wherein

X represents a group represented by formula (II-2);

A represents a five or six membered heteroaryl group containing one or more heteroatoms selected from the group consisting of nitrogen atom, oxygen atom and sulfur atom, which may be optionally substituted with one or more substituents.

[9] The compound according to [8] or salts thereof wherein A represents a five or six membered heteroaryl group containing two or three heteroatoms selected from the group consisting of nitrogen atom, oxygen atom and sulfur atom, provided that at least two nitrogen atoms are included, which may be optionally substituted with one or more substituents, and the substituents is selected independently of each other a group consisting of a $C_{1-3}$ alkyl group which may be optionally substituted with one or more halogen atoms, a halogen atom, and an amino group which may be optionally substituted with one or more $C_{1-3}$ alkyl group.

[10] The compound according to [9] or salts thereof wherein the five or six membered heteroaryl group represents a group consisting of a triazolyl group, an oxadiazolyl group, a thiadiazolyl group, a pyrimidinyl group, and a pyrazinyl group, each may be optionally substituted with one or more substituents.

[11] The compound according to [10] or salts thereof wherein the triazolyl group which may be optionally substituted with one or more substituents represents 1,5-dimethyl-1,2,4-triazol-3-yl group.

[12] The compound according to [10] or salts thereof wherein the oxadiazolyl group which may be optionally substituted with one or more substituents represents 5-methyl-1,2,4-oxadiazol-3-yl group.

[13] The compound according to [10] or salts thereof wherein the thiadiazol group which may be optionally substituted with one or more substituents represents 3-methyl-1,2,4-thiadiazol-5-yl group.

[14] The compound according to any one of [1] to [3] or salts thereof wherein

X represents a group represented by formula (II-3); and

M represents a sulfonyl group which is substituted with one or more substituents selected from the group consisting of a $C_{1-6}$ alkyl group which may be optionally substituted with one or more substituents, and an aryl group which may be optionally substituted with one or more substituents.

[15] The compound according to [14] or salts thereof wherein M represents a sulfonyl group which is substituted with one or more substituents selected from the group consisting of a methyl group and a phenyl group.

[16] The compound according to according to any one of claims [1] to [15] or salts thereof wherein $R_6$ represents a hydrogen atom or DMTr group, and $R_5$ represents a hydrogen atom or $—P(O(CH_2)_2CN)(N(ipr)_2)$.

[17] A compound selected from the group consisting of

3-[[(1R,4R,6R,7S)-4-[[bis(4-methoxyphenyl)-phenyl-methoxy]methyl]-6-(5-methyl-2,4-dioxo-pyrimidin-1-yl)-2-methylsulfonyl-5-oxa-2-azabicyclo[2.2.1]heptan-7-yl]oxy-(diisopropylamino)phosphanyl] oxypropanenitrile (Present compound 1);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-5-methyl-2-oxo-pyrimidin-4-yl]benzamide (Present compound 2);

[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-2-(2-methylpropanoylamino)purin-6-yl]N,N-diphenylcarbamate (Present compound 3);

N-[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-purin-6-yl]benzamide (Present compound 4);

3-[[(1R,3R,4R,7S)-5-(benzenesulfonyl)-1-[[bis(4-methoxyphenyl)-phenylmethoxy]methyl]-3-(5-methyl-2,4-dioxopyrimidin-1-yl)-2-oxa-5-azabicyclo[2.2.1]heptan-7-yl]oxy-(diisopropylamino)phosphanyl]oxypropanenitrile (Present compound 5);

N-[1-[(1R,3R,4R,7S)-5-(benzenesulfonyl)-1-[[bis(4-methoxyphenyl)-phenyl-methoxy]methyl]-7-[2-cyanoethoxy-(diisopropylamino)phosphanyl)oxy-2-oxa-5-azabicyclo[2.2.1]heptan-3-yl]-5-methyl-2-oxo-pyrimidin-4-yl]benzamide (Present compound 6);

(1R,3R,4R,7S)-1-[[bis(4-methoxyphenyl)-phenyl-methoxy]methyl]-7-[2-cyanoethoxy-(diisopropylamino)phosphanyl]oxy-N-methyl-3-(5-methyl-2,4-dioxo-pyrimidin-1-yl)-2-oxa-5-azabicyclo[2.2.1]heptane-5-carboxamide (Present compound 7);

(1R,3R,4R,7S)-3-(4-benzamide-5-methyl-2-oxo-pyrimidin-1-yl)-1-[[bis(4-methoxyphenyl)-phenyl-methoxy]methyl]-7-[2-cyanoethoxy-(diisopropylamino)phosphanyl]oxy-N-methyl-2-oxa-5-azabicyclo[2.2.1]heptane-5-carboxamide (Present compound 8);

[9-[(1R,3R,4R,7S)-1-[[bis(4-methoxyphenyl)-phenyl-methoxy]methyl]-7-[2-cyanoethoxy-(diisopropylamino)phosphanyl]oxy-5-(methylcarbamoyl)-2-oxa-5-azabicyclo[2.2.1]heptan-3-yl]-2-(2-methylpropanoylamino)purin-6-yl]N,N-diphenylcarbamate (Present compound 9);

(1R,3R,4R,7S)-3-(6-benzamidepurin-9-yl)-1-[[bis(4-methoxyphenyl)phenylmethoxy]methyl]-7-[2-cyanoethoxy-(diisopropylamino)phosphanyl]oxy-N-methyl-2-oxa-5-azabicyclo[2.2.1]heptane-5-carboxamide (Present compound 10);

(1R,3R,4R,7S)-1-[[bis(4-methoxyphenyl)phenyl-methoxy]methyl]-7-[2-cyanoethoxy-(diisopropylamino)phosphanyl]oxy-N-isopropyl-3-(5-methyl-2,4-dioxopyrimidin-1-yl)-2-oxa-5-azabicyclo[2.2.1]heptane-5-carboxamide (Present compound 11);

(1R,3R,4R,7S)-3-(4-benzamide-5-methyl-2-oxopyrimidin-1-yl)-1-[[bis(4-methoxyphenyl)phenyl-methoxy]methyl]-7-[2-cyanoethoxy-(diisopropylamino)phosphanyl]oxy-N-isopropyl-2-oxa-5-azabicyclo[2.2.1]heptane-5-carboxamide (Present compound 12);

[9-[(1R,3R,4R,7S)-1-[[bis(4-methoxyphenyl)-phenyl-methoxy]methyl]-7-[2-cyanoethoxy-(diisopropylamino)phosphanyl]oxy-5-(isopropylcarbamoyl)-2-oxa-5-azabicyclo[2.2.1]heptan-3-yl]-2-(2-methylpropanoylamino)purin-6-yl]N,N-diphenylcarbamate (Present compound 13);

(1R,3R,4R,73)-3-(6-benzamidepurin-9-yl)-1-[[bis(4-methoxyphenyl)-phenyl-methoxy]methyl]-7-[2-cyanoethoxy-(diisopropylamino)phosphanyl]oxy-N-isopropyl-2-oxa-5-azabicyclo[2.2.1]heptane-5-carboxamide (Present compound 14);

(1R,3R,4R,7S)-1-[[bis(4-methoxyphenyl)-phenyl-methoxy]methyl]-7-[2-cyanoethoxy-(diisopropylamino)phosphanyl]oxy-N,N-dimethyl-3-(5-methyl-2,4-dioxopyrimidin-1-yl)-2-oxa-5-azabicyclo[2.2.1]heptane-5-carboxamide (Present compound 15);

(1R,3R,4R,7S)-3-(4-benzamide-5-methyl-2-oxo-pyrimidin-1-yl)-1-[[bis(4-methoxyphenyl)-phenylmethoxy]methyl]-7-[2-cyanoethoxy-(diisopropylamino)phosphanyl]oxy-N,N-dimethyl-2-oxa-5-azabicyclo[2.2.1]heptane-5-carboxamide (Present compound 16);

3-[(1R,3R,4R,7S)-1-[[bis(4-methoxyphenyl)-phenyl-methoxy]methyl]-3-(5-methyl-2,4-dioxo-pyrimidin-1-yl)-5-pyrimidin-2-yl-2-oxa-5-azabicyclo[2.2.1]heptan-7-yl]oxy-(diisopropylamino)phosphanyl]oxypropanenitrile (Present compound 17);

1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]-5-methyl-2-oxo-pyrimidin-4-yl]benzamide (Present compound 18);

N'-[9-(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]-6-oxo-1H-purin-2-yl]-N,N-dimethyl-6-formamidine (Present compound 19);

N'-[9-(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]purin-6-yl]benzamide (Present compound 20);

3-[(1R,3R,4R,7S)-1-[[bis(4-methoxyphenyl)-phenyl-methoxy]methyl]-3-(5-methyl-2,4-dioxopyrimidin-1-yl)-5-4-yl-2-oxa-5-azabicyclo[2.2.1]heptan-7-yl]oxy-(diisopropylamino)phosphanyl]oxypropanenitrile (Present compound 21);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-4-yl-2-oxa-5-azabicyclo[2.2.1]heptan-3-yl]-5-methyl-2-oxo-pyrimidin-4-yl]benzamide (Present compound 22);

3-[[(1R,3R,4R,7S)-1-[[bis(4-methoxyphenyl)-phenyl-methoxy]methyl]-3-(5-methyl-2,4-dioxo-pyrimidin-1-yl)-5-[4-(trifluoromethyl)pyrimidin-2-yl]-2-oxa-5-azabicyclo[2.2.1]heptan-7-yl]oxy-(diisopropylamino)phosphanyl]oxypropanenitrile (Present compound 23);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-[4-(trifluoromethyl)pyrimidin-2-yl]-2-oxa-5-azabicyclo[2.2.1]heptan-3-yl]-5-methyl-2-oxo-pyrimidin-4-yl]benzamide (Present compound 24);

3-[[(1R,3R,4R,7S)-1-[[bis(4-methoxyphenyl)-phenyl-methoxy]methyl]-5-(5-chloropyrimidin-2-yl)-3-(5-methyl-2,4-dioxo-pyrimidin-1-yl)-2-oxa-5-azabicyclo[2.2.1]heptan-7-yl]oxy-(diisopropylamino)phosphanyl]oxypropanenitrile (Present compound 25);

N-[1-[(1R,3R,4R,7S)-1-[[bis(4-methoxyphenyl)-phenyl-methoxy]methyl]-5-(5-chloropyrimidin-2-yl)-7-[2-cyanoethoxy-(diisopropylamino)phosphanyl]oxy-2-oxa-5-azabicyclo[2.2.1]heptan-3-yl]-5-methylpyrimidin-4-yl]benzamide (Present compound 26);

3-[[(1R,3R,4R,7S)-1-[[bis(4-methoxyphenyl)-phenyl-methoxy]methyl]-5-[6-(dimethylamino)pyrimidin-4- yl]-3-(5-methyl-2,4-dioxo-pyrimidin-1-yl)-2-oxa-5-azabicyclo[2.2.1]heptan-7-yl]oxy-(diisopropylamine)phosphanyl]oxypropanenitrile (Present compound 27);

N-[1-[(1R,3R,4R,7S)-1-[[bis(4-methoxyphenyl)-phenyl-methoxy]methyl]-7-[2-cyanoethoxy(diisopropylamino)phosphanyl]oxy-5-[(6-dimethylamino)pyrimidin-4-yl]-2-oxa-5-azabicyclo[2.2.1]heptan-3-yl]-5-methyl-2-oxo-pyrimidin-4-yl]benzamide (Present compound 28);

3-[[(1R,3R,4R,7S)-1-[[bis(4-methoxyphenyl)-phenyl-methoxy]methyl]-5-[2-(dimethylamino)pyrimidin-4-yl]-3-(5-methyl-2,4-dioxo-pyrimidin-1-yl)-2-oxa-5-azabicyclo[2.2.1]heptan-7-yl]oxy-(diisopropylamino)oxypropanenitrile (Present compound 29);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-[2-(dimethylamino)pyrimidin-4-yl]-7-hydroxy-2-oxa-5-azabicyclo[2.2.1]heptan-3-yl]-5-methyl-2-oxo-pyrimidin-4-yl]benzamide (Present compound 30);

3-[1-[(1R,3R,4R,7S)-1-[[bis(4-methoxyphenyl)-phenyl-methoxy]methyl]-3-(5-methyl-2,4-dioxopyrimidin-1-yl)-5-pyrazin-2-yl-2-oxa-5-azabicyclo[2.2.1]heptan-7-yl]oxy-(diisopropylamino)phosphanyl]oxypropanenitrile (Present compound 31);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrazine-2-yl-2-oxa-5-azabicyclo[2.2.1]heptan-3-yl]-5-methyl-2-oxo-pyrimidin-4-yl]benzamide (Present compound 32);

3-([(1R,3R,4R,7S)-1-[[bis(4-methoxyphenyl)-phenyl-methoxy]methyl)-5-(1,5-dimethyl-1,2,4-triazol-3-yl)-3-(5-methyl-2,4-dioxopyrimidin-1-yl)-2-oxa-5-azabicyclo[2.2.1]heptan-7-yl]oxy-(diisopropylamino)phosphanyl]oxypropanenitrile (Present compound 33);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-5-methyl-2-oxo-pyrimidin-4-yl]benzamide (Present compound 34);

N'-[9-[(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-6-oxo-1H-purin-2-yl]-N,N-dimethylformamidine (Present compound 35);

N-[9-(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]purin-6-yl]benzamide (Present compound 36);

3-[[(1R,3R,4R,7S)-1-[[bis(4-methoxyphenyl)-phenyl-methoxy]methyl]-3-(5-methyl-2,4-dioxopyrimidin-1-yl)-5-(5-methyl-1,2,4-oxadiazol-3-yl)-2-oxa-5-azabicyclo[2.2.1]heptan-7-yl]oxy-(diisopropylamino)phosphanyl]oxypropanenitrile (Present compound 37);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(5-methyl-1,2,4-oxadiazol-3-yl)-2-oxa-5-azabicyclo[2.2.1]heptan-3-yl]-5-methyl-2-oxo-pyrimidin-4-yl]benzamide (Present compound 38);

3-[[(1R,3R,4R,7S)-1-[[bis(4-methoxyphenyl)-phenyl-methoxy]methyl]-3-(5-methyl-2,4-dioxopyrimidin-1-yl)-5-(3-methyl-1,2,4-thiadiazol-5-yl)-2-oxa-5-azabicyclo[2.2.1]heptan-7-yl]oxy-(diisopropylamino)phosphanyl]oxypropanenitrile (Present compound 39);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(3-methyl-1,2,4-thiadiazol-5-yl)-2-oxa-5-azabicyclo[2.2.1]heptan-3-yl]-5-methyl-2-oxo-pyrimidin-4-yl]benzamide (Present compound 40);

N-[1-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-5-methyl-2-oxo-pyrimidin-4-yl]dihydropyrimidin-2-one (Present compound 41);

N'-[9-[(1R,3R,4R,7S)-1-[[bis(4-methoxyphenyl)-phenyl-methoxy]methyl]-7-[2-cyanoethoxy(diisopropylamino)phosphanyl]oxy-5-methylsulfonyl-2-oxa-5-azabicyclo[2.2.1]heptan-3-yl]-6-oxo-1H-purin-2-yl]-N,N-dimethylformamidine (Present compound 42);

N-[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-6-oxo-1H-purin-2-yl]-2-methylpropane amide (Present compound 43); and N-[9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-6-oxo-1H-purin-2-yl]-2-methylpropane amide (Present compound 44).

(Oligonucleotide)

[18] An oligonucleotide compound comprising one or more nucleosides represented by general formula (I'):

(I')

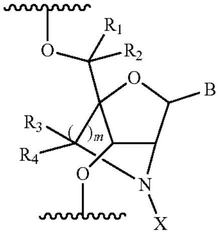

[wherein,

B represents a base moiety of nucleic acid wherein the base moiety may be optionally substituted with one or more substituents;

$R_1$, $R_2$, $R_3$ and $R_4$ represent independently of each other a hydrogen atom, or a $C_{1-6}$ alkyl group which may be optionally substituted with one or mere substituents;

m is an integer of 1 or 2;

X represents a group represented by the following formula (II'-1), (II'-2), or (II'-3):

(II'-1)

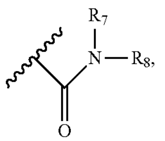

(II'-2)

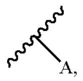

-continued (II'-3)

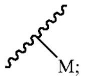

the symbols:

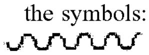

which is described in the formula (II'-1), (II'-2) or (II'-3) represents a binding point to 2'-amino group;

A represents an aromatic group containing one or more heteroatoms selected from the group consisting of nitrogen atom, oxygen atom and sulfur atom, which may be optionally substituted with one or more substituents;

M represents a sulfonyl group which is substituted with one or more substituents selected from the group consisting of a $C_{1-6}$ alkyl group which may be optionally substituted with one or more substituents, and an aromatic group which may be optionally substituted with one or more substituents.]

or salts thereof (hereinafter, the compound represented by formula (I') or salts thereof is referred to as "Present oligonucleotide compound" or "Oligonucleotide compound of the present invention").

[19] The compound according to [18] or salts thereof wherein B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents or an uracilyl group which may be optionally substituted with one or more substituents.

[20] The oligonucleotide compound according to [18] or [19] or salts thereof wherein $R_1$, $R_2$, $R_3$ and $R_4$ represent independently of each other a hydrogen atom; and m is an integer of 1.

[21] (Urea compound) The oligonucleotide compound according to any one of [18] to [20] or salts thereof, wherein X represents a group represented by formula (II'-1); and $R_7$ and $R_8$ represent independently of each other a hydrogen atom, a C1-6 alkyl group which may be optionally substituted with one or more substituents, or an aromatic group which may be optionally substituted with one or more substituents.

[22] The oligonucleotide compound according to [21] or salts thereof wherein $R_7$ and $R_8$ represent independently of each ocher a hydrogen atom, a C1-3 alkyl group which may be optionally substituted with one or more substituents.

[23] The oligonucleotide compound according to [22] or salts thereof wherein one of $R_7$ and $R_8$ represents a hydrogen atom, and the ether thereof represents a methyl group.

[24] The oligonucleotide compound according to [23] or salts thereof wherein one of $R_7$ and $R_8$ represents a hydrogen atom, and the other thereof represents an isopropyl group.

[25] (Aryl type compound) The oligonucleotide compound according to any one of claims 18 to 20 or salts thereof wherein X represents a group represented by formula (II'-2); and A represents a five or six membered heteroaryl group containing one or more heteroatoms selected from the group consisting of nitrogen atom, oxygen atom and sulfur atom, which may be optionally substituted with one or more substituents.

[26] The oligonucleotide compound according to [25] or salts thereof wherein

A represents a five or six membered heteroaryl group containing two or three heteroatoms selected from nitrogen atom, oxygen atom, and sulfur atom, provided that at least two nitrogen atoms are included, which may be optionally substituted with one or more substituents, and the substituent is selected independently of each other from a group consisting of a C1-3 alkyl group which may be optionally substituted with one or more halogen atoms, a halogen atom, and an amino group which may be optionally substituted with one or more C1-3 alkyl groups.

[27] The oligonucleotide compound according to [26] or salts thereof wherein the five or six membered heteroaryl group is selected from the group consisting of a triazolyl group, an oxadiazolyl group, a thiadiazolyl group, a pyrimidinyl group, and a pyrazinyl group, each may be optionally substituted with one or more substituents.

[28] The oligonucleotide compound according to [27] or salts thereof wherein the triazolyl group which may be optionally substituted with one or more substituents represents 1,5-dimethyl-1,2,4-triazol-3-yl group.

[29] The oligonucleotide compound according to [27] or salts thereof wherein the oxadiazolyl group which may be optionally substituted with one or more substituents represents 5-methyl-1,2,4-oxadiazol-3-yl group.

[30] The oligonucleotide compound according to [27] or salts thereof wherein the thiadiazolyl group which may be optionally substituted with one or more substituents represents 3-methyl-1,2,4-thiadiazol-5-yl group.

[31] (Sulfonamide type compound) The oligonucleotide compound according to any one of [18] to [20] or salts thereof, wherein X represents a group represented by formula (II'-3); and M represents a sulfonyl group which is substituted with one or more substituents selected from the group consisting of a C1-6 alkyl group which may be optionally substituted with one or more substituents, and an aryl group which may be optionally substituted with one or more substituents.

[32] The compound according to any one of [18] to [31] or salts thereof wherein M represents a sulfonyl group which is substituted with one or more substituents selected from the group consisting of a methyl group and a phenyl group.

[33] The oligonucleotide compound according to any one of [1] to [32] or salts thereof wherein one or more phosphate bonds between nucleotides represent a phosphorothioate bond.

Effect of Invention

According to the present invention, novel 2'-amino LNA (hereinafter, is abbreviated as "ALNA") and oligomer comprising these ALNA as a monomer (hereinafter, is abbreviated as "ALNA oligomer") can be prepared. The ALNA oligomer of the present invention has a functional inhibition of a target microRNA in vitro, or a potential target gene knockdown activity, and when administered to a living body, has a potential target gene knockdown activity in many organs (such as muscle), which accordingly can be expected to use as novel nucleic acid medicine.

MODE FOR CARRYING OUT THE INVENTION

Hereinafter, the present invention is further explained in details. All of the publications cited herein are incorporated herein by reference.

Definition

First, the definitions of the terms as used herein are described.

The term of "$C_{1-6}$ alkyl which may be optionally substituted with one or more substituents" as used herein encompasses any straight chain alkyl group having 1 to 6 carbon atoms ($C_{1-6}$), preferably 1 to 4 carbon atoms ($C_{1-4}$), more preferably 1 to 3 carbon atoms ($C_{1-3}$), any branched chain alkyl group having 3 to 6 carbon atoms in which the identical or different branched chains are contained, any cyclic alky group having 3 to 6 carbon atoms, and any combinations thereof which have 4 to 6 carbon atoms. Specific examples of the straight chain alkyl group having 1 to 6 carbon atoms include methyl, ethyl, normal (which is abbreviated as "n")-propyl, iso (which is abbreviated as "i")-propyl, n-butyl, n-pentyl, and n-hexyl. Specific examples of the branched chain alkyl group having 3 to 6 carbon atoms in which the identical or different branched chains are contained include i-propyl, i-butyl, tert (which is abbreviated as "t")-butyl, sec (which is abbreviated as "s")-butyl, neopentyl, isopentyl, and the others, and also examples of the cyclic alkyl group having 3 to 6 carbon atoms include preferably a 3 to 6 membered monocyclic cycloalkyl group, and specific examples thereof include cyclopropyl, cyclobutyl, cyclopentyl, cyclohexyl, and the others, which are not limited thereto. Examples of the substituents include one or more (or preferably one to three) identical or different groups selected from the group consisting of a hydroxy group, a halogen atom, a nitro group, a cyano group, a $C_{1-6}$ alkyl group, a $C_{2-t}$ alkenyl group, a $C_{2-6}$ alkynyl group, a $C_{1-6}$ alkoxy group, an aryl group, an aryloxy group, an amino group which may be optionally substituted with $C_{1-3}$ alkyl group, an oxo group, a thioxo group, and a $C_{1-6}$ alkyl group which may be optionally substituted with one or more halogen atoms, and any groups not being affected under a reaction condition for oligomerization is preferably included.

The term of "$C_{1-3}$ alkyl group which may be optionally substituted with one or more substituents" as used herein represents methyl, ethyl, n-propyl, or i-propyl, each may be substituted with one or more halogens, as defined in the above term of "$C_{1-3}$ alkyl group which may be optionally substituted with one or more substituents". Specific examples thereof include perfluoroalkyl (such as trifluoromethyl, pentafluoroethyl, or heptafluoropropyl) and the others.

The term of "$C_{2-6}$ alkenyl which may be optionally substituted with one or more substituents" as used herein encompasses any straight chain alkenyl group having 2 to 6 carbon atoms ($C_{2-6}$), preferably having 2 to 4 carbon atoms ($C_{2-4}$), more preferably having 2 to 3 carbon atoms ($C_{2-3}$), any branched chain alkenyl group having 3 to 6 carbon atoms in which the identical or different branched chains are contained, any cyclic alkenyl group having 3 to 6 carbon atoms, and any combinations thereof that have 4 to 6 carbon atoms. Specific examples of the straight chain alkenyl group having 2 to 6 carbon atoms include ethenyl, 1-propenyl, 2-propenyl, 1-butenyl, 2-butenyl, 1-pentenyl, 2-pentenyl, 3-pentenyl, 4-pentenyl, 1-hexenyl, and the others. Specific examples the branched chain alkenyl group having 3 to 6 carbon atoms in which the identical or different branched chains are contained include isopropenyl, 1-methyl-1-propenyl, 1-methyl-2-propenyl, 2-methyl-1-propenyl, 2-methyl-2-propenyl, 1-methyl-2-butenyl and the others, and also examples of the cyclic alkenyl group having 3 to 6 carbon atoms include a three to six membered monocyclic cycloalkenyl group, and specific examples thereof include cyclopropenyl, cyclobutenyl, cyclopentenyl, cyclohexenyl, and the others. Examples of the substituents include one or more (or preferably one to three) identical or different groups selected from the group consisting of a hydroxy group, a halogen atom, a nitro group, a cyano group, a $C_{1-6}$ alkyl group, a $C_{2-4}$ alkenyl group, a $C_{2-6}$ alkynyl group, a $C_{1-6}$ alkoxy group, an aryl group, an aryloxy group, an amino group which may be optionally substituted with $C_{1-3}$ alkyl group, an oxo group, a thioxo group, and a $C_{1-6}$ alkyl group which may be optionally substituted with one or more halogen atoms, and any groups not being affected under a reaction condition for oligomerization is preferably included.

The term of "a $C_{2-6}$ alkynyl which may be optionally substituted with one or more substituents" as used herein encompasses any straight chain alkynyl group having 2 to 6 carbon atom ($C_{2-6}$), preferably any straight chain alkynyl group having 2 to 4 carbon atoms ($C_{2-4}$), more preferably any straight chain alkynyl group having 2 to 3 carbon atoms ($C_{2-3}$), any branched chain alkynyl group having 3 to 6 carbon atoms which have the identical or different branched chains, any cyclic alkynyl group having 3 to 6 carbon atoms, and any combinations thereof which have 4 to 6 carbon atoms. Specific examples of the straight chain alkynyl group having 2 to 6 carbon atoms include ethynyl, 1-propynyl, 2-propynyl, 1-butynyl, 2-butynyl, 1-pentynyl, 2-pentynyl, 3-pentynyl, 4-pentynyl, 1-hexynyl and the others. Specific examples of the branched chain alkynyl group having 3 to 6 carbon atoms in which the identical or different branched chains are contained include isopropynyl, 1-methyl-1-propynyl, 1-methyl-2-propynyl, 2-methyl-1-propynyl, 2-methyl-2-propynyl, l-methyl-2-butynyl, and the others, and also examples of the cyclic alkynyl group having 3 to 6 carbon atoms include preferably a three to six membered monocyclic cycloalkynyl group, and specific examples thereof include cyclobutynyl, cyclopentynyl, cyclohexynyl and the others, which are not limited thereto. Examples of the substituents include one or more (or preferably one to three) identical or different groups selected from the group consisting of a hydroxy group, a halogen atom, a nitro group, a cyano group, a $C_{1-6}$ alkyl group, a $C_{2-6}$ alkenyl group, a $C_{2-6}$ alkynyl group, a $C_{1-6}$ alkoxy group, an aryl group, an aryloxy group, an amino group which may be optionally substituted with $C_{1-3}$ alkyl group, an oxo group, a thioxo group, and a $C_{1-6}$ alkyl group which may be optionally substituted with one or more halogen atoms, and any groups not being affected under a reaction condition for oligomerization is preferably included.

The term of "an aromatic group which may be optionally substituted with one or more substituents" as used herein means to encompass both of an aryl group and a heteroaryl group. The aryl group and the heteroaryl group may be independently of each other substituted with one or more substituents. Examples of the substituents include one or more (or preferably one to three) identical or different groups selected from the group consisting of a hydroxy group, a halogen atom, a nitro group, a cyano group, a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, a hydroxy group, a $C_{1-6}$ alkoxy group, an aryloxy group, an amino group which may be optionally substituted with one or more $C_{1-3}$ alkyl groups, an $C_{1-6}$ alkyl groups which may be optionally substituted with one or mere halogen atoms, and an aryl group, preferably a $C_{1-6}$ alkyl group which may be optionally substituted with one or more substituents, an amino group which may be optionally substituted with one or more $C_{1-3}$ alkyl groups, and a halogen atom, and more preferably a trifluoromethyl group, a dimethylamino group, a chloro atom and the others, and any groups being affected under a reaction condition for oligomerization is preferably included.

The term of "aryl (group)" as used herein represents a functional group or a substituent group which is derivatized from aromatic hydrocarbon group and encompasses a group composed of a plurality of cycles, and specifically, represents a monovalent group having 6 to 14 carbon atoms in which one hydrogen atom is excluded from aromatic hydrocarbon atom, consisting of one or more five membered and/or six membered ring, and include, for example, phenyl, indenyl, naphthyl, phenanthrenyl, anthracenyl and the others. Also examples of the substituents for the aryl group include one or more (or preferably one to three) identical or different groups selected from the group consisting of a hydroxy group, a halogen atom, a nitro group, a cyano group, a $C_{1-6}$ alkyl group which may be optionally substituted with one or more substituents, a $C_{2-4}$ alkenyl group which may be optionally substituted with one or more substituents, a $C_{2-6}$ alkynyl group which may be optionally substituted with one or more substituents, a $C_{1-6}$ alkoxy group, an aryloxy group, an amino group, an amino group which may be optionally substituted with one or more $C_{1-3}$ alkyl groups, and an aryl group, preferably a $C_{1-6}$ alkyl group which may be optionally substituted with one or more substituents, an amino group which may be optionally substituted with one or more $C_{1-3}$ alkyl groups, and a halogen atom, and more preferably a trifluoromethyl group, a dimethylamino group, a chloro atom and the others, and any groups being affected under a reaction condition for oligomerization is preferably included.

Specific examples of the aryl group which may be optionally substituted with one or mere substituents include 2-methylphenyl, 3-methylphenyl, 4-methylphenyl, 2,6-dimethylphenyl, 2,4-dimethylphenyl, 2-chlorophenyl, 3-chlorophenyl, 4-chlorophenyl, 2,4-dichlorophenyl, 2,5-dichlorophenyl, 2,6-dichlorophenyl, 2-bromophenyl, 4-methoxyphenyl, 4-chlorophenyl, 2-nitrophenyl, 4-nitrophenyl, 2-nitrophenyl, 2,6-dinitrophenyl, 2-trifluoromethylphenyl, 3-trifluoromethylphenyl, 4-trifluoromethylphenyl, 2-dimethylaminophenyl, 3-dimethylaminophenyl, 4-dimethylaminophenyl, and biphenyl and the others. Preferred examples of the aryl group include a phenyl group which is substituted with halogen atom, $C_{1-6}$ alkoxy group or nitro group, or an unsubstituted phenyl group.

The term of "heteroaryl (group)" as used herein represents a monovalent group in which one hydrogen atom is excluded from optional heteroaromatic compound containing one or more heteroatoms (such as nitrogen atom, oxygen atom, and/or sulfur atom) in a ring structure and having 5 to 12 carbon atoms, consisting of one or more five membered and/or six membered ring, and preferably five membered cyclic or six membered cyclic heteroaryl group. Specific examples of the heteroaryl group include a five membered cyclic heteroaryl group selected from pyrrolyl, furyl, thienyl, pyrazolyl, imidazolyl, triazolyl, tetrazolyl, oxazolyl, isoxazolyl, thiazolyl, isothiazolyl, oxadiazolyl, and thiadiazolyl; a six membered cyclic heteroaryl group selected from pyridyl, pyridazinyl, pyrimidinyl, and pyrazinyl, and preferably triazolyl, oxadiazolyl, thiadiazolyl group, pyrimidinyl, or pyrazinyl. Also examples of the substituents for the heteroaryl group include one or more (or preferably one to three) identical or different groups selected from the group consisting of a hydroxy group, a halogen atom, a nitro group, a cyano group, a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, a $C_{1-6}$ alkoxy group, an aryloxy group, an amino group, an amino group which may be optionally substituted with one or more $C_{1-3}$ alkyl groups, and an aryl group, preferably a $C_{1-6}$ alkyl group which may be optionally substituted with one or more substituents, an amino group which may be optionally substituted with one or more $C_{1-3}$ alkyl groups, and a halogen atom, and more preferably a trifluoromethyl group, a dimethylamino group, a chloro atom and the others, and any groups being affected under a reaction condition for oligomerization is preferably included.

Specific examples of the heteroaryl group which may be optionally substituted with one or more substituents include 1,2,4-triazolyl, 1,5-dimethyl-1,2,4-triazolyl, 1,2,4-oxadiazolyl, 5-methyl-1,2,4-oxadiazol-3-yl, 1,2,4-thiadiazolyl, 3-methyl-1,2,4-thiadiazol-5-yl, 1,3-pyrimidinyl, 1,5-pyrimidinyl, 4-trifluoromethyl, 1,5-pyrimidinyl, 4-dimethylamino-2,4-pyrimidinyl, 3-dimethylamino-2,4-pyrimidinyl, 3-chloro-1,5-pyrimidinyl, and 1,4-pyridazinyl, and preferably 1,5-dimethyl-1,2,4-triazol-3-yl, 1,2,4-oxadiazolyl, 3-methyl-1,2,4-thiadiazol-5-yl, 1,5-pyrimidinyl, 4-trifluoromethyl-1,5-pyrimidinyl, 4-dimethylamino-2,4-pyrimidinyl, 3-dimethylamino-2,4-pyrimidinyl, 3-chloro-1,5-pyrimidinyl, and 1,4-pyridazinyl, and more preferably 1,5-dimethyl-1,2,4-triazol-3-yl, 1,2,4-oxadiazol-3-yl, and 3-methyl-1,2,4-thiadiazol-5-yl.

Examples of the term of "five or six membered heteroaryl group containing one or more heteroatoms selected from the group consisting of nitrogen atom, oxygen atom and sulfur atom, which may be optionally substituted with one or more substituents" as used herein include a five membered cyclic or six membered cyclic heteroaryl group which may optionally substituted with one or more substituents, which is defined in the above-mentioned term of "heteroaryl group".

The term of "five or six membered heteroaryl group containing two or three heteroatoms selected from nitrogen atom, oxygen atom, and sulfur atom, provided that at least two nitrogen atoms are included, which may be optionally substituted with one or more substituents" as used herein represents triazolyl, oxadiazolyl, thiadiazolyl, pyrimidinyl, and pyridazinyl, each may be substituted with one or more substituents, which is defined in the above-mentioned term of "heteroaryl group.

The term of "sulfonyl group which is substituted with one substituent selected from the group consisting of a C1-6 alkyl group which may be optionally substituted with one or more substituents and an aromatic group which may be optionally substituted with one or more substituents" represents a sulfonyl ($S(O)_2$) group which is substituted with one substituents thereof. The $C_{1-6}$ alkyl group which may be optionally substituted with one or more substituents, or the aromatic group which may be optionally substituted with one or more substituents are as defined above, and specific examples of the substituents include methyl, trifluoromethyl, phenyl, 4-methylphenyl, and the others, preferably methyl and phenyl.

The term of "$C_{1-6}$ alkoxy group" as used herein represents a monovalent group in which the $C_{1-6}$ alkyl binds to an oxygen atom, and represents a $C_{1-6}$ alkyl-O group. Specific examples thereof include methoxy, ethoxy, n-propoxy, i-propoxy, n-butoxy, t-butoxy, s-butoxy, 3-methylbutoxy, and the others, which are not limited thereto.

The term of "aryloxy (group)" as used herein represents a monovalent group in which the aryl group is bonded to an oxygen atom. Specific examples thereof include phenoxy, p-tolyl and the others, which are not limited thereto.

The term of "amino group which may be optionally substituted with one or more $C_{1-3}$ alkyl groups" as used herein represents an amino group which may be optionally substituted with one or more hydrogen atoms may be optionally substituted with a $C_{1-3}$ alkyl group. Specific examples thereof include methylamino, ethylamino, isopropylamino, dimethylamino, diethylamino, methylethylamino, and the others, which are not limited thereto.

Examples of the term of "halogen (atom)" as used herein include fluorine atom (fluoro), chlorine atom (chloro), bromine atom (bromo), and iodine atom (iodo), and fluorine atom or chloro atom is preferred.

Herein when the compound of the present invention, an intermediate compound, or a starting material and the others has a functional group (such as, a hydroxy group, an amino group, a carboxyl group and the others), the functional group may be protected with a protecting group that is usually used in an organic synthetic chemistry according to the method described in Theodora W. Greene, Peter G. M. Wuts, "Protective Groups in Organic Synthesis" 4th. ed., John Wiley & Sons, Inc. 1999, and after the reaction, the protecting group may be then removed to obtain the desirable compound. Examples of the protecting group include the protecting group that is usually used in an organic synthetic chemistry as described in the sane document, and is also usually used in an organic synthetic chemistry, and examples of each of the protecting group depending on the functional group are described below.

The term of "protecting group" described in terms of "a protecting group for hydroxy group", "a protecting group for amino group", "a protecting group for phosphate group", or "a protecting group for mercapto group" as used herein is nor particularly limited to any group as long as it can protect amino group, hydroxy group, phosphate group or mercapto group stably during a nucleic acid synthesis. Specific examples thereof include a protecting group that is stable under acidic or neutral condition and also can be cleaved by a chemical method such as a hydrogenolysis, a hydrolysis, an electrolysis, and a photolysis. Examples of the protecting group includes an alkyl group having 1 to 6 carbon atoms; an alkenyl group having 2 to 6 carbon atoms; an alkynyl group having 2 to 6 carbon atoms; an acyl group; a tetrahydropyranyl group or a tetrahydrothiopyranyl group; a tetrahydrofuranyl group or a tetrahydrothiofuranyl group; a silyl group; a methyl group substituted with alkoxy group having 1 to 6 carbon atoms; a methyl group substituted with alkoxy group having 1 to 6 carbon atoms, said alkoxy group being substituted with alkoxy group having 1 to 6 carbon atoms; a methyl group substituted with alkoxy group having 1 to 6 carbon atoms said alkoxy group being substituted with halogen atom; an ethyl group substituted with alkoxy group having 1 to 6 carbon atoms; an ethyl group substituted with halogen atom; a methyl group substituted with one to three aryl groups; a methyl group substituted with one to three aryl groups, said aryl groups being substituted with alkyl group having 1 to 6 carbon atoms, alkenyl group having 2 to 6 carbon atoms, alkynyl group having 2 to 6 carbon atoms, alkoxy group having 1 to 6 carbon atoms, halogen atom, and/or cyano group; a carbonyl group substituted with alkoxy group having 1 to 6 carbon atoms; an aryl group substituted with halogen atom, alkoxy group having 1 to 6 carbon atoms and/or nitro group; a carbonyl group substituted with alkoxy group having 1 to 6 carbon atoms, said alkoxy group being substituted with halogen atom and/or silyl group substituted with alkyl group having 1 to 6 carbon atoms; an alkenyloxycarbonyl group; an aralkyloxycarbonyl group which may be optionally substituted with alkoxy group having 1 to 6 carbon atoms and/or aryl group substituted with nitro group; and the others.

The term of "protecting group for hydroxy group" represents a protecting group that is usually used in an organic synthetic chemistry (in particular, nucleic acid synthesis), and includes, for example, an aliphatic acyl group; an aromatic acyl group; an aminocarbonyl group which may be substituted; an alkoxycarboyl group which may be substituted; an aliphatic sulfonyl group; an aromatic sulfonyl group; a methyl group substituted with one to three aryl groups; a methyl group substituted with one to three groups, said aryl group being substituted with alkyl group having 1 to 6 carbon atoms, alkoxy group having 1 to 6 carbon atoms, halogen atom and/or cyano group; or a silyl group. Specific examples thereof include benzyl (Bn), 4,4'-dimethoxytrityl (DMTr), 4-methoxytrityl, triphenylmethyl, 2-naphthylmethyl, diphenylaminocarbonyl (DPC), cyanoethoxycarbonyl, tetrahydropyranyl, trimethylsilyl, triethylsilyl, triisopropylsilyl, t-butyldimethylsilyl, t-butyldiphenylsilyl, triphenylsilyl, 4-methoxybenzyl (p-methoxybenzyl), 3,4-dimethoxybenzyl, 2,6-dimethoxybenzyl, p-phenylbenzyl, methanesulfonyl, trifluoromethansulfonyl, methoxymethyl, benzoyl (Br), phenoxyacetyl, and acetyl and the others, which should not be limited thereto. Benzyl (Bn), 4,4'-dimethoxytrityl (DMTr), t-butyldimethylsilyl, t-butyldiphenylsilyl, trimethylsilyl (TMS), diphenylaminocarbonyl (DPC), methanesulfonyl, and trifluoromethansulfonyl are preferably included, and 4,4'-dimethoxytrityl (DMTr) is more preferably included.

The term of "phosphate group which may be optionally substituted" as used herein represents a phosphate, a phosphite, or a hydrophosphite, each of which may have optionally substituents (which encompasses protecting group). The term encompasses a phosphate group represented by a formula of $—P(R^{P1})R^{P2}$, wherein $R^{P1}$ and $R^{P2}$ represent independently of each other a hydroxy group, a hydroxy group that is protected with a protecting group for nucleic acid synthesis, a mercapto group, a mercapto that is protected with a protecting group for nucleic acid synthesis, an amino group, an alkoxy group having 1 to 5 carbon atoms, an alkylthio group having 1 to 6 carbon atoms, a cyanoalkoxy group having 1 to 6 carbon atoms, or an amine group that is substituted with alkyl group having 1 to 6 carbon atoms.

Here the groups of the above-mentioned formula wherein $R_{P1}$ represents $OR^{P1}$ and $R^{P2}$ represents $NR^{P1}$ is referred to as "phosphoramidite group", which is a preferred example. The $R^{P1a}$ represents an alkyl group having 1 to 5 carbon atoms or a cyanoalkyl group having 1 to 6 carbon atoms, and the $R^{P2a}$ represents an alkyl group having 1 to 6 carbon atoms. Specific examples of "phosphoramidite group" include a group represented by a formula of $—P(O(CH_2)_2CN)(N(iPr)_2)$, or a group represented by a formula of $—P(OCH_3)(N(iPr)_2)$ and the others, which is not limited thereto. The group represented by —$P(O(CH_2)_2CN)(N(iPr)_2)$ is preferably included. Herein "iPr" represents an isopropyl group.

The term of "phosphate group which may be optionally substituted with substituents" as used herein may form a chiral auxiliary containing a phosphorus atom. Specific examples of the chiral auxiliary containing a phosphorus atom include an optical active bicyclic oxazaphospholidine, which is described in non-patent document, N. Oka et al., J. AM. CHEM. SOC. 2008, 130, 16031, and an optical active 2-thio-1,3,2-oxa-thiaphospharane containing five valent phosphorus atom, which is described in non-patent document, K. W. Knouse et al., Science 10. 1126/science. aau3369 (2018), which is not limited thereto.

The term of "protecting group for amino group" represents a protecting group that is usually used in an organic synthetic chemistry (in particular, nucleic acid synthesis), and include, for example, an aliphatic acyl group; an aromatic acyl group; an alkoxycarboyl group which may be optionally substituted; a methyl group substituted with one to three aryl groups; and a methyl group substituted with aryl groups, said aryl group being substituted with halogen atom and/or cyano group. Specific examples thereof include acetyl (Ac), phenoxyacetyl (Pac), t-butylphenoxyacetyl group (Tac), p-isopropyl phenoxyacetyl group (iPc-Pac), trifluoroacetyl, propionyl group, isobutyryl, benzoyl (Bz), methoxycarbonyl, ethoxycarbonyl, t-butoxycarbonyl (Boc), trimethylsilylethoxycarbonyl (Teoc), cyanoethoxycarbonyl (Ceoc), benzyloxycarbonyl (Cbz), allyloxycarbonyl, 9-fluorenylmethoxycarbonyl (Fmoc), dimethylaminomethylenyl, 2,2,2-trichloroethoxycarbonyl, t-amyloxycarbonyl, 4-methoxybenzyl, triphenylmethyl, 2-nitrobenzenesulfonyl, 2,4-dinitrobenzenesulfonyl or 2-(trimethylsilyl)ethoxymethyl and the others, which are not limited thereto. Preferably, isobutyryl, benzoyl (Bz), t-butoxycarbonyl (Boc), and trimethylsilylethoxycarbonyl (Teoc) are included.

The term of "protecting group for a phosphate group" represents a protecting group that is usually used in an organic synthetic chemistry (in particularly, nucleic acid synthesis), and examples thereof include an alkyl group having 1 to 6 carbon atoms and/or an alkyl group having 1 to 6 carbon atoms substituted with cyano group; an aralkyl group; an aralkyl group substituted with aryl group, said aryl group being substituted with nitro group and/or halogen atom; an aryl group substituted with alkyl group having 1 to 6 carbon atoms, halogen atom, or nitro group; 2-cyanoethyl group; 2,2,2-trichloroethyl group; benzyl group; 2-chlorophenyl group; and 4-chlorophenyl group, and the ethers, which are not limited thereto.

The term of "protecting group for mercapto group" represents a protecting group that is usually used in an organic synthetic chemistry (in particularly, nucleic acid synthesis), and includes, for example, an aliphatic acyl group, an aromatic acyl group, a benzoyl group (Bz), and the others, which are not limited thereto.

The term of "leaving group" as used herein represents a partial substrate having electron pairs that is created when the substrate is cleaved by a cleavage of heterolysis during reaction(s), and encompasses a halogen atom (such as fluorine atom, chlorine atom, bromine atom, iodine atom), and "a leaving group for hydroxy". Examples of the leaving group for hydroxyl include a sulfonyloxy group (such as paratolunesulfonyloxy, mesyloxy, and trifluoromethanesulfonyloxy), an acyloxy group (preferably, saturated or unsaturated acyloxy group having 1 to 8 carbon atoms, for example, aryl group represented by $R^L$—C(═O)—O— wherein the $R^L$ represents an aryl group which may be optionally substituted with alkyl group (the total number of carbon atom is preferably 6 to 8, for example, phenyl, or p-tolyl), an aryloxy group which may be optionally substituted with alkyl group (the total number of carbon atom is preferably 6 to 8, for example, phenoxy, or p-tolyloxy), an aralkyl group (the total number of carbon atom is preferably 7 to 9, for example, benzyl), an arylalkenyl group (the total number of carbon atom is preferably 8 or 9, for example, cinnamyl), an aralkyloxy group (the total number of carbon atom is 7 to 15, for example, benzyloxy, or 9-fluorenylmethyloxy), an alkoxy group (a straight chain or branched chain alkoxy group, for example, methoxy, ethoxy, t-butoxy), and specific examples of the leaving group include iodo, bromo, chloro, fluoro, mesyloxy, methanesulfonyloxy, trifluoromethanesulfonyloxy, ethanesulfonyloxy, 2,2,2-trifluoroethanesulfonyloxy, propanesulfonyloxy, iso-propanesulfonyloxy, butanesulfonyloxy, nonafluorobutanesulfonyloxy, heptafluoropropan-1-sulfonyloxy, pentanesulfonyloxy, pentafluoroethanesulfonyloxy, pentanesulfonyloxy, cyclopentanesulfonyloxy, hexanesulfonyloxy, cyclohexanesulfonyloxy, o-toluenesulfonyloxy, m-toluenesulfonyloxy, p-toluenesulfonyloxy, benzenesulfonyloxy, o-bromobenzenesulfonyloxy, m-bromobenzenesulfonyloxy, p-bromobenzenesulfonyloxy, o-nitrobenzenesulfonyloxy, m-nitrobenzenesulfonyloxy, and p-nitrobenzenesulfonyloxy, and the others, which are not limited thereto. Preferred examples of the leaving group include methanesulfonyloxy (mesyloxy; Ms-O—), trifluoromethanesulfonyloxy, and p-toluenesulfonyloxy.

Examples of the term of "acyl group" as used herein include an aliphatic acyl group and aromatic acyl group. Specific examples of the aliphatic acyl group include an alkylcarbonyl group, such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and henaicosanoyl; an aryloxyalkycarbonyl group such as phenoxyacetyl (pac); a carboxylated alkylcarbonyl group such as succinoyl, glutaroyl, and adipoyl; a carbonyl group that is substituted with alkyl group having 1 to 6 carbon atoms, said alkyl group being substituted with halogen atom, such as chloroacetyl group, dichloroacetyl, trichloroacetyl, trifluoroacetyl; an alkoxyalkylcarbonyl group having 1 to 6 carbon atoms such as methoxyacetyl; and an unsaturated alkylcarbonyl group such as (E)-2-methyl-2-butenoyl. Also, examples of the aromatic acyl group include an arylcarbonyl group such as benzoyl, α-naphthoyl, and β-naphthoyl; a halogenoarylcarbonyl group such as 2-bromobenzoyl and 4-chlorobenzoyl; an arylcarbonyl group that is substituted with alkyl group having 1 to 6 carbon atoms, such as 2,4,6-trimethylbenzoyl, and 4-toluoyl; an arylcarbonyl group that is substituted with alkoxy group having 1 to 6 carbon atoms, such as 4-anisoyl; a carboxylated arylcarbonyl group such as 2-carboxybenzoyl, 3-carboxybenzoyl, and 4-carboxybenzoyl; a nitrolated arylcarbonyl group such as 4-nitrobenzolyl and 2-nitrobenzoyl; a carbonylated arylcarbonyl group that is substituted with alkoxy group having 1 to 6 carbon atoms, such as 2-(methoxycarbonyl)benzoyl; and an arylated arylcarbonyl group such as 4-phenylbenzoyl, which are not limited thereto.

The term of "aralkyl group" as used herein represents an alkyl group of 1 to 6 carbon atoms, preferably 1 to 4 carbon atoms, more preferably 1 to 3 carbon atoms, said alkyl group being substituted with aromatic hydrocarbon group (such as, 6 to 14 membered monocyclic, bicyclic, or tricyclic aromatic hydrocarbon group). Specific examples thereof include benzyl, phenethyl, 1-naphthylmethyl, 2-naphthylmethyl, and the others, but which are not limited thereto.

Examples of term of "silyl group" as used herein include a silyl group that is substituted with alkyl group having 1 to 6 carbon atoms, such as trimethylsilyl, triethylsilyl, isopropyldimethylsilyl, t-butyldimethylsilyl, methyldiisopropylsilyl, methyl di-t-butylsilyl, triisopropylsilyl; a silyl group that is substituted with one or two aryl group and also three alkyl groups having 1 to 6 carbon atoms, such as t-butyldiphenylsilyl, diphenylmethylsilyl, butyldiphenylbutylsilyl, diphenylisopropylsilyl, and phenyldiisopropylsilyl; and triphenylsilyl, but which are not limited thereto.

The term of "β form" as used herein represents the a compound having a stereochemistry in which the direction of substituting the substituted base moiety of nucleic acid at 1' position of a ribose of nucleic acid and the direction of substituting the substituted 5'-position side chain at 4' position of a ribose of nucleic acid are the same direction of the substitution. For a bridged artificial nucleic acid 2',4'-LNA, the β form represents the compound having the stereo configuration in which the direction of substituting the substituted base moiety of nucleic acid at 1' position of a ribose of nucleic acid and the direction of substituting the substituted 5'-position side chain that is not used for bridging substituted at 4' position of ribose of nucleic acid are the same direction of the substitution.

The term of "β selective" as used herein represents that a β form can be obtained.

The "a base moiety of nucleic acid" in the term of "a base moiety of nucleic acid which may be optionally substituted with one or more substituents" as used herein includes, for example, a base moiety of natural nucleic acid, and a base moiety of unnatural nucleic acid, which contains an aromatic heterocycle, and encompasses a monocyclic ring, a bicyclic ring, and a tricyclic ring. Here it should be clearly understood that base moieties of various nucleic acid that has been now considered "unnatural" to a skilled person in the art, could be found in nature hereafter. Thus "nucleic acid base moiety" includes not only any heterocycle contained in publicly known purine and pyrimidine, but also their heterocyclic analogues and tautomers. Specific examples of the base moiety of nucleic acid include adenine, guanine, thymine, cytosine, uracil, purine, xanthine, diaminopurine, 8-oxo-$N^6$-methyladenine, 7-deazaxanthine, 7-deazaguanine, $N^4$,$N^4$-ethanocytosine, $N^6$,$N^6$-ethano-2,6-diaminopurine, 5-methylcytosine, 5-($C^3$-$C^6$)-alkynylcytosine, 5-fluorocytosine, 5-bromouracil, pseudoisocytosine, 2-hydroxy-5-methyl-4-triazolopyridine, isocytosine, isoguanine, inosine, $N^6$-arylpurine, $N^6$-acylpurine, $N^4$-benzylpurine, $N^6$-halopurine, $N^6$-vinylpurine, $N^4$-acetylenic purine, $N^6$-acylpurine, $N^6$-hydroxyalkylpurine, $N^6$-thioalkylpurine, $N^2$-alkylpurine, $N^6$-alkylpyrimidine, $N^4$-acylpyrimidine, $N^4$-benzylpurine, $N^4$-halopyrimidine, $N^4$-vinylpyrimidine, $N^4$-acetylenic pyrimidine-, $N^4$-acetylpyrimidine, $N^4$-hydroxyalkylpyrimidine, $N^4$-thioalkylpyrimidine, 6-azapyrimidine, 6-azacytosine, 2- and/or 4-mercaptcpyrimidine, uracil, $C^5$-alkylpyrimidine, $C^5$-benzylpyrimidine, $C^5$-halopyrimidine, $C^5$-vinylpyrimidine, $C^5$-acetylenicpyrimidine, $C^5$-acylpyrimidine, $C^5$-hydroxyalkylpurine, $C^5$-amidopyrimidine, $C^5$-cyanopyrimidinyl, $C^5$-nitropyrimidine, $C^5$-aminopyrimidine, $N^2$-alkylpurine, $N^2$-alkyl-6-thiopurine, 5-cytidinyl, 5-azauracilyl, triazolopyridinyl, imidazolopyridinyl, pyrrolopyrimidinyl, pyrazolopyrimidinyl, and the others, which are not limited thereto. Preferred examples of the base moiety of nucleic acid include adenine, guanine, 2,6-diaminopurine, thymine, 2-thiothymine, cytosine, 5-methylcytosine, uracil, 5-fluorocytosine, xanthine, 6-aminopurine, 2-aminopurine, 6-chloro-2-aminopurine, and 6-chloropurine, and particular preferred examples of the base moiety of nucleic acid include adenine, guanine, cytosine, 5-methylcytosine, thymine, and uracil. The base moiety of the nucleic acid may be further substituted with one or more substituents, and examples of the substituents include hydroxy group, $C_{1-6}$ alkoxy group, mercapto group, $C_{1-6}$ alkylthio group, amino group, amino group substituted with $C_{1-6}$ alkyl group, $C_{1-6}$ alkyl group, $C_{1-6}$ alkynyl group, oxo group, thioxo group, and halogen atom. If necessary or if desirable, the functional oxygen atom, sulfur atom and nitrogen atom on the base moiety may be protected and/or deprotected. The appropriate protecting group is well known to a skilled person in the art, and encompasses, for example, the above-mentioned protecting group for hydroxy group and protecting group for amino group, and includes diphenylaminocarbonyl group, silyl group (such as trimethylsilyl group, dimethylhexylsilyl group, t-butyldimethylsilyl group, and t-butyldiphenylsilyl group), trityl group, alkyl group, acyl group (such as acetyl group, propionyl group, isobutyryl group, benzoyl group (Bz), phenoxyacetyl group (Fac)), alkoxycarboyl group (such as t-butoxycarbonyl group (Boc), benzyloxycarbonyl group (Cbz), diphenylaminocarbonyl group (DPC), cyanoethoxycarbonyl group (Ceoc)), sulfonyl group (such as methanesulfonyl group, and p-toluenesulfonyl group), dimethylaminomethylenyl group, and the others, which are not limited thereto.

The term of "artificial nucleic acid" as used herein encompasses artificial nucleoside, artificial nucleotide (herein, one nucleoside or nucleotide is sometimes referred to as a monomer) or artificial oligonucleotide. These artificial nucleic acids are not natural nucleic acids, but nucleic acids that can be produced only artificially. Examples of these artificial nucleic acids include those in which the nucleic acid base moiety contains an unnatural base, those having a sugar in which the sugar moiety is modified, and/or those containing an unnatural phosphate group as a phosphate moiety, and the artificial nucleic acids as used herein represents those in which the sugar moiety contains an unnatural sugar, in particular, those containing a (deoxy) ribose in which the carbon atoms at 2' position and 4' position are bridged.

The term of "artificial oligonucleotide" as used herein represents a substance in which two or more of the identical or different "artificial nucleosides" are bonded with each other via a phosphodiester bond or a thiophosphodiester bond and the like, and includes a substance in which preferably 2 up to 100, more preferably 5 up to 50, most preferably 10 up to 30 artificial nucleosides are bonded, or a substance in which the nucleotides together with these complementary strands forms a double strand. Herein, an oligonucleotide in which two or more nucleosides are bonded with each other is sometimes referred to as oligomer.

Embodiments of the compounds of the present invention are described.

Compound Represented by General Formula I

According to one embodiment of the present application, a compound represented by general formula I:

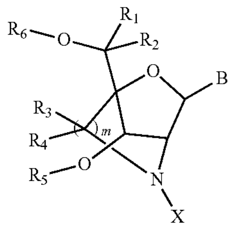

(I)

[wherein

B represents a base moiety of nucleic acid wherein the base moiety may be optionally substituted with one or more substituents;

$R_1$, $R_2$, $R_3$ and $R_4$ represent independently of each other a hydrogen atom, or a $C_{1-6}$ alkyl group which may be optionally substituted with one or more substituents;

$R_5$ and $R_6$ represent independently of each other a hydrogen atom, a protecting group for hydroxy group, or a phosphate group which may be optionally substituted with substituents;

m is an integer of 1 or 2;

X represents a group represented by the following formula (II-1), (II-2) or (II-3):

(II-1)

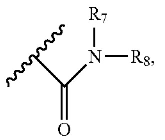

(II-2)

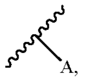

(II-3)

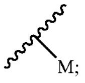

the symbols:

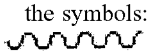

which is described in the formula (II-1), (II-2) or (II-3) represents a binding point to 2'-amino group;

$R_7$ and $R_8$ represent independently of each other a hydrogen atom, a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, or an aromatic group which may be optionally substituted with one or more substituents;

A represents an aromatic group;

M represents a sulfonyl group which is substituted with one substituent selected from the group consisting of a $C_{1-6}$ alkyl group which may be optionally substituted with one or more substituents and an aromatic group which may be optionally substituted with one or more substituents.]

or salts thereof is provided.

According to one embodiment of the present application, the compound represented by general formula (I) or salts thereof represents a compound represented by general formula I-a:

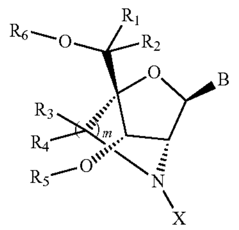

(I-a)

or salts thereof is preferably included (wherein $R_1$, $R_2$, $R_3$, $R_4$, $R_5$, $R_6$, B, X and m are the same as defied in a general formula (I)).

According to one embodiment of the present application, the compound represented by formula (I) or salts thereof wherein a ring B in the formula (I) represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents or an uracilyl group which may be optionally substituted with one or more substituents is provided.

According to one embodiment of the present application, the compound represented by formula (I) or salts thereof wherein in the formula (I), a ring B represents a 5-methylcytosinyl group which may be optionally substituted with one or more substituents or a 5-uracilyl group which may be optionally substituted with one or more substituents is provided.

According to one embodiment of the present application, the compound represented by formula (I) or salts thereof wherein in the formula (I), $R_1$, $R_2$, $R_3$ and $R_4$ represent independently of each other a hydrogen atom, and m is an integer of 1 is provided.

According to one embodiment of the present application, the compound represented by formula (I) or salts thereof wherein in the formula (I), $R_6$ represents a hydrogen atom or DMTr group, and $R_5$ represents a hydrogen atom or $—P(O(CH_2)_2CN)(N(ipr)_2)$.

According to one embodiment of the present application, the compound represented by formula (I) or salts thereof wherein in the formula (I), $R_6$ represents DMTr group, and $R_5$ represents a hydrogen atom or $—P(O(CH_2)_2CN)(N(ipr)_2)$.

According to one embodiment of the present application, the compound represented by formula (I) is roughly divided into the formula (II-1), (II-2) or (II-3).

First, the compound wherein in the formula (I), X represents a group represented by formula (II-1) (hereinafter, referred to as "Urea type compound") is included.

According to one embodiment of the present application, a compound represented by general formula (I) or salts thereof wherein X represents a group represented by formula (II-1); and $R_7$ and $R_8$ represent independently of each other a hydrogen atom, a C1-6 alkyl group which may be optionally substituted with one or more substituents, or an aromatic group which may be optionally substituted with one or more substituents is provided.

According to one embodiment of the present application, a compound represented by general formula (I) or salts thereof wherein X represents a group represented by formula (II-1); and $R_7$ and $R_8$ represent independently of each other a hydrogen atom, a $C_{1-3}$ alkyl group which may be optionally substituted with one or more substituents, or an aromatic group which may be optionally substituted with one or more substituents is provided.

According to one embodiment of the present application, a compound represented by general formula (I) or salts thereof wherein X represents a group represented by formula (II-1); and $R_7$ and $R_8$ represent independently of each other a hydrogen atom, a methyl group, an isopropyl group, or a phenyl group is provided.

According to one embodiment of the present application, a compound represented by general formula (I) or salts thereof wherein X represents a group represented by formula (II-1), and a combination of $R_7$ and $R_8$ represents a combination wherein both of $R_7$ and $R_8$ represent a hydrogen atom; a combination wherein both of $R_7$ and $R_8$ represent a methyl group; a combination wherein $R_7$ represents a hydrogen atom and $R_8$ represents a methyl group; a combination wherein $R_7$ represents a hydrogen atom and $R_8$ represents an isopropyl group; or a combination wherein $R_7$ represents a hydrogen atom and $R_8$ represents a phenyl group is provided.

According to one embodiment of the present application, a compound represented by formula (I) or salts thereof wherein X represents a group represented by formula (II-1); and a combination of $R_7$ and $R_8$ represents a combination wherein both of $R_7$ and $R_8$ represent a hydrogen atom; a combination wherein both of $R_7$ and $R_8$ represent a methyl group; a combination wherein one of $R_7$ and $R_8$ represents a hydrogen atom and the other thereof represents a methyl group; combination wherein one of $R_7$ and $R_8$ represents a hydrogen atom and the other thereof represents an isopropyl group; or a combination wherein one of $R_7$ and $R_8$ represents a hydrogen atom and the other thereof represents a phenyl group is provided.

According to one embodiment of the present application, a compound represented by formula (I) or salts thereof wherein X represents a group represented by formula (II-1); and one of $R_7$ and $R_8$ represents a hydrogen atom, and the other thereof represents a methyl group, is provided.

According to one embodiment of the present application, a compound represented by formula (I) or salts thereof wherein X represents a group represented by formula (II-1); and one of $R_7$ and $R_8$ represents a hydrogen atom, and the other thereof represents an isopropyl group, is provided.

Also the compound wherein in the formula (I), X represents a group represented by formula (II-2) (hereinafter, referred to as "heteroaryl type compound") may be included.

According to one embodiment of the present application, a compound represented by formula (I) or salts thereof wherein X represents a group represented by formula (II-2); and A represents a five or six membered heteroaryl group containing one or more heteroatoms selected from the group consisting of nitrogen atom, oxygen atom and sulfur atom, which may be optionally substituted with one or more substituents, is provided.

According to one embodiment of the present application, a compound represented by formula (I) or salts thereof wherein X represents a group represented by formula (II-2); and A represents a five or six membered heteroaryl group containing two or three heteroatoms selected from nitrogen atom, oxygen atom, and sulfur atom, provided that at least two nitrogen atoms are included, which may be optionally substituted with one or more substituents, is provided.

According to one embodiment of the present application, a compound represented by formula (I) or salts thereof wherein X represents a group represented by formula (II-2); and A represents a five or six membered heteroaryl group containing one or more heteroatoms selected from the group consisting of nitrogen atom, oxygen atom and sulfur atom, provided that at least two nitrogen atoms are included, which may be optionally substituted with one or more substituents, and the substituent is selected independently of each other from a group consisting of a $C_{1-3}$ alkyl group which may be optionally substituted with one or more halogen atoms, a halogen atom, and an amino group which may be optionally substituted with one or more $C_{1-3}$ alkyl group, is provided.

According to one embodiment of the present application, a compound represented by formula (I) or salts thereof wherein X represents a group represented by formula (II-2); and A represents a five or six membered heteroaryl group consisting one or more heteroatoms selected from the group consisting of nitrogen atom, oxygen atom and sulfur atom, provided that at least two nitrogen atoms are included, which may be optionally substituted with one or more substituents, and the substituent is selected independently of each other from a group consisting of a $C_{1-3}$ alkyl group which may be optionally substituted with one or more halogen adorns, a halogen atom, and an amino group which may be optionally substituted with one or more $C_{1-3}$ alkyl group, is provided.

According to one embodiment of the present application, a compound represented by formula (I) or salts thereof wherein X represents a group represented by formula (II-2); and the five or six membered heteroaryl group as A group is selected from the group consisting of a triazolyl group, an oxadiazolyl group, a thiadiazolyl group, a pyrimidinyl group, and a pyrazinyl group, each may be optionally substituted with one or more substituents, is provided.

According to one embodiment of the present application, a group represented by formula (I) or salts thereof wherein X represents a group represented by formula (II-2); and the triazolyl group which may be optionally substituted with one or more substituents represents 1,5-dimethyl-1,2,4-triazol-3-yl group, is provided.

According to one embodiment of the present application, a group represented by formula (I) or salts thereof wherein X represents a group represented by formula (II-2); and the oxadiazolyl group which may be optionally substituted with one or more substituents represents 5-methyl-1,2,4-oxadiazol-3-yl group, is provided.

According to one embodiment of the present application, a group represented by formula (I) or salts thereof wherein X represents a group represented by formula (II-2); and the thiadiazolyl group which may be optionally substituted with one or more substituents represents 3-methyl-1,2,4-thiadiazol-5-yl group, is provided.

According to one embodiment of the present application, a group represented by formula (I) or salts thereof wherein X represents a group represented by formula (II-3); and M represents a sulfonyl group which is substituted with one substituent selected from a $C_{1-6}$ alkyl group which may be optionally substituted with one or more substituents, and an aryl group which may be optionally substituted with one or more substituents, is provided.

According to one embodiment of the present application, a group represented by formula (i) or salts thereof wherein X represents a group represented by formula (II-3); and M represents a sulfonyl group which is substituted with one substituent selected from the group consisting of a methyl group which may be optionally substituted with one or more substituents, and a phenyl group which may be optionally substituted with one or more substituents, is provided.

According to one embodiment of the present application, a group represented by formula (I) or salts thereof wherein X represents a group represented by formula (II-3); and M represents a sulfonyl group which is substituted with one or more substituents selected from the group consisting of a methyl group and a phenyl group, is provided.

According to one embodiment of the present application, as specific examples of the compound represented by formula (I) or salts thereof, one or more compounds selected from the following compounds or salts thereof are provided.

The compounds selected from the group consisting of the following compounds:

3-[[(1R,4R,6R,7S)-4-[[bis(4-methoxyphenyl)-phenyl-methoxy]methyl]-6-(5-methyl-2,4-dioxo-pyrimidin-1-yl)-2-methylsulfonyl-5-oxa-2-azabicyclo[2.2.1]heptan-7-yl]oxy-(diisopropylamino)phosphanyl]oxypropanenitrile (Present compound 1);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-5-methyl-2-oxo-pyrimidin-4-yl]benzamide (Present compound 2);

[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-2-(2-methylpropanoylamino)purin-6-yl]N,N-diphenylcarbamate (Present compound 3);

N-[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-purin-6-yl]benzamide (Present compound 4);

3-[[(1R,3R,4R,7S)-5-(benzenesulfonyl)-1-[[bis(4-methoxyphenyl)-phenylmethoxy]methyl]-3-(5-methyl-2,4-dioxopyrimidin-1-yl)-2-oxa-5-azabicyclo[2.2.1]heptan-7-yl]oxy-(diisopropylamino)phosphanyl]oxypropanenitrile (Present compound 5);

N-[1-[(1R,3R,4R,7S)-5-(benzenesulfonyl)-1-[[bis(4-methoxyphenyl)-phenyl-methoxy]methyl]-7-[2-cyanoethoxy-(diisopropylamino)phosphanyl)oxy-2-oxa-5-azabicyclo[2.2.1]heptan-3-yl]-5-methyl-2-oxo-pyrimidin-4-yl]benzamide (Present compound 6);

(1R,3R,4R,7S)-1-[[bis(4-methoxyphenyl)-phenyl-methoxy]methyl]-7-[2-cyanoethoxy-(diisopropylamino)phosphanyl]oxy-N-methyl-3-(5-methyl-2,4-dioxo-pyrimidin-1-yl)-2-oxa-5-azabicyclo[2.2.1]heptane-5-carboxamide (Present compound 7);

(1R,3R,4R,7S)-3-(4-benzamide-5-methyl-2-oxo-pyrimidin-1-yl]-1-([bis(4-methoxyphenyl)-phenyl-methoxy]methyl]-7-[2-cyanoethoxy-(diisopropylamino)phosphanyl]oxy-N-methyl-2-oxa-5-azabicyclo[2.2.1]heptane-5-carboxamide (Present compound 8);

[9-[(1R,3R,4R,7S)-1-[[bis(4-methoxyphenyl)-phenyl-methoxy]methyl]-7-[2-cyanoethoxy-(diisopropylamino)phosphanyl]oxy-5-(methylcarbamoyl)-2-oxa-5-azabicyclo[2.2.1]heptan-3-yl]-2-(2-methylpropanoylamino)purin-6-yl]N,N-diphenylcarbamate (Present compound 9);

(1R,3R,4R,7S)-3-(6-benzamidepurin-9-yl)-1-[[bis(4-methoxyphenyl)phenylmethoxy]methyl]-7-[2-cyanoethoxy-(diisopropylamino)phosphanyl]oxy-N-methyl-2-oxa-5-azabicyclo[2.2.1]heptane-5-carboxamide (Present compound 10);

(1R,3R,4R,7S)-1-[[bis(4-methoxyphenyl)phenyl-methoxy]methyl]-7-[2-cyanoethoxy-(diisopropylamino)phosphanyl]oxy-N-isopropyl-3-(5-methyl-2,4-dioxopyrimidin-1-yl)-2-oxa-5-azabicyclo[2.2.1]heptane-5-carboxamide (Present compound 11);

(1R,3R,4R,7S)-3-(4-benzamide-5-methyl-2-oxopyrimidin-1-yl)-1-[[bis(4-methoxyphenyl)phenyl-methoxy]methyl]-7-[2-cyanoethoxy-(diisopropylamino)phosphanyl]oxy-N-isopropyl-2-oxa-5-azabicyclo[2.2.1]heptane-5-carboxamide (Present compound 12);

[9-[(1R,3R,4R,7S)-1-[[bis(4-methoxyphenyl)-phenyl-methoxy]methyl]-7-[2-cyanoethoxy-(diisopropylamino)phosphanyl]oxy-5-(isopropylcarbamoyl)-2-oxa-5-azabicyclo[2.2.1]heptan-3-yl]-2-(2-methylpropanoylamino)purin-6-yl]N,N-diphenylcarbamate (Present compound 13);

(1R,3R,4R,7S)-3-(6-benzamidepurin-9-yl)-1-[[bis(4-methoxyphenyl)-phenyl-methoxy]methyl]-7-[2-cyanoethoxy-(diisopropylamino)phosphanyl]oxy-N-isopropyl-2-oxa-5-azabicyclo[2.2.1]heptane-5-carboxamide (Present compound 14);

(1R,3R,4R,7S)-1-[[bis(4-methoxyphenyl)-phenyl-methoxy]methyl]-7-[2-cyanoethoxy-(diisopropylamino)phosphanyl]oxy-N,N-dimethyl-3-(5-methyl-2,4-dioxopyrimidin-1-yl)-2-oxa-5-azabicyclo[2.2.1]heptane-5-carboxamide (Present compound 15);

(1R,3R,4R,7S)-3-(4-benzamide-5-methyl-2-oxo-pyrimidin-1-yl)-1-[[bis(4-methoxyphenyl)-phenylmethoxy]methyl]-7-[2-cyanoethoxy-(diisopropylamino)phosphanyl]oxy-N,N-dimethyl-2-oxa-5-azabicyclo[2.2.1]heptane-5-carboxamide (Present compound 16);

3-[(1R,3R,4R,7S)-1-[[bis(4-methoxyphenyl)-phenyl-methoxy]methyl]-3-(5-methyl-2,4-dioxo-pyrimidin-1-yl)-5-pyrimidin-2-yl-2-oxa-5-azabicyclo[2.2.1]heptan-7-yl]oxy-(diisopropylamino)phosphanyl]oxypropanenitrile (Present compound 17);

1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]-5-methyl-2-oxo-pyrimidin-4-yl]benzamide (Present compound 19);

N'-[9-(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]-6-oxo-1H-purin-2-yl]-N,N-dimethyl-6-formamidine (Present compound 19);

N'-[9-(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]purin-6-yl]benzamide (Present compound 20);

3-[(1R,3R,4R,7S)-1-[[bis(4-methoxyphenyl)-phenyl-methoxy]methyl]-3-(5-methyl-2,4-dioxopyrimidin-1-yl)-5-pyrimidin-4-yl-2-oxa-5-azabicyclo[2.2.1]heptan-7-yl]oxy-(diisopropylamino)phosphanyl] oxypropanenitrile (Present compound 21);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-4-yl-2-oxa-5-azabicyclo[2.2.1]heptan-3-yl]-5-methyl-2-oxo-pyrimidin-4-yl]benzamide (Present compound 22);

3-[[(1R,3R,4R,7S)-1-([bis(4-methoxyphenyl)-phenyl-methoxy]methyl]-3-(5-methyl-2,4-dioxo-pyrimidin-1-yl)-5-[4-(trifluoromethyl)pyrimidin-2-yl]-2-oxa-5-azabicyclo[2.2.1]heptan-7-yl]oxy-(diisopropylamino) phosphanyl]oxypropanenitrile (Present compound 23);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-[4-(trifluoromethyl)pyrimidin-2-yl]-2-oxa-5-azabicyclo[2.2.1]heptan-3-yl]-5-methyl-2-oxo-pyrimidin-4-yl]benzamide (Present compound 24);

3-[[(1R,3R,4R,7S)-1-[[bis(4-methoxyphenyl)-phenyl-methoxy]methyl]-5-(5-chloropyrimidin-2-yl)-3-(5-methyl-2,4-dioxo-pyrimidin-1-yl)-2-oxa-5-azabicyclo [2.2.1]heptan-7-yl)oxy-(diisopropylamino) phosphanyl]oxypropanenitrile (Present compound 25);

N-[1-[(1R,3R,4R,7S)-1-[[bis(4-methoxyphenyl)-phenyl-methoxy]methyl]-5-(5-chloropyrimidin-2-yl)-7-[2-cyanoethoxy-(diisopropylamino)phosphanyl]oxy-2-oxa-5-azabicyclo[2.2.1]heptan-3-yl]-5-methylpyrimidin-4-yl]benzamide (Present compound 26);

3-[[(1R,3R,4R,7S)-1-[[bis(4-methoxyphenyl)-phenyl-methoxy]methyl]-5-[6-(dimethylamino)pyrimidin-4-yl]-3-(5-methyl-2,4-dioxo-pyrimidin-1-yl)-2-oxa-5-azabicyclo[2.2.1]heptan-7-yl]oxy-(diisopropylamine) phosphanyl]oxypropanenitrile (Present compound 27);

N-[1-[(1R,3R,4R,7S)-1-[[bis(4-methoxyphenyl)-phenyl-methoxy]methyl]-7-[2-cyanoethoxy(diisopropylamino)phosphanyl]oxy-5-[(6-dimethylamino)pyrimidin-4-yl]-2-oxa-5-azabicyclo[2.2.1]heptan-3-yl]-5-methyl-2-oxo-pyrimidin-4-yl]benzamide (Present compound 28);

3-[[(1R,3R,4R,7S)-1-[[bis(4-methoxyphenyl)-phenyl-methoxy]methyl]-5-[2-(dimethylamino)pyrimidin-4-yl]-3-(5-methyl-2,4-dioxo-pyrimidin-1-yl)-2-oxa-5-azabicyclo[2.2.1]heptan-7-yl]oxy-(diisopropylamino) oxypropanenitrile (Present compound 29);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-[2-(dimethylamino)pyrimidin-4-yl]-7-hydroxy-2-oxa-5-azabicyclo[2.2.1]heptan-3-yl]-5-methyl-2-oxo-pyrimidin-4-yl]benzamide (Present compound 30);

3-[1-[(1R/3R,4R,7S)-1-[[bis(4-methoxyphenyl)-phenyl-methoxy]methyl]-3-(5-methyl-2,4-dioxopyrimidin-1-yl)-5-pyrazin-2-yl-2-oxa-5-azabicyclo[2.2.1]heptan-7-yl]oxy-(diisopropylamino)phosphanyl] oxypropanenitrile (Present compound 31);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrazine-2-yl-2-oxa-5-azabicyclo(2.2.1]heptan-3-yl]-5-methyl-2-oxo-pyrimidin-4-yl]benzamide (Present compound 32);

3-[[(1R,3R,4R,7S)-1-[[bis(4-methoxyphenyl)-phenyl-methoxy]methyl]-5-(1,5-dimethyl-1,2,4-triazol-3-yl)-3-(5-methyl-2,4-dioxopyrimidin-1-yl)-2-oxa-5-azabicyclo[2.2.1]heptan-7-yl]oxy-(diisopropylamino) phosphanyl]oxypropanenitrile (Present compound 33);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-5-methyl-2-oxo-pyrimidin-4-yl]benzamide (Present compound 34);

N'-[9-[(1R,3R,4R,7S)-1-[[bis(4-methoxyphenyl)-phenyl-methoxy]methyl)-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-6-oxo-1H-purin-2-yl]-N,N-dimethylformamidine (Present compound 35);

N-[9-(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]purin-6-yl] benzamide (Present compound 36);

3-[[(1R,3R,4R,7S)-1-[[bis(4-methoxyphenyl)-phenyl-methoxy]methyl]-3-(5-methyl-2,4-dioxopyrimidin-1-yl)-5-(5-methyl-1,2,4-oxadiazol-3-yl)-2-oxa-5-azabicyclo[2.2.1]heptan-7-yl]oxy-(diisopropylamino) phosphanyl]oxypropanenitrile (Present compound 37);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(5-methyl-1,2,4-oxadiazol-3-yl)-2-oxa-5-azabicyclo[2.2.1]heptan-3-yl]-5-methyl-2-oxo-pyrimidin-4-yl]benzamide (Present compound 38);

3-[[(1R,3R,4R,7S)-1-[[bis(4-methoxyphenyl)-phenyl-methoxy]methyl]-3-(5-methyl-2,4-dioxopyrimidin-1-yl)-5-(3-methyl-1,2,4-thiadiazol-5-yl)-2-oxa-5-azabicyclo[2.2.1]heptan-7-yl]oxy-(diisopropylamino) phosphanyl]oxypropanenitrile (Present compound 39);

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(3-methyl-1,2,4-thiadiazol-5-yl)-2-oxa-5-azabicyclo[2.2.1]heptan-3-yl]-5-methyl-2-oxo-pyrimidin-4-yl]benzamide (Present compound 40);

N-[1-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-5-methyl-2-oxo-pyrimidin-4-yl]dihydropyrimidin-2-one (Present compound 41);

N'-[9-[(1R,3R,4R,7S)-1-[[bis(4-methoxyphenyl)-phenyl-methoxy]methyl]-7-[2-cyanoethoxy(diisopropylamino)phosphanyl]oxy-5-methylsulfonyl-2-oxa-5-azabicyclo[2.2.1]heptan-3-yl]-6-oxo-1H-purin-2-yl]-N,N-dimethylformamidine (Present compound 42);

N-[9-[(1R,3R,4R,7S)-1-[[bis(4-methoxyphenyl)-phenyl-methoxy]methyl]-7-[2-cyanoethoxy-(diisopropy-lamino)phosphanyl]oxy-5-methylsulfonyl-2-oxa-5-azabicyclo[2.2.1]heptan-3-yl]-6-oxo-1H-purin-2-yl]-2-methylpropane amide (Present compound 43); and N-[9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-6-oxo-1H-purin-2-yl]-2-methylpropane amide (Present compound 44).

Oligonucleotide

Compound Represented by General Formula (I')

According to one embodiment of the present application, an oligonucleotide compound comprising one or more nucleosides represented by general formula (I'):

(I')

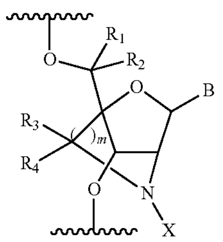

[wherein,

B represents a base moiety of nucleic acid wherein the base moiety may be optionally substituted with one or more substituents;

$R_1$, $R_2$, $R_3$ and $R_4$ represent independently of each other a hydrogen atom, or a $C_{1-6}$ alkyl group which may be optionally substituted with one or more substituents;

m is an integer of 1 or 2;

X represents a group represented by the following formula (II'-1), (II'-2), or (II'-3):

(II'-1)

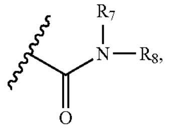

(II'-2)

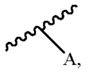

(II'-3)

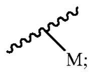

the symbols:

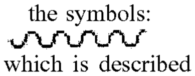

which is described in the formula (II'-1), (II'-2) or (II'-3) represents a binding point to 2'-amino group;

A represents an aromatic group containing one or more heteroatoms selected from the group consisting of nitrogen atom, oxygen atom and sulfur atom, which may be optionally substituted with one or more substituents;

M represents a sulfonyl group which is substituted with one or more substituents selected from the group consisting of a $C_{1-6}$ alkyl group which may be optionally substituted with one or more substituents, and an aromatic group which may be optionally substituted with one or more substituents.]

or salts thereof, is provided.

According to one embodiment of the present application, an oligonucleotide compound represented by formula ( )') or salts thereof wherein in the formula (I'), the ring B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents or an uracilyl group which may be optionally substituted with one or more substituents, is provided.

According to one embodiment of the present application, wherein in the formula (I'), the ring B represents a 5-methylcytosinyl group which may be optionally substituted with one or more substituents or a 5-uracilyl group which may have one or more protecting groups, is provided.

According to one embodiment of the present application, an oligonucleotide compound represented by formula (I') or salts thereof wherein in the formula (I'), $R_1$, $R_2$, $R_3$ and $R_4$ represent independently of each other a hydrogen atom, and m is an integer of 1, is provided.

According to one embodiment of the present application, an oligonucleotide compound represented by formula (I') or salts thereof wherein in the formula (I'), one or more phosphate bonds between nucleotides represent a phosphorothioate bond, and is/are sulfurized, is provided.

The compound wherein in the formula (I'), X represents a group represented by formula (II'-1) (hereinafter, referred to as "Urea type compound" may be included.

According to one embodiment of the present application, an oligonucleotide compound represented by formula (I') or salts thereof wherein X represents a group represented by formula and $R_7$ and $R_8$ represent independently of each other a hydrogen atom, a $C_{1-6}$ alkyl group which may be optionally substituted with one or more substituents, or an aromatic group which may be optionally substituted with one or more substituents, is provided.

According to one embodiment of the present application, an oligonucleotide compound represented by formula (I') or salts thereof wherein X represents a group represented by formula (II'-1); and $R_7$ and $R_8$ represent independently of each other a hydrogen atom, a $C_{1-6}$ alkyl group which may be optionally substituted with one or more substituents, or an aromatic group which may be optionally substituted with one or more substituents, is provided.

According to one embodiment of the present application, an oligonucleotide compound represented by formula (I') or salts thereof wherein X represents a group represented by formula (II'-1); and $R_7$ and $R_8$ represent independently of each other a hydrogen atom, a $C_{1-3}$ alkyl group which may be optionally substituted with one or more substituents, or an aromatic group which may be optionally substituted with one or more substituents, is provided.

According to one embodiment of the present application, an oligonucleotide compound represented by formula (I') or salts thereof wherein X represents a group represented by formula (II'-1); and $R_7$ and $R_8$ represent independently of each other a hydrogen atom, a methyl group, an isopropyl group, or a phenyl group, is provided.

According to one embodiment of the present application, an oligonucleotide compound represented by formula (I') or salts thereof wherein X represents a group represented by formula (II'-1); and a combination of $R_7$ and $R_8$ represents a combination wherein both of $R_7$ and $R_8$ represent a hydrogen atom; a combination wherein both of $R_7$ and $R_8$ represent a methyl group; a combination wherein $R_7$ represents a hydrogen atom and $R_8$ represents a methyl group; a combination wherein $R_7$ represents a hydrogen atom and $R_8$ represents an isopropyl group; or a combination wherein $R_7$ represents a hydrogen atom and $R_8$ represents a phenyl group, is provided.

According to one embodiment of the present application, an oligonucleotide compound represented by formula (I') or salts thereof wherein X represents a group represented by formula (II'-1); and a combination of $R_7$ and $R_8$ represents a combination wherein both of $R_7$ and $R_8$ represent a hydrogen atom; a combination wherein both of $R_7$ and $R_8$ represent a methyl group; a combination wherein one of $R_7$ and $R_8$ represents a hydrogen atom and the other thereof represents an isopropyl group; a combination wherein one of $R_7$ and $R_8$ represents a hydrogen atom and the other thereof represents an isopropyl group; or a combination wherein one of $R_7$ and $R_8$ represents a hydrogen atom and the other thereof represents a phenyl group, is provided.

According to one embodiment of the present application, an oligonucleotide compound represented by formula (I') or salts thereof wherein X represents a group represented by formula (II'-1); and one of $R_7$ and $R_8$ represents a hydrogen atom and the other thereof represents a methyl group, is provided.

According to one embodiment of the present application, an oligonucleotide compound represented by formula (I') or salts thereof wherein X represents a group represented by formula (II'-1); and one of $R_7$ and $R_8$ represents a hydrogen atom and the ether thereof represents an isopropyl group, is provided.

Also a compound wherein in the formula (I'), X represents a group represented by formula (II'-2) (hereinafter, referred to as "heteroaryl type compound") may be included.

According to one embodiment of the present application, an oligonucleotide compound represented by formula (I') or salts thereof wherein X represents a group represented by formula (II'-2); and A represents a five or six membered heteroaryl group containing one or mere heteroatoms selected from the group consisting of nitrogen atom, oxygen atom and sulfur atom, which may be optionally substituted with one or mere substituents, is provided.

According to one embodiment of the present application, an oligonucleotide compound represented by formula (I') or salts thereof wherein X represents a group represented by formula (II'-2); and A represents a five or six membered heteroaryl group containing two or three heteroatoms selected from nitrogen atom, oxygen atom, and sulfur atom, provided that at least two nitrogen atoms are included, which may be optionally substituted with one or more substituents, is provided.

According to one embodiment of the present application, an oligonucleotide compound represented by formula (I') or salts thereof wherein X represents a group represented by formula (II'-2); and A represents a five or six membered heteroaryl group containing one or more heteroatoms selected from nitrogen atom, oxygen atom, and sulfur atom, provided that at least two nitrogen atoms are included, which may be optionally substituted with one or more substituents, and the substituent is selected independently of each other from a C1-3 alkyl group which may be optionally substituted with one or more halogen atoms, a halogen atom, and an amino group which may be optionally substituted with one or more C1-3 alkyl groups, is provided.

According to one embodiment of the present application, an oligonucleotide compound represented by formula (I') or salts thereof wherein X represents a group represented by formula (II'-2); and A represents a five or six membered heteroaryl group containing one or more heteroatoms selected from nitrogen atom, oxygen atom, and sulfur atom, provided that at least two nitrogen atoms are included, which may be optionally substituted with one or more substituents, and the substituent is selected independently of each other from a C1-3 alkyl group which may be optionally substituted with one or more halogen atoms, a halogen atom, and an amino group which may be optionally substituted with one or more C1-3 alkyl groups, is provided.

According to one embodiment of the present application, an oligonucleotide compound represented by formula (I') or salts thereof wherein X represents a group represented by formula (II'-2); and the five or six membered heteroaryl group as A group is selected from the group consisting of a triazolyl group, an oxadiazolyl group, a thiadiazolyl group, a pyrimidinyl group, and a pyrazinyl group, each may be optionally substituted with one or more substituents, is provided.

According to one embodiment of the present application, an oligonucleotide compound represented by formula (I') or salts thereof wherein X represents a group represented by formula (II'-2), and the triazole group which may be optionally substituted with one or more substituents represents 1,5-dimethyl-1,2,4-triazol-3-yl group, is provided.

According to one embodiment of the present application, an oligonucleotide compound represented by formula (I') or salts thereof wherein X represents a group represented by formula (II'-2), and the oxadiazolyl group which may be optionally substituted with one or more substituents represents 5-methyl-1,2,4-oxadiazol-3-yl group, is provided.

According to one embodiment of the present application, an oligonucleotide compound represented by formula (I') or salts thereof wherein X represents a group represented by formula (II'-2); and the thiadiazolyl group which may be optionally substituted with one or more substituents represents 3-methyl-1,2,4-thiadiazol-5-yl group, is provided.

According to one embodiment of the present application, an oligonucleotide compound represented by formula (I') or salts thereof wherein X represents a group represented by formula (II'-3); and M represents a sulfonyl group which is substituted with one substituent selected from the group consisting of a C1-6 alkyl group which may be optionally substituted with one or more substituents and an aryl group which may be optionally substituted with one or more substituents, is provided.

According to one embodiment of the present application, an oligonucleotide compound represented by formula (I') or salts thereof wherein X represents a group represented by formula (II'-3); and M represents a sulfonyl group which is substituted with one substituent selected from the group consisting of a methyl group which may be optionally substituted with one or more substituents, and a phenyl group which may be optionally substituted with one or mere substituents, is provided.

According to one embodiment of the present application, an oligonucleotide compound represented by formula (I') or salts thereof wherein X represents a group represented by formula (II'-3); and M represents a sulfonyl group which is substituted with one or more substituents selected from the group consisting of a methyl group and a phenyl group, is provided.

According to one embodiment of the present application, an oligonucleotide compound represented by formula (I') or salts thereof wherein X represents a group represented by formula (II'-3); and M represents a sulfonyl group which is substituted with one or more substituents selected from the group consisting of a methyl group and a phenyl group, is provided.

According to one embodiment of the present application, the oligonucleotide or salts thereof is made by binding two or more the nucleosides and preferably contains 2 to 100 nucleosides, more preferably 5 to 50 nucleosides, and particularly preferably those in which 10 to 30 artificial nucleosides are bonded or are combined together with these complementary strands forms a double strand.

The term of “salt” in the expression of “salts of compound” used herein alkali metal salts such as sodium salt, potassium salt, lithium salt; alkaline earth metal salts such as calcium salt, and magnesium salts; metal salts such as aluminium salt, iron salt, zinc salt, copper salt, nickel salt, and cobalt salt; inorganic salts such as ammonium salt; amine salts, for example, organic salts such as t-octylamine salt, dibenzylamine salt, morpholine salt, glucosamine salt, phenylglysine alkyl ester salt, ethylenediamine salt, N-methylglucamine salt, guanidine salt, diethylamine salt, triethylamine salt, hexylamine salt, dicyclohexylamine salt, N,N'-dibenzylethylenediamine salt, chloroprocaine salt, procaine salt, diethanolamine salt, N-benzyl phenethylamine salt, piperazine salt, tetramethylammonium salt, and tris(hydroxymethyl)aminomethane salt; inorganic acid salts, for example, hydrohalic acids (such as hydrofluoric acid, hydrochloric acid, hydrobromic acid, and hydroiodic acid), nitrate salt, perchloric acid salt, sulfate salt, and phosphate salt; salts of alkanesulfonic acid having one to six carbon atoms, such as methanesulfonate salt, trifluoro methanesulfonate salt, ethanesulfonate salt; arylsulfonic acid salts such as benzene sulfonate salt, and p-toluene sulfonate salt; organic acid salts such as acetate salt, malate salt, fumarate salt, succinate salt, citrate salt, tartrate salt, oxalate salt, and maleate salt; and amino acid salts such as glycine salt, lysine salt, arginine salt, ornithine salt, glutamic acid salt, and aspartic acid salt, which should not be limited thereto. The salts are encompassed by pharmaceutically acceptable salts.

Each compound represented by general formula (I) described herein encompasses enantiomer form, diastereomer form, or mixtures thereof. For example, a stereo configuration of sugar moiety in the structure of each compound encompasses α form and β form, however, β form is preferred. When the above-mentioned compounds represented by the above formula (I) is obtained in the form of diastereomer or enantiomer, they can be separated by well-known methods in organic synthesis (for example, sugar synthesis), such as chromatography method or fractional crystallization method. For example, the compound 2Td represented by the following formula:

2Td

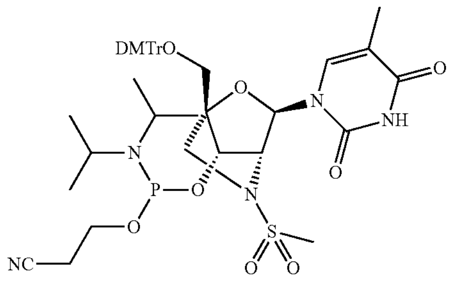

has β form as a stereo configuration of sugar moiety.

Each compound represented by general formula I described herein compasses the compounds labeled with isotopes (such as $^{3}H$, $^{13}C$, $^{14}C$, $^{15}N$, $^{18}F$, $^{32}P$, $^{35}S$ or $^{125}I$) and deuterated transformers.

The oligonucleotide or analogues thereof described herein may be mixed with auxiliary agents that are usually used in the formulation of pharmaceuticals, such as excipients, binders, preservatives, antioxidants, disintegrants, lubricants, and flavors, to make parenterally-administered formulation or liposome formulations. Also, the oligonucleotide or analogues thereof is mixed with pharmaceutical carriers that are usually used in the pharmaceutical arts to formulate into topical formulations such as solutions, creams and ointments.

(Preparation Method)

Hereinafter, the preparation method of the compound of the present invention is described.

Optically active substances having absolute configuration in each compound represented by the below-mentioned starting materials and intermediate compounds may be prepared by using as starting material optically active substance(s) or separating the isomers that created in the intermediate stages for synthesis. Also, the below-mentioned replacement reaction of nucleic acid base in which nucleic acid base is replaced may proceed a β-selective transglycosylation effectively, and the obtained compound represented by general formula I may be obtained as a desired β former selectively.

The compound of the present invention or pharmaceutically acceptable salts thereof may be prepared according to the following method, but which should not be limited thereto.

For starting materials, unless specific processes therefor are stated, they may be used as commercially available ones, or can be prepared according to the publicly known method or a similar method thereto.

The abbreviated symbols as used herein mean the following meanings respectively.

THF: tetrahydrofuran

DMSO: dimethyl sulfoxide

MsCl: methanesulfonyl chloride

DMAP: N,N-dimethyl-4-aminopyridine $iPr_2NEt$, DIPEA: N,N-diisopropylethylamine

BSA: N,O-bis(trimethylsilyl)acetamide

TMSOTf: trimethylsilyl trifluoro-methanesulfonate

TBSOTf: t-butyldimethylsilyl trifluoro methanesulfonate

Bn: benzyl

TMS: trimethylsilyl

TBDPS: tert-butyldiphenylsilyl

Ac: acetyl

MOE: methoxyethyl $CH_2Cl_2$: dichloromethane

MeCN: acetonitrile

DMTr: 4,4'-dimethoxytrityl

First, the summary of a preparation method for the compound of the present invention (monomer) is described.

(Sulfonamide Type Compound)

The preparation method of the compound of the present invention represented by general formula I wherein X represents a group represented by formula (II-3), so-called sulfonamide type compound is described. The typical example of the preparation scheme is described, and is not limited thereto.

Reaction scheme 1

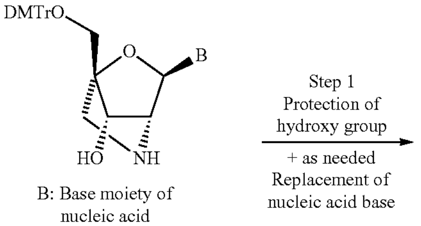

B: Base moiety of nucleic acid

Starting compound 1

-continued

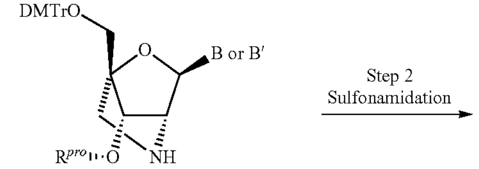

$R^{pro}$: Protecting group of hydroxy group

Intermediate compound 2

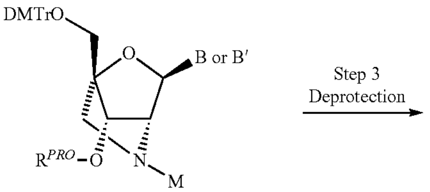

Intermediate compound 3

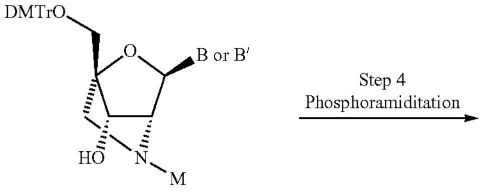

Intermediate compound 4

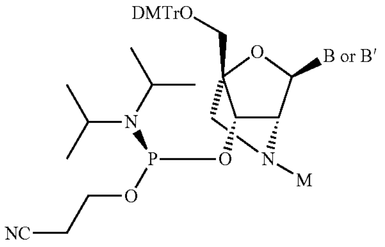

Present compound

M: 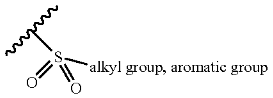

(Step 1)

A protecting group for hydroxy group is introduced as $R_5$ group in the general formula (I) by using a starting material 1 (for example, which can be prepared according to the process described in WO 2017/047816 A1) which is a sugar compound, according to a publicly known method to prepare an intermediate compound 2. Alternatively, a basic moiety of nucleic acid in the starting material 1 (abbreviated as "B") is subjected to a nucleic acid base exchange reaction with ether basic moiety of nucleic acid which may be optionally protected (abbreviated as "B'") and a protecting group for hydroxy group is also introduced at the same time as the nucleic acid base exchange reaction to prepare an intermediate compound 2.

This introduction of the protecting group for hydroxy group can be conducted under a reaction condition which is known in organic synthetic chemistry (for example, nucleic acid synthesis) depending on a kind of protecting group. For example, when a protecting group for hydroxy group is a silyl type protecting group (such as TMS), a silyl agent (such as BSA, hexamethyl disilazane, TMS chloride) can be used. In the reaction, Lewis acid (such as TMSOTf, TBSOTf, and tin chloride) may be added.

The silylating agent may be used in about 1 to about 20 molar equivalent(s), and the Lewis acid may be used in a catalytic amount (about 0.05 molar equivalents) to about 2 molar equivalents as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; hydrocarbons such as benzene toluene; acetonitrile; water; or mixed solvents thereof). The reaction may proceed preferably at 0° C. to high temperature, and particularly preferably at room temperature to about 60° C.

Also, according to a nucleic acid exchange reaction (transglycosylation reaction), a pyrimidine base moiety of nucleic acid base such as thymine group (T) and uracil group (U) can be replaced with other nucleic acid base moiety (for example, adenine (A), guanine (G), uracil (U), thymine (T), cytosine (C), or 5-methylcytosine ($^{Me}C$) to obtain an intermediate compound 2 wherein the nucleic acid base moiety is replaced. The base exchange reaction can be carried out, for example, in the presence of Lewis acid (such as TMSOTf and TBSOTf), and the reaction can be facilitated by reacting with the silylating agent.

(Step 2)

Next, using the intermediate compound 2 as a starting material, an alkyl sulfonyl halide or an aromatic sulfonyl halide can be reacted with the intermediate compound 2 according to a publicly known method to undergo a sulfonamidation on an amino nitrogen atom, resulting in preparing an intermediate compound 3.

Examples of the sulfone amidation reagent used in a sulfone amidation reaction include an alkyl sulfonyl halide reagent (such as methane sulfonyl chloride (MsCl)), an alkyl sulfonic anhydride reagent (such as methane sulfonic anhydride), an aromatic sulfonyl halide reagent (such as benzene sulfonyl chloride), or an aromatic sulfonic anhydride (such as benzene sulfonic anhydride), and these reagents can be used in the presence of a base (such as triethyl amine, and DIPEA).

The sulfonamidation reagent may be used in approximately molar equivalents to somewhat excess molar equivalents (for example, about 1.0 molar equivalent) as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; hydrocarbons such as benzene and toluene; acetonitrile; water; or mixed solvents thereof). The reaction can proceed preferably at −25° C. to room temperature, and particularly preferably at 0° C. to room temperature.

(Step 3)

Next, the protecting groups for hydroxy group which is introduced in the step 1 is deprotected by using the intermediate compound 3 as a starting material according to a publicly known method to prepare an intermediate compound 4.

The present deprotection reaction can be carried out in appropriate reaction condition (for example, reagents to be used) depending on the kinds of the protecting group. For example, when a protecting group for hydroxy group (abbreviated as "$R^{PRC}$") is a silly type protecting group (such as TMS), the reaction can be carried out by hydrolysis under acidic condition (such as acetic acid-THF-water) or by treating with a fluoride ion-donating reagent (such as TBAF).

The solvents may be any ones unless they affect the reaction adversely, and the reaction may be carried out in an appropriate solvents (for example, ethers such as THF, halogenated hydrocarbon atoms such as dichloromethane, water, or mixed solvents thereof).

The reaction may proceed preferably at −25° C. to 100° C., particularly preferably at 0° C. to 50° C. as a reaction temperature.

(Step 4)

Further, the intermediate compound 4 as a starting material is subjected to a phosphoramiditation reaction under reaction conditions that have been generally known in organic synthesis (in particular, nucleic acid synthesis) (for example, in terms of reagent(s)) to prepare a desired compound of the present invention as a sulfone amide type j compound.

Examples of the phosphoramiditation reagent include agents by the following formula:

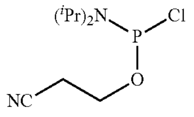
and
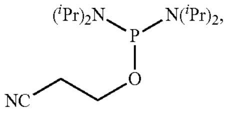
, which should not be limited thereto.

The phosphoramiditation reaction may be conducted in the presence of appropriate bases (such as DIPEA) or appropriate acids (such as diisopropyl ammonium tetrazolide, and 4,5-dicyanoimidazole).

The phosphoramiditation reagent may be used in 1 to about 10 molar equivalent(s), preferably 1 to about 5 molar equivalent(s) (such as 3 molar equivalents) as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; acetonitrile; water; or mixed solvents thereof). The reaction can proceed preferably at −25° C. to 60° C., and particularly preferably at 0° C. to room temperature.

Here in any stages from the timing of before the above step 1 to the timing of after the above step 4, a substituent on the ring of the nucleic acid base may be appropriately modified (for example, a benzoylation reaction or a acetylation reaction on an amino substituent on a cytosine ring).

Also, among the above step (1) to step (4), a plural steps (for example, step (1) and step (2), and step (2) and step (3)) may be carried out successively.

(Urea Type Compound)

A method for preparing a compound of the present invention represented by general formula I wherein X represents a group represented by formula (II-1), which is so-called urea type compound, is described. Typical examples of the preparation scheme is indicated in the following reaction scheme 2, which should not be limited thereto.

Reaction scheme 2

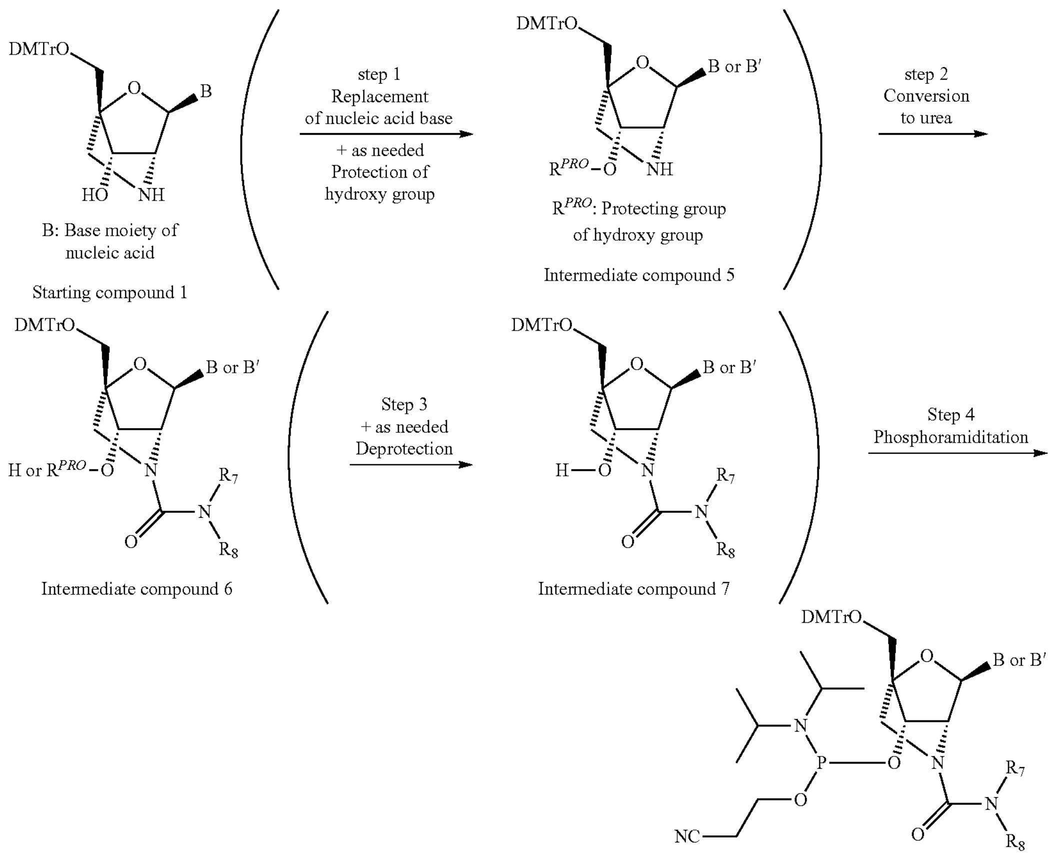

Present compound (Step 1)

Before undergoing a reaction for converting into an urea according to a publicly known method, similarly to the above reaction scheme 1 using the above starting compound 1 as a starting material, a basic moiety of nucleic acid in the starting compound 1 (abbreviated as "3") is subjected to a nucleic acid base exchange reaction with other basic moiety of nucleic acid which may be optionally protected (abbreviated as "B'"), and thereafter, the reaction for converting into an urea may be carried out. Also, similarly to the above reaction scheme, after the nucleic acid base exchange reaction is carried out, a protecting group for hydroxy group may be introduced appropriately.

In a nucleic acid exchange reaction (transglycosylation reaction), according to a publicly known method, a pyrimidine base moiety of nucleic acid base such as thymine group (T) and uracil group (U) can be replaced with other nucleic acid base moiety (for example, adenine (A), guanine (G), uracil (U), thymine (T), cytosine (C), or 5-methylcytosine ($^{Me}C$) to obtain an intermediate compound 5 wherein the nucleic acid base moiety is replaced. The base exchange reaction can be carried out, for example, in the presence of Lewis acid (such as TMSOTf and TBSOTf), and the reaction can be facilitated by reacting with the silylating agent (such as BSA).

This introduction of the protecting group for hydroxy group can be conducted under a reaction condition which is known in organic synthetic chemistry (for example, nucleic acid synthesis) depending on a kind of protecting group. For example, when a protecting group for hydroxy group is a silyl type protecting group (such as TMS), a silyl agent (such as BSA, hexamethyl disilazane, TMS chloride) can be used. In the reaction, Lewis acid (such as TMSOTf, TBSOTf, and tin chloride) may be added.

The silylating agent may be used in about 1 to about 20 molar equivalent(s), and the Lewis acid may be used in a catalytic amount (about 0.05 molar equivalents) to about 2 molar equivalents as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; hydrocarbons such as benzene and toluene; acetonitrile; water; or mixed solvents thereof). The reaction may proceed preferably at 0° C. to high temperature, and particularly preferably at room temperature to about 60° C.

(Step 2)

Next, using the starting compound 1 or the intermediate compound 5 as a starting material, according to a publicly known method, the reagent for converting into urea is reacted with the starting compound 1 or the intermediate compound 5 to undergo a conversion reaction to a urea on the amine nitrogen atom, results m preparing an intermediate compound 6.

Examples of the reagent for converting into urea used in the reaction for converting into urea include isocyanate, alkyl carbamoyl halide reagent (such as N-methylcarbamoyl chloride) or N,N-dialkyl carbamoyl halide reagent (such as N,N-dialkyl carbamoyl chloride), and these reagents can be used in the presence or absence of a base (such as DIPEA).

The reagent for converting into urea may be used in approximately molar equivalents to somewhat excess molar equivalents (for example, about 1.0 molar equivalent) as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; or mixed solvents thereof). The reaction may proceed preferably at −25° C. to room temperature, and particularly preferably at 0° C. to room temperature.

(Step 3)

Next, as needed, when a protecting group for hydroxy group is introduced in the above-mentioned step 1, using the intermediate compound 6 as a starting material, according to a publicly known method, the introduced protecting group for hydroxy group is deprotected to prepare an intermediate compound 7.

The present deprotection reaction can be carried out in appropriate reaction condition (for example, reagents to be used) depending on the kinds of the protecting group. For example, when a protecting group for hydroxy group (abbreviated as "$R^{PRC}$") is a silyl type protecting group (such as TMS), the reaction can be carried out by hydrolysis under acidic condition (such as acetic acid-THF-water) or by treating with a fluoride ion-donating reagent (such as TBAF).

The solvents may be any ones unless they affect the reaction adversely, and the reaction may be carried out in an appropriate solvents (for example, ethers such as THF, halogenated hydrocarbon atoms such as dichloromethane, water, or mixed solvents thereof).

The reaction may proceed preferably at −25° C. to 100° C., particularly preferably at 0° C. to 50° C. as a reaction temperature.

(Step 4)

Further, similarly to the step 4 of the above-mentioned reaction scheme 1, the intermediate compound 6 or the intermediate compound 7 as a starting material is subjected to a phosphoramiditation reaction according to a publicly known method to prepare a desired urea type (for example, methyl urea type, and isopropyl urea type) of the present compound.

Examples of the phosphoramiditation reagent include 2-cyanoethyl-N,N-diisopropylchlorophosphoramidite, and the reagent can be used in the presence of a base (such as triethylamine, DIPEA).

The phosphoramiditation reagent may be used in 1 to about 10 molar equivalent(s), preferably 1 to about 5 molar equivalent(s) (such as 3 molar equivalents) as opposed to 1 mole of the reaction substrates.

The solvents may be any ones unless they affect the reaction adversely, and the reaction may be carried cut in appropriate solvents (for example, ethers such as THF; halogenated hydrocarbons such as dichloromethane, dichloroethane, and chloroform; acetonitrile; water; or mixed solvents thereof). The reaction can proceed preferably at −25° C. to 60° C., and particularly preferably at 0° C. to room temperature.

Also, among the above step (1) to step (4), a plural steps (for example, step (1) and step (2), step (2) and step (3), and step (1) to step (3)) may be carried out successively.

Here in any stages from the timing of before the above step 1 to the timing of after the above step 4, a substituent on the ring of the nucleic acid base may be appropriately modified (for example, a benzoylation reaction or a acetylation reaction on an amino substituent on a cytosine ring).

(Aryl Type Compound)

A preparation method of the compound represented by formula I wherein X represents formula (II-2), so-called an aryl type of the present compound is described. Examples of the preparation scheme is shown in the following reaction scheme 3.

Reaction scheme 3

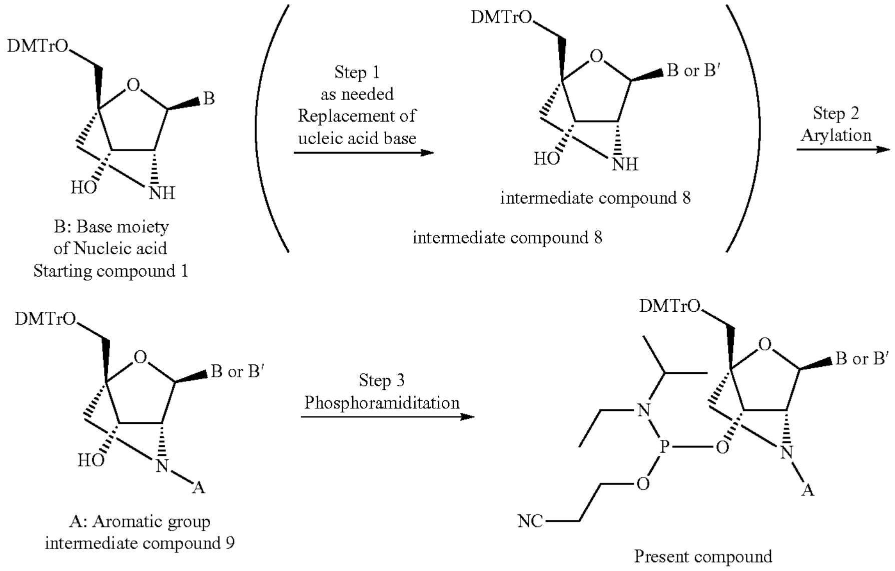

B: Base moiety of Nucleic acid
Starting compound 1 intermediate compound 8 intermediate compound 8

A: Aromatic group
intermediate compound 9

Present compound (Step 1)

Before undergoing an arylation reaction according to a publicly known method, similarly to the above reaction scheme 1 using the above starting compound 1 as a starting material, a basic moiety of nucleic acid in the starting compound 1 (abbreviated as "B") is subjected to a nucleic acid base exchange reaction with other basic moiety of nucleic acid which may be optionally protected (abbreviated as "B'"), and thereafter, the arylation reaction may be carried out.

In a nucleic acid exchange reaction (transglycosylation reaction), according to a publicly known method, a pyrimidine base moiety of nucleic acid base such as thymine group (T) and uracil group (U) can be replaced with other nucleic acid base moiety (for example, adenine (A), guanine (G), uracil (U), thymine (T), cytosine (C), or 5-methylcytosine ($^{Me}$C) to obtain an intermediate compound 8 wherein the nucleic acid base moiety is replaced. The base exchange reaction can be carried out, for example, in the presence of Lewis acid (such as TMSOTf and TBSOTf), and the reaction can be facilitated by reacting with the silylating agent (such as BSA).

This introduction of the protecting group for hydroxy group can be conducted under a reaction condition which is known in organic synthetic chemistry (for example, nucleic acid synthesis) depending on a kind of protecting group. For example, when a protecting group for hydroxy group is a silyl type protecting group (such as TMS), a silyl agent (such as BSA, hexamethyl disilazane, TMS chloride) can be used. In the reaction, Lewis acid (such as TMSOTf, TBSOTf, and tin chloride) may be added.

The silylating agent may be used in about 1 to about 20 molar equivalent(s), and the Lewis acid may be used in a catalytic amount (about 0.05 molar equivalents) to about 2 molar equivalents as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; hydrocarbons such as benzene and toluene; acetonitrile; water; or mixed solvents thereof). The reaction may proceed preferably at 0° C. to high temperature, and particularly preferably at room temperature to about 60° C.

(Step 2)

Next, using the starting compound 1 or the intermediate compound 8 as a starting material, according to a publicly known method, the arylation reagent is reacted with the starting compound 1 or the intermediate compound 8 to undergo an aromatization reaction on the amino nitrogen atom, results in preparing an intermediate compound 9.

Examples of the arylation reagent used in the arylation reaction include a desired aryl halide compound (such as chloropyrimidine, dichloropyrimidine, fluoropyrazine, chlorotriazole, chlorooxadiazole, or chlorothiadiazole), and these reagents can be used in the presence of a base (such as DIPEA).

The arylation reagent can be used in about one to about five molar equivalent(s) (for example, three molar equivalents) as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; aprotic polar solvents such as DMSO; or mixed solvents thereof). The reaction may proceed preferably at room temperature to high temperature, and particularly preferably at high temperature (such as 120 to 130° C.).

(Step 3)

Further, similarly to the step 4 of the above-mentioned reaction scheme 1, the intermediate compound 9 or the intermediate compound 8 as a starting material is subjected to a phosphoramiditation reaction according to a publicly known method to prepare a desired aryl type (for example, aromatic type or heteroaryl type) of the present compound. Examples of the phosphoramiditation reagent include 2-cyanoethyl-N,N-diisopropylchlorophosphoramidite, and the reagents can be used in the presence of a base (such as triethylamine, CIPEA).

The phosphoramiditation reagent may be used in about 1 to about 10 molar equivalent(s), and preferably 1 to about molar equivalent(s) (such as 1 to 3 molar equivalent(s)) as opposed to 1 mole of the reaction substrates.

The solvents may be any ones unless they affect the reaction adversely, and the reaction may be carried out in appropriate solvents (for example, ethers such as THF; halogenated hydrocarbons such as dichloromethane, dichloroethane, and chloroform; acetonitrile; or mixed solvents thereof). The reaction may proceed preferably at −25° C. to 60° C., and particularly preferably at 0° C. to room temperature.

Also, among the above step (1) to step (3), a plural steps (for example, step (1) and step (2)) may be carried out successively.

Here in any stages from the timing of before the above step 1 to the timing of after the above step 3, a substituent on the ring of the nucleic acid base may be appropriately modified (for example, a benzoylation reaction or a acetylation reaction on an amino substituent on a cytosine ring), or the substituents on the aromatic ring of the introduced aryl group may be modified (for example, a transformation of the chloro group into an amino group), or both of these substituents may be modified.

(Alternative Preparation Method of Nucleic Acid Base Exchange Reaction)

Instead of the nucleic acid base exchange reaction described in step 1, the partial transformation of nucleic acid base may be carried out by using a series of reaction as shown in the following reaction scheme 4. The series of reaction can be carried out according to the method described in the literature (for example, C. H. Kim. et al., J. Med. Chem. 1987, 330, 862).

Reaction scheme 4

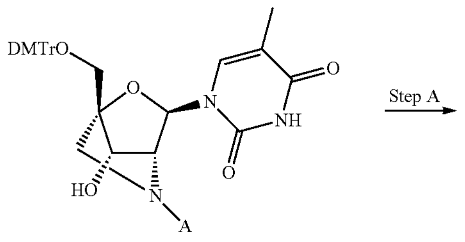

Intermediate compound 9'

-continued

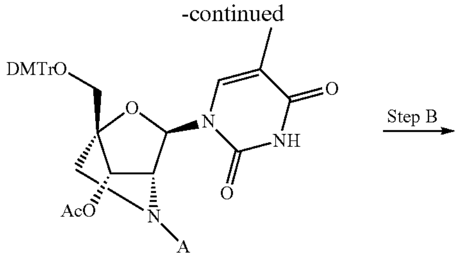

Intermediate compound A

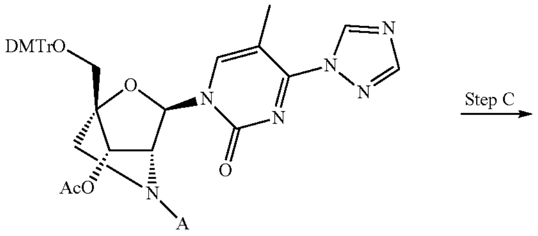

Intermediate compound B

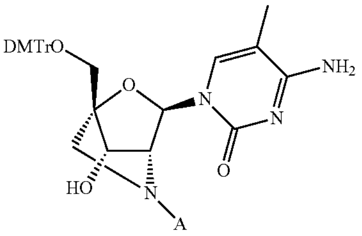

Intermediate compound X (Step A)

The intermediate compound 9' wherein the nucleic acid base moiety represents a thymine (such as the intermediate compound 2 obtained in the above step 2) as a starting material is reacted with an acetylation reagent (such as acetic anhydride) in the presence of a base (such as pyridine) to prepare an intermediate compound A wherein a hydroxy group is acylated. As needed, a catalytic amount of DMAP may be added as a reaction activating reagent.

The acetylation reagent can be used in about 1 to 3 molar equivalent(s) (such as about 1.5 molar equivalents) as opposed to 1 mole of the reaction substrates.

The solvents may be any ones unless they affect the reaction adversely, and the reaction may be carried out in appropriate solvents (for example, ethers such as THF; or pyridine used as a base). The reaction can proceed preferably at 0° C. to high temperature (such as room temperature).

(Step B)

Next, after the thymine moiety is activated with a chlorinating reagent such as phosphoryl chloride, the intermediate compound A as a starting material is reacted with 1,2,4-triazole in the presence of a base (such as DIPEA) to prepare an intermediate compound B wherein the nucleic acid base moiety is substituted with 1,2,4-triazole group.

The 1,2,4-triazole can be used m excess molar equivalents (for example, about five to about 20 molar equivalents, including about 9 to 10 molar equivalents).

The solvents may be any ones unless they affect the reaction adversely, and the reaction may be carried out in appropriate solvents (for example, ethers such as THF; halogenated hydrocarbons such as dichloromethane, dichloroethane, and chloroform; acetonitrile; or mixed solvents thereof). The reaction can proceed preferably at −25° C. to room temperature, and particularly preferably at 0° C. to room temperature.

(Step C)

Also the intermediate compound B as a starting material is reacted with a base (such as ammonia water) to remove the acetyl group which is introduced in the above step A, and the 1,2,4-triazole group which is modified in the step B, to prepare an intermediate compound C wherein the nucleic acid base moiety is 5-methylcytosine.

The ammonia water (such as 28% ammonia water) can be used in excess molar equivalents as opposed to 1 mole of the reaction substrates.

The solvents may be any ones unless they affect the reaction adversely, and the reaction may be carried out in appropriate solvents (for example, ethers such as THF; acetonitrile; or mixed solvents thereof). The reaction can proceed preferably at 0° C. to room temperature, and particularly preferably at room temperature.

Using the obtained intermediate compound C as a starting material, as needed, the substituent on the ring of nucleic acid base is modified (for example, benzoylation or acetylation of amino substituent of the cytosine ring), or the substituent on the aromatic ring of the introduced aryl group is modified (for example, a transformation of a chloro group into an amino group), and thereafter, the substituent is subjected to a phosphoramidation reaction to prepare a desired aryl type (for example, aromatic type, and heteroaryl type) of the present compound.

(Alternative Preparation Method 1 for Aromatization)

Further, instead of an aromatization reaction with an aryl reagent as described in step 2, a series of reaction as shown in the following reaction step 5 can be used for an aromatization reaction.

Reaction scheme 5

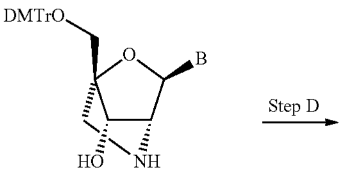

B: Base moiety of nucleic acid

Starting compound 1

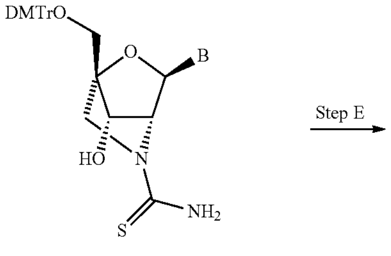

Intermediate compound D

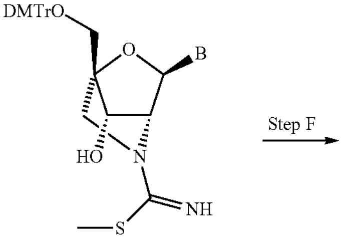

Intermediate compound E

-continued

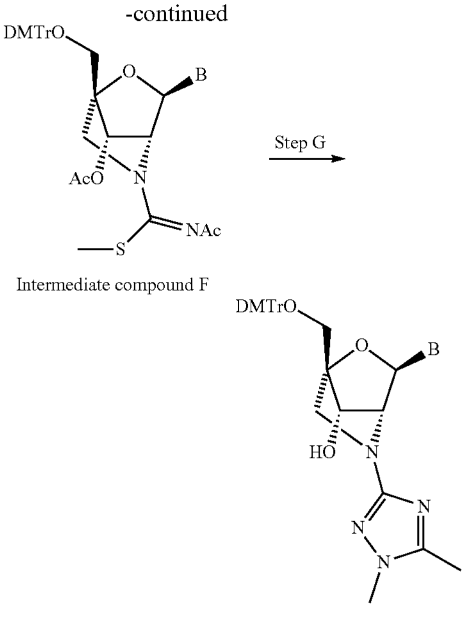

Intermediate compound F

Intermediate compound G (Step D)

The above starting material 1 is reacted with a reagent for converting into thiourea (such as 1,1-thiocarbonyl imidazole), followed by treating with ammonia water, to prepare an intermediate compound D wherein a group on the amino nitrogen atom is converted into a thiourea.

The reagent for converting into thiourea can be used in about 1 to 5 molar equivalent(s), particularly about 2 molar equivalents, as opposed to 1 mole of the reaction substrates.

The solvents may be any ones unless they affect the reaction adversely, and the reaction may be carried out in appropriate solvents (for example, ethers such as THF). The reaction can proceed preferably at 0° C. to room temperature (for example, room temperature).

(Step E)

Next, the intermediate compound D as a starting material is reacted with a methylation reagent (such as methyl iodide) to prepare an intermediate compound having S-methylated and carboimidated group or moiety.

The methylation reagent can be used in about 1 to 5 molar equivalent(s), particularly, 3 molar equivalents, as opposed to 1 mole of the reaction substrates.

The solvents may be any ones unless they affect the reaction adversely, and the reaction may be carried out in appropriate solvents (for example, ethers such as THF). The reaction can proceed preferably at C ° C. to room temperature, (for example, room temperature).

(Step F)

Also the intermediate compound E as a starting material is reacted with an acetylation reagent (such as acetic anhydride) in the presence of a base (such as pyridine) to prepare an intermediate compound F having acylation on a carbodiimide group and a hydroxy group. As needed, a catalytic amount of DMAP may be added as a reaction activating reagent.

The acetylation reagent can be use in about 1 to 5 molar equivalent(s) (for example, about 3 molar equivalent(s)) as opposed to 1 mole of the reaction substrates.

The solvents may be any ones unless they affect the reaction adversely, and the reaction may be carried out in appropriate solvents (for example, ethers such as THF, or pyridine used as a base). The reaction can proceed preferably at 0° C. to room temperature, (for example, room temperature).

(Step G)

Also the intermediate compound F as a starting material is subjected to a ring closure reaction with methyl hydrazine to prepare an intermediate compound G wherein a 1,2,4-triazole ring is formed.

The methyl hydrazine can be used in excess molar equivalent (for example, about 5 to 20 molar equivalents (such as about 10 molar equivalents)) as opposed to 1 mole of the reaction substrate.

The solvents may be any ones unless they affect the reaction adversely, and the reaction may be carried out in appropriate solvents (for example, alcohols such as ethanol). The reaction can proceed preferably at 0° C. to high temperature (for example, room temperature).

Using the obtained intermediate compound G as a starting material, as needed, the substituent on the ring of nucleic acid base is modified (for example, benzoylation or the other ones of amino substituent of the cytosine ring), or the substituent on the aromatic ring of the introduced aryl group is modified (for example, a transformation of a chloro group into an amino group), and thereafter, the substituent is subjected to a phosphoramidation reaction to prepare a desired aryl type (for example, aromatic type, and heteroaryl type) of the present compound.

(Preparation Method of Oligomer)

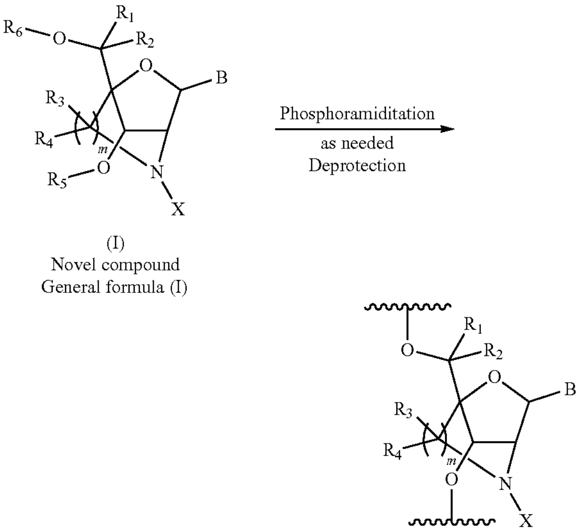

(I)
Novel compound
General formula (I)

(I')
Novel oligomer compound
General formula (I')

(II-1) or (II'-1)

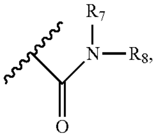

(II-2) or (II'-2)

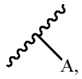

(II-3) or (II'-3)

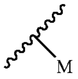

The present compound or salts thereof can be used as a monomer starting material for preparation of oligonucleotide. The oligonucleotide can be synthesized by subjecting to oligomerization reaction of the compound represented by general formula (I) or salts thereof, as needed followed by deprotecting the protecting group for amino group and the protecting group for hydroxy group.

For example, the oligomerization is not limited to any method as long as it is the method that has been generally known in the synthetic chemistry (in particular, nucleic acid synthesis), and it can be used by an phosphoramidite method. The phosphoramidite method can be conducted, for example, according to the method described in WO 2014/046212 A1.

Using this oligomerization, oligonucleotide containing one or more nucleosides represented by general formula (I) can be prepared.

That is, the method for preparing oligonucleotide represented by general formula (I') comprises the following step.

a) a step of oligomerization of the compound represented by general formula (I) or salts thereof, if necessary, followed by deprotecting a protecting group for amino group, and a protecting group for hydroxy group.

Also, the method for preparing the compound represented by general formula (I) or salts thereof may comprise at least one of the following steps among the steps described herein.

a step of preparing the present compound or salts thereof;

a step of phosphoramiditation of the above intermediate compound 4, 7 or 9 or salts thereof to prepare a compound represented by general formula (I') or salts thereof, and a step of deprotecting a protecting group for hydroxy group in the intermediate compound 3 or 6 to prepare the above intermediate compound 4, 7 or 9.

(Preparation Method of Phosphorothioate Oligomer)

In the synthesis of oligonucleotide by phosphoramiditation, an oxidizing agent is used in a conversion reaction of a phosphite group into a phosphate group. DDTT (((dimethylaminomethylidene)amino)-3H-1,2,4-dithiazaoline-3-one) or Beaucage reagent (3H-1,2-benzodithiol-3-one 1,1-dioxide) is used instead of the oxidizing agent used in the reaction to obtain a phosphorothioate oligomer having a protecting group wherein an oxygen atom at P═O of phosphate group is replaced with a sulfur atom like P═S to make a thiophosphate group.

EXAMPLES

Hereinafter, the present invention is further specifically described by Examples, however, the present invention is not limited thereto. The identification of compound was carried out by Mass spectrum, High performance liquid chromatography mass spectrometer; LCMS, NMR spectrum, High-performance liquid chromatography (HPLC) and the like. In NMR spectrum, for proton nuclear magnetic resonance ($^1$H-NMR), an apparatus with 400 MHz of the resonance frequency was used, and for phosphorus nuclear magnetic resonance ($^{31}$P-NMR), an apparatus with 161.8 MHz of the resonance frequency was used. As symbols used in NMR spectrum, "s" is "singlet", "d" is "doublet", "dd" is "double of doublet", "t" is "triplet", "td" is "double of triplet", "q" is "quartet", "quin" is "quintet", "sept" is "septet", "m" is "multiplet", "br" is "broad", "brs" is "broad singlet", "brd" is "bread doublet", "brt" is "broad triplet", and "J" is "coupling constant".

A structure and abbreviation of each artificial nucleic acid (hereinafter, as needed, described by abbreviation) is shown in the following structural formula.

Structure and Abbreviation of Each Artificial Nucleic Acid

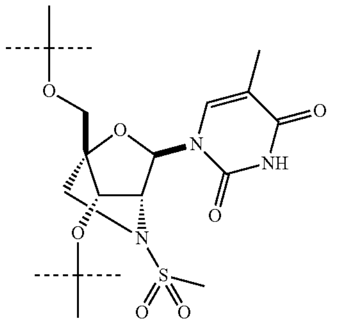

ALNA[Ms]

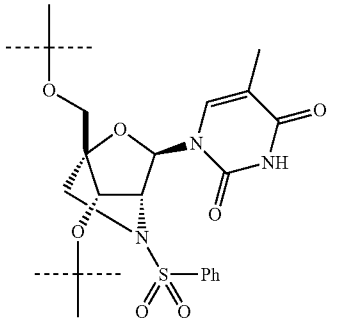

ALNA[Bs]

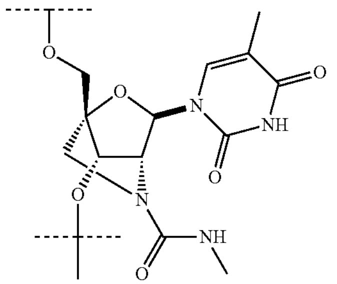

ALNA[mU]

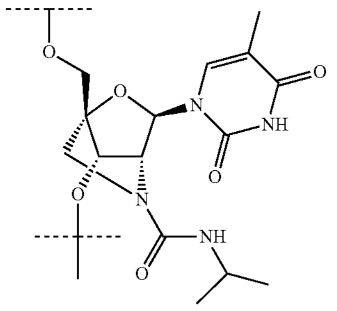

ALNA[IpU]

-continued
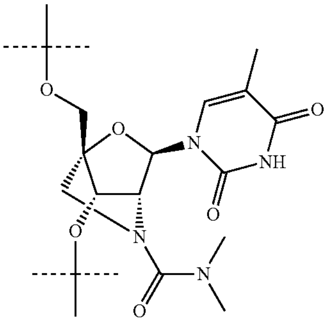
ALNA[dmU]
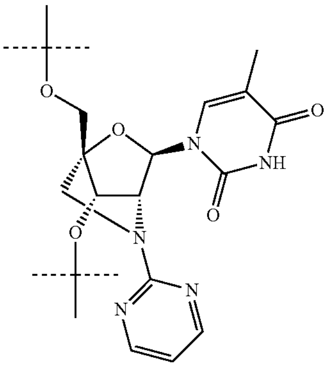
ALNA[2Pym]
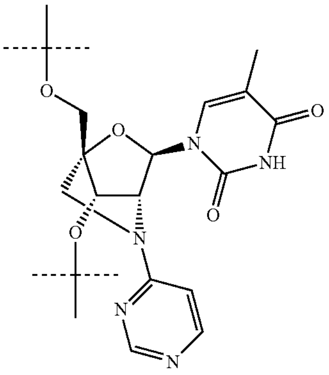
ALNA[4Pym]
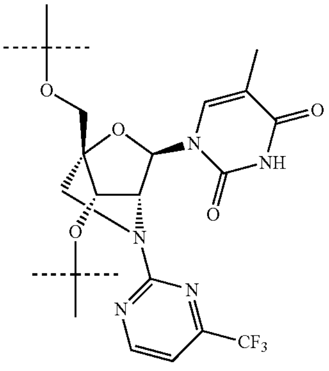
ALNA[4CF3-2Pym]
-continued
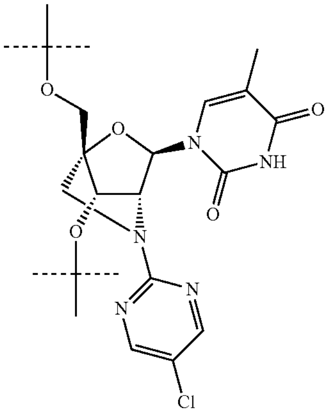
ALNA[5Cl-2Pym]
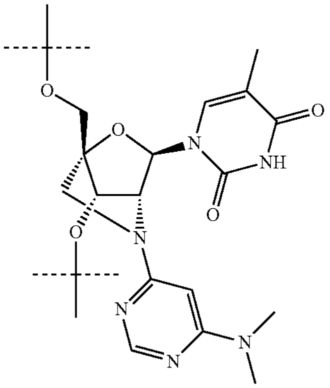
ALNA[6NMe2-4Pym]
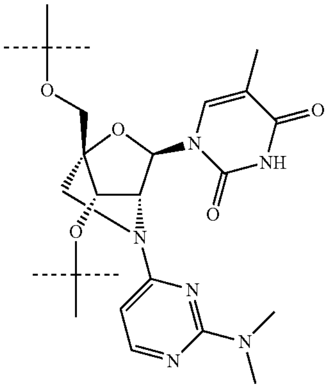
ALNA[2NMe2-4Pym]
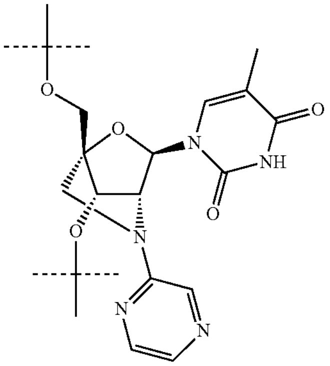
ALNA[Prz]

-continued

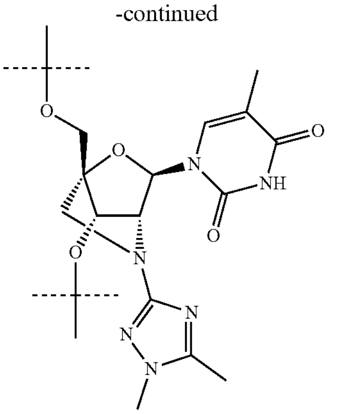

ALNA[Trz]

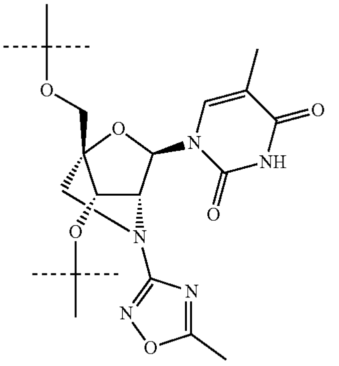

ALNA[Oxz]

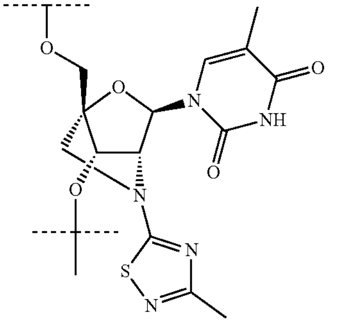

ALNA[Tdz]

Synthesis of ALNA[Ms]-T

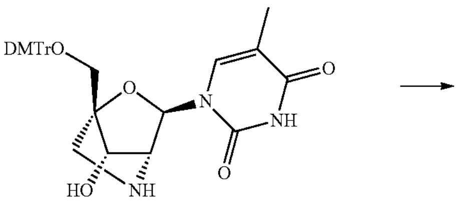

1a

-continued

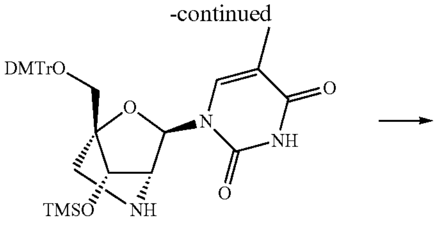

2Ta

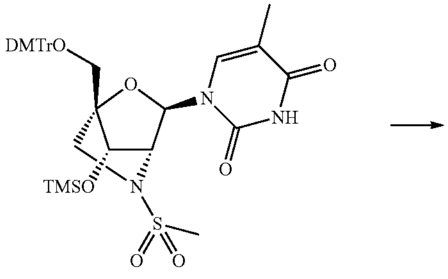

2Tb

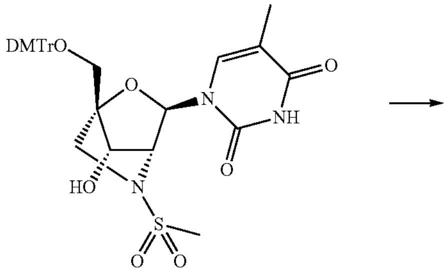

2Tc

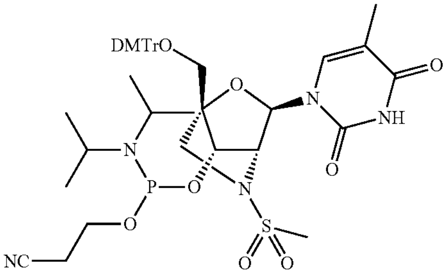

2Td

Example 1 Synthesis of Compound 2Ta

1-[(1R,3R,4R,7S)-1-[[bis(4-methoxyphenyl)-phenyl-methoxy]methyl]-7-trimethylsilyloxy-2-oxa-5-azabicyclo[2.2.1]heptan-3-yl]-5-methylpyrimidin-2,4-dione A mixed solution of 1-[(1R,3R,4R,7S)-1-[[bis(4-methoxyphenyl)-phenylmethoxy]methyl]-7-hydroxy-2-oxa-5-azabicyclo[2.2.1]heptan-3-yl]-5-methylpyrimidin-2,4-dione (1a) (which was prepared according to the method described in WO 2017/047816 A1) (12.35 g, 21.61 mmol) in dichloromethane was added BSA (13 mL, 53.17 mmol), and the mixture was stirred at room temperature for 8 hours. Thereto were added BSA (5.2 mL, 21 mmol) and TMSOTf (200 μL, 1.0 mmol), and the mixture was stirred again at room temperature for 15 hours. To the reaction solution was added 5% sodium bicarbonate water (50 mL), and the mixture was stirred, and extracted with dichloromethane.

The aqueous layer was mixed with dichloromethane (61 mL), and extracted, and the dichloromethane organic layer was combined. After the solvent was evaporated from the organic layer, the resulting residue was purified by silica gel chromatography (chloroform/methanol, 100/0 to 98/2)) to obtain a compound 2Ta (10.49 g, yield 75%).

MS(ESI): m/z=644 $(M+H)^+$

Example 2 Synthesis of Compound 2Tb

1-[(1R,3R,4R,7S)-1-[[bis(4-methoxyphenyl)-phenylmethoxy]methyl]-5-methylsulfonyl-7-trimethylsilyloxy-2-oxa-5-azabicyclo[2.2.1]heptan-3-yl]-5-methylpyrimidin-2,4-dione To a mixed solution of compound 2Ta (10.19 g, 15.83 mmol) in dichloromethane (50 mL) was added DIPEA (5.4 mL, 31 mmol), and thereto was added mesyl chloride (1.4 mL, 18 mmol) under ice bath, and the mixture was stirred in ice bath for 1.5 hours. To the reaction solution was added 5% sodium bicarbonate water (20 mL), and the mixture was stirred, and extracted with dichloromethane. The aqueous layer was mixed with dichloromethane (20 mL), and extracted, and combined and mixed with a dichloromethane organic layer. After the solvent was evaporated from the organic layer, the resulting residue was purified by silica gel chromatography (chloroform/methanol, 100/0 to 98/2)) to obtain a compound 2Tb (6.56 g, yield 57%).

MS (ESI): m/z=720 $(M-H)^-$

Example 3 Synthesis of Compound 2Tc

1-[(1R,3R,4R,7S)-1-[[bis(4-methoxyphenyl)-phenylmethoxy]methyl]-7-hydroxy-5-methylsulfonyl-2-oxa-5-azabicyclo[2.2.1]heptan-3-yl]-5-methylpyrimidin-2,4-dione To a mixed solution of compound 2Tb (3.02 g, 4.13 mmol) in tetrahydrofuran (15 mL) was added TBAF (1.35 mL, 4.58 mmol, 1M tetrahydrofuran solution) in ice bath, and the mixture was stirred for 30 minutes. To the reaction solution were added 10% aqueous ammonium chloride solution (20 mL) and dichloromethane (20 mL), and the mixture was stirred, and extracted with dichloromethane. The aqueous layer was mixed with dichloromethane (20 mL), extracted, and the dichloromethane organic layer was mixed. After the solvent was evaporated from the organic layer, the resulting residue was purified by silica gel chromatography (chloroform/methanol, 100/0 to 98/2) to obtain a compound 2tc (2.47 g, yield 92%).

MS(ESI): m/z=648 $(M-H)^-$

Example 4 Synthesis of Compound 2Td

3-[[(1R,4R,6R,7S)-4-[[bis(4-methoxyphenyl)-phenyl-methoxy]methyl]-6-(5-methyl-2,4-dioxopyrimidin-1-yl)-2-methylsulfonyl-5-oxa-2-azabicyclo[2.2.1]heptan-7-yl]oxy(diisopropylamino)phosphanyl]oxypropanenitrile (Present Compound 1)

To a solution of the compound 2Tc (2.47 g, 3.80 mmol) in dichloromethane (12.5 mL) were added DIPEA (2.00 mL, 12.0 mmol), and 2-cyanoethyl N,N-diisopropylchlorophosphoramidite (2.10 mL, 9.40 mmol), and the mixture was stirred at room temperature for 5 hours. Then thereto was added 5% aqueous sodium hydrocarbonate solution (15 mL) and dichloromethane (10 mL) under ice-cooling, and the mixture was stirred at room temperature, and then extracted with dichloromethane. The aqueous layer was extracted with dichloromethane (10 mL), and combined and mixed with the dichloromethane organic layer. After the solvent was evaporated from the mixture under reduced pressure, the mixture was purified by silica gel chromatography (hexane/ethyl acetate, 60/40 to 40/60) to obtain a compound 2Td as the present compound 1 (2.13 g, yield 66%).

MS(ESI): m/z=850 $(M+H)^+$ $^{31}$P-NMR ($CDCl_3$) δ: 150.30, 149.12

Synthesis of ALNA[Ms]-mC

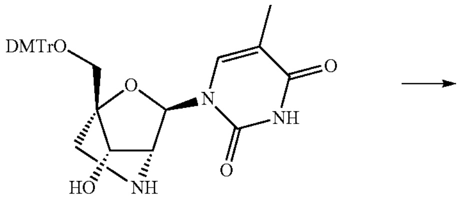

1a

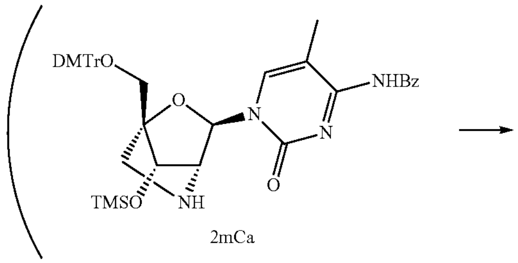

2mCa

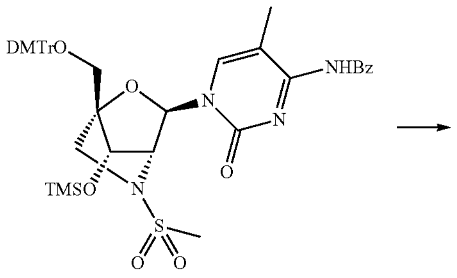

2mCb

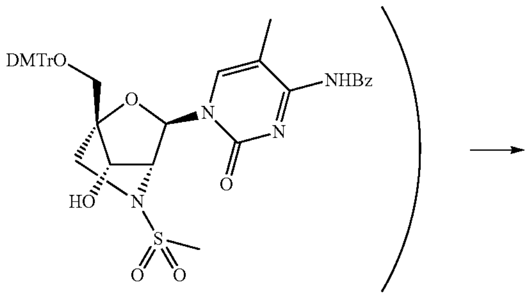

2mCc

-continued

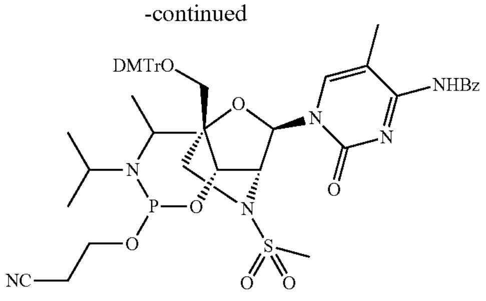

2mCd

Example 5 Synthesis of Compound 2mCc

N-[1-[(1R,3R,4R,7S)-1-[[bis(4-methoxyphenyl)-phenylmethoxy]methyl]-7-hydroxy-5-methylsulfonyl-2-oxa-5-azabicyclo[2.2.1]heptan-3-yl]-5-methyl-2-oxo-pyrimidin-4-yl]benzamide To a suspension solution of the compound 1a (10.33 g, 18.1 mmol) and N-(5-methyl-2-oxo-1H-pyrimidin-4-yl) benzamide (12.42 g, 54.2 mmol) in toluene solution (180 ml) was added BSA (44 mL, 180 mmol), and the mixture was stirred at room temperature for 15 minutes. Thereto was added TMSOTf (0.52 mL, 2.71 mmol), and the mixture was stirred at room temperature for 2 hours. The reaction solution was added to a mixed solution of IPS (100 mL), saturated sodium bicarbonate water (50 mL) and water (50 mL), and the mixture was stirred for 10 minutes, and insoluble materials were removed through Celite™. The aqueous layer was removed from the filtrates, and the organic layer was washed with water (50 mL) and saturated brine (50 mL) successively. The organic layer was passed through a phase separator, and the solvent was evaporated. The residue was solubilized with dichloromethane (90 mL), and thereto were added triethylamine (5.0 mL, 36.0 mmol) and methane sulfonic anhydride (3463 mg, 19.9 mmol), and the mixture was stirred at room temperature for 40 minutes. Thereto was added methane sulfonic anhydride (S44 mg, 5.42 mmol), and the mixture was stirred at room temperature for 30 minutes. Thereto was added further methane sulfonic anhydride (944 mg, 5.42 mmol) and triethylamine (1.3 mL, 9.06 mmol), and the mixture was stirred at room temperature for 20 minutes. The mixture was diluted with ethyl acetate (80 mL), and thereto were added water (40 mL) and saturated sodium bicarbonate water (40 mL), and the mixture was stirred. The aqueous layer was removed, and the organic layer was washed with saturated brine (50 mL), and then passed through a phase separator, and a solvent was evaporated, and the resulting mixture was dried under vacuum. A residue was added by THF (90 mL) to make a solution, and thereto was added TBAF (0.1 M, THF solution, 21.7 mL, 21.7 mmol) under ice-cooling, and the mixture was stirred under ice-cooling for 15 minutes. The mixture was diluted with ethyl acetate (90 mL), and thereto were added aqueous ammonium chloride solution (40 mL) and water (40 mL), and the mixture was stirred. The aqueous layer was removed, and the organic layer was passed through a phase separator, and the solvent was evaporated. The resulting residue was purified by silica gel chromatography (chloroform/methanol, 100/0 to 95/5) to obtain a compound 2mCc (5702 mg, yields over three steps 38%).

MS(ESI): m/z=753 $(M+H)^+$

Example 6 Synthesis of Compound 2mCd

N-[1-[(1R,3R,4R,7S)-1-[[bis(4-methoxyphenyl)-phenylmethoxy]methyl]-7-[2-cyanoethoxy-(diisopropylamino)phosphanyl]oxy-5-methylsulfonyl-2-oxa-5-azabicyclo[2.2.1]heptan-3-yl]-5-methyl-2-oxo-pyrimidin-4-yl]benzamide (Present Compound 2)

The compound 2mCd as the present compound 2 (6809 mg, yield 72%) was obtained from the compound 2mCc (8099 mg, 9.89 mmol) similarly to the Example 4.

MS(APCI): m/z=954 $(M+H)^+$

Synthesis of ALNA[Ms]-G

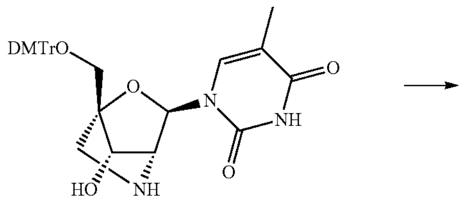

1a

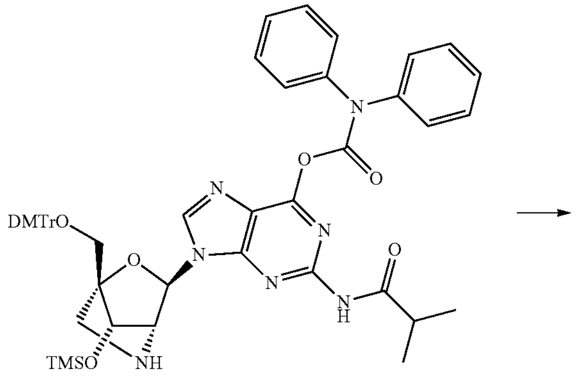

2Ga

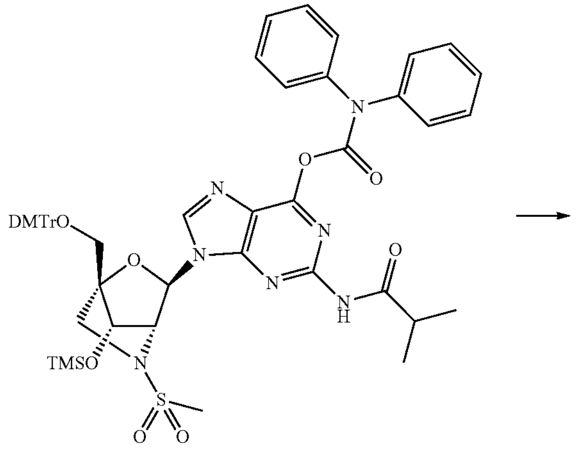

2Gb

-continued

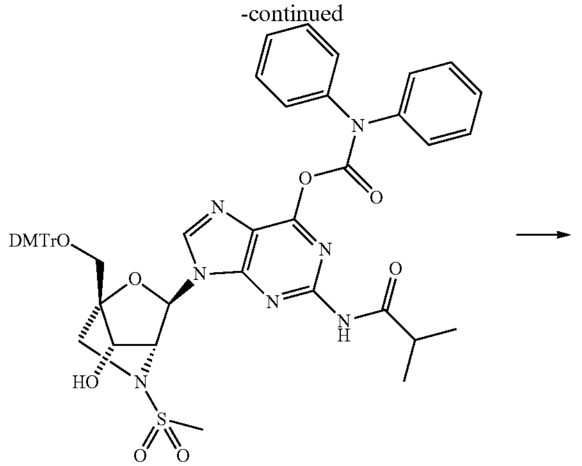

2Gc

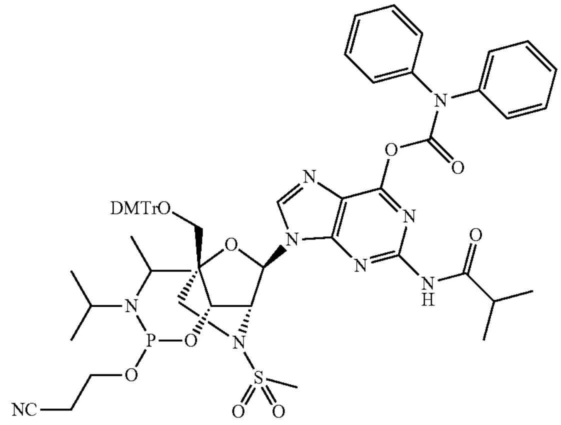

2Gd

Example 7 Synthesis of Compound 2Ga

[9-[(1R,3R,4R,7S)-1-[[bis(4-methoxyphenyl)-phenylmethoxy]methyl]-7-trimethylsilyloxy-2-oxa-5-azabicyclo[2.2.1]heptan-3-yl]-2-(2-methylpropanoylamino)purin-6-yl]N,N-diphenylcarbamate To a solution of the compound 1a (5040 mg, 8.817 mmol) and a solution of [2-(2-methylpropanoylamino)-9H-purin-6-yl]N,N-diphenyl carbamate (5400 mg, 12.97 mmol) in 1,2-dichloroethane (24.7 mL) was added BSA (14.8 mL, 60.46 mmol), and the mixture was stirred at 64° C. for 1 hour. Successively, thereto was added TMSOTf (0.167 ml, 0.864 mmol) was added gradually while maintaining the inner temperature at 60° C., and the mixture was stirred for 1 hour. After allowed to stand to cool, the reaction solution was added gradually to a mixed solution of chloroform (40 ml) and saturated aqueous sodium hydrogen carbonate solution (40 mL), which was prepared separately, and the mixture was stirred. After suction filtering insoluble materials off, the filtrates were extracted with ethyl acetate (50 mL). The organic layer was washed with saturated brine (50 mL), and then dried over sodium sulfate. Successively, after the filtrates were evaporated under reduced pressure, the resulting residue was purified by silica gel chromatography (chloroform/methanol, 100/0 to 97/3) to obtain a compound 2Ga (6350 mg, yield 79%).

MS (ESI): m/z=935 $(M+H)^+$

Example 8 Synthesis of Compound 2Gb

[9-[(1R,3R,4R,7S)-1-[[bis(4-methoxyphenyl)-phenylmethoxy]methyl]-5-methylsulfonyl-7-trimethylsilyloxy-2-oxa-5-azabicyclo[2.2.1]heptan-3-yl]-2-(2-methylpropanoylamino)purin-6-yl]N,N-diphenylcarbamate To a solution of the compound 2Ga (2370 mg, 2.537 mmol) in dichloromethane (24.9 mL) was added triethylamine (0.692 mL, 4.984 mmol), and the mixture was stirred at room temperature for 5 minutes. Successively, thereto was added methanesulfonyl chloride (0.193 mL, 2.488 mmol) under ice-cooling, and the mixture was stirred for 1 hour. To the reaction solution were added methylene chloride (30 mL) and saturated aqueous sodium hydrogen carbonate solution (30 mL) under ice-cooling, and the mixture was separated with a separatory funnel. The organic layer was washed with saturated brine (30 mL), and then dried over sodium sulfate. Successively, after the filtrates were evaporated under reduced pressure, the resulting mixture was purified by silica gel chromatography (hexane/ethyl acetate, 67/33 to 50/50) to obtain a compound 2Gb (2210 mg, yield 88%).

MS(ESI): m/z=1013 $(M+H)^+$

Example 9 Synthesis of Compound 2Gc

[9-[(1R,3R,4R,7S)-1-[[bis(4-methoxyphenyl)-phenylmethoxy]methyl]-7-hydroxy-5-methylsulfonyl-2-oxa-5-azabicyclo[2.2.1]heptan-3-yl]-2-(2-methylpropanoylamino)purin-6-yl]N,N-diphenylcarbamate To a solution of the compound 2Gb (2200 mg, 2.173 mmol) in THF (11 mL) was added TBAF (2.4 mL, 3.407 mmol) under ice-cooling, and the mixture was stirred at room temperature for 5 hours. To the reaction solution were added ethyl acetate (30 mL) and aqueous ammonium chloride solution (30 mL) under ice-cooling, and the mixture was filtered and separated with a separatory funnel. The organic layer was washed with saturated brine (30 mL), and then dried over sodium sulfate. Successively, after the filtrates were evaporated under reduced pressure, the resulting residue was purified by silica gel chromatography (hexane/ethyl acetate, 60/40 to 50/50). In order to remove raw materials, the mixture was purified again by silica gel chromatography (chloroform/methanol, 100/0 to 97/3) to obtain a compound 2Gc (1070 mg, yield 52%).

MS(ESI): m/z=941 $(M+H)^+$

Example 10 Synthesis of Compound 2Gd

[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-2-(2-methylpropanoylamino)purin-6-yl]N,N-diphenylcarbamate (Present Compound 3)

To a solution of the compound 2Gc (1070 mg, 1.139 mmol) in dichloromethane (5.690 mL) were added DIPEA (0.590 mg, 3.407 mmol) and 2-cyanoethyl N,N-diisopropylchloro phosphoramidite (0.510 mL, 2.282 mmol) under ice-cooling, and the mixture was stirred at room temperature for 22 hours. To the reaction solution were added dichloromethane (20 mL) and saturated sodium bicarbonate water (20 mL) under ice-cooling, and the mixture was separated with a separatory funnel. The aqueous layer was removed, and the organic layer was passed through a phase separator. After the filtrates were evaporated under reduced pressure, the result-ng residue was purified by silica gel chromatography (hexane/ethyl acetate, 50/50 to 40/60) to obtain a compound 2Gd as the present compound 3 (548 mg, yield 42%).

MS(ESI): m/z=1141 $(M+H)^+$

Synthesis of ALNA[Ms]-A

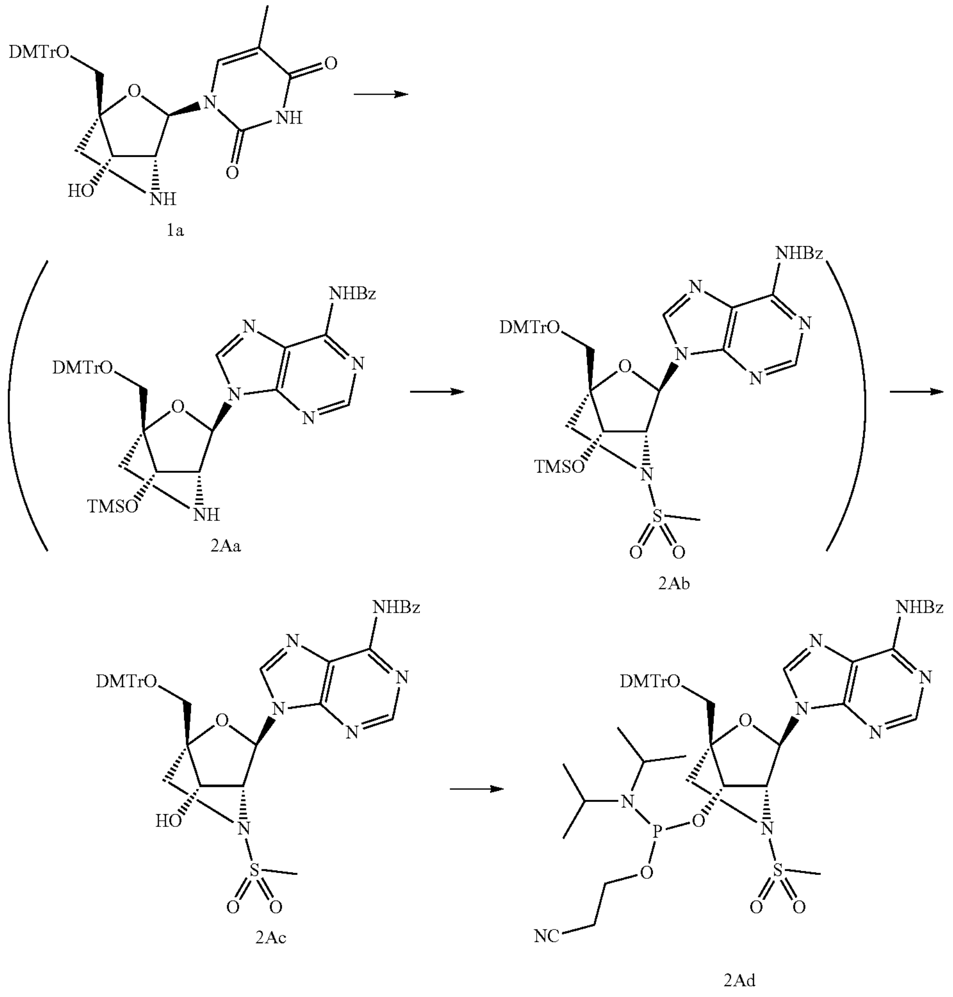

1a

2Aa

2Ab

2Ac

2Ad

Example 11 Synthesis of Compound 2Ac

N-[9-[(1R,3R,4R,7S)-1-[[bis(4-methoxyphenyl)-phenylmethoxy]methyl]-7-hydroxy-5-methylsulfonyl-2-oxa-5-azabicyclo[2.2.1]heptan-3-yl]-purin-6-yl]benzamide To a suspension of the compound 1a (10.0 g, 17.6 mmol) and N-(9H-purin-6-yl)benzamide (5.04 g, 21.1 mmol) in toluene (176 mL) was added dropwise BSA (30 mL, 123 mmol), and the mixture was warmed to 60° C., and stirred for 30 minutes. Thereto was added TMSOTf (1.03 mL, 5.34 mmol) and the mixture was stirred at 60° C. for 15 minutes. The reaction solution was added to the mixture solution of IPE (100 mL) and saturated sodium bicarbonate water (100 mL) while stirring under ice-cooling, and the mixture was stirred for 20 minutes, and insoluble materials were filtered off. After the filtered residue was washed with $Et_2O$ (20 mL) twice, the filtrates were separated with a separatory funnel, and washed with saturated brine (50 mL). After the mixture was passed through a phase separator, the mixture was concentrated under reduced pressure. The residue was solubilized with dichloromethane (24.9 mL), and thereto were added pyridine (4.57 mL, 56.5 mmol) and methane sulfonic anhydride (3614 mg, 20.75 mmol), and the mixture was stirred at room temperature for 30 minutes. Thereto were added saturated aqueous sodium hydrogen carbonate solution (50 mL) and water (50 mL), and the mixture was stirred, and separated with a separatory funnel. After the organic layer was washed with saturated brine (50 mL), the mixture was passed through a phase separator, and the solvent was evaporated under reduced pressure. The residue was added by THF (88 mL) to make a solution, and thereto was added TBAF (1M THF solution, 21.1 mL, 21.1 mmol) under ice-cooling, and the mixture was stirred under ice-cooling for 30 minutes. The mixture was diluted with ethyl acetate (80 mL), and thereto were added aqueous ammonium chloride solution (50 mL) and water (50 mL), and the mixture was stirred at room temperature. The mixture was separated with a separatory funnel, and the organic layer was washed with saturated brine (50 mL), and then passed through a phase separator, and the solvent was evaporated. The resulting residue was purified by silica gel chromatography (chloroform/methanol, 100/0 to 95/5) to a compound 2Ac (10.6 g, yields over three steps 75%).

MS(ESI): m/z=763 $(M+H)^+$

Example 12 Synthesis of Compound 2Ad

N-[9-[(1R,3R,4R,7S)-1-[[bis(4-methoxyphenyl)-phenylmethoxy]methyl]-7-[2-cyanoethoxy-(diisopropylamino)phosphanyl]oxy-5-methylsulfonyl-2-oxa-5-azabicyclo[2.2.1]heptan-3-yl]-purin-6-yl] benzamide (Present compound 4)

To a solution of the compound 2Ac (5.60 g, 7.01 mmol) in dichloromethane (40 mL) were added DIPEA (4.8 mL, 28.0 mmol) and 2-cyanoethyl N,N-diisopropylchloro phosphoramidite (4.7 mL, 21.0 mmol) in ice-cooling, and the mixture was stirred at room temperature for 4 hours. Thereto was added ethanol (1.2 mL, 21.0 mmol) under ice-cooling, and the mixture was stirred at room temperature for 5 minutes. The mixture was placed again under ice-cooling, and thereto were added saturated sodium bicarbonate water (20 mL), and saturated brine (20 mL), and the mixture was stirred, and the organic layer was passed through a phase separator. After the filtrates were evaporated under reduced pressure, the resulting residue was purified by silica gel chromatography (hexane/ethyl acetate, 67/33 to 10/90) to obtain a compound 2Ad as the present compound 4 (5.44 g, yield 77%).

MS(ESI): m/z=964 $(M+H)^+$

Synthesis of ALNA[Bs]-T

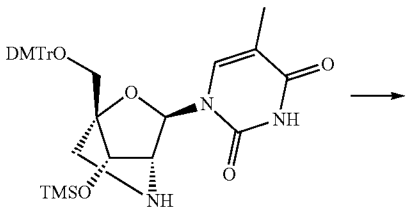

2Ta

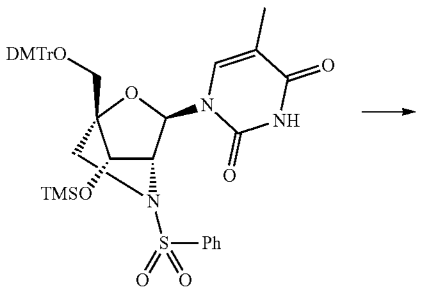

3Tb

-continued

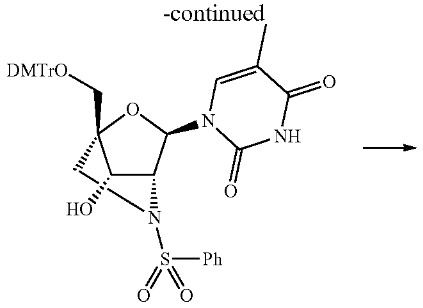

3Tc

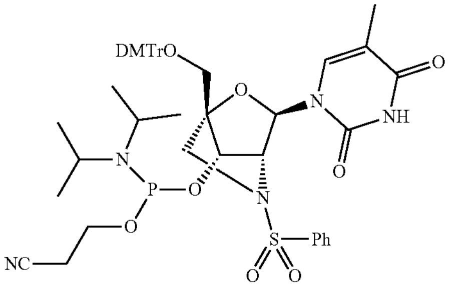

3Td

Example 13 Synthesis of Compound 3Tb

1-[(1R,3R,4R,7S)-5-(benzenesulfonyl)-1-[[bis(4-methoxyphenyl)-phenylmethoxy]methyl]-7-trimethylsilyloxy-2-oxa-5-azabicyclo[2.2.1]heptan-3-yl]-5-methyl-pyrimidin-2,4-dione A compound 2Ta (1.00 g, 1-56 mmol) was azeotroped with toluene. Tc the residue were added dichloromethane (5 mL) and triethylamine (0.43 mL, 3.1 mmol), and the mixture was solubilized completely. The mixture solution was cooled under ice-cooling, and thereto was added benzenesulfonyl chloride (0.21 mL, 1.6 mmol), and the mixture was stirred under ice-cooling for 4 hours. Tc the reaction solution was added 5% potassium carbonate solution (20 mL), and the mixture was stirred, and extracted with dichloromethane (5 mL). The aqueous layer was mixed with dichloromethane (5 mL), extracted, and the extracts were combined and mixed with the dichloromethane organic layer. After the solvent was evaporated from the organic layer, the resulting residue was purified by silica gel chromatography (hexane/ethyl acetate, 40/60 to 20/80) to obtain a compound 3Tb (0.78 g, yield 64%).

MS(ESI): m/z=782 $(M-H)^-$

Example 14 Synthesis of Compound 3Tc

1-[(1R,3R,4R,7S)-5-(benzenesulfonyl)-1-[[bis(4-methoxyphenyl)-phenylmethoxy]methyl]-7-hydroxy-2-oxa-5-azabicyclo[2.2.1]heptan-3-yl]-5-methylpyrimidin-2,4-dione A compound 3Tc (0.59 g, yield 84%) was synthesized from the compound 3Tb (0.78 g, 0.99 mmol) similarly to the Example 3.

MS(ESI): m/z=710 $(M-H)^-$

Example 15 Synthesis of Compound 3Td

3-[[(1R,3R,4R,7S)-5-(benzenesulfonyl)-1-[[bis(4-methoxyphenyl)-phenylmethoxy]methyl]-3-(5-methyl-2,4-dioxo-pyrimidin-1-yl)-2-oxa-5-azabicyclo[2.2.1]heptan-7-yl]oxy-(diisopropylamino) phosphanyl]oxypropanenitrile (Present Compound 5)

To a solution of the compound 3Tc (599 mg, 0.765 mmol) in acetonitrile (3 mL) were added diisopropylammonium tetrazolide (171 mg, 0.996 mmol), 2-Cyanoethyl N,N,N',N'-Tetraisopropylphosphordiamidite (0.36 mL, 1.1 mmol), and the mixture was stirred at room temperature for 19 hours. To the reaction solution were added ethyl acetate (10 mL) and water (5 mL), and after the mixture was stirred, the aqueous layer was separated. To the aqueous layer was added ethyl acetate (10 mL), and after the mixture was mixed, the organic layer was separated. The organic layer was combined and mixed with above organic layer, and the mixture was concentrated at 40° C. under reduced pressure. The resulting residue was purified by silica gel chromatography (hexane/ethyl acetate, 67/33 to 10/90) to obtain a compound 3Td as the present compound 5 (0.65 g, yield 86%).

MS(ESI): m/z=912 $(M+H)^+$ $^{31}$P-NMR ($CDCl_3$) δ: 149.68, 149.22

Synthesis of ALNA[Bs]-mC

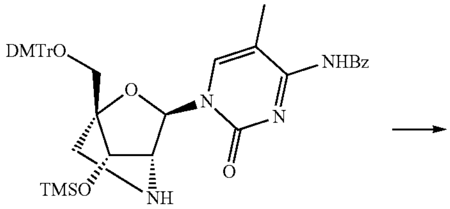

1b

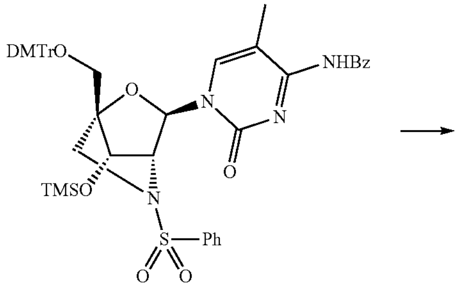

3mCb

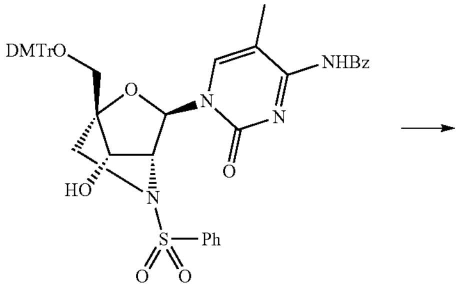

3mCc

-continued

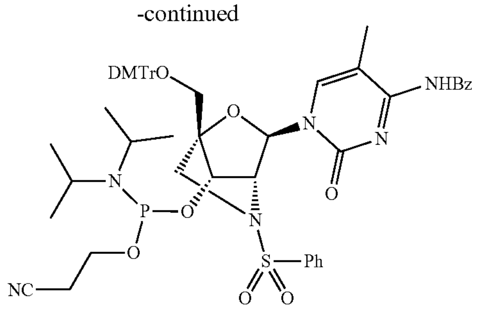

3mCd

Example 16 Synthesis of Compound 3Cb

N-[1-[(1R,3R,4R,7S)-5-(benzenesulfonyl)-1-[[bis(4-methoxyphenyl)-phenylmethoxy]methyl]-7-trimethylsilyloxy-2-oxa-5-azabicyclo[2.2.1]heptan-3-yl]-5-methyl-2-oxo-pyrimidin-4-yl]benzamide A compound 3mCb (0.85 g, yield 71%) was synthesized from the compound 1b (1.00 g, 1.34 mmol) which was synthesized according to the method described in WC 2017/047816 A1 similarly to the Example 13.

MS(ESI): m/z=887 $(M+H)^+$

Example 17 Synthesis of Compound 3mCb

N-[1-[(1R,3R,4R,7S)-5-(benzenesulfonyl)-1-[[bis(4-methoxyphenyl)-phenylmethoxy]methyl]-7 hydroxy 2 oxa 5-azabicyclo[2.2.1]heptan-3-yl]-5-methyl-2-oxo-pyrimidin-4-yl]benzamide A compound 3mCc (0.78 g, yield 99%) was synthesized from the compound 3mCb (0.85 q, 0.96 mmol) similarly to the Example 14.

MS(SSI): m/z=813 $(M+H)^+$

Example 18 Synthesis of Compound 3mCd

N-[1-[(1R,3R,4R,7S)-5-(benzenesulfonyl)-1-[[bis(4-methoxyphenyl)-phenylmethoxy]methyl]-7-[2-cyanoethoxy-(diisopropylamino)phosphanyl)oxy-2-oxa-5-azabicyclo[2.2.1]heptan-3-yl]-5-methyl-2-oxo-pyrimidin-4-yl]benzamide (Present Compound 6)

A compound 3mCd (0.53 q, yield 55%) as the present compound 6 was synthesized from the compound 3mCc (0.78 g, 0.89 mmol) similarly to the Example 15.

MS(ESI): m/z=1015 $(M+H)^+$ $^{31}$P-NMR ($CDCl_3$) δ: 149.94, 149.34

Synthesis of ALNA[mU]-T

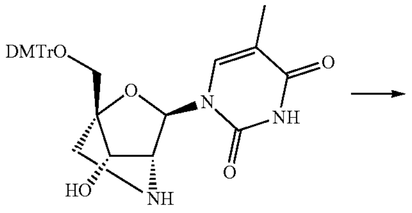

1a

-continued

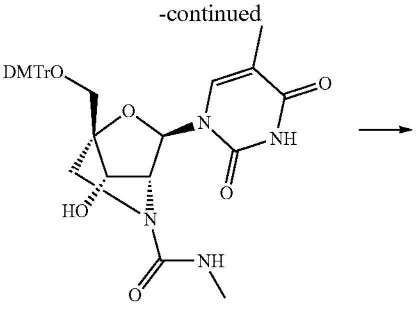

4Tc

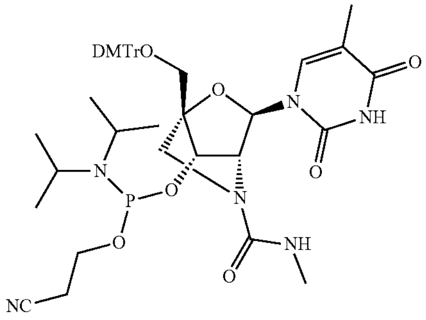

4Td

Example 19 Synthesis of Compound 4Tc (1R,3R,4R,7S)-1-[[bis(4-methoxyphenyl)-phenyl-methoxy]methyl]-7-hydroxy-N-methyl-3-(5-methyl-2,4-dioxopyrimidin-1-yl)-2-oxa-5-azabicyclo[2.2.1] heptane-5-carboxamide A compound 1a (1.20 g, 2.10 mmol) was azeotroped with toluene, and to the mixture solution of the residue in tetrahydrofuran (6 mL) was added N,N-diisopropylethylamine (0.61 mL, 3.5 mmol), and thereto was added a solution of N-methylcarbamoyl chloride (0.20 g, 2.2 mmol) in tetrahydrofuran (1 mL) in ice bath, and the mixture was stirred for 3 hours in ice bath. To the reaction solution were added 5% sodium bicarbonate water (20 ml) and ethyl acetate (10 mL), and the mixture was stirred, and the mixture was extracted with ethyl acetate. The aqueous layer (10 mL) was extracted with ethyl acetate (10 mL) twice, and the extracts were combined and mixed with the organic layer. After the solvent was evaporated from the organic layer, the resulting residue was purified by silica gel chromatography (chloroform/methanol, 100/0 to 97/3) to obtain a compound 4Tc (1.28 g, yield 97%).

MS (ESI): m/z=627 $(M-H)^-$

Example 20 Synthesis of Compound 4Td (1R,3R,4R/7S)-1-[[bis(4-methoxyphenyl)-phenyl-methoxy]methyl]-7-[2-cyanoethoxy-(diisopropylamino)phosphanyl]oxy-N-methyl-3-(5-methyl-2,4-dioxopyrimidin-1-yl)-2-oxa-5-azabicyclo[2.2.1] heptane-5-carboxamide (Present Compound 7)

A compound 4Td (0.56 g, yield 37%) as the present compound 7 was synthesized from the compound 4Tc (1.16 g, 1.8 mmol) similarly to the Example 15.

MS(ESI): m/z=828 $(M-H)^-$ $^{31}$P-NMR ($CDCl_3$) δ: 149.31, 147.44

Synthesis of ALNA[mU]-mC

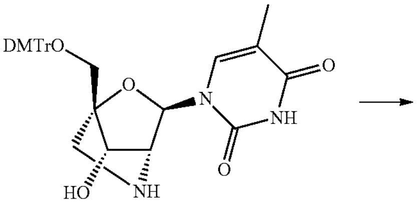

1a

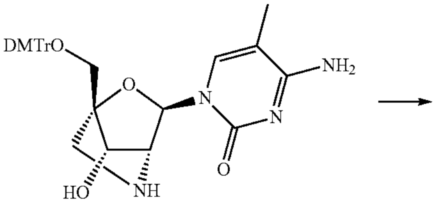

4mCa

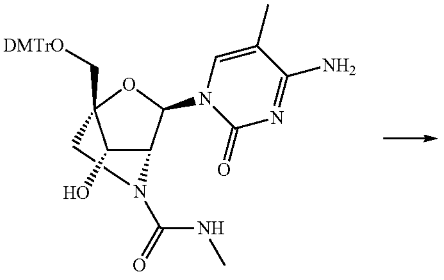

4mCb

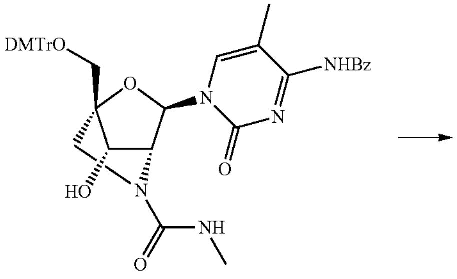

4mCc

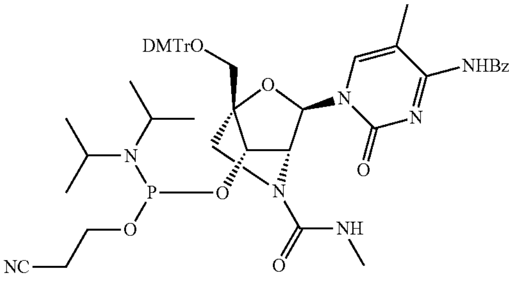

4mCd

Example 21 Synthesis of Compound 4mCa 4-amino-1-[(1R,3R,4R,7S)-1-[[bis(4-methoxyphenyl)-phenylmethoxy] methyl]-7-hydroxy-2-oxa-5-azabicyclo[2.2.1]heptan-3-yl]-5-methyl-pyrimidin-2-one To a mixed solution of the compound 1a (105.0 g, 184 mmol), 5-methylcytosine (69.0 g, 551 mmol) and 1,2-dichloroethane (918 mL) was added dropwise BSA (584 mL, 2390 mmol) over 18 minutes. The mixture was warmed to 60° C., and stirred for 20 minutes. After an inner temperature was cooled to 19.5° C. under ice-cooling, thereto was added TMSOTf (10 mL, 55.2 mmol), and the mixture was warmed to 60° C. After the mixture was stirred for 40 minutes, the reaction solution was cooled under ice-cooling, and thereto was added dropwise 5% aqueous sodium hydrocarbonate solution (525 mL). Next, thereto were added chloroform (1050 mL) and aqueous 15% sodium chloride solution (525 mL). After the resulting slurry was filtered through Celite, the filtered residue were washed with chloroform (525 mL) to obtain a residue 1 and a filtrate 1. To the residue 1 were added ethyl acetate (2100 mL) and water (2100 mL), and the mixture was stirred for 1 hour. After the mixture was filtered through Celite, the residue was washed with ethyl acetate (1050 mL) to obtain the filtrates 2. The filtrates 2 were separated with a separatory funnel, and the organic layer washed with water (525 mL) twice. On the other hand, the filtrates 1 were separated with a separatory funnel, and the aqueous layer was extracted with chloroform (525 mL). The organic layers were combined, and washed with water 1050 mL twice. The resulting organic layer was concentrated under reduced pressure to obtain pale yellow solids (125.6 g). Thereto was added THF (550 mL), and the mixture was stirred, and thereto was added 1M TBAF/THF solution (276 mL, 276 mmol). After the mixture was stirred at room temperature for 3 hours, the reaction solution was quenched with water (550 mL), and thereto was added chloroform (550 mL), and the mixture was separated with a separatory funnel. The aqueous layer was extracted with chloroform (275 mL) again, and the organic layers were combined. The organic layer was washed with water, and then concentrated under reduced pressure. The resulting residue was purified by silica gel chromatography (chloroform/methanol, 20/1 to 4/1) to obtain a compound 4mCa (69.62 g, yield 62%).

MS(ESI): m/z=593 $(M+Na)^+$

Example 22 Synthesis of Compound 4mCb (1R,3R,4R,7S)-3-(4-amino-5-methyl-2-oxo-pyrimidin-1-yl)-1-[[bis(4-methoxyphenyl)-phenylmethoxy] methyl]-7-hydroxy-N-methyl-2-oxa-5-azabicyclo [2.2.1]heptane-5-carboxamide The compound 4mCa (1.00 g, 1.75 mmol) was azeotroped with toluene, and to the mixture solution of the residue in tetrahydrofuran (5 mL) was added triethylamine (0.49 mL, 3.5 mmol), and thereto was added a solution of N-methylcarbamoyl chloride (0.17 g, 1.8 mmol) in tetrahydrofuran (1 mL) under ice-cooling, and the mixture was stirred for 3 hours in ice bath. To the reaction solution were added tap water (15 mL), ethyl acetate (1 mL) and chloroform (15 mL), and the mixture was stirred, and extracted with organic solvent. The aqueous layer was extracted with chloroform (5 mL), and the organic layers were combined and mixed. The organic layer was dried over magnesium sulfate, and the solids were filtered. The solvents were evaporated from the filtrates to obtain a compound 4mCb (1.18 g, yield quant.). The residue was used to a next reaction without purification.

MS (ESI): m/z=627 $(M-H)^-$

Example 23 Synthesis of Compound 4mCc (1R,3R,4R,7S)-3-(4-benzamide-5-methyl-2-oxo-pyrimidin-1-yl)-1-[[bis(4-methoxyphenyl)-phenyl-methoxy]methyl]-7-hydroxy-N-methyl-2-oxa-5-azabicyclo[2.2.1]heptane-5-carboxamide The compound 4mCb (1.18 g) was azeotroped with toluene, and to a mixture solution of the residue in tetrahydrofuran (5 mL) were added benzoic anhydride (0.51 g, 2.27 mmol) and methanol (0.01 mL, 0.25 mmol) at room temperature, and the mixture was stirred at 70° C. as a temperature of outer bath for 4 hours. Thereto were added 5% sodium bicarbonate water (10 mL) and ethyl acetate (10 mL), and the mixture was stirred, and extracted with organic solvent(s). The aqueous layer was extracted with ethyl acetate (15 mL), and the organic layers were combined and mixed. After the solvent was evaporated from the organic layer, the resulting residue was purified by silica gel chromatography (chloroform/methanol, 130/0 to 97/3) to obtain a compound 4mCc (0.99 g, yield 77%).

MS(ESI): m/z=731 $(M-H)^-$

Example 24 Synthesis of Compound 4mCd (1R,3R,4R,7S)-3-(4-benzamide-5-methyl-2-oxo-pyrimidin-1-yl)-1-[[bis(4-methoxyphenyl)-phenyl-methoxy]methyl]-7-[2-cyanoethoxy-(diisopropylamino)phosphanyl]oxy-N-methyl-2-oxa-5-azabicyclo[2.2.1]heptane-5-carboxamide (Present Compound 8)

A compound 4mCd (0.96 g, yield 77%) as the present compound 8 was synthesized from the compound 4mCc (0.98 g, 1.34 mmol) similarly to the Example 15.

MS(ESI): m/z=933 $(M+H)^+$

Synthesis of ALNA[mU]-G

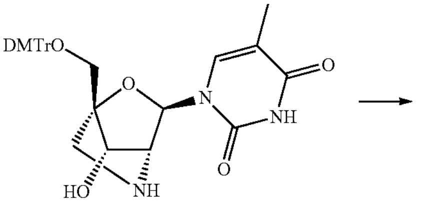

1a

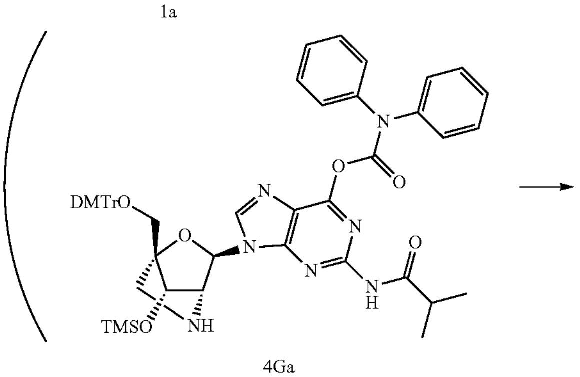

4Ga

-continued

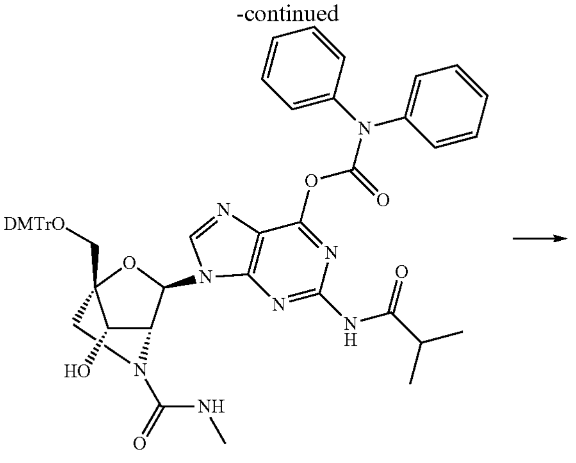

4Gb

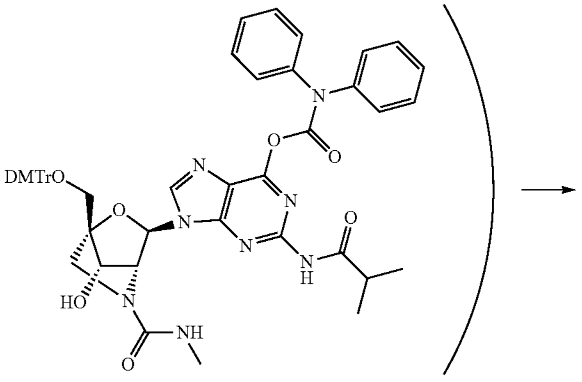

4Gc

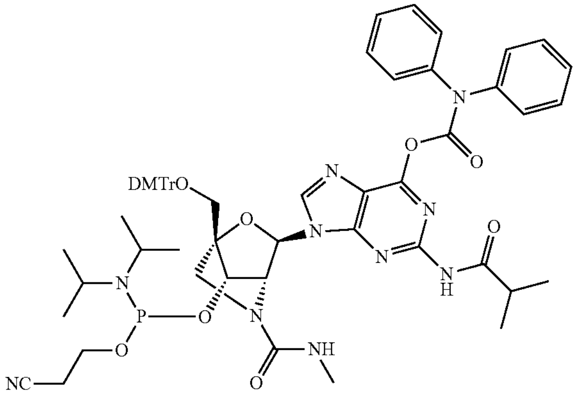

4Gd

Example 25 Synthesis of Compound 4Ga

[9-[(1R,3R,4R,7S)-1-[[bis(4-methoxyphenyl)-phenylmethoxy]methyl]-7-trimethylsilyloxy-2-oxa-5-azabicyclo[2.2.1]heptan-3-yl]-2-(2-methylpropanoylamino)purin-6-yl]N,N-diphenylcarbamate To a suspension of the compound 1a (30.5 g, 53.4 mmol) and [2-(2-methylpropanoylamino)-9H-purin-6-yl]N,N-diphenylcarbamate (26.7 g, 64.1 mmol) in toluene (267 mL) was added dropwise BSA (91 mL, 372 mmol) ever about 20 minutes, and the mixture was warmed to 60° C., and stirred for 5 minutes. Thereto was added further toluene (100 mL), and the mixture was stirred at 60° C. for additional 10 minutes. Thereto was added TMSOTf (1.03 mL, 5.34 mmol) and the mixture was stirred at 60° C. for 20 minutes. The reaction solution was added to a mixture solution of IPE (100 mL), saturated sodium bicarbonate water (50 mL) and water (50 mL) while stirring under ice-cooling, and the mixture was stirred for 2 hours, and insoluble materials were filtered off. After the residue was washed with $Et_2O$ (20 mL) twice, the filtrate were separated with a separatory funnel, and the organic layer was washed with water (50 mL) and saturated brine (50 mL) successively. The mixture was passed through a phase separator, concentrated under reduced pressure, and dried under vacuum to Compound 4Ga as crude product (48.67 g).

MS(ESI): m/z=954 $(M+H)^+$

Example 26 Synthesis of Compound 4Gc

[9-[(1R,3R,4R,7S)-1-[[bis(4-methoxyphenyl)-phenyl-methoxy]methyl]-7-hydroxy-N-methyl-2-oxa-5-azabicyclo[2.2.1]heptan-3-yl]-2-(2-methylpropanoylamino)purin-6-yl]N,N-diphenylcarbamate The compound 4Ga (17.4 g, 18.6 mmol) was solubilized by THE (100 mL), and thereto were added DIPEA (4.87 mL, 28.0 mmol), and N-methylcarbamoyl chloride (1830 mg, 19.6 mmol) under ice-cooling, and the mixture was stirred for 30 minutes. Thereto were added saturated sodium bicarbonate water (100 mL) and ethyl acetate (100 mL) successively, and the mixture was stirred at room temperature for 5 minutes. After the mixture was separated with a separatory funnel, the organic layer was washed with water (50 mL) and saturated brine (50 mL) successively, and the mixture was passed through a phase separator, and the solvent was evaporated, and dried under vacuum. The residue was added by THF (90 mL) to make a solution, and thereto was added TBAF (1M THF solution, 4.54 mL, 4.54 mmol) under ice-cooling, and the mixture was stirred under ice-cooling for 20 minutes. The mixture was diluted with ethyl acetate (100 mL), and thereto were added aqueous ammonium chloride solution (50 mL) and water (50 mL), and the mixture was stirred at room temperature for 5 minutes. The mixture was separated with a separatory funnel, and the organic layer was passed through a phase separator and the solvents were evaporated. The resulting residue was purified by silica gel chromatography (chloroform/methanol, 100/0 to 95/5) to obtain a compound 4Gc (9030 mg, yields over three steps 54%).

MS(ESI): m/z=919 $(M+H)^+$

Example 21

Synthesis of Compound 4Gd

[5-[(1R,3R,4R,7S)-1-[[bis(4-methoxyphenyl)-phenylmethoxy]methyl]-7-[2-cyanoethoxy-(diisopropylamino)phosphanyl]oxy-5-(methylcarbamoyl)-2-oxa-5-azabicyclo[2.2.1]heptan-3-yl]-2-(2-methylpropanoylamino)purin-6-yl]N,N-diphenylcarbamate (Present Compound 9)

A compound 4Dc as the present compound 9 (8700 mg, yield 79%) was synthesized from the compound 4Gc (9020 mg, 9.82 mmol) similarly to the Example 12.

MS(ESI): m/z=1197 $(M+H)^+$

Synthesis of ALNA[mU]-A

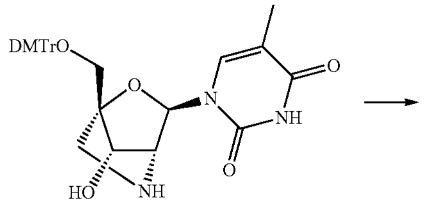

1a

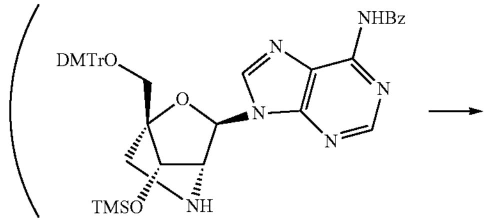

4Aa

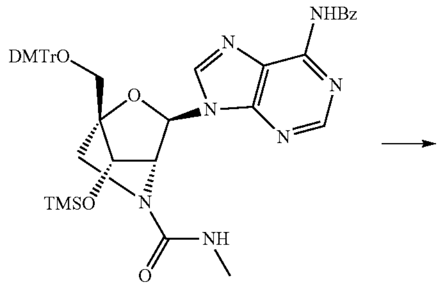

4Ab

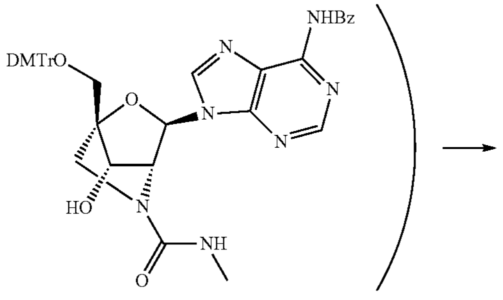

4Ac

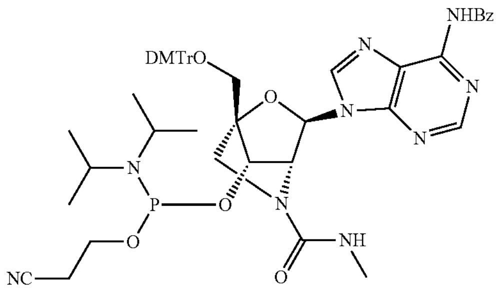

4Ad

Example 28 Synthesis of Compound 4Aa

N-[9-[(1R,3R,4R,7S)-1-[[bis(4-methoxyphenyl)-phenylmethoxy]methyl]-7-trimethylsilyloxy-2-oxa-5-azabicyclo[2.2.1]heptan-3-yl]purin-6-yl]benzamide To a suspension of the compound 1a (30.0 g, 52.5 mmol) and N-(9H-purin-6-yl)benzamide (15.0 g, 62.7 mmol) in toluene (500 mL) was added dropwise BSA (90 mL, 368 mmol), and the mixture was warmed to 80° C., and stirred for 20 minutes. Thereto was added TMSOTf (1.0 mL, 5.17 mmol) under ice-cooling, and the mixture was stirred at 60° C. for 20 minutes. To a mixed solution of IPE (200 mL) and saturated sodium bicarbonate water (200 mL) was added the reaction solution under ice-cooling while stirring, and the mixture was stirred for 20 minutes, and insoluble materials were filtered off. After the residues were washed with $Et_2O$ (40 mL) twice, the filtrates were separated with a separatory funnel, and washed with saturated brine. After the organic layer was dried over sodium sulfate, insoluble materials were filtered off, and the filtrates were concentrated under reduced pressure, and dried under vacuum to obtain a compound 4Aa as a crude product (40.5 g).

MS(ESI): m/z=757 $(M+H)^+$

Example 29 Synthesis of Compound 4Ab (1R,3R,4R,7S)-3-(6-benzamidepurin-9-yl)-1[[bis(4-methoxyphenyl)-phenylmethoxy]methyl]-N-methyl-7-trimethylsilyloxy-2-oxa-5-azabicyclo[2.2.1]heptane-5-carboxamide The crude product 4Aa (8.20 g) was solubilized by THF (87 mL), and thereto were added DIPEA (3.00 mL, 17.2 mmol), and N-methyl carbamoyl chloride (970 mg, 10.4 mmol) successively at room temperature, and the mixture was stirred for 30 minutes. Thereto were added ethyl acetate (100 mL), saturated sodium bicarbonate water (50 mL) and water (50 mL), and the mixture was separated with a separatory funnel, and the organic layer was then washed with saturated brine (50 mL), and passed through a phase separator and the solvents were evaporated, and dried under vacuum to obtain a crude product 4Ab (8.70 g).

MS(ESI): m/z=813 $(M-H)^-$

Example 30 Synthesis of Compound 4Ac (1R,3R,4R,7S)-3-(6-benzamidepurin-9-yl)-1[[bis(4-methoxyphenyl)phenylmethoxy]methyl]-7-hydroxy-N-methyl-2-oxa-5-azabicyclo[2.2.1]heptane-5-carboxamide The crude product 4Ab (8.00 g) was added by THF (100 mL) to make a solution, and thereto was added TBAF (1M THF solution, 5.00 mL, 5.00 mmol) under ice-cooling, and the mixture was stirred under ice-cooling for 1 hour. The mixture was diluted with ethyl acetate (90 mL), and thereto were added aqueous ammonium chloride solution (50 mL), and water (50 mL), and the mixture was stirred at room temperature. The mixture was separated with a separatory funnel, the organic layer was washed with saturated brine (50 mL), and passed through a phase separatory, and the solvents were evaporated. The resulting residue was purified by silica gel chromatography (chloroform/methanol, 100/0 to 97/3) to obtain a compound 4Ac (6100 mg, yields over three steps 84%).

MS(ESI): m/z=742 $(M+H)^+$

Example 31 Synthesis of Compound 4Ad (1R,3R,4R,7S)-3-(6-benzamidepurin-9-yl)-1-[[bis(4-methoxyphenyl)phenylmethoxy]methyl]-7-[2-cyano-ethoxy-(diisopropylamino)phosphanyl]oxy-N-methyl-2-oxa-5-azabicyclo[2.2.1]heptane-5-carboxamide (Present Compound 10)

A compound 4Ad as the present compound 10 (3830 mg, yield 48%) was obtained from the compound 4Ac (6100 mg, 8.20 mmol) similarly to the Example 12.

MS(APCI): m/z=942 $(M+H)^+$

Synthesis of ALNA[ipU]-T

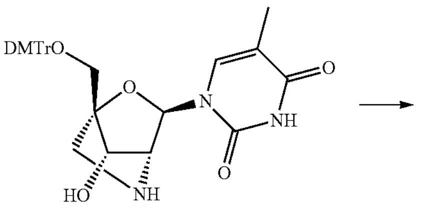

1a

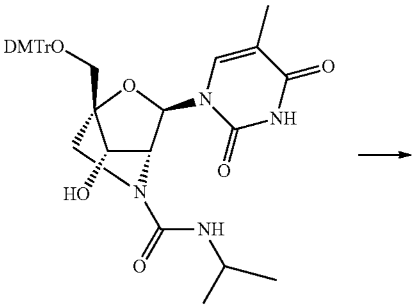

5Tc

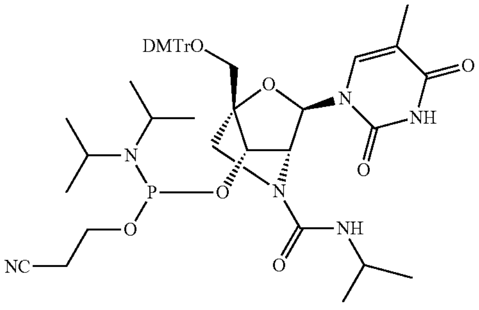

5Td

Example 32 Synthesis of Compound 5Tc (1R,3R,4R,7S)-1-[[bis(4-methoxyphenyl)-phenyl-methoxy]methyl]-7-hydroxy-N-isopropyl-3-(5-methyl-2,4-dioxopyrimidin-1-yl)-2-oxa-5-azabicyclo[2.2.1]heptane-5-carboxamide To a solution of the compound 1a (1500 mg, 2.624 mmol) in dichloromethane (26 mL) was added 2-isocyanate-propane (0.27 mL, 2.7 mmol) under ice-cooling, and the mixture was stirred at room temperature for 1 hour. Thereto were added a mixed solution of ethyl acetate (10 mL) and saturated bicarbonate solution (20 mL), and the mixture was separated with a separatory funnel, and the aqueous layer was then extracted with ethyl acetate 10 mL twice, and the combined organic layer was washed with saturated brine 10 mL. The organic layer was dried over anhydrous sodium sulfate, and filtered, and the solvents were then evaporated. The mixture was purified by silica gel chromatography (hexane/ethyl acetate, 50/50 to 0/100 to obtain a compound 5tc (1904 mg, yield quant.).

MS(ESI): m/z=656 $(M-H)^-$

Example 33 Synthesis of Compound 5Td (1R,3R,4R,7S)-1-[[bis(4-methoxyphenyl)-phenyl-methoxy]methyl]-7-[2-cyanoethoxy-(diisopropy-lamino)phosphanyl]oxy-N-isopropyl-3-(5-methyl-2,4-dioxo-pyrimidin-1-yl)-2-oxa-5-azabicyclo[2.2.1]heptane-5-carboxamide (Present Compound 11)

A compound 5td as the present compound 11 (1272.9 mg, yield 52%) was obtained from the compound 5Tc (2020 mg, 2.85 mmol) similarly to the Example 4.

MS(ESI): m/z=855 $(M-H)^-$

Synthesis of ALNA[ipU]-mC

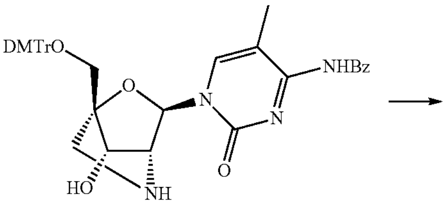

1c

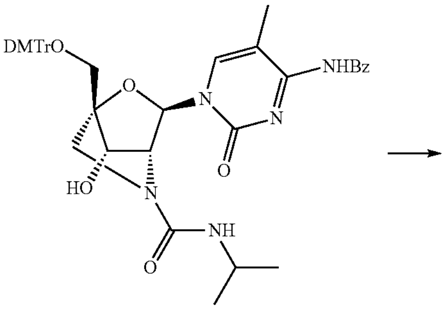

5mCc

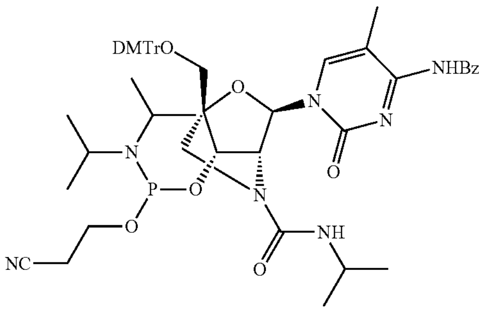

5mCd

Example 34 Synthesis of Compound 5mCc (1R,3R,4R,7S)-3-(4-benzamide-5-methyl-2-oxo-pyrimidin-1-yl)-1-[[bis(4-methoxyphenyl)phenyl-methoxy]methyl]-7-hydroxy-N-isopropyl-2-oxa-5-azabicyclo[2.2.1]heptane-5-carboxamide A compound 5mCc (1168 mg, yield 93%) was obtained from the compound 1c (1300 mg, 1.657 mmol) which was synthesized according to the method described in WO 2017/047816 A1.

MS(ESI): m/z=761 $(M+H)^+$

Example 35 Synthesis of Compound 5mCd (1R,3R,4R,7S)-3-(4-benzamide-5-methyl-2-oxo-pyrimidin-1-yl)-1-[[bis(4-methoxyphenyl)-phenyl-methoxy]methyl]-7-[2-cyanoethoxy-(diisopropy-lamino)phosphanyl]oxy-N-isopropyl-2-oxa-5-azabicyclo[2.2.1]heptane-5-carboxamide (Present Compound 12)

A compound 5mCd as the present compound 12 (1002.8 mg, yield 75%) was obtained from the compound 5mCc (1168 mg, 1.137 mmol) similarly to the Example 4.

MS(ESI): m/z=961 $(M+H)^+$

Synthesis of ALNA[ipU]-G

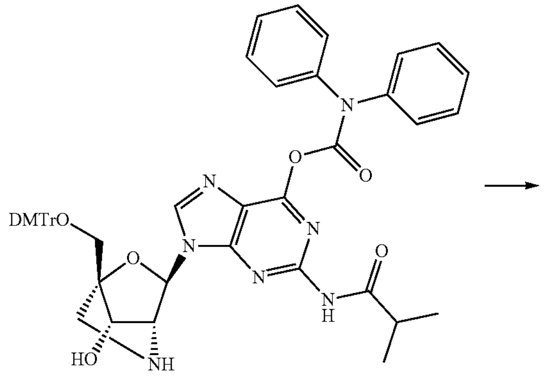

1d

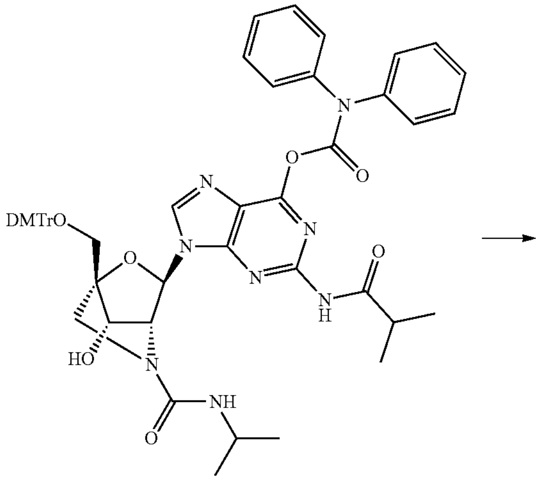

5Gc

-continued

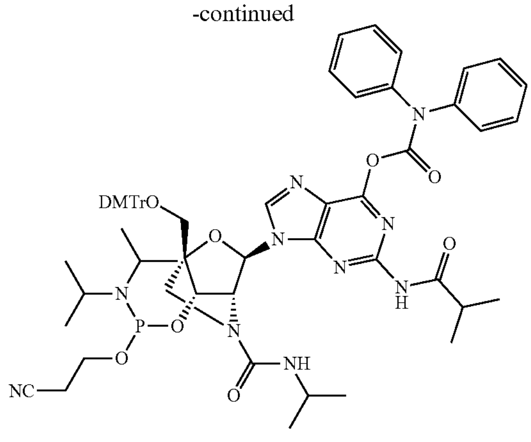

5Gd

Example 36 Synthesis of Compound 5Gc

N-[9-[(1R,3R,4R,7S)-1-[[bis(4-methoxyphenyl)-phenylmethoxy]methyl]-7-hydroxy-5-(isopropylcar-bamoyl)-2-oxa-5-azabicyclo[2.2.1]heptan-3-yl]-2-(2-methylpropanoylamino)purin-6-yl]N,N-diphenylcarbamate To a solution of the compound Id which was synthesized according to the method described in Working examples of WO 2017/047816 A1 (2.42 g, 2.81 mmol) in dichlorometh-ane (28 mL) was added isopropyl isocyanate (0.31 mL, 3.09 mmol) under ice-cooling, and the mixture was stirred at room temperature for three hours. To the reaction solution was added saturated sodium bicarbonate water, and the mixture was stirred, passed through a phase separator, and the solvents were then evaporated. The residue was purified by silica gel chromatography (hexane/ethyl acetate, 50/50 to 20/80) to obtain a compound 5Gc (1.41 g, yield 53%).

MS(ESI): m/z=948 $(M+H)^+$

Example 37 Synthesis of Compound 5Gd

[9-[(1R,3R,4R,7S)-1-[[bis(4-methoxyphenyl)-phe-nylmethoxy]methyl]-7-[2-cyanoethoxy-(diisopropy-lamino)phosphanyl]oxy-5-(isopropylcarbamoyl)-2-oxa-5-azabicyclo[2.2.1]heptan-3-yl]-2-(2-methylpropanoylamino)purin-6-yl]N,N-diphenylcarbamate (Present Compound 13)

A compound 5Gd as the present compound 13 (1.20 g, yield 70%) was obtained from the compound 5Gc (1.41 g, 1.49 mmol) similarly to the Example 4.

MS(ESI): m/z=1148 $(M+H)^+$ $^{31}P$-NMR ($CDCl_3$) δ: 149.42, 149.39

Synthesis of ALNA[ipU]-A

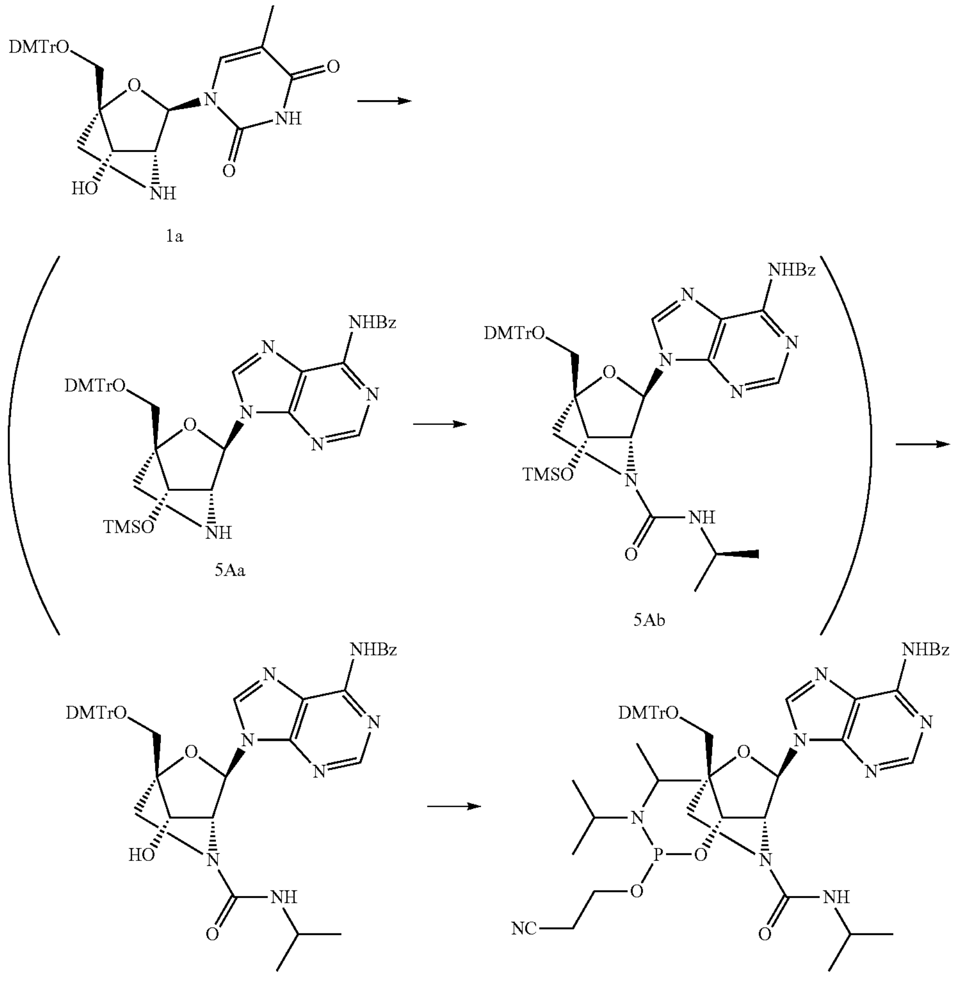

1a

5Aa

5Ab

5Ac

5Ad

Example 38 Synthesis of Compound 5Ac (1R,3R,4R,7S)-3-(6-benzamidepurin-9-yl)-1-[[bis(4-methoxyphenyl)-phenylmethoxy)methyl]-7-hydroxy-N-isopropyl-2-oxa-5-azabicyclo[2.2.1]heptan-3-yl]-5-carboxamide To a suspension of the compound 1a (10.0 g, 17.5 mmol) and N-(9H-purin-6-yl)benzamide (5.0 g, 21.0 mmol) in toluene (175 mL) was added dropwise BSA (30 mL, 122 mmol), and the mixture was warmed to 60° C. and stirred for 10 minutes, and thereto was added TMSOTf (0.34 mL, 1.8 mmol), and the mixture was stirred at 60° C. for 15 minutes. The reaction solution was added to a mixed solution of the IPE (100 mL) and saturated sodium bicarbonate water (100 mL) under ice-cooling while stirring, and the mixture was stirred for 20 minutes, and insoluble materials were filtered off. After the filtered residue was washed with $Et_2O$ (10 mL), the filtrates were separated with a separatory funnel, and washed with saturated brine. The organic layer was dried over sodium sulfate, and insoluble materials were then filtered off, and concentrated under reduced pressure. The residue was solubilized by dichloromethane (162 mL), and thereto was added isopropyl isocyanate (1.8 mL, 18 mmol) at room temperature, and the mixture was stirred for 60 minutes. Thereto were added ethyl acetate (100 mL), saturated sodium bicarbonate water (50 mL) and water (50 mL), and the mixture was separated with a separatory funnel, and the organic layer was washed with saturated brine (50 ml), dried over sodium sulfate, filtered, and the solvents were then evaporated. The residue was added by THF (162 mL) to make a solution, and thereto was added TBAF (1M THF solution, 2.39 mL, 8.11 mmol) under ice-cooling, and the mixture was stirred at room temperature for 24 hours. The mixture was diluted with ethyl acetate (30 mL), and thereto were added aqueous ammonium chloride solution (50 mL) and water (50 mL), and the mixture was stirred at room temperature, The mixture was separated with a separatory funnel, and the organic layer was washed with saturated brine (50 mL), and then dried over sodium sulfate, filtered, and solvents were evaporated. The resulting residue was purified by silica gel chromatography (hexane/ethyl acetate, 50/50 to 0/100) to obtain a compound 5Ac (10.1 g, yields over three steps 77%).

MS(SSI): m/z=770 $(M+H)^+$

Example 39 Synthesis of Compound 5Ad (1R,3R,4R,7S)-3-(6-benzamidepurin-9-yl)-1-([bis(4-methoxyphenyl)-phenylmethoxy]methyl]-7-[2-cyanoethoxy-(diisopropylamino)phosphanyl]oxy-N-isopropyl-2-oxa-5-azabicyclo[2.2.1]heptane-5-carboxamide (Present Compound 14)

A compound 5d as the present compound 14 (4.6 g, yield 51%) was obtained from the compound 5c (7.0 g, 9.09 mmol) similarly to the Example 4.

MS(ESI): m/z=970 $(M+H)^+$ $^{31}$P-NMR ($CDCl_3$) δ: 149.4

Synthesis of ALNA[dmU]-T

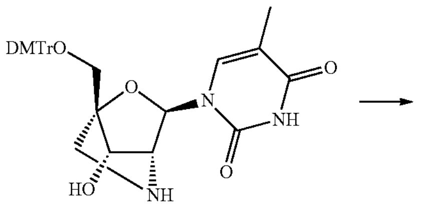

1a

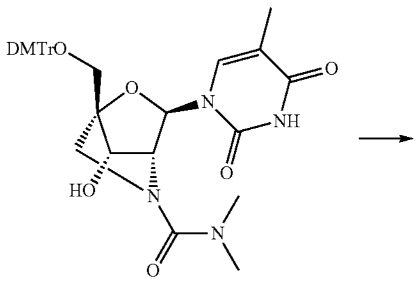

6Tc

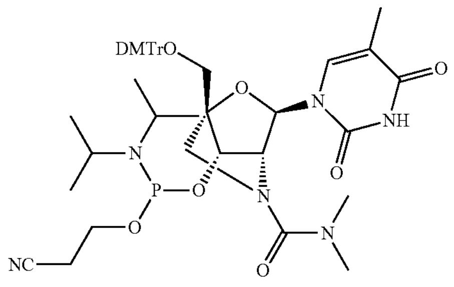

6Td

Example 40 Synthesis of Compound 6Tc (1R,3R,4R,7S)-1-[[bis(4-methoxyphenyl)-phenylmethoxy]methyl]-7-hydroxy-N,N-dimethyl-3-(5-methyl-2,4-dioxo-pyrimidin-1-yl)-2-oxa-5-azabicyclo[2.2.1]heptane-5-carboxamide To a solution of the compound 1a (1512 mg, 2.645 mmol) in tetrahydrofuran (26 mL) was added N,N-diisopropylethylamine (0.483 mL, 2.773 mmol) and the mixture was cooled under ice-cooling, and thereto was added N,N-dimethyl carbamoyl chloride (0.255 mL, 2.77 mmol). The mixture was warmed to room temperature, and thereto was then added N,N-dimethyl formamide (1 mL, 12.9 mmol), and the mixture was stirred for 4 hours. Thereto was added a mixed solution of ethyl acetate (10 mL) and saturated bicarbonate water (20 mL), and the mixture was stirred, and the mixture was separated with a separatory funnel, and the aqueous layer was then extracted with ethyl acetate 10 mL twice, and the organic layers were combined, and the combined organic layers were then washed with saturated brine 10 mL. The organic layer was dried over anhydrous sodium sulfate, filtered, and the solvents were evaporated. The mixture was purified by silica gel chromatography (hexane/ethyl acetate, 50/50 to 0/100) to obtain a compound 6Tc1 (1705 mg, yield quant.).

MS(ESI): m/z=642 $(M-H)^-$

Example 41 Synthesis of Compound 6Td (1R,3R,4R,7S)-1-[[bis(4-methoxyphenyl)-phenylmethoxy]methyl]-7-[2-cyanoethoxy-(diisopropylamino)phosphanyl]oxy-N,N-dimethyl-3-(5-methyl-2,4-dioxopyrimidin-1-yl)-2-oxa-5-azabicyclo[2.2.1]heptane-5-carboxamide (Present Compound 15)

A compound 6Td as the present compound 15 (1565 mg, yield 66%) was obtained from the compound 6Tc (1758 mg, 2.735 mmol) similarly to the Example 4.

MS(ESI): m/z=842 $(M-H)^-$

Synthesis of ALNA[dmU]-mC

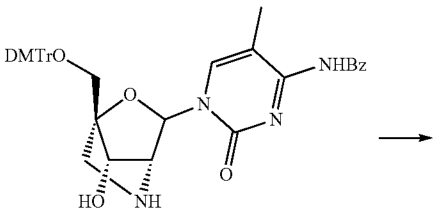

1c

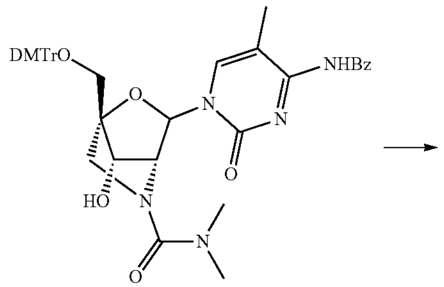

6mCc

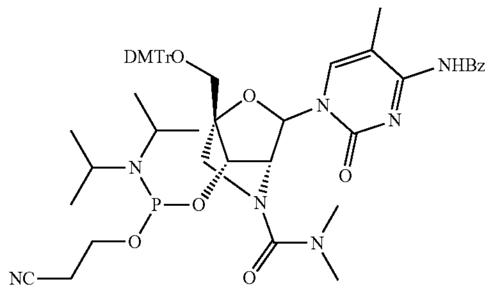

6mCd

Example 42 Synthesis of Compound 6mCc (1R,3R,4R,7S)-3-(4-benzamide-5-methyl-2-oxo-pyrimidin-1-yl)-1-[[bis(4-methoxyphenyl)-phenyl-methoxy]methyl]-7-hydroxy-N,N-dimethyl-2-oxa-5-azabicyclo[2.2.1]heptane-5-carboxamide To a solution of the compound 1c (1300 mg, 1.657 mmol) in tetrahydrofuran (16.6 mL) was added N,N-diisopropyl ethyl amine (0.317 mL, 1.820 mmol), and the mixture was cooled under ice-cooling, and thereto was added N,N-dimethyl carbamoyl chloride (0.168 mL, 1.83 mmol), and the mixture was stirred at room temperature for 10 minutes. After the mixture was heated under reflux for 2 hours, thereto was added a mixed solution of ethyl acetate (10 mL) and saturated sodium bicarbonate water (20 mL) at room temperature, and the mixture was separated with a separatory funnel, the aqueous layer was extracted with ethyl acetate 10 mL twice, and the combined organic layers were washed with saturated brine 10 mL. The organic layer was dried over anhydrous sodium sulfate, and filtered, and the solvents were then evaporated. The mixture was purified by silica gel chromatography (hexane/ethyl acetate, 70/30 to 30/70) to obtain a compound 6mCc (1705 mg, yield 79%).

MS(ESI): m/z=747 $(M+H)^+$

Example 43 Synthesis of Compound 6mCd (1R,3R,4R,7S)-3-(4-benzamide-5-methyl-2-oxo-pyrimidin-1-yl)-1-[[bis(4-methoxyphenyl)-phenyl-methoxy]methyl]-7-[2-cyanoethoxy-(diisopropylamino)phosphanyl]oxy-N,N-dimethyl-2-oxa-5-azabicyclo[2.2.1]heptane-5-carboxamide (Present Compound 16)

A compound 6mCd as the present compound 16 (936.5 mg, yield 76%) was obtained from the compound 6mCc (1019 mg, 1.312 mmol) similarly to the Example 4.

MS(ESI): m/z=947 $(M+H)^+$

Synthesis of ALNA [2Pym]-T

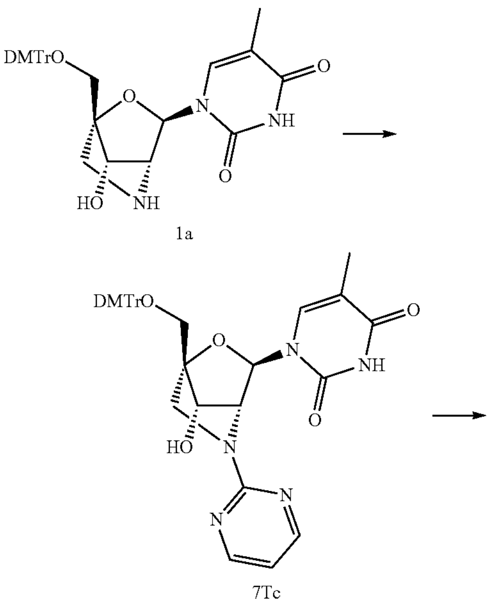

1a

7Tc

-continued

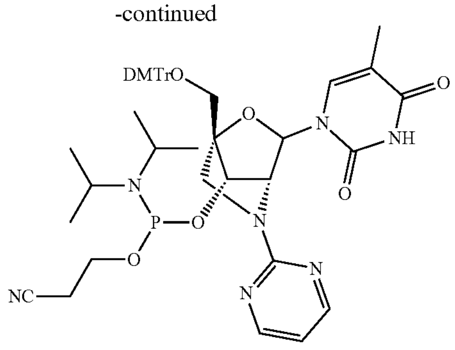

7Td

Example 44 Synthesis of Compound 7Tc

1-[(1R,3R,4R,7S)-1-[[bis(4-methoxyphenyl)-phenyl-methoxy]methyl]-7-hydroxy-5-pyrimidin-2-yl-2-oxa-5-azabicyclo[2.2.1]heptan-3-yl]-5-methylpyrimidin-2,4-dione A mixture of the compound 1a (2.00 g, 3.50 mmol), 2-chloropyrimidine (1.20 g, 10.5 mmol), DIPEA (3.05 mL, 17.5 mmol), and DMSO (17.5 mL) was stirred at 130° C. under nitrogen atmosphere for 6 hours. Ethyl acetate was added to the reaction solution, and the mixture was washed with water and saturated brine. The organic layer was dried over anhydrous magnesium sulfate, and insoluble materials were filtered off, and the filtrates were concentrated under reduced pressure. The residue was purified by column chromatography ($SiO_2$:chloroform/methanol=100/0 to 90/10) to obtain a compound 7Tc (1.74 g, yield 77%).

HRMS(MALDI): calculated value as $C_{36}H_{35}N_5O_7$ $[M+Na]^+$: 672.2429, measured value: 672.2427

Example 45 Synthesis of Compound 7Td

3-[(1R,3R,4R,7S)-1-[[bis(4-methoxyphenyl)-phenyl-methoxy]methyl]-3-(5-methyl2,4-dioxo-pyrimidin-1-yl)-5-pyrimidin-2-yl-2-oxa-5-azabicyclo[2.2.1]heptan-7-yl]oxy-(diisopropylamino)phosphanyl]oxypropanenitrile (Present Compound 17)

To a mixture of the compound 7Tc (1.73 g, 2.66 mmol), dichloromethane (13 mL), and DIPEA (1.39 mL, 7.98 mmol) was added 2-cyanoethyl N,N-diisopropyl chloro phosphoroamidite (1.19 mL, 5.32 mmol) under ice-cooling, and the mixture was stirred at room temperature under nitrogen atmosphere overnight. A saturated aqueous sodium hydrogen carbonate solution was added to the reaction solution, and the mixture was extracted with chloroform. The organic layer was passed through a phase separator, and evaporated under reduced pressure. The residue was purified by column chromatography ($SiO_2$:hexane/ethyl acetate=60/40 to 10/90, Diol:hexane/ethyl acetate=70/30 to 20/80, NH:chloroform/methanol=100/0 to 95/5) to obtain a compound 7Td as the present compound 17 (1.53 g, yield 68%).

HRMS(FAB): calculated value as $C_{45}H_{52}N_7O_8P$ $[M+H]^+$: 850.3693, measured value: 850.3699

$^{31}P$-NMR ($CDCl_3$) δ: 148.72, 148.83

Synthesis of ALNA[2Pym]-mC

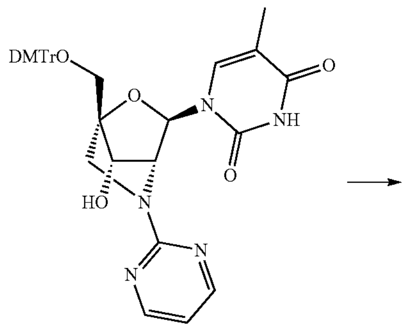

7Ta

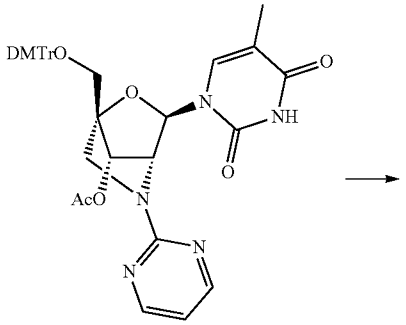

7mCa

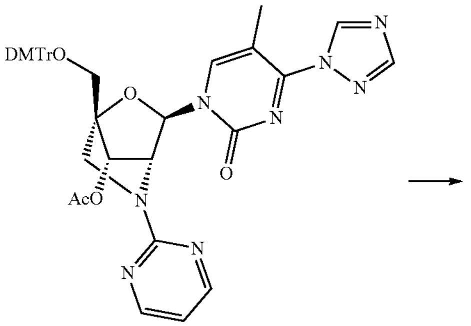

7mCb

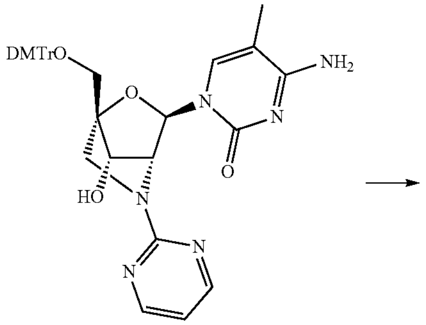

7mCc

-continued

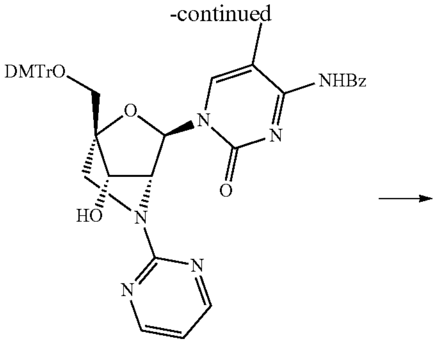

7mCd

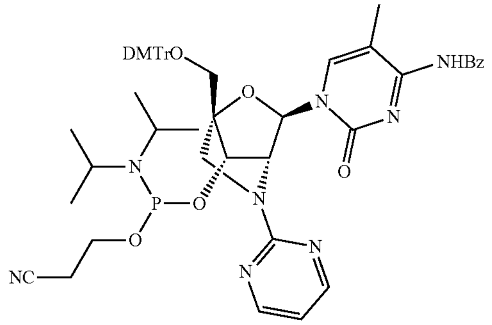

7mCe

Example 46 Synthesis of Compound 7mCa

[(1R,3R,4R,7S)-1-[[bis(4-methoxyphenyl)-phenyl-methoxy]methyl]-3-(5-methyl-2,4-dioxo-pyrimidin-1-yl)-5-pyrimidin-2-yl-2-oxa-5-azabicyclo[2.2.1]heptan-7-yl]acetate To a mixture of the compound 7Ta (3.68 g, 5.67 mmol), DMAP (69.3 mg, 0.567 mmol), and pyridine (28 mL) was added acetic anhydride (0.804 mL, 8.51 mmol), and the mixture was stirred at room temperature overnight. Ethyl acetate was added to the reaction solution, and the mixture was washed with saturated aqueous sodium hydrogen carbonate solution, and saturated brine. The organic layer was dried over anhydrous magnesium sulfate, and insoluble materials are filtered off, and concentrated under reduced pressure. Pyridine was azeotroped with ethyl acetate, and the mixture was triturated with diisopropyl ether to obtain the compound 7mCa (3.49 g, yield 89%).

HRMS(FAB): calculated value as $C_{38}H_{38}N_5O_8$ $[M+H]^+$: 692.2720, measured value: 692.2713

Example 47 Synthesis of Compound 7mCb

[(1R,3R,4R,7S)-1-[[bis(4-methoxyphenyl)-phenyl-methoxy]methyl]-3-[5-methyl-2-oxo-4-(1,2,4-triazol-1-yl)pyrimidin-1-yl]-5-pyrimidin-2-yl-2-oxa-5-azabicyclo[2.2.1]heptan-7-yl]acetate To a mixture of the compound 7mCa (3.46 g, 5.00 mmol), 1,2,4-triazole (3.11 g, 45.0 mmol), DIPEA (8.71 mL, 50.0 mmol) and acetonitrile (50 ml) was added phosphoryl chloride (0.792 mL, 8.50 mmol) under ice-cooling, and the mixture was stirred at room temperature under nitrogen atmosphere overnight. Ethyl acetate was added to the reaction solution, and the mixture was washed with saturated aqueous sodium hydrogen carbonate solution, and saturated brine. The organic layer was dried over anhydrous magnesium sulfate, and insoluble materials were filtered off, and the filtrates were concentrated under reduced pressure. The mixture was triturated with diisopropyl ether to obtain a compound 7mCb1 (3.40 g, yield 92%).

HRMS(FAB): calculated value as $C_{40}H_{38}N_8O_7$ $[M+H]^+$: 743.2942, measured value: 743.2545

Example 48 Synthesis of Compound 7mCc 4-amino-1-[(1R,3R,4R,7S)-1-[[bis(4-methoxyphenyl)-phenylmethoxy]methyl]-7-hydroxy-5-pyrimidin-2-yl-2-oxa-5-azabicyclo[2.2.1]heptan-3-yl]-5-methylpyrimidin-2-one To a mixture of the compound 7mCb (3.40 g, 4.58 mmol) and acetonitrile (46 ml) was added 28% ammonia water (31 mL), and the mixture was stirred at room temperature for 3 days. Water was added to the reaction solution, and the mixture was extracted with chloroform. The organic layer was dried ever anhydrous magnesium sulfate, and insoluble materials were filtered off, and concentrated under reduced pressure. The mixture was triturated with diisopropyl ether and small amounts of ethyl acetate to obtain a compound 7mCc (2.65 g, yield 89%).

HRMS(FAB): calculated value as $C_{36}H_{36}N_6O_6$ $[M+H]^+$: 649.2775, measured value: 649.2766

Example 49 Synthesis of Compound 7mCd

N-[1-[(1R,3R,4R,7S)-1-[[bis(4-methoxyphenyl)-phenylmethoxy]methyl]-7-hydroxy-5-pyrimidin-2-yl-2-oxa-5-azabicyclo[2.2.1]heptan-3-yl]-5-methyl-2-oxo-pyrimidin-4-yl]benzamide To a mixture of the compound 7mCc (2.62 g, 4.04 mmol), and DMF (20 mL) was added benzoic anhydride (959 mg, 4.24 mmol), and the mixture was stirred at room temperature under nitrogen atmosphere overnight. Ethyl acetate was added to the reaction solution, and the mixture was washed with saturated aqueous sodium hydrogen carbonate solution, water, and saturated brine. The organic layer was dried over anhydrous magnesium sulfate, insoluble materials were filtered off, and concentrated under reduced pressure. The residue was purified by column chromatography ($SiO_2$: chloroform/methanol=100/0 to 90/10) to obtain the compound 7mCd (1.42 g, yield 47%).

HRMS(FAB): calculated value as $C_{43}H_{40}N_6O_7$ $[M+H]^+$: 753.3037, measured value: 753.3035

Example 50 Synthesis of Compound 7mCe

N-[1-[(1R,3R,4R,7S)-1-[[bis(4-methoxyphenyl)-phenylmethoxy]methyl]-7-[2-cyanoethoxy-(diisopropylamino)phosphanyl]oxy-5-pyrimidin-2-yl-2-oxa-5-azabicyclo[2.2.1]heptan-3-yl]-5-methyl-2-oxo-pyrimidin-4-yl]benzamide (Present Compound 18)

To a mixture of the compound 7mCd (1.40 g, 1.86 mmol), dichloromethane (S mL), and DIPEA (0.972 mL, 5.58 mmol) was added 2-cyanoethyl N,N-diisopropylchlorophosphoramidite (0.830 mL, 3.72 mmol), and the mixture was stirred at room temperature under nitrogen atmosphere overnight. To reaction solution was added saturated aqueous sodium hydrogen carbonate solution, and the mixture was extracted with chloroform. The organic layer was passed through a phase separator, and the solvents were evaporated. The residue was purified by column chromatography ($SiO_2$: hexane/ethyl acetate=80/20 to 30/70, NH:hexane/ethyl acetate=50/50 to 0/100) to obtain a compound 7mCe as the present compound 18 (1.01 g, yield 57%).

HRMS(FAB): calculated value as $C_{52}H_{57}N_8O_8P$ $[M+Na]^+$: 975.3935, measured value: 975.3931

$^{31}$P-NMR ($CDCl_3$) δ: 149.17, 149.23

Synthesis of ALNA[2Pym]-G

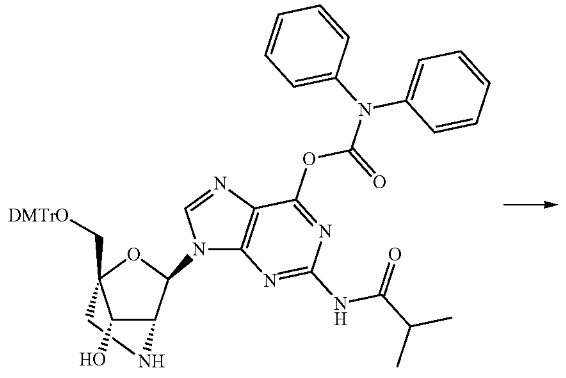

1d

-continued

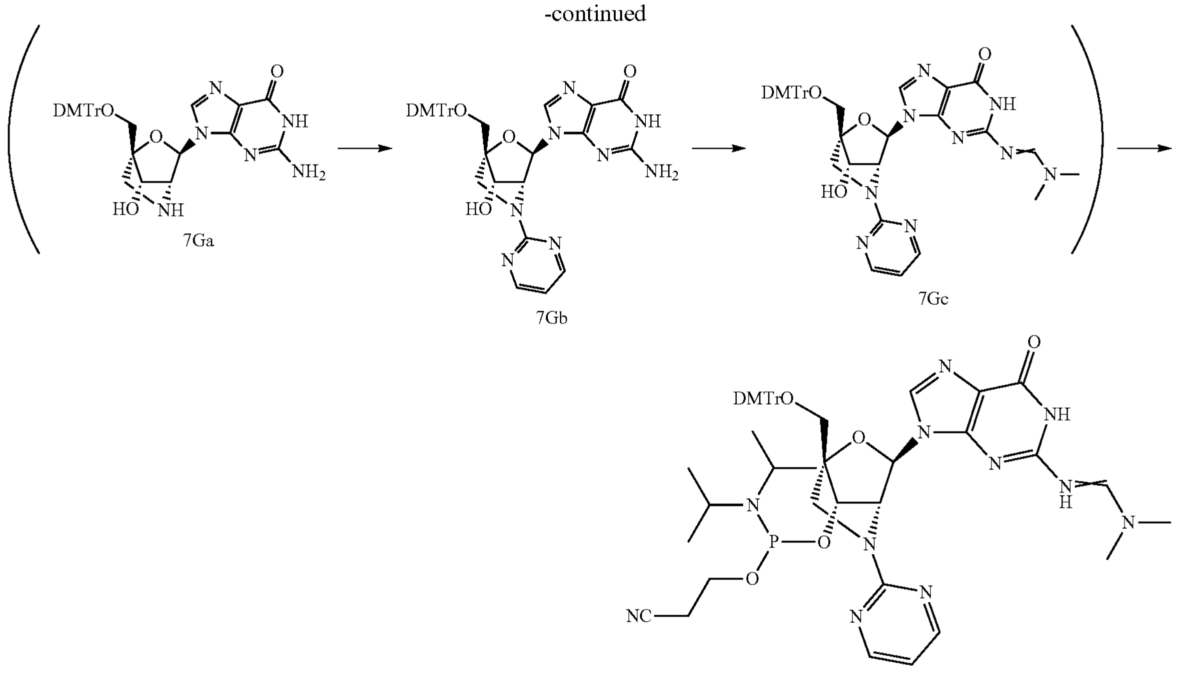

7Ga 7Gb 7Gc 7Gd

Example 51 Synthesis of Compound 7Gc

N'-[9-(1R,3R,4R; 7S)-1-[[bis(4-methoxyphenyl)-phenylmethoxy]methyl]-7-hydroxy-5-pyrimidin-2-yl-2-oxa-5-azabicyclo[2.2.1]heptan-3-yl]-6-oxo-1H-purin-2-yl]-N,N-dimethyl-formamidine To a solution of the compound Id (3.00 g, 3.50 mmol) in methanol (20 mL) and THF (20 mL) was added 28% ammonia water (40 mL). Thereto were added methanol (20 mL) and THF (20 mL), and the mixture was allowed to stand at room temperature for 16 hours. Thereto was a solution of 40% methyl amine in methanol (40 mL), and the mixture was allowed to stand at room temperature for 4 hours. After solvents were evaporated, the residue was azeotroped with toluene, and dried under reduced pressure. The residue was solubilized with DMSO (35 mL), and thereto were added DIPEA (4.8 mL, 28.0 mmol), and 2-fluoropyrimidine (0.66 mL, 10.5 mmol), and the mixture was stirred at 80° C. for 2 hours, and then stirred at 100° C. for additional 2 hours. Thereto was added 2-fluoropyrimidine (0.22 mL, 3.5 mmol) and DIPEA (1.6 mL, 9.3 mmol) additionally, and the mixture was stirred at 100° C. for 2 hours. To the reaction solution was N,N-dimethyl formamide dimethyl acetal (2.3 mL, 17.0 mmol) and the mixture was stirred at room temperature. After 1 hour, thereto were added ethyl acetate (200 mL), saturated sodium bicarbonate water (20 mL) and water (80 mL), and the mixture was separated with a separatory funnel. The organic layer was washed with water (50 mL) three times, and then washed with saturated brine. After the mixture was died over sodium sulfate, insoluble materials were filtered off, and solvents were evaporated under reduced pressure. The aqueous layer at the separation with a separatory funnel was further extracted with chloroform (100 mL) three times, followed by washing with water (100 mL) and saturated brine. The chloroform layer was dried over sodium sulfate, and insoluble materials were then filtered off, and solvents were evaporated from the filtrates under reduced pressure, and the residue was combined with the above extracts, and the mixture was purified by silica gel chromatography (chloroform/methanol, 100/0 to 92/8) to obtain a compound 7Gc (1.66 g, yields over three steps 65%).

MS (ESI): m/z=731 $(M+H)^+$

Example 52 Synthesis of Compound 7Gd

N'-[9-(1R,3R,4R,7S)-1-[[bis(4-methoxyphenyl)-phenylmethoxy]methyl]-7-[2-cyanoethoxy-(diiso-propylamino)phosphanyl]oxy-5-pyrimidin-2-yl-2-oxa-5-azabicyclo[2.2.1]heptan-3-yl]-6-oxo-1H-purin-2-yl]-N,N-dimethyl-6-formamidine (Present Compound 19)

A compound 7Gd as the present compound 19 (1.07 g, yield 53%) was obtained from the compound 7Gc (1.58 g, 2.16 mmol) similarly to the Example 4.

MS(ESI): m/z=931 $(M+H)^+$

Synthesis of ALNA[2Pym]-A

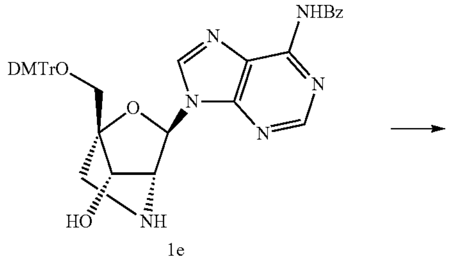

1e

-continued

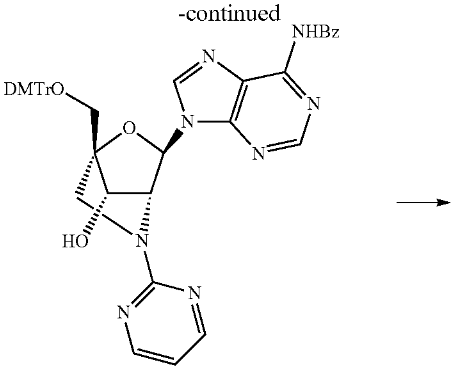

7Aa

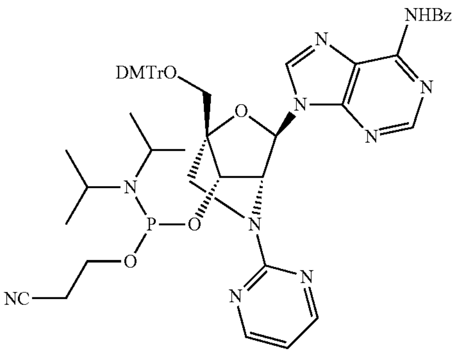

7Ab

Example 53 Synthesis of Compound 7Aa

N-[9-(1R,3R,4R,7S)-1-[[bis(4-methoxyphenyl)-phenylmethoxy]methyl]-7-hydroxy-5-pyrimidin-2-yl-2-oxa-5-azabicyclo[2.2.1]heptan-3-yl]purin-6-yl]benzamide A mixture of the compound 1e which was synthesized according to the method described in WO 2017/047816 A1 (500 mg, 0.730 mmol), 2-fluoropyrimidine (215 mg, 2.19 mmol), DIPEA (0.509 mL, 2.92 mmol) and DMSO (7 mL) was stirred at 130° C. under nitrogen atmosphere for 7 hours. Ethyl acetate was added to the reaction solution, and the mixture was washed with water and saturated brine. The organic layer was dried ever anhydrous sodium sulfate, and insoluble materials were filtered off, and the filtrates were concentrated by evaporating solvents under reduced pressure. The residue was purified by column chromatography ($SiO_2$:hexane/ethyl acetate=50/50 to 0/100) to obtain a compound 7Aa (207 mg, yield 37%).

HRMS(FAB): calculated value as $C_{43}H_{38}N_8O_6$ $[M+Na]^+$: 785.2807, measured value: 785.2807

Example 54 Synthesis of Compound 7Ab

N'-[9-(1R,3R,4R,7S)-1-[[bis(4-methoxyphenyl)-phenylmethoxy]methyl]-7-[2-cyanoethoxy-(diisopropylamino)phosphanyl]oxy-5-pyrimidin-2-yl-2-oxa-5-azabicyclo[2.2.1]heptan-3-yl]purin-6-yl]benzamide (Present Compound 20)

To a mixture of the compound 7Aa (126 mg, 0.165 mmol), dichloromethane (3 mL) and DIPEA (86.2 μL, 0.495 mmol) was added 2-cyanoethyl N,N-diisopropylchlorophosphoramidite (73.6 ML, 0.330 mmol), and the mixture was stirred at room temperature under nitrogen atmosphere for 5 hours. Saturated aqueous sodium hydrogen carbonate solution was added to the reaction solution, and the mixture was extracted with chloroform. The organic layer was passed through a phase separator, and the solvent was evaporated. The residue was purified by column chromatography (NH: hexane/ethyl acetate=50/50 to 0/100, $SiO_2$:hexane/ethyl acetate=50/50 to 0/100, diol: hexane/ethyl acetate=60/40 to 10/90 to obtain a compound 7Ab as the present compound 20 (110 mg, yield 69%).

HRMS(FAB): calculated value as $C_{52}H_{55}N_{10}O_7P$ $[M+Na]^+$: 985.3885, measured value: 985.3878

$^{31}P$-NMR ($CDCl_3$) δ: 149.33, 149.47

Synthesis of ALNA[4Pym]-T

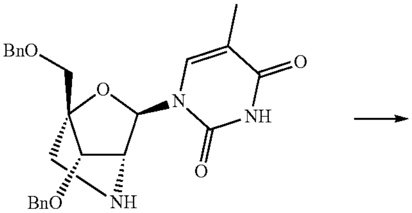

1f

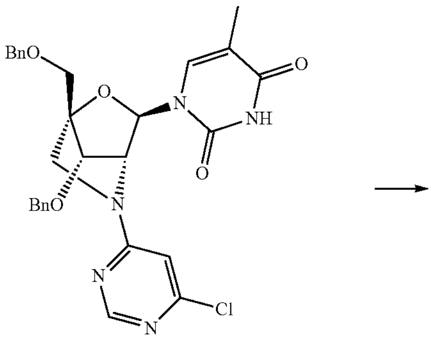

8Ta

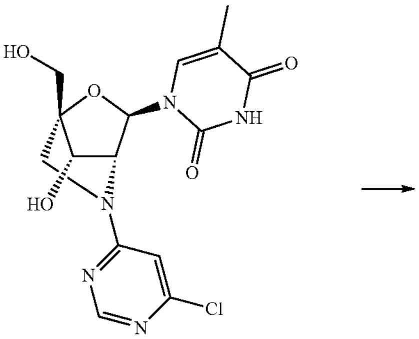

8Tb

-continued

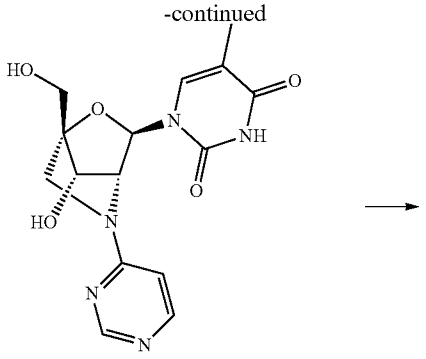

8Tc

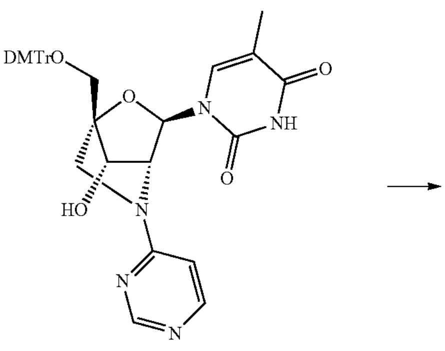

8Td

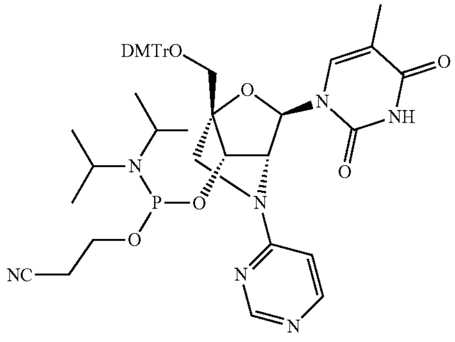

8Te

Example 55 Synthesis of Compound 8Ta

1-[(1R,3R,4R,7S)-7-benzyloxy-1-(benzyloxymethyl)-5-(6-chloropyrimidin-4-yl)-2-oxa-5-azabicyclo[2.2.1]heptan-3-yl]-5-methyl-pyrimidin-2,4-dione A mixture of the compound 1f which was synthesized according to the method described in WO 2017/047816 A1 (1.00 g, 2.22 mmol), 4,6-dichloropyrimidine (398 mg, 2.66 mmol), DIPEA (1.16 mL, 6.66 mmol) and EtOH (20 mL) (2 batches) was stirred at 120° C. under microwave irradiation for 5 hours for each batch. The batches were combined and insoluble materials of the reaction solutions were collected by filtration, washed with EtOH, and dried under reduced pressure to obtain a compound 8Ta (1.54 g, yield 62%).

HRMS(FAB): calculated value as $C_{29}H_{28}ClN_5O_5$ $[M+H]^+$: 562.1857, measured value: 562.1859

Example 56 Synthesis of Compound 8Tb

1-[(1R,3R,4R,7S)-5-(6-chloropyrimidin-4-yl)-7-hydroxyl-(hydroxymethyl)-2-oxa-5-azabicyclo[2.2.1]heptan-3-yl]-5-methyl-pyrimidin-2,4-dione To a mixture of the compound 8Ta (3.49 g, 6.21 mmol) and dichloromethane (62 ml) was added trichloroborane (1.0 mol/L dichloromethane solution, 62 mL, 62.1 mmol) at −78° C. under nitrogen atmosphere, and the mixture was warmed to room temperature gradually overnight. MeOH (62 mL) was added to the reaction solution slowly under ice-cooling, and the mixture was stirred for a while. The reaction solution was concentrated, and the residue was then triturated with ethyl acetate to obtain a compound 8Tb (3.28 g) as a crude product.

HRMS(FAB): calculated value as $C_{15}H_{16}ClN_5O_5$ $[M+H]^+$: 382.0918, measured value: 382.0919

Example 57 Synthesis of Compound 8Tc

1-[(1R,3R,4R,7S)-7-hydroxy-1-(hydroxymethyl)-5-pyrimidin-4-yl-2-oxa-5-azabicyclo[2.2.1]heptan-3-yl]-5-methyl-pyrimidin-2,4-dione To a mixture of the compound 6Tb (3.26 g, 6.21 mmol, crude product) and MeOH (62 mL) was added 20% palladium hydroxide (654 mg, 20 wt %), and the mixture was stirred at room temperature under nitrogen atmosphere overnight. Water (31 mL) was added to the reaction solution to dissolve insoluble materials, and palladium was filtered through Celite. The filtrates were concentrated, and water was azeotroped with toluene. The residue was triturated with MeOH to obtain a compound 8Tc (1.75 g, yields over two steps 81%).

HRMS(FAB): calculated value as $C_{15}H_{17}N_5O_5$ $[M+H]^+$: 348.1302, measured value: 348.1308

Example 58 Synthesis of Compound 8Td

1-[(1R,3R,4R,7S)-1-[[bis(4-methoxyphenyl)-phenyl-methoxy]methyl]-7-hydroxy-5-pyrimidin-4-yl-2-oxa-5-azabicyclo[2.2.1]heptan-3-yl]-5-methylpyrimidin-2,4-dione To a mixture of the compound 8Tc (444 mg, 1.28 mmol) and pyridine (13 ml) was added 4,4'-dimethoxy trityl chloride (520 mg, 1.54 mmol), and the mixture was stirred at room temperature overnight. Saturated aqueous sodium hydrogen carbonate solution was added dropwise to the reaction solution under ice-cooling, and thereto was added ethyl acetate. The organic layer was washed with saturated aqueous sodium hydrogen carbonate solution, water and saturated brine. The organic layer was dried over anhydrous sodium sulfate, and concentrated. Pyridine was azeotroped with ethyl acetate, and the residue was triturated with diisopropyl ether to obtain a compound 8Td (652 mg, yield 78%).

HRMS(FAB): calculated value as $C_{36}H_{35}N_5O_7$ $[M+H]^+$: 650.2609, measured value: 650.2600

Example 59 Synthesis of Compound 8Te

3-[(1R,3R,4R,7S)-1-[[bis(4-methoxyphenyl)-phenyl-methoxy]methyl]-3-(5-methyl-2,4-dioxopyrimidin-1-yl)-5-pyrimidin-4-yl-2-oxa-5-azabicyclo[2.2.1]heptan-7-yl]oxy-(diisopropylamino)phosphanyl]oxypropanenitrile (Present Compound 21)

To a mixture of the compound 8Td (300 mg, 0.462 mmol), dichloromethane (5 mL) and DIPEA (322 μL, 1.85 mmol) was added 2-cyanoethyl N,N-diisopropylchlorophosphoramidite (309 μL, 1.39 mmol) under ice-cooling, and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and solvents were evaporated. The residue was purified by column chromatography ($SiO_2$:chloroform/methanol=100/0 to 90/10, diol:hexane/ethyl acetate=50/50 to 0/100) to obtain a compound 8Te as the present compound 21 (263 mg, yield 67%).

HRMS(FAB): calculated value as $C_{45}H_{52}N_7O_8$ $[M+H]^+$: 850.3693, measured value: 850.3665

$^{31}$P-NMR ($CDCl_3$) δ: 148.93, 149.47

Synthesis of ALNA[4Pym]-mC

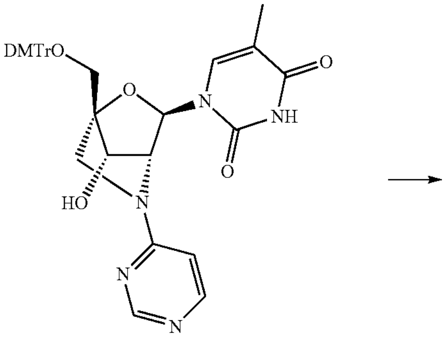

8Td

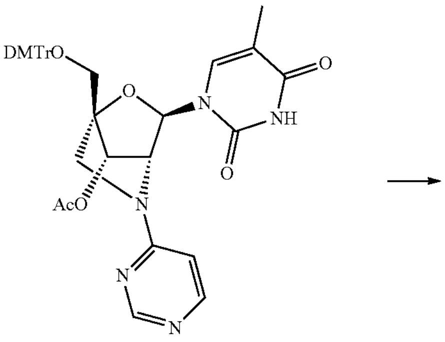

8Ca

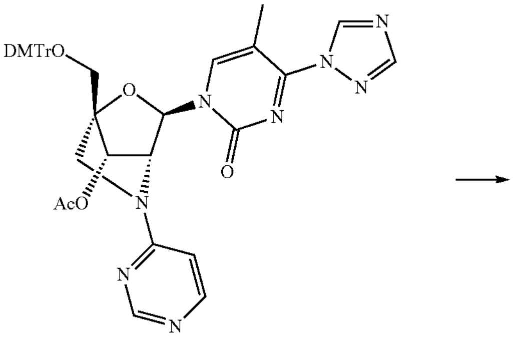

8Cb

-continued

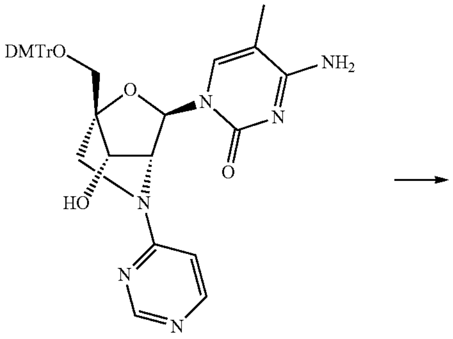

8Cc

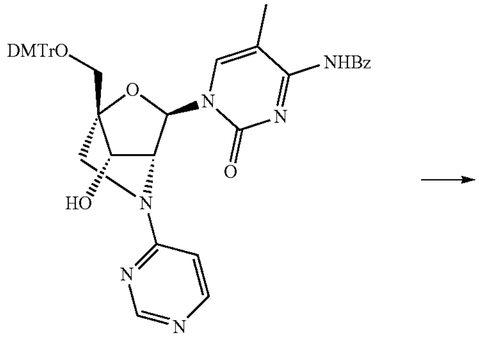

8Cd

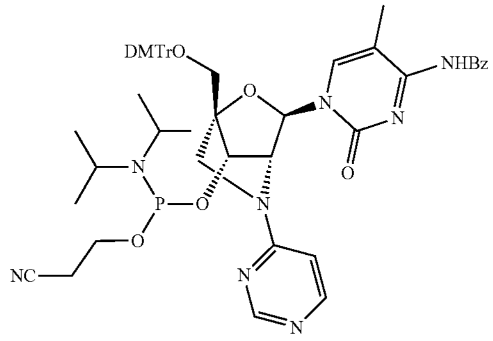

8Ce

Example 60 Synthesis of Compound 8Ca

[(1R,3R,4R,7S)-1-[[bis(4-methoxyphenyl)-phenyl-methoxy]methyl]-3-(5-methyl-2,4-dioxopyrimidin-1-yl)-5-pyrimidin-4-yl-2-oxa-5-azabicyclo[2.2.1]heptan-7-yl]acetate To a mixture of the compound 8Td (234 mg, 0.360 mmol), DMAP (4.4 mg. 0.0360 mmcl) and pyridine (3.6 mL) was added acetic anhydride (51.1 μL, 0.540 mmol), and the mixture was stirred at room temperature overnight. Ethyl acetate was added to the reaction solution, and the mixture was washed with 5% aqueous copper sulfate solution, water and saturated brine. The organic layer was dried over anhydrous magnesium sulfate, and concentrated. The residue was triturated with diisopropyl ether to obtain a compound 8Ca (219 mg, yield 88%).

HRMS(FAB): calculated value as $C_{38}H_{27}N_5O_8$ $[M+H]^+$: 692.2720, measured value: 692.2720

Example 61 Synthesis of Compound 8Cb

[(1R,3R,4R,7S)-1-[[bis(4-methoxyphenyl)-phenyl-methoxy]methyl]-3-[5-methyl-2-oxo-4-(1,2,4-triazol-1-yl)pyrimidin-1-yl)-5-pyrimidin-4-yl-2-oxa-5-azabicyclo[2.2.1]heptan-7-yl]acetate To a mixture of the compound 8Ca (201 mg, 0.291 mmol), 1,2,4-triazole (181 mg, 2.62 mmol), DIPEA (507 μL, 2.91 mmol) and acetonitrile (3 mL) was added phosphoryl chloride (46.1 μL, 0.494 mmol) under ice-cooling, and the mixture was stirred at room temperature under nitrogen atmosphere overnight. Ethyl acetate was added to the reaction solution, and the mixture was washed with saturated aqueous sodium hydrogen carbonate solution, and saturated brine. The organic layer was dried over anhydrous magnesium sulfate, and concentrated. The mixture was triturated with diisopropyl ether to obtain a compound 8Cb (211 mg yield 98%).

HRMS(FAB): calculated value as $C_{40}H_{38}N_8O_7$ $[M+H]^+$: 743.2942, measured value: 743.2939

Example 62 Synthesis of Compound 8Cc 4-amino-1-[(1R,3R,4R,7S)-1-[[bis(4-methoxyphenyl)-phenylmethoxy]methyl]-7-hydroxy-5-pyrimidin-4-yl-2-oxa-5-azabicyclo[2.2.1]heptan-3-yl]-5-methylpyrimidin-2-one To a mixture of the compound 8Cb (613 mg, 0.825 mmol) and acetonitrile (8.3 mL) was added 28% ammonia water (5.5 mL), and the mixture was stirred at room temperature overnight. Acetonitrile of the reaction solution was concentrated. Insoluble materials were collected by filtration, and washed with water. The crude product was triturated with ethyl acetate to obtain a compound 8Cc (380 mg, yield 71%).

HRMS(FAB): calculated value as $C_{36}H_{36}N_6O_6$ $[M+H]^+$: 649.2775, measured value: 649.2773

Example 63 Synthesis of Compound 8Cd

N-[1-[(1R,3R,4R,7S)-1-[[bis(4-methoxyphenyl)-phenylmethoxy]methyl]-7-hydroxy5-pyrimidin-4-yl-2-oxa-5-azabicyclo[2.2.1]heptan-3-yl]-5-methyl-2-oxo-pyrimidin-4-yl]benzamide To a mixture of the compound 8Cc (378 mg, 0.583 mmcl) and pyridine (6 mL) was added benzoic anhydride (198 mg, 0.875 mmol), and the mixture was stirred at room temperature for 3 days. The reaction solution was concentrated, and the residue was purified by column chromatography (diol: 0.5% triethylaminechloroform/methanol=100/0 to 90/10, $SiO_2$:0.55% triethylaminechloroform/methanol=100/0 to 90/10) to obtain a compound 8Cd (247 mg, yield 56%).

HRMS(FAB): calculated value as $C_{43}H_{40}N_6O_7$ $[M+H]^+$: 753.3037, measured value: 753.3040

Example 64 Synthesis of Compound 8Ce

N-[1-[(1R,3R,4R,7S)-1-[[bis(4-methoxyphenyl)-phenylmethoxy]methyl]-7-[2-cyanoethoxy-(diisopropylamino)phosphanyl]oxy-5-pyrimidin-4-yl-2-oxa-5-azabicyclo[2.2.1]heptan-3-yl]-5-methyl-2-oxo-pyrimidin-4-yl]benzamide (Present Compound 22)

To a mixture of the compound 8Cd (135 mg, 0.179 mmol), dichloromethane (2 mL), and DIPEA (125 μL, 0.716 mmol) was added 2-cyanoethyl N,N-diisopropylchlorophosphoramidite (120 μL, 0.537 mmol), and the mixture was stirred at room temperature under nitrogen atmosphere for 2 days. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$: hexane/ethyl acetate=50/50 to 0/100, diol:hexane/ethyl acetate=60/40 to 10/90, NH:hexane/ethyl acetate=50/50 to 0/100) to obtain a compound 8Ce as the present compound 22 (61.9 mg, yield 36%).

HRMS(FAB): calculated value as $C_{52}H_{57}N_8O_8$ $[M+H]^+$: 953.4115, measured value: 953.4109

$^{31}$P-NMR ($CDCl_3$) δ: 149.65, 150.24

Synthesis of ALNA[4-$CF_{3-2}$Pym]-T

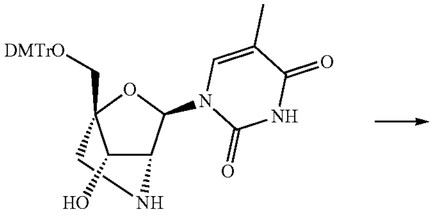

1a

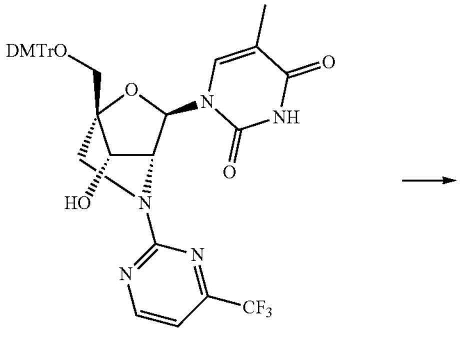

9Ta

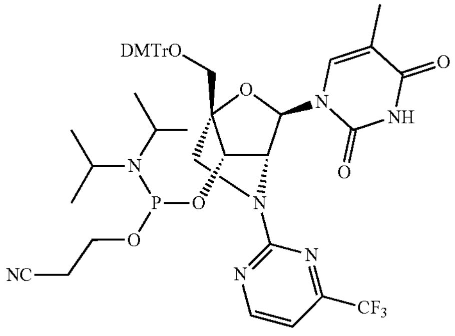

9Tb

Example 65 Synthesis of Compound 9Ta

1-[(1R,3R,4R,7S)-1-[[bis(4-methoxyphenyl)-phenylmethoxy]methyl]-7-hydroxy5-[4-(trifluoromethyl)pyrimidin-2-yl]-2-oxa-5-azabicyclo[2.2.1]heptan-3-yl]-5-methylpyrimidin-2,4-dione A mixture of the compound 1a (500 mg, 0.875 mmol), 2-chloro-4-(trifluoromethyl)pyrimidine (239 mg, 1.31 mmol), DIPEA (457 μL, 2.63 mmol) and EtOH (4.4 ml) was stirred at 120° C. under microwave irradiation for 30 minutes. 2-Chloro-4-(trifluoromethyl)pyrimidine (239 mg, 1.31 mmol) and DIPEA (457 μL, 2.63 mmol) were added additionally to the reaction solution, and the mixture was stirred at 120° C. under microwave irradiation for 1 hour. The reaction solution was concentrated, and thereto was added ethyl acetate, and the mixture was washed with water and saturated brine. The organic layer was dried over anhydrous magnesium sulfate, and concentrated. The residue was purified by column chromatography ($SiO_2$:chloroform/methanol=100/0 to 95/5) to obtain a compound 9Ta (545 mg, yield 87%).

HRMS(FAB): calculated value as $C_{37}H_{34}F_3N_5O_7$ $[M+H]^+$: 718.2489, measured value: 713.2491

Example 66 Synthesis of Compound 9Tb

3-[[(1R,3R,4R,7S)-1-[[bis(4-methoxyphenyl)-phenylmethoxy]methyl]-3-(5-methyl-2,4-dioxopyrimidin-1-yl)-5-(4-(trifluoromethyl)pyrimidin-2-yl]-2-oxa-5-azabicyclo[2.2.1]heptan-7-yl]oxy-(diisopropylamino)phosphanyl]oxopropanenitrile (Present Compound 23)

To a mixture of the compound 9Ta (527 mg, 0.734 mmol), dichlor erne thane (7 mL) and DIPEA (384 pw 2.20 mmol) was added 2-cyanoethyl N,N-diisopropylchlorophosphoramidite (328 μL, 1.47 mmol) under ice-cooling, and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$:hexane/ethyl acetate=80/20 to 30/70, diol:hexane/ethyl acetate=70/30 to 20/80) to obtain a compound 9Tb as the present compound 23 (530 mg, yield 79%). HRMS(FAB): calculated value as $C_{46}H_{51}F_3N_7O_8P$ $[M+H]^+$: 918.3567, measured value: 918.3568

$^{31}$P-NMR ($CDCl_3$) δ: 149.04, 149.12, 149.20, 149.47

Synthesis of ALNA[4-$CF_3$-2Pym]-mC

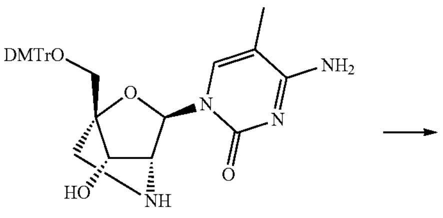

4Ca

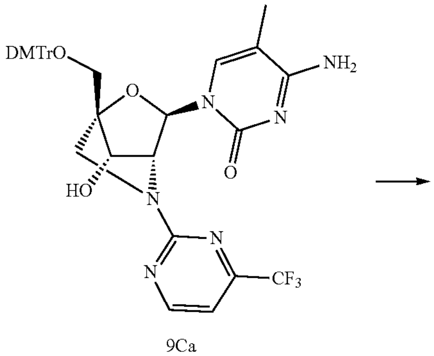

9Ca

-continued

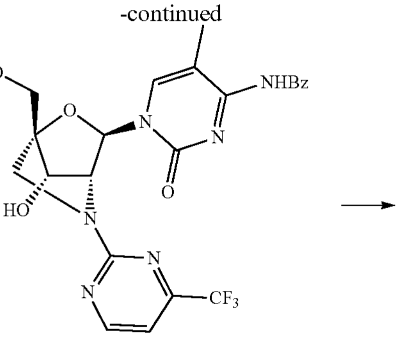

9Cb

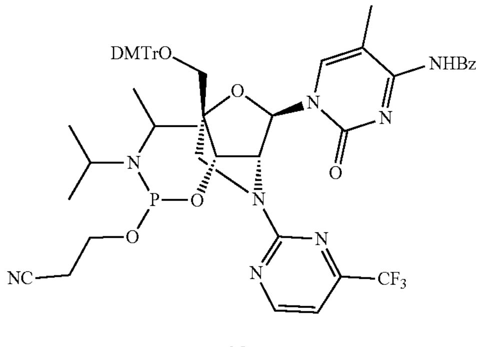

9Cc

Example 67 Synthesis of Compound 9Ca 4-amino-1-[(1R,3R,4R,7S)-1-[[bis(4-methoxyphenyl)-phenylmethoxy]methyl]-7-hydroxy-5-[4-(trifluoromethyl)pyrimidin-2-yl]-2-oxa-5-azabicyclo[2.2.1]heptan-3-yl]-5-methylpyrimidin-2-one A mixture of the compound 4Ca (500 mg, 0.876 mmol), 2-chloro-4-(trifluoromethyl)pyrimidine (317 μL, 2.63 mmol), DIPEA (610 μL, 3.50 mmol), and EtOH (4.4 mL) was stirred at 150° C. under microwave irradiation for 1 hour. The reaction solution was concentrated, and thereto was added ethyl acetate, and the mixture was washed with water and saturated brine. The organic layer was dried over anhydrous magnesium sulfate, and concentrated. The residue was purified by column chromatography ($SiO_2$:chloroform/methanol=100/0 to 90/10) to obtain a compound 9Ca (186 mg, yield 30%).

HRMS(FAB): calculated value as $C_{37}H_{35}F_3N_6O_6$ $[M+H]^+$: 717.2648, measured value: 717.2651

Example 68 Synthesis of Compound 9Cb

N-[1-[[1R,3R,4R,7S)-1-[[bis(4-methoxyphenyl)-phenylmethoxy]methyl]-7-hydroxy5-[4-(trifluoromethyl)pyrimidin-2-yl]-2-oxa-5-azabicyclo[2.2.1]heptan-3-yl]-5-methyl-2-oxo-pyrimidin-4-yl]benzamide To a mixture of the compound 9Ca (395 mg, 0.551 mmol), and DMF (5.5 mL) was added benzoic anhydride (131 mg, 0.579 mmol), and the mixture was stirred at room temperature overnight. Ethyl acetate was added to the reaction solution, and the mixture was washed with saturated aqueous sodium hydrogen carbonate solution, water, and saturated brine. The organic layer was dried over anhydrous magnesium sulfate, and concentrated. The residue was purified by column chromatography ($SiO_2$:chloroform/methanol=100/0 to 95/15) to obtain a compound 9Cb (335 mg, yield 74%).

HRMS(FAB): calculated value as $C_{44}H_{39}F_3N_6O_7$ $[M+H]^+$: 821.2911, measured value: 821.2932

Example 69 Synthesis of Compound 9Cc

N-[1-[(1R,3R,4R,7S)-1-[[bis(4-methoxyphenyl)-phenylmethoxy]methyl]-7-[2-cyanoethoxy-(diisopropylamino)phosphanyl]oxy-5-[4-(trifluoromethyl)pyrimidin-2-yl]-2-oxa-5-azabicyclo[2.2.1]heptan-3-yl]-5-methyl-2-oxo-pyrimidin-4-yl]benzamide (Present Compound 24)

To a mixture of the compound 9Cb (316 mg, 0.385 mmol), dichloromethane (4 mL), and DIPEA (201 μL, 1.16 mmol) was added 2-cyanoethyl N,N-diisopropylchlorophosphoramidite (172 μL, 0.770 mmol), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and solvents were evaporated. The residue was purified by column chromatography ($SiO_2$: hexane/ethyl acetate=100/0 to 50/50, Diol:hexane/ethyl acetate=100/0 to 50/50) to obtain a compound 9Cc as the present compound 24 (227 mg, yield 58%).

HRMS(FAB): calculated value as $C_{53}H_{56}F_3N_8O_8P$ $[M+H]^+$: 1021.3989, measured value: 1021.3993

$^{31}P$-NMR ($CDCl_3$) δ: 149.15, 149.28, 149.36, 149.60

Synthesis of ALNA[5-Cl-2Pym]-T

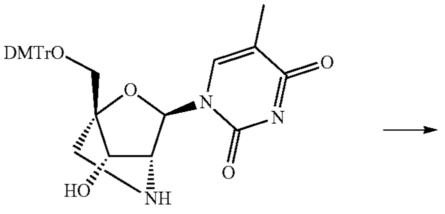

1a

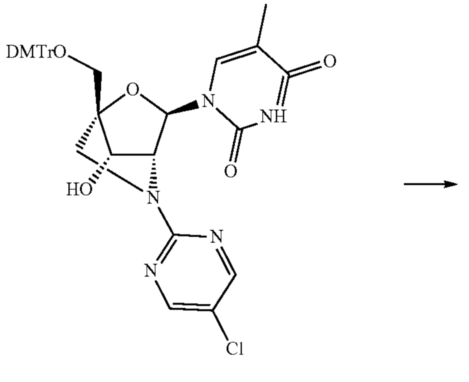

10Ta

-continued

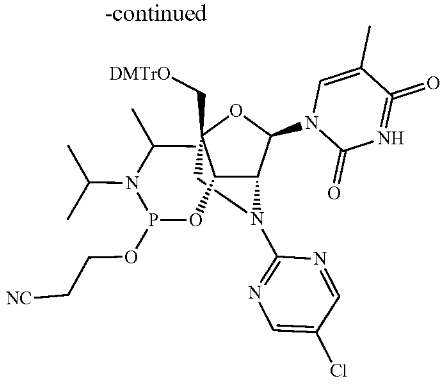

10Tb

Example 70 Synthesis of Compound 10Ta

1-[(1R,3R,4R,7S)-1-[[bis(4-methoxyphenyl)-phenylmethoxy]methyl]-5-(5-chloropyrimidin-2-yl]-7-hydroxy-2-oxa-5-azabicyclo[2.2.1]heptan-3-yl]-5-methylpyrimidin-2,4-dione A mixture of the compound 1a (500 mg, 0.875 mmol, 2.5-dichloropyrimidine (196 mg, 1.31 mmol), DIPEA (457 μL, 2.63 mmol) and EtOH (4.4 mL) was stirred at 150° C. under microwave irradiation for 1 hour. Insoluble materials of the reaction solutions were solubilized with chloroform, and the mixture was concentrated. The residue was purified by column chromatography ($SiO_2$:chloroform/methanol=100/0 to 90/10) to obtain a compound 10Ta (263 mg, yield 44%).

HRMS(FAB): calculated value as $C_{36}H_{34}ClN_5O_7$ $[M+H]^+$: 684.2225, measured value: 684.2226

Example 71 Synthesis of Compound 10Tb

3-[[(1R,3R,4R,7S)-1-[[bis(4-methoxyphenyl)-phenylmethoxy]methyl]-5-(5-chloropyrimidin-2-yl)-3-(5-methyl-2,4-dioxopyrimidin-1-yl)-2-oxa-5-azabicyclo[2.2.1]heptan-7-yl]oxy-(diisopropylamino)phosphanyl]oxypropanenitrile (Present Compound 25)

To a mixture of the compound 10Ta (240 mg, 0.351 mmol), dichloromethane (3.5 mL) and DIPEA (183 μL, 1.05 mmol) was added 2-cyanoethyl N,N-diisopropylchlorophosphoramidite (157 μL, 0.702 mmol) under ice-cooling, and the mixture was stirred at room temperature under nitrogen atmosphere for 4 days. Saturated aqueous sodium hydrogen carbonate solution was added to the reaction solutions, and the mixture was extracted with chloroform. The organic layer was passed through a phase separator, and the solvents were evaporated. The residue was purified by column chromatography ($SiO_2$:hexane/ethyl acetate=70/30 to 20/80, diol: hexane/ethyl acetate=70/30 to 20/80) to obtain a compound 10Tb (201 mg, yield 65%).

HRMS(FAB): calculated value as $C_{45}H_{51}ClN_7O_6P$ $[M+H]^+$: 884.3304, measured value: 884.3303

$^{31}P$-NMR ($CDCl_3$) δ: 149.12

Synthesis of ALNA[5-Cl-2Pym]-mC

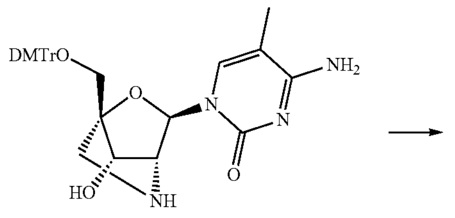

4Ca

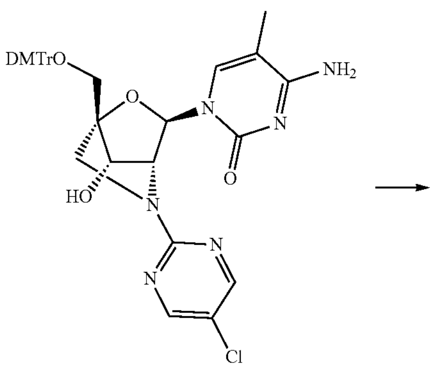

10mCa

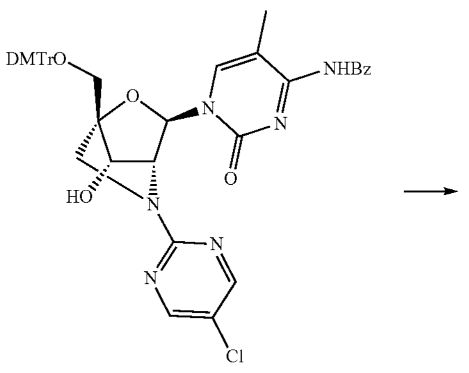

10mCb

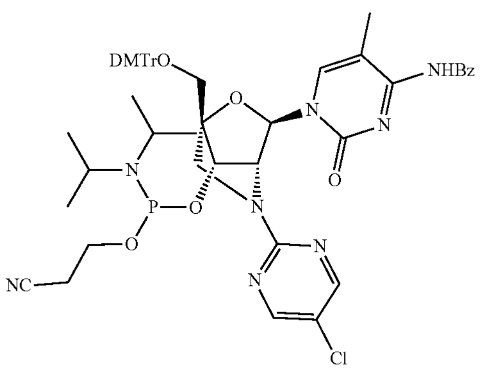

10mCc

Example 72 Synthesis of Compound 10mCa 4-amino-1-[(1R,3R,4R,7S)-1-[[bis(4-methoxyphenyl)-phenylmethoxy]methyl]-5-(5-chloropyrimidin2-yl)-7-hydroxy-2-oxa-5-azabicyclo[2.2.1]heptan-3-yl]-5-methylpyrimidin-2-one A mixture of the compound 4Ca (500 mg, 0.876 mmol), 2,5-dichloropyrimidine (391 mg, 2.63 mmol), and DIPEA (610 μL, 3.50 mmol) and EtOH (4.4 mL) (2 batches) was stirred at 150° C. under microwave irradiation for 1 hour for each batch. The reaction solution was concentrated, and water was added thereto, and the mixture was extracted with chloroform. The combined organic layer was passed through a phase separator, and the solvents were evaporated. The residue was purified by column chromatography ($SiO_2$: chloroform/methanol=100/0 to 90/10) to obtain a compound 10mCa (381 mg, yield 32%).

HRMS(FAB): calculated value as $C_{36}H_{35}ClN_6O_6$ $[M+H]^+$: 683.2385, measured value: 683.2389

Example 73 Synthesis of Compound 10mCb

N-[1-[(1R,3R,4R,7S)-1-L[bis(4-methoxyphenyl)-phenylmethoxy]methyl]-5-(5-chloropyrimidin-2-yl)-7-hydroxy-2-oxa-5-azabicyclo[2.2.1]heptan-3-yl]-5-methyl-2-oxo-pyrimidin-4-yl]benzamide To a mixture of the compound 10mCa (375 mg, 0.549 mmol) and DMF (5.5 mL) was added benzoic anhydride (130 mg, 0.576 mmol), and the mixture was stirred at room temperature overnight. To the reaction solution was added benzoic anhydride (24.8 mg, 0.110 mmol) additionally, and the mixture was further stirred at room temperature overnight. Ethyl acetate was added to the reaction solution, and the mixture was washed with saturated aqueous sodium hydrogen carbonate solution, water, and saturated brine. The organic layer was dried over anhydrous magnesium sulfate, and concentrated. The residue was purified by column chromatography ($SiO_2$:chloroform/methanol=100/0 to 95/5) to obtain a compound 10mCb (422 mg, yield 98%).

HRMS(MALDI): calculated value as $C_{43}H_{39}ClN_6O_7$ $[M+Na]^+$: 809.2461, measured value: 809.2463

Example 74 Synthesis of Compound 10mCc

N-[1-[(1R,3R,4R,7S)-1-[[bis(4-methoxyphenyl)-phenylmethoxy]methyl]-5-(5-chloropyrimidin-2-yl)-7-[2-cyanoethoxy-(diisopropylamino)phosphanyl]oxy-2-oxa-5-azabicyclo[2.2.1]heptan-3-yl]-5-methylpyrimidin-4-yl]benzamide (Present Compound 26)

To a mixture of the compound 10mCb (409 mg, 0.520 mmol), dichloromethane (5 ml), and DIPEA (272 μL, 1.56 mmol) was added 2-cyanoethyl N,N-diisopropylchlorophosphoramidite (232 μL, 1.04 mmol), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$: hexane/ethyl acetate=100/0 to 50/50, diol: hexane/ethyl acetate=100/0 to 50/50) to obtain a compound 10mCc as the present compound 26 (264 mg, yield 51%).

HRMS(MALDI): calculated value as $C_{52}H_{56}ClN_8O_8P$ $[M+Na]^+$: 1009.3540, measured value: 1009.3521

$^{31}P$-NMR ($CDCl_3$) δ: 149.28

Synthesis of ALNA[6-$NMe_2$-4Pym]-T

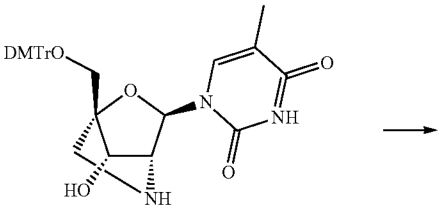

1a

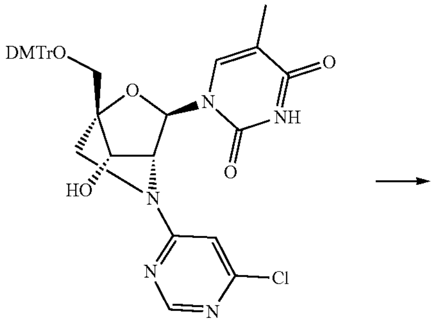

11Ta

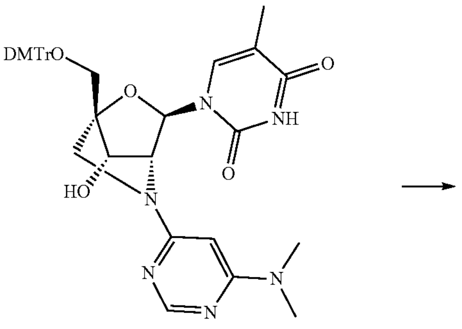

11Tb

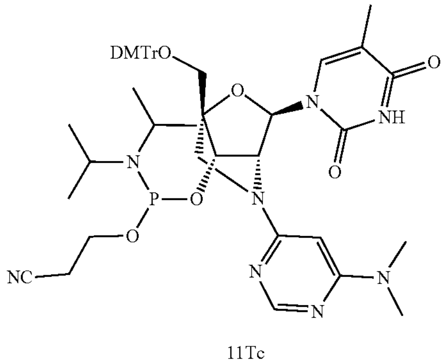

11Tc

Example 75 Synthesis of Compound 11Ta

1-[(1R,3R,4R,7S)-1-[[bis(4-methoxyphenyl)-phenyl-methoxy]methyl]-5-(6-chloropyrimidin-4-yl)-7-hydroxy-2-oxa-5-azabicyclo[2.2.1]heptan-3-yl]-5-methylpyrimidin-2,4-dione A mixture of the compound 1a (1.00 g, 1.75 mmol), 4,6-dichloropyrimidine (391 mg, 2.63 mmol), DIPEA (914 μL, 5.25 mmol) and EtOH (18 mL) was stirred at 120° C. under microwave irradiation for 1 hour. The reaction was concentrated, the residue was purified by column chromatography ($SiO_2$:chloroform/methanol=100/0 to 95/5) to obtain a compound 11Ta (1.00 g, yield 84%).

HRMS(FAB): calculated value as $C_{36}H_{34}ClN_5O_7$ $[M+H]^+$: 684.2225, measured value: 684.2214

Example 76 Synthesis of Compound 11Tb

1-[(1R,3R,4R,7S)-1-[[bis(4-methoxyphenyl)-phenyl-methoxy]methyl]-5-[6-(dimethylamino)pyrimidin-4-yl]-7-hydroxy-2-oxa-5-azabicyclo[2.2.1]heptan-3-yl]-5-methylpyrimidin-2,4-dione To a mixture of the compound 11Ta (500 mg, 0.731 mmol), DIPEA (637 μL, 3.66 mmol), and EtOH (5 mL) was added dimethyl amine hydrochloride (179 mg, 2.19 mmol), and the mixture was stirred at 150° C. under microwave irradiation for 30 minutes. Insoluble materials were collected by filtration, and dried under reduced pressure to obtain a compound 11Tb (386 mg, yield 76%).

HRMS(FAB): calculated value as $C_{38}H_{40}N_6O_7$ $[M+H]^+$: 693.3037, measured value: 693.3030

Example 77 Synthesis of Compound 11Tc

3-[[(1R,3R,4R,7S)-1-[[bis(4-methoxyphenyl)-phenylmethoxy]methyl]-5-[6-(dimethylamino)pyrimidin-4-yl]-3-(5-methyl-2,4-dioxopyrimidin-1-yl)-2-oxa-5-azabicyclo[2.2.1]heptan-7-yl]oxy-(diisopropylamine)phosphanyl]oxypropanenitrile (Present Compound 27)

To a mixture of the compound 11Tb (335 mg, 0.484 mmol), dichloromethane (5 mL), DIPEA (253 μL, 1.45 mmol) was added 2-cyanoethyl N,N-diisopropylchlorophosphoramidite (216 μL, 0.968 mmol) under ice-cooling, and the mixture was stirred at room temperature under nitrogen atmosphere overnight. DMF (2 mL) was added to the reaction solution, and the mixture was stirred at room temperature under nitrogen atmosphere overnight. To the reaction solution were added DIPEA (253 μL, 1.45 mmol), and 2-cyanoethyl N,N-diisopropylchlorophosphoramidite (216 μL, 0.968 mmol) additionally, and the mixture was stirred at room temperature under nitrogen atmosphere for 2 days. Ethyl acetate was added to the reaction solution, and the mixture was washed with saturated aqueous sodium hydrogen carbonate solution, and saturated brine. The organic layer was dried ever anhydrous magnesium sulfate, and concentrated. The residue was purified by column chromatography ($SiO_2$:chloroform/methanol=100/0 to 90/10, Diol:hexane/ethyl acetate=50/50 to 0/100) to obtain a compound 11Tc as the present compound 27 (189 mg, yield 44%).

HRMS(FAB): calculated value as $C_{47}H_{57}N_8O_6P$ $[M+H]^+$: 893.4115, measured value: 893.4115

$^{31}P$-NMR ($CDCl_3$) δ: 149.83, 148.99

Synthesis of ALNA[6-$NMe_2$-4Pym]-mC

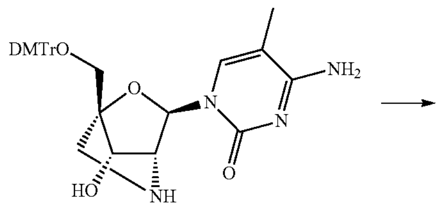

4mCa

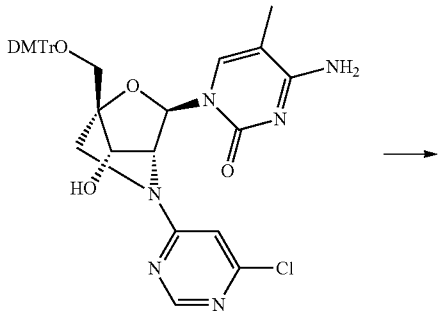

11mCa

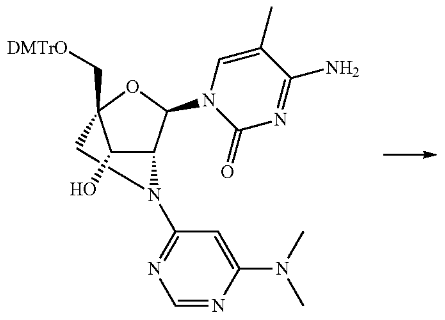

11mCb

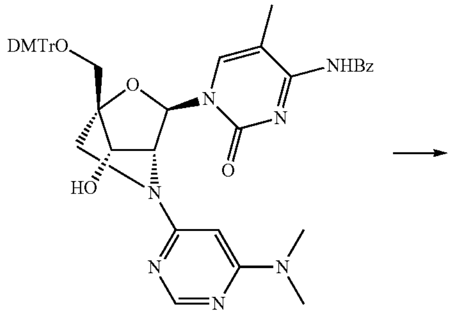

11mCc

-continued

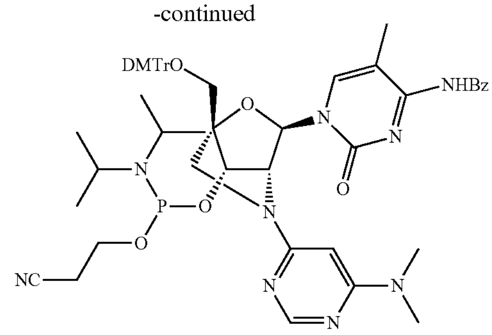

11mCd

Example 78 Synthesis of Compound 11mCa 4-amino-1-[(1R,3R,4R,7S)-1-[[bis(4-methoxyphenyl)-phenylmethoxy]methyl]-5-(6-chloropyrimidin-4-yl)-7-hydroxy-2-oxa-5-azabicyclo[2.2.1]heptan-3-yl]-5-methylpyrimidin-2-one A mixture of the compound 4mCa (2.00 g, 3.50 mmol), 4,6-dichloropyrimidine (626 mg, 4.20 mmol), DIPEA (1.83 mL, 10.5 mmol) and EtOH (17.5 ml) was stirred at 100° C. for 4 hours. The reaction solution was concentrated, and water was added thereto, and the mixture was extracted with chloroform. The organic layer was passed through a phase separator, and the solvents were evaporated. The residue was purified by column chromatography ($SiO_2$:chloroform/methanol=100/0 to 90/10) to obtain a compound 11mCa (1.34 g, yield 56%).

HRMS(FAB): calculated value as $C_{36}H_{35}ClN_6O_6$ $[M+H]^+$: 683.2385, measured value: 683.2384

Example 79 Synthesis of Compound 11mCb 4-amino-1-[(1R,3R,4R,7S)-1-[[bis(4-methoxyphenyl)-phenylmethoxy]methyl]-5-[8-(dimethylamino)pyrimidin-4-yl]-7-hydroxy-2-oxa-5-azabicyclo[2.2.1]heptan-3-yl]-5-methylpyrimidin-2-one A mixture of the compound 11mCa (1.12 g, 1.64 mmol), dimethylamine (50% aqueous solution, 863 μL, 8.20 mmol), and EtOH (1 mL) was stirred at 150° C. under microwave irradiation for 30 minutes. The reaction was concentrated, and the residue was purified by column chromatography (NH:chloroform/methanol=100/0 to 95/5) to obtain a compound 11mCb (1.09 g, yield 56%).

HRMS(MALDI): calculated value as $C_{38}H_{41}N_7O_6$ $[M+Na]^+$: 714.3011, measured value: 714.3003

Example 80 Synthesis of Compound 11mCc

N-[1-[(1R,3R,4R,7S)-1-[[bis(4-methoxyphenyl)-phenyl-methoxy]methyl]-5-[6-(dimethylamino)pyrimidin-4-yl]-7-hydroxy-2-oxa-5-azabicyclo[2.2.1]heptan-3-yl]-5-methyl-2-oxo-pyrimidin-4-yl]benzamide To a mixture of the compound 11mCb (1.08 g, 1.56 mmol) and DMF (8 mL) was added benzoic anhydride (389 mg, 1.72 mmol), and the mixture was stirred at room temperature overnight. Ethyl acetate was added to the reaction solutions, and the mixture was washed with saturated aqueous sodium hydrogen carbonate solution, water, and saturated brine. The organic layer was dried over anhydrous magnesium sulfate, and concentrated. The residue was purified by column chromatography ($SiO_2$:chloroform/methanol=100/0 to 95/5) to obtain a compound 11Cc (1.02 g, yield 82%).

HRMS(MALDI): calculated value as $C_{45}H_{45}N_7O_7$ $[M+H]^+$: 796.3453, measured value: 796.3466

Example 81 Synthesis of Compound 11mCd

N-[1-[(1R,3R,4R,7S)-1-[[bis(4-methoxyphenyl)-phenyl-methoxy]methyl]-1-[2-cyanoethoxy(diisopropylamino)phosphanyl]oxy-5-[(6-dimethylamino)pyrimidin-4-yl]-2-oxa-5-azabicyclo[2.2.1]heptan-3-yl]-5-methyl-2-oxo-pyrimidin-4-yl]benzamide (Present Compound 28)

To a mixture of the compound 11mCc (972 mg, 1.22 mmol), dichloromethane (12 mL) and DIPEA (637 μL, 3.66 mmcl) was added 2-cyanoethyl N,N-diisopropylchlorophosphoramidite (545 μL, 2.44 mmol), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$: hexane/ethyl acetate=50/50 to 0/100, NH:hexane/ethyl acetate=50/50 to 0/100) to obtain a compound 11mCd as the present compound 28 (788 mg, yield 65%).

HRMS(MALDI): calculated value as $C_{54}H_{62}N_9O_9P$ $[M+H]^+$: 996.4532, measured value: 996.4513

$^{31}P$-NMR ($CDCl_3$) δ: 149.06, 149.17

Synthesis of ALNA[2-$NMe_2$-4Pym]-T

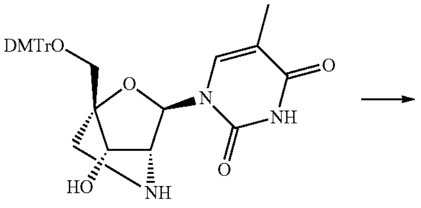

1a

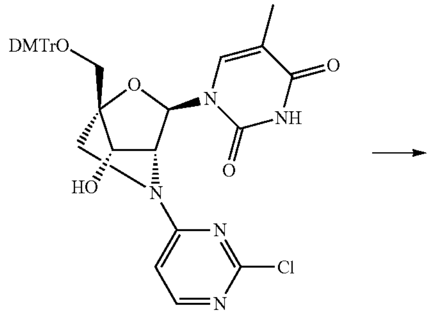

12Ta

-continued

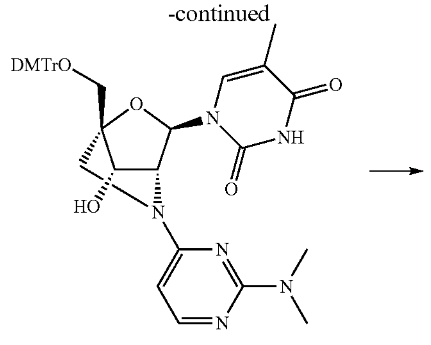

12Tb

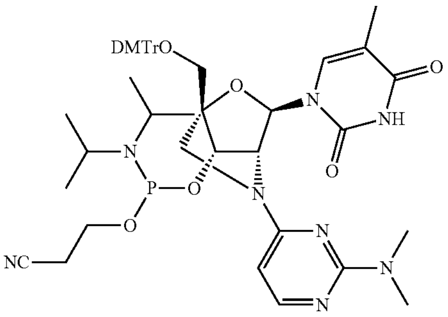

12Tc

Example 82 Synthesis of Compound 12Ta

1-[(1R,3R,4R,7S)-1-[[bis(4-methoxyphenyl)-phenyl-methoxy]methyl]-5-(2-chloropyrimidin-4-yl)-7-hydroxy-2-oxa-5-azabicyclo[2.2.1]heptan-3-yl]-5-methylpyrimidin-2,4-dione A mixture of the compound 1a (2.00 g, 3.50 mmol), 2,4-dichloropyrimidine (782 mg, 5.25 mmol), DIPEA (1.83 mL, 10.5 mmol), and EtOH (17.5 mL) was stirred at 100° C. for 4.5 hours. The reaction solutions were concentrated, and water was added thereto, and the mixture was extracted with chloroform. The organic layer was passed through a phase separator, and the solvents were evaporated. The residue was purified by column chromatography ($SiO_2$:chloroform/methanol=100/0 to 55/5) to obtain a compound 12Ta (1.86 g, yield 78%).

HRMS(FAB): calculated value as $C_{36}H_{34}ClN_5O_7$ $[M+H]^+$: 684.2225, measured value: 684.2223

Example 83 Synthesis of Compound 12Tb

1-[(1R,3R,4R,7S)-1-[[bis(4-methoxyphenyl)-phenyl-methoxy]methyl]-5-[2-(dimethylamino)pyrimidin-4-yl]-7-hydroxy-2-oxa-5-azabicyclo[2.2.1]heptan-3-yl]-5-methylpyrimidin-2,4-dione To a mixture of the compound 12Ta (500 mg, 0.731 mmol), DIPEA (637 μL, 3.66 mmol), and EtOH (5 mL) was added dimethyl amine hydrochloride (179 mg, 2.19 mmol), and the mixture was stirred at 150° C. under microwave irradiation for 30 minutes. The reaction solutions were concentrated, and the residue was purified by column chromatography ($SiO_2$:chloroform/methanol=100/0 to 95/5). The mixture was triturated with diisopropyl ether to obtain a compound 12Tb (648 mg) as a crude product.

HRMS(FAB): calculated value as $C_{38}H_{40}N_6O_7$ [M+H]$^+$: 693.3037, measured value: 693.3041

Example 64 Synthesis of Compound 12Tc

3-[[(1R,3R,4R,7S)-1-[[bis(4-methoxyphenyl)-phenyl-methoxy]methyl]-5-[2-(dimethylamino)pyrimidin-4-yl]-3-(5-methyl-2,4-dioxopyrimidin-1-yl)-2-oxa-5-azabicyclo[2.2.1]heptan-7-yl]oxy-(diisopropylamino)oxypropanenitrile (Present Compound 29)

To a mixture of the compound 12Tb (638 mg, 0.731 mmol, crude product), dichloromethane (7 mL) and DIPEA (382 μL, 2.19 mmol) was added 2-cyanoethyl N,N-diisopropylchlorophosphoramidite (326 μL, 1.46 mmol), and the mixture was stirred at room temperature under nitrogen atmosphere for 5 days. Saturated aqueous sodium hydrogen carbonate solution was added to the reaction solutions, and the mixture was extracted with chloroform. The organic layer was passed through a phase separator, and the solvents were evaporated. The residue was purified by column chromatography ($SiO_2$:chloroform/methanol=100/0 to 90/10, diol:hexane/ethyl acetate=50/50 to 0/100) to obtain a compound 12Tc as the present compound 29 (304 mg, yields 47% over two steps).

HRMS(FAB): calculated value as $C_{47}H_{57}N_8O_8P$ [M+H]$^+$: 893.4115, measured value: 893.4128

$^{31}$P-NMR ($CDCl_3$) δ: 148.91, 149.33

Synthesis of ALNA[2-NMe$_2$-4Pym]-mC

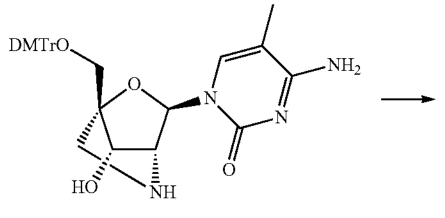

4mCa

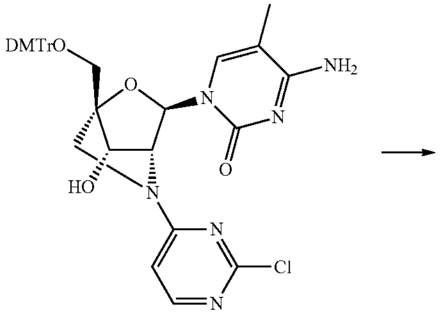

12mCa

-continued

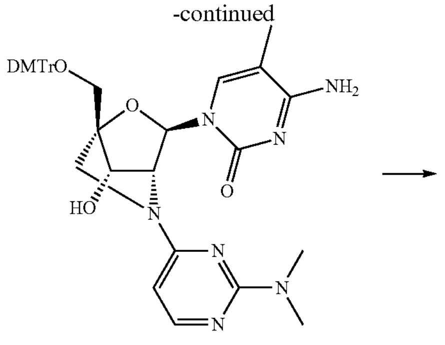

12mCb

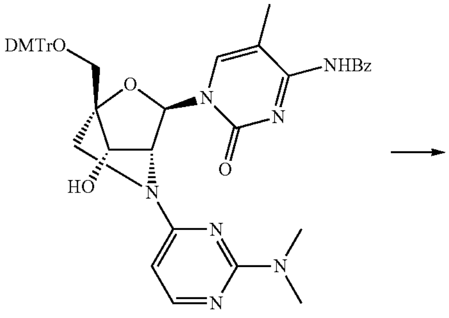

12mCc

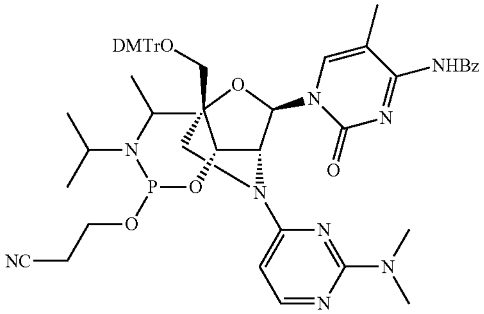

12mCd

Example 85 Synthesis of Compound 12mCa 4-amino-1-[(1R,3R,4R,7S)-1-[[bis(4-methoxyphenyl)-phenyl-methoxy]methyl]-5-(2-chloropyrimidin-4-yl)-7-hydroxy-2-oxa-5-azabicyclo[2.2.1]heptan-3-yl]-5-methylpyrimidin-2-one A mixture of the compound 4mCa (2.00 g, 2.50 mmol), 2.4-dichloropyrimidine (627 mg, 4.20 mmol), DIPEA (1.83 mL, 10.5 mmol) and EtOH (17.5 mL) was stirred at 100° C. for 3 hours. The reaction solution was concentrated, and water was added thereto, and the mixture was extracted with chloroform. The organic layer was dried ever anhydrous magnesium sulfate, and concentrated. The residue was purified cy column chromatography ($SiO_2$:chloroform/methanol=100/0 to 90/10) to obtain a compound 12mCa (1.28 g, yield 54%).

HRMS (MALDI): calculated value as $C_{36}H_{35}ClN_6O_6$ [M+Na]$^+$: 705.2199, measured value: 705.2199

Example 86 Synthesis of Compound 12mCb 4-amino-1-[(1R,3R,4R,7S)-1-[[bis(4-methoxyphenyl)-phenyl-methoxy]methyl]-5-[2-(dimethylamino)pyrimidin-4-yl]-7-hydroxy-2-oxa-5-azabicyclo[2.2.1]heptan-3-yl]-5-methylpyrimidin-2-one A mixture of the compound 12mCa (941 mg, 1.38 mmol), dimethyl amine (aqueous 50% solution, 725 μL, 6.90 mmol), and EtOH (14 mL, 0.1 M) was stirred at 150° C. under microwave irradiation for 30 minutes. The reaction solution was concentrated, and the residue was purified by column chromatography (NH: chloroform/methanol=100/0 to 90/10) to obtain a compound 12mCb (784 mg, yield 82%).

HRMS (MALDI): calculated value as $C_{38}H_{41}N_7O_6$ $[M+H]^+$: 692.3191, measured value: 692.3167

Example 87 Synthesis of Compound 12mCc

N-[1-[(1R,3R,4R,7S)-1-[[bis(4-methoxyphenyl)-phenyl-methoxy]methyl]-5-[2-(dimethylamino)pyrimidin-4-yl]-7-hydroxy-2-oxa-5-azabicyclo[2.2.1]heptan-3-yl]-5-methyl-2-oxo-pyrimidin-4-yl]benzamide To a mixture of the compound 12mCb (754 mg, 1.09 mmol) and DMF (5.5 mL) was added benzoic anhydride (271 mg, 1.20 mmol), and the mixture was stirred at room temperature overnight. Ethyl acetate was added to the reaction solution, and the mixture was washed with saturated aqueous sodium hydrogen carbonate solution, water, and saturated brine. The organic layer was dried over anhydrous magnesium sulfate, and concentrated. The residue was purified by column chromatography ($SiO_2$:chloroform/methanol=100/0 to 95/5) to obtain a compound 12mCc (731 mg, yield 84%).

HRMS(MALDI): calculated value as $C_{45}H_{45}N_7O_7$ $[M+H]^+$: 796.3453, measured value: 796.3440

Example 88 Synthesis of Compound 12mCd

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-[2-(dimethylamino)pyrimidin-4-yl]-7-hydroxy-2-oxa-5-azabicyclo[2.2.1]heptan-3-yl]-5-methyl-2-oxo-pyrimidin-4-yl]benzamide (Present Compound 30)

To a mixture of the compound 12mCc (709 mg, 0.891 mmol), dichloromethane (9 mL) and DIPEA (466 μL, 2.67 mmol) was added 2-cyanoethyl N,N-diisopropylchlorophosphoramidite (397 μL, 1.78 mmol), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$: hexane/ethyl acetate=50/50 to 0/100, NH:hexane/ethyl acetate=50/50 to 0/100) to obtain a compound 12mCd as the present compound (482 mg, yield 54%).

HRMS (MALDI): calculated value as $C_{54}H_{62}N_9O_9P$ $[M+H]^+$: 996.4532, measured value: 996.4526

$^{31}P$-NMR ($CDCl_3$) δ: 149.19, 149.46, 149.65

Synthesis of ALNA[Prz]-T

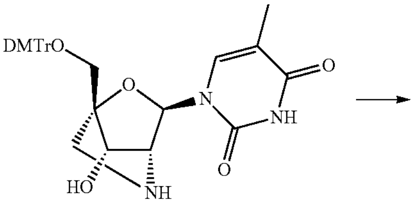

1a

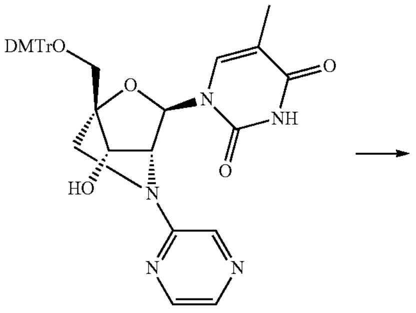

13Ta

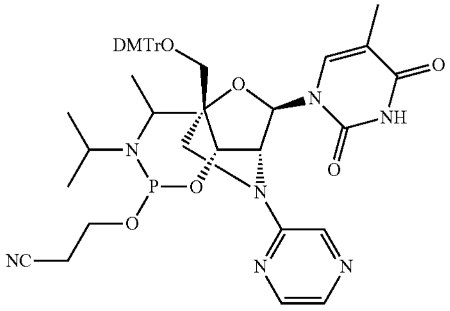

13Tb

Example 89 Synthesis of Compound 13Ta

[1-[(1R,3R,4R,7S)-1-[[bis(4-methoxyphenyl)-phenyl-methoxy]methyl]-7-hydroxy-5-pyrazine-2-yl-2-oxa-5-azabicyclo[2.2.1]heptan-3-yl]-5-methyl-pyrimidin-2,4-dione A mixture of the compound 1a (500 mg, 0.875 mmol), 2-fluoropyrazine (201 μL, 2.63 mmol), DIPEA (610 μL, 3.50 mmol; and DMSO (8.8 mL) was stirred at 140° C. for 1.5 hours and at 150° C. for 4.5 hours under nitrogen atmosphere. Ethyl acetate was added to the reaction solutions, and the mixture was washed with water, and saturated brine. The organic layer was dried over anhydrous magnesium sulfate, and concentrated. The residue was purified by column chromatography $SiO_2$:chloroform/methanol 100/0 to 90/10, $SiO_2$:hexane/ethyl acetate=50/50 to 0/100) to obtain a compound 13Ta (227 mg, yield 40%).

HRMS(MALDI): calculated value as $C_{36}H_{35}N_5O_7$ $[M+Na]^+$: 672.2429, measured value: 672.2409

Example 90 Synthesis of Compound 13Tb

3-[1-[(1R,3R,4R,7S)-1-[[bis(4-methoxyphenyl)-phenyl-methoxy]methyl]-3-(5-methyl-2,4-dioxopy-rimidin-1-yl)-5-pyrazine-2-yl-2-oxa-5-azabicyclo[2.2.1]heptan-7-yl]oxy-(diisopropylamino)phosphanyl]oxypropanenitrile (Present Compound 31)

To a mixture of the compound 13Ta (214 mg, 0.329 mmol), dichloromethane (6.6 mL), and DIPEA (172 μL, 0.987 mmol, was added 2-cyanoethyl N,N-diisopropylchlorophosphoramidite (147 μL, 0.658 mmol), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$:hexane/ethyl acetate e=50/50 to C/100, NH:ethyl acetate/methanol=100/0 to 90/10) to obtain a compound 13Tb as the present compound 31 (204 mg, yield 73%).

HRMS(MALDI): calculated value as $C_{45}H_{52}N_7O_6P$ $[M+Na]^+$: 872.3507, measured value: 672.3507

$^{31}$P-NMR ($CDCl_3$) δ: 149.12, 149.31

Synthesis of ALNA[Prz]-mC

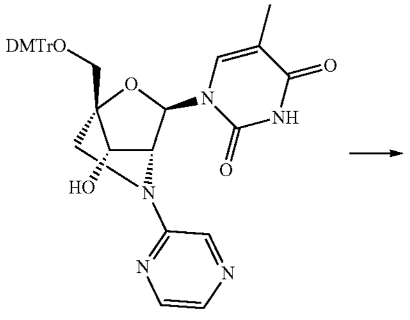

13Ta

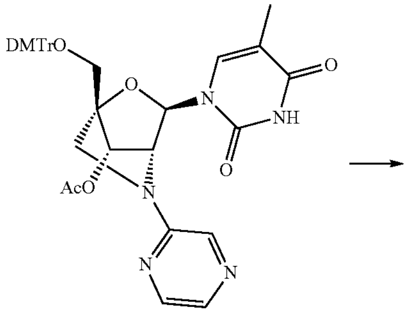

13mCb

-continued

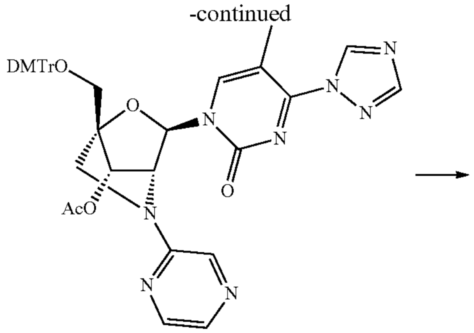

13mCc

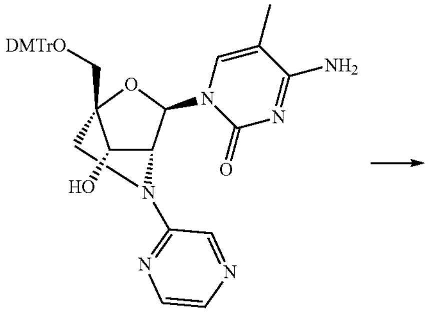

13mCd

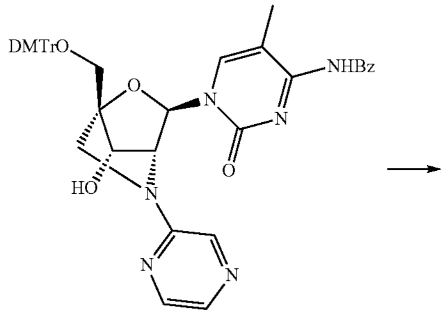

13mCe

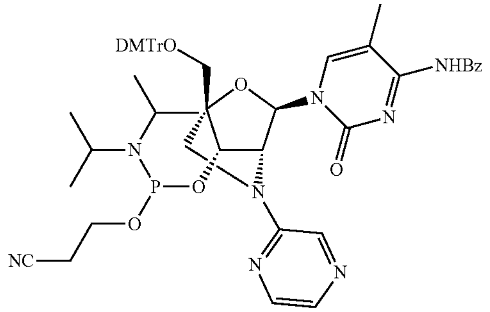

13mCf

Example 91 Synthesis of Compound 13mCb

[(1R,3R,4R,7S)-1-[[bis(4-methoxyphenyl)-phenyl-methoxy]methyl]-3-(5-methyl-2,4-dioxopyrimidin-1-yl)-5-pyrazin-2-yl-2-oxa-5-azabicyclo[2.2.1]heptan-7-yl]acetate To a mixture of the compound 13Ta (746 mg, 1.15 mmol), DMAP (14.0 mg, 0.115 mmol) and pyridine (5.3 mL) was added acetic anhydride (163 μL, 1.73 mmol), and the mixture was stirred at room temperature overnight. Ethyl acetate was added to the reaction solution, and the mixture was washed with saturated aqueous sodium hydrogen carbonate solution, and saturated brine. The organic layer was dried over anhydrous magnesium sulfate, and concentrated. Pyridine was azeotroped with ethyl acetate, and the residue was triturated with diisopropyl ether to obtain a compound 13MCb (712 mg, yield 50%).

HRMS(MALDI): calculated value as $C_{38}H_{37}N_5O_8$ $[M+Na]^+$: 714.2534, measured value: 714.2520

Example 52 Synthesis of Compound 13mCc

[(1R,3R,4R,7S)-1-[[bis(4-methoxyphenyl)-phenyl-methoxy]methyl]-3-(5-methyl-2-oxo-(4-1,2,4-triazol-1-yl)pyrimidin-1-yl]-5-pyrazin-2-yl-2-oxa-5-azabicyclo[2.2.1]heptan-7-yl]acetate To a mixture of the compound 13mCb (692 mg, 1.00 mmol), 1,2,4-triazole (622 mg, 5.00 mmol), DIPEA (1.74 mL, 10.0 mmol; and acetonitrile (10 mL) was added phosphoryl chloride (158 μL, 1.70 mmol) under ice-cooling, and the mixture was stirred at room temperature under nitrogen atmosphere for 1 hour. Ethyl acetate was added to the reaction solution, and the mixture was washed with saturated aqueous sodium hydrogen carbonate solution, and saturated brine. The organic layer was dried over anhydrous magnesium sulfate, and concentrated to obtain a compound 13mCc (753 mg) as a crude product.

HRMS(MALDI): calculated value as $C_{40}H_{38}N_8O_7$ $[M+Na]^+$: 765.2756, measured value: 765.2750

Example 93 Synthesis of Compound 13mCd 4-amino-1-[(1R,3R,4R,7S)-1-[[bis(4-methoxyphenyl)-phenyl-methoxy]methyl]-7-hydroxy-5-pyrazin-2-yl-2-oxa-5-azabicyclo[2.2.1]heptan-3-yl]-5-methylpyrimidin-2-one To a mixture of the compound 13mCc (744 g, 1.00 mmol, crude product) and acetonitrile (10 mL) was added 28% ammonia water (6.7 mL), and the mixture was stirred at room temperature overnight. Water was added to the reaction solution, and the mixture was extracted with chloroform. The organic layer was dried over anhydrous magnesium sulfate, and concentrated to obtain a compound 13mCd (638 mg, yields over two steps 98%).

HRMS(MALDI): calculated value as $C_{36}H_{36}N_6O_6$ $[M+Na]^+$: 671.2589, measured value: 671.2591

Example 54 Synthesis of Compound 13mCe

N-[1-[(1R,3R,4R,7S)-1-[[bis(4-methoxyphenyl)-phenyl-methoxy]methyl]-7-hydroxy-5-pyrazin-2-yl-2-oxa-5-azabicyclo[2.2.1]heptan-3-yl]-5-methyl-2-oxo-pyrimidin-4-yl]benzamide To a mixture of the compound 13mCd (625 mg, 0.963 mmol) and DMF (4.8 mL) was added benzoyl anhydride (327 mg, 1.44 mmcl), and the mixture was stirred at room temperature overnight. Ethyl acetate was added to the reaction solution, and the mixture was washed with saturated aqueous sodium hydrogen carbonate solution, water, and saturated brine. The organic layer was dried ever anhydrous magnesium sulfate, and concentrated. The residue was purified by column chromatography ($SiO_2$:chloroform/methanol=100/0 to 95/5) to obtain a compound 13mCe (245 mg, yield 34%).

HRMS (MALDI): calculated value as $C_{43}H_{40}N_6O_7$ $[M+Na]^+$: 775.2851, measured value: 775.2845

Example 95 Synthesis of Compound 13mCf

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrazin-2-yl-2-oxa-5-azabicyclo[2.2.1]heptan-3-yl]-5-methyl-2-oxo-pyrimidin-4-yl]benzamide (Present Compound 32)

To a mixture of the compound 13mCe (565 mg, 0.751 mmol), dichloromethane (7.5 ml) and DIPEA (392 μL, 2.25 mmol) was added 2-cyanoethyl N,N-diisopropylchlorophosphoramidite (335 μL, 1.50 mmcl), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$: hexane/ethyl acetate=70/30 to 20/80, NH:hexane/ethyl acetate=50/50 to 0/100) to obtain a compound 13mCf as the present compound 32 (369 mg, yield 52%).

HRMS(MALDI): calculated value as $C_{50}H_{44}N_8O_8$ $[M+Na]^+$: 975.3929, measured value: 975.3923

$^{31}P$-NMR ($CDCl_3$) δ: 149.25, 149.49

Synthesis of ALNA[Trz]-T

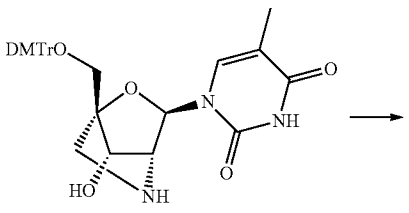

1a

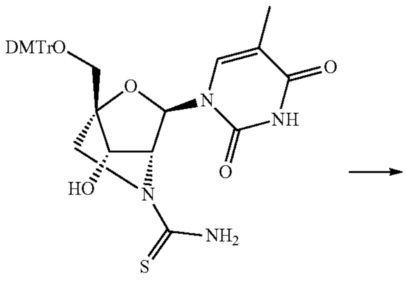

14Ta

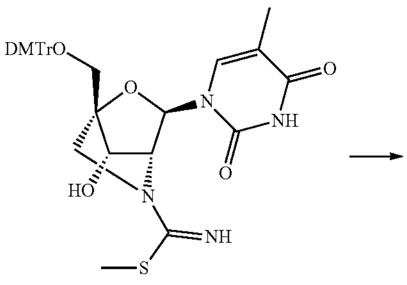

14Tb

-continued

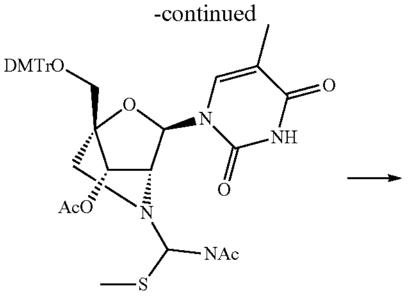

14Tc

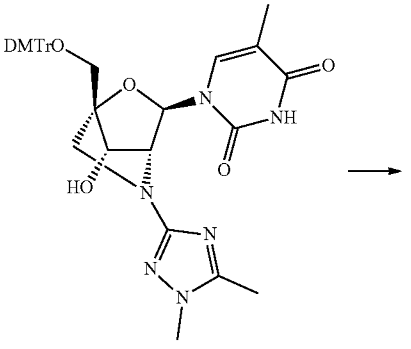

14Td

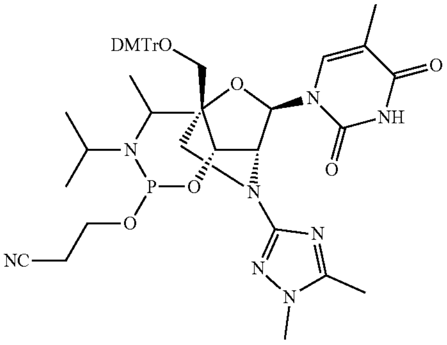

14Te

Example 96 Synthesis of Compound 14Ta (1R,3R,4R,7S)-1-[[bis(4-methoxyphenyl)-phenyl-methoxy]methyl]-7-hydroxy-3-(5-methyl-2,4-dioxopyrimidin-1-yl)-2-oxa-5-azabicyclo[2.2.1]heptane-5-carbothioamide To a mixture of the compound 1a (2.00 g, 3.50 mmol) and THF (17.5 mL) was added 1,1-thiocarbonyl diimidazole (1.25 g, 7.00 mmol), and the mixture was stirred at room temperature overnight. 28% Ammonia water (17.5 mL) was added to the reaction solution, and the mixture was stirred at room temperature overnight. The reaction solution was concentrated, and insoluble materials were filtered off. The insoluble materials were washed with water to obtain a compound 14Ta (2.35 g) as a crude product.

HRMS (MALDI): calculated value as $C_{33}K_{34}N_4O_7$ $[M+Na]^+$: 653.2040, measured value: 653.2026

Example 97 Synthesis of Compound 14Tb methyl (1R,3R,4R,7S)-1-[[bis(4-methoxyphenyl)-phenyl-methoxy]methyl]-7-hydroxy-3-(5-methyl-2,4-dioxopyrimidin-1-yl)-2-oxa-5-azabicyclo[2.2.1]heptane-5-carboxyimidothioate To a mixture of the compound 14Ta (2.35 g, 3.50 mmol, crude product) and THF (17.5 mL), was added methyl iodide (654 μL, 10.5 mmol), and the mixture was stirred at room temperature for 2 days. Saturated aqueous sodium hydrogen carbonate solution was added to the reaction solution, and the mixture was extracted with chloroform. The organic layer was dried over anhydrous magnesium sulfate, and insoluble materials were filtered off, and concentrated under reduced pressure. The residue was purified by column chromatography ($SiO_2$:chloroform/methanol=100/0 to 80/20) to obtain a compound 14Tb (1.88 g, yields over two steps 83%).

HRMS(MALDI): calculated value as $C_{34}H_{36}N_4O_7$ $[M+H]^+$: 645.2377, measured value: 645.2374

Example 98 Synthesis of Compound 14Tc

[(1R,3R,4R,7S)-5-[(Z)—N-acetyl-C-methylsulfanyl-carbamimidoyl]-1-[[bis(4-methoxyphenyl)-phenyl-methoxy]methyl]-3-(5-methyl2,4-dioxopyrimidin-1-yl)-2-oxa-5-azabicyclo[2.2.1]heptan-7-yl]acetate To a mixture of the compound 14Tb (1.87 g, 2.90 mmol, DMAP (35.4 mg, 0.290 mmol) and pyridine (14.5 mL) was added acetic anhydride (822 μL, 8.70 mmol), and the mixture was stirred at room temperature overnight. Ethyl acetate was added to the reaction solution, and the mixture was washed with 5% aqueous copper sulfate solution, water, and saturated brine. The organic layer was dried over anhydrous magnesium sulfate, and insoluble materials were filtered off, and the filtrates were then concentrated under reduced pressure to obtain a compound 14Tc (2.11 g, yield 100%).

HRMS(MALDI): calculated value as $C_{38}H_{40}N_4O_9S$ $[M+Na]^+$: 751.2408, measured value: 751.2398

Example 99 Synthesis of Compound 14Td

1-[(1R,3R,4R,7S)-1-[[bis(4-methoxyphenyl)-phenyl-methoxy]methyl]-5-(1,5-dimethyl-1,2,4-triazol-3-yl)-7-hydroxy-2-oxa-5-azabicyclo[2.2.1]heptan-3-yl]-5-methylpyrimidin-2,4-dione To a mixture of the compound 14Tc (1.66 g, 2.28 mmci) and EtOH (23 mL) was added methyl hydrazine (1.20 mL, 22.8 mmol), and the mixture was stirred at room temperature overnight. The reaction solution was concentrated, and the residue was purified by column chromatography ($SiO_2$: chloroform/methanol=100/0 to 90/10) to obtain a compound 14td (985 mg, yield 65%).

HRMS(MALDI): calculated value as $C_{36}H_{38}N_6O_7$ $[M+Na]^+$: 689.2694, measured value: 689.2684

Example 100 Synthesis of Compound 14Te

3-[[(1R,3R,4R,7S)-1-[[bis(4-methoxyphenyl)-phenyl-methoxy]methyl]-5-(1,5-dimethyl-1,2,4-triazol-3-yl)-3-(5-methyl-2,4-dioxopyrimidin-1-yl)-2-oxa-5-azabicyclo[2.2.1]heptan-7-yl]oxy-(diisopropylamino)phosphanyl]oxypropanenitrile (Present Compound 33)

To a mixture of the compound 14Td (576 mg, 0.864 mmol), dichloromethane (8.6 mL) and DIPEA (451 μL, 2.59 mmol) was added 2-cyanoethyl N,N-diisopropylchlorophosphoramidite (385 μL, 1.73 mmol), and the mixture was stirred at room temperature under nitrogen atmosphere for 2 days. Saturated aqueous sodium hydrogen carbonate solution was added to the reaction solutions, and the mixture was extracted with chloroform. The organic layer was passed through a phase separator, and the solvents were evaporated. The residue was purified by column chromatography ($SiO_2$: hexane/ethyl acetate=50/50 to 0/100, diol:hexane/ethyl acetate=50/50 to 0/100) to obtain a compound 14Te as the present compound 33 (517 mg, yield 69%).

HRMS(MALDI): calculated value as $C_{45}H_{55}N_8O_8P$ $[M+Na]^+$: 889.3773, measured value: 889.3778

$^{31}P$-NMR ($CDCl_3$) δ: 148.40, 146.45

Synthesis of ALNA[Trz]-mC

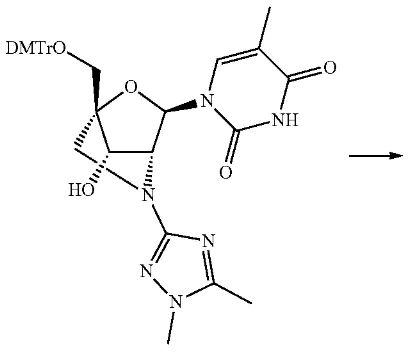

14Td

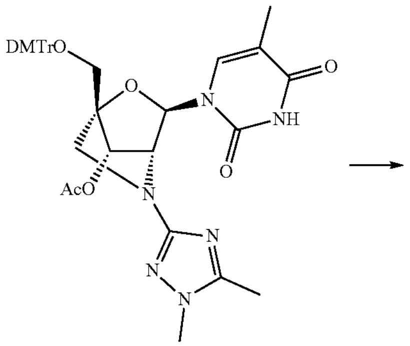

14Ca

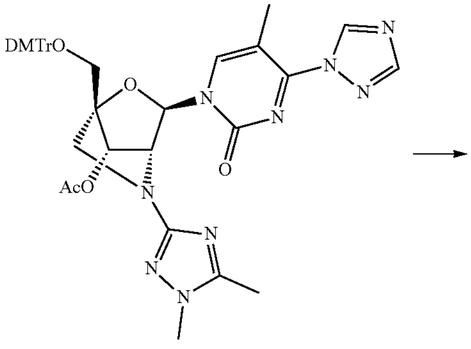

14Cb

-continued

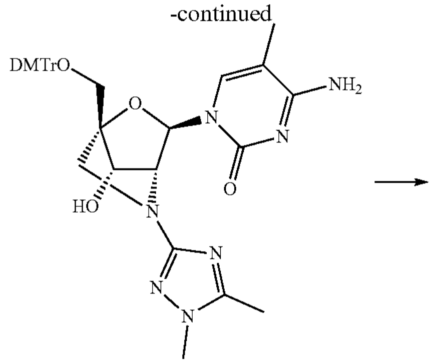

14Cc

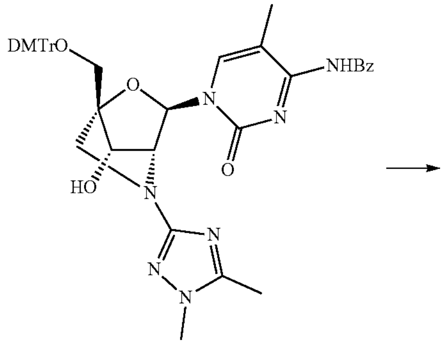

14Cd

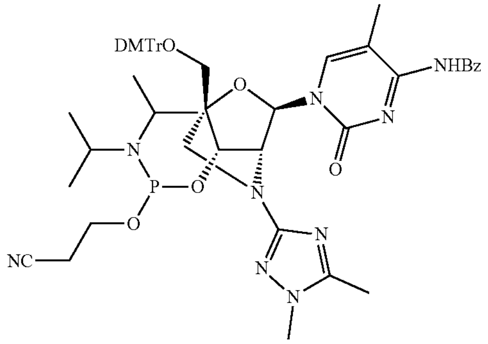

14Ce

Example 101 Synthesis of Compound 14Ca

[(1R,3R,4R,7S)-1-[[bis(4-methoxyphenyl)-phenyl-methoxy]methyl]-5-(1,5-dimethyl-1,2,4-triazol-3-yl)-3-(5-methyl-2,4-dioxopyrimidin-1-yl)-2-oxa-5-azabicyclo[2.2.1]heptan-7-yl]acetate To a mixture of the compound 14Td (918 mg, 1.38 mmol), DMAP (16.9 mg, 0.138 mmol) and pyridine (6.9 ml) was added acetic anhydride (196 μL, 2.07 mmcl), and the mixture was stirred at room temperature overnight. Ethyl acetate was added to the reaction solution, and the mixture was washed with saturated aqueous sodium hydrogen carbonate solution, water, and saturated brine. The organic layer was dried over anhydrous magnesium sulfate, and insoluble materials were filtered off, and the filtrates were then concentrated under reduced pressure to obtain a compound 14Ca (955 mg, yield 98%).

HRMS(MALDI): calculated value as $C_{38}H_{40}N_6O_8$ $[M+Na]^+$: 731.2800, measured value: 731.2791

Example 102 Synthesis of Compound 14Cb

[(1R,3R,4R,7S)-1-[[bis(4-methoxyphenyl)-phenyl-methoxy]methyl]-5-(1,5-dimethyl-1,2,4-triazol-3-yl)-3-(5-methyl-2-oxo-4-(1,2,4-triazol-1-yl)pyrimidin-1-yl]-2-oxa-5-azabicyclo[2.2.1]heptan-7-yl [acetate To a mixture of the compound 14Ca (915 mg, 1.29 mmol), 2,4-triazole (802 mg, 11.6 mmol), DIPEA (2.25 mL, 12.9 mmol) and acetonitrile (12.9 mL) was added phosphoryl chloride (204 μL, 2.19 mmol) under ice-cooling, and the mixture was stirred at room temperature under nitrogen atmosphere overnight. Ethyl acetate was added to the reaction solution, and the mixture was washed with saturated aqueous sodium hydrogen carbonate solution, and saturated brine. The organic layer was dried over anhydrous magnesium sulfate, and insoluble materials were filtered off, and the filtrates were concentrated under reduced pressure to obtain a compound 14Cb (1.08 g) as a crude product.

HRMS(MALDI): calculated value as $C_{40}H_{41}N_9O_7$ $[M+Na]^+$: 782.3021, measured value: 782.3019

Example 103 Synthesis of Compound 14Cc 4-amino-[(1R,3R,4R,7S)-1-[[bis(4-methoxyphenyl)-phenyl-methoxy]methyl]-5-(1,5-dimethyl-1,2,4-triazol-3-yl)-7-hydroxy-2-oxa-5-azabicyclo[2.2.1]heptan-3-yl]-5-methylpyrimidin-2-one To a mixture of the compound 14Cb (1.07 g, 1.29 mmol), crude product) and acetonitrile (12.9 ml) was added 28% ammonia water (8.6 mL), and the mixture was stirred at room temperature overnight. Water was added to the reaction solution, and the mixture was extracted with chloroform. The organic layer was passed through a phase separator, and the filtrates were concentrated to obtain a compound 14Cc (748 mg, yields ever two steps 87%).

HRMS (MALDI): calculated value as $C_{36}H_{39}N_7O_6$ $[M+Na]^+$: 688.2854, measured value: 688.2857

Example 104 Synthesis of Compound 14Cd

N-[1-[(1R,3R,4R,7S)-1-[[bis(4-methoxyphenyl)-phenyl-methoxy]methyl]-5-(1,5-dimethyl-1,2,4-triazol-3-yl)-7-hydroxy-2-oxa-5-azabicyclo[2.2.1]heptan-3-yl]-5-methyl-2-oxo-pyrimidin-4-yl]benzamide To a mixture of the compound 14Cc (733 mg, 1.10 mmol) and pyridine (5.5 mL) was added benzoic anhydride (374 mg, 1.64 mmol), and the mixture was stirred at room temperature overnight. A 2N aqueous sodium hydroxide solution (5.5 mL) was added to the reaction solution, and the mixture was stirred at room temperature for 1 hour. Ethyl acetate was added to the reaction solution, and the mixture was washed with saturated aqueous sodium hydrogen carbonate solution, and saturated brine. The organic layer was dried over anhydrous magnesium sulfate, and insoluble materials were filtered off, and the filtrates were concentrated under reduced pressure. The residue was purified by column chromatography ($SiO_2$:chloroform/methanol=100/0 to 90/10) to obtain a compound 14Cd (744 mg, yield 88%).

HRMS(MALDI): calculated value as $C_{43}H_{43}N_7O_7$ $[M+Na]^+$: 792.3116, measured value: 792.3111

Example 105 Synthesis of Compound 14Ce

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-5-methyl-2-oxo-pyrimidin-4-yl]benzamide (Present Compound 34)

To a mixture of the compound 14Cd (730 mg, 0.948 mmol), dichloromethane (9.5 mL) and DIPEA (0.495 mL, 2.84 mmol) was added 2-cyanoethyl N,N-diisopropylchlorophosphoramidite (0.423 mL, 1.90 mmol) under ice-cooling, and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$:hexane/ethyl acetate=50/50 to 0/100, NH:hexane/ethyl acetate=50/50 to 0/100) to obtain a compound 14Ce as the present compound 34 (672 mg, yield 73%).

HRMS(MALDI): calculated value as $C_{52}H_{60}N_9O_8P$ $[M+Na]^+$: 952.4195, measured value: 992.4186

$^{31}P$-NMR ($CDCl_3$) δ: 148.50, 148.56

Synthesis of ALNA[Trz]-G

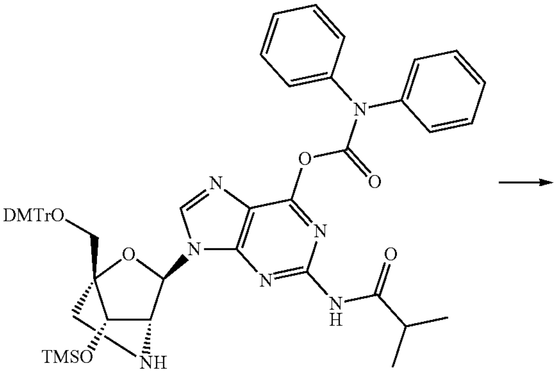

1g

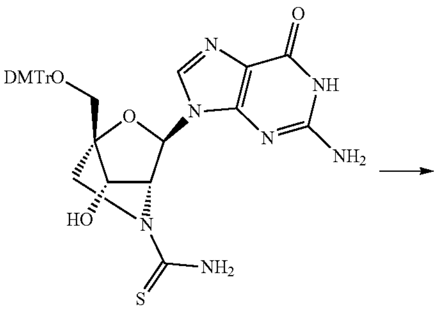

14Ga

-continued

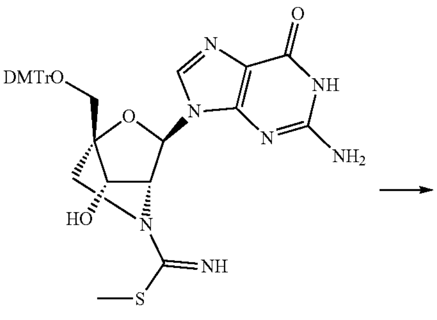

14Gb

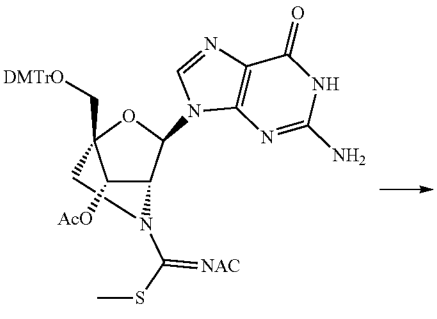

14Gc

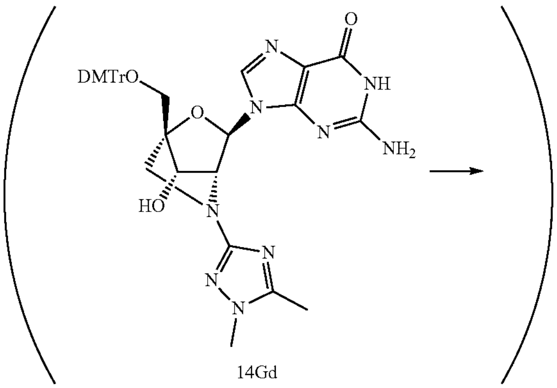

14Gd

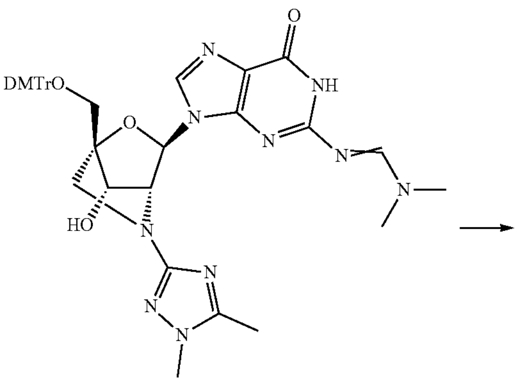

14Ge

-continued

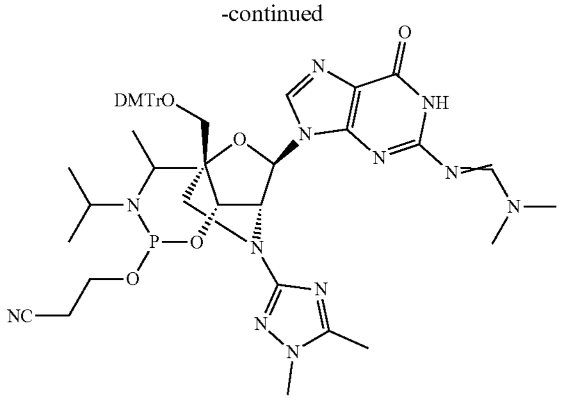

14Gf

Example 106 Synthesis of Compound 14Ga (1R,3R,4R,7S)-3-(2-amino-6-oxo-1H-purin-9-yl)-1-[[bis(4-methoxyphenyl)-phenyl-methoxy]methyl]-7-hydroxy-2-oxa-5-azabicyclo[2.2.1]heptane-5-carbothioamide To a solution of the compound 1g which was synthesized according to the method described in WO 2017/047816 A1 (55.0 g, 58.9 mmcl) in THF (270 mL) was injected 1,1-thiocarbonyl diimidazole (21.0 g, 118 mmol), and the mixture was stirred at room temperature for 2 hours. 28% Ammonia water (270 mL) was added to the reaction solution, and the mixture was stirred at room temperature for 30 minutes, followed by stirring at 50° C. for 46 hours. Chloroform (700 mL) was added to the reaction solution, and after stirring for a while, the organic layer was separated with a separatory funnel, and dried over anhydrous sodium sulfate. Insoluble materials were filtered off, and the solvents were then evaporated under reduced pressure, and the resulting residue was roughly purified by silica gel chromatography ($SiO_2$:chloroform/methanol=100/0 to 90/10). The resulting residue was solubilized in ethyl acetate (250 mL), and thereto was added toluene (250 mL). The solvents were evaporated under reduced pressure to about 300 mL (solids were precipitated out), and to the resulting suspensions was added diisopropyl ether (IPE) (50 mL), and the mixture was stirred at room temperature for 30 minutes. The precipitated materials were collected by filtration, and the filtered materials were washed with IPE (50 mL), and then dried under reduced pressure to obtain a compound 14Ga (27.9 g, yields 72%).

MS (ESI): m/z=656 $[M+H]^+$

Example 107 Synthesis of Compound 14Gb methyl (1R,3R,4R,7S)-3-(2-amino-6-oxo-1H-purin-9-yl)-1-[[bis(4-methoxyphenyl)-phenyl-methoxy]methyl]-7-hydroxy-2-oxa-5-azabicyclo[2.2.1]heptane-5-carboxyimidothioate To a solution of the compound 14Ga (27.9 g, 42.5 mmol) in THF (400 mL) was added dropwise methyl iodide (4.24 mL, 68.1 mmol) under ice-cooling, and the mixture was stirred at room temperature for 24 hours. The reaction solution was added to a mixed solution of sodium bicarbonate water (which was prepared from saturated sodium bicarbonate water (400 mL) and water (400 mL)) and chloroform (1400 mL) while stirring. After stirring for w while, the organic layer was separated with a separatory funnel, and dried over anhydrous sodium sulfate. The mixture was filtered through Celite, and the filtrates were azeotroped with toluene to obtain a compound 14Gb (26.9 g, yield 82%).

MS (ESI): m/z=670 $[M+H]^+$

Example 108 Synthesis of Compound 14Gc

[(1R,3R,4R,7S)-5-(N-acetyl-C-methylsulfanyl carboxyimidoyl)-3-(2-amino-6-oxo-1H-purin-9 yl) 1 [[bis(methoxyphenyl)-phenyl-methoxy]methyl]-2-oxa-5-azabicyclo[2.2.1]heptan-7-yl]acetate To a mixture of the compound 14Gb (26.9 g, 34.7 mmol) in pyridine (100 mL) were added acetic anhydride (9.83 mL, 104 mmol) and DMAP (424 mg, 3.47 mmol), and the mixture was stirred at room temperature for 4 hours. To the reaction solution were added ethyl acetate (400 mL) and saturated sodium bicarbonate water (200 mL), and the mixture was stirred vigorously for 20 minutes, and the organic layer was separated with a separatory funnel. The organic layer was washed with water (2×200 mL) and saturated brine (200 mL), and then dried over anhydrous sodium sulfate. After insoluble materials were filtered off, the solvents were evaporated under reduced pressure, and the resulting residue was azeotroped with toluene to obtain a compound 14Gc (30.5 g). The product was used as itself without purification in a next step.

MS (ESI): m/Z=754 $[M+H]^+$

Example 109 Synthesis of Compound 14Gd

N'-[9-[(1R,3R,4R,7S)-1-[[bis(4-methoxyphenyl)-phenyl-methoxy]methyl]-5-(1,5-dimethyl-1,2,4-triazol-3-yl)-7-hydroxy-2-oxa-5-azabicyclo[2.2.1]heptan-3-yl]-6-oxo-1H-purin-2-yl]-N,N-dimethylformamidine To a solution of the compound 14Gc (30.5 g, 35.9 mmol) in 1,4-dioxane (300 mL) was added methyl hydrazine (16.9 mL, 359 mmol), and the mixture was stirred at room temperature for 2 hours, followed by stirring at 50° C. for 3 hours. Water (100 mL) was added to the reaction solutions, the mixture was evaporated under recued pressure. Chloroform (250 mL) was added thereto, and after stirring for a while, the mixture was passed through a phase separator, and the organic layer was separated with a separatory funnel. After the solvents were evaporated, the solvents were azeotroped with toluene. The resulting residue was suspended with IPE (100 ml), the mixture was placed in ultrasonic bath for 20 minutes, and the precipitated materials were then collected by filtration, and the filtered materials were air dried followed by drying under reduced pressure.

To the solution of the resulting residue in DMF (75 mL, 970 mmol) was added N,N-dimethyl formamide dimethylacetal (50 mL, 375 mmol), and the mixture was stirred at room temperature for 2 hours. The reaction solvents were evaporated under reduced pressure, and the resulting concentrated residue was purified roughly by silica gel chromatography ($SiO_2$:chloroform/methanol=100/0 to 90/10, $SiO_2$:ethyl acetate/methanol=90/10 to 72/28). The crude products were washed by suspending in ethyl acetate (200 mL), and collected by filtration, and the filtered materials were dried under reduced pressure to a compound 14Gd (11.2 g, yield 40%).

MS (ESI): m/Z=748 $[M+H]^+$

Example 110 Synthesis of Compound 14Ge

N'-[9-[(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-6-oxo-1H-purin-2-yl]-N,N-dimethylformamidine (Present Compound 35)

To a solution of the compound 14Gd (6.00 g, 7.60 mmol) in dichloromethane (60 mL) was added DIPEA (5.30 mL, 30.6 mmol) under ice-cooling, followed by adding dropwise 2-cyanoethyl N,N-diisopropylchlorophosphoramidite (5.12 mL, 23.0 mmol), and the mixture was stirred at room temperature for 6 hours. The reaction solution was cooled under ice-cooling, and thereto were added saturated sodium bicarbonate water (120 mL) and chloroform (160 mL), and the mixture was stirred vigorously for 15 minutes, and the organic layer was then separated with a separatory funnel, and dried over anhydrous sodium sulfate. After insoluble materials were filtered off, the solvents were evaporated under reduced pressure, and the resulting residue was purified by silica gel chromatography ($SiO_2$:ethyl acetate/methanol=100/0 to 84/16) to obtain a compound 14Ge as the present compound 35 (5.59 g, yield 74%).

MS (ESI): m/Z=948 $[M+H]^+$ $^{31}$P-NMR ($CDCl_3$) δ: 148.52, 148.59

Synthesis of ALNA[Trz]-A

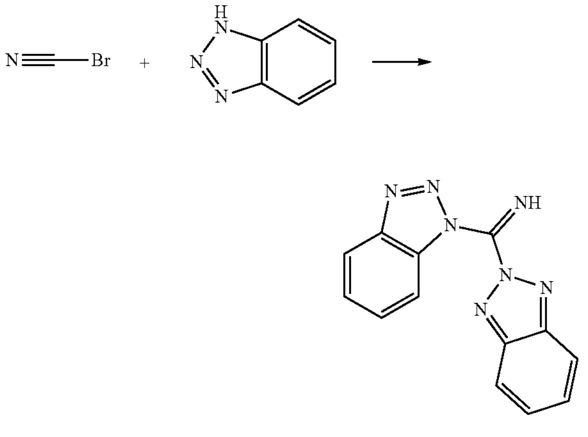

14Aa

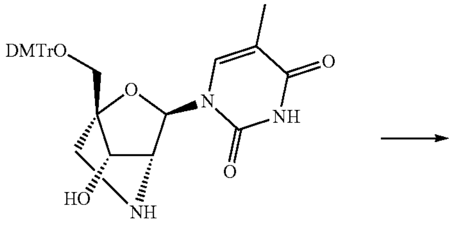

1a

-continued

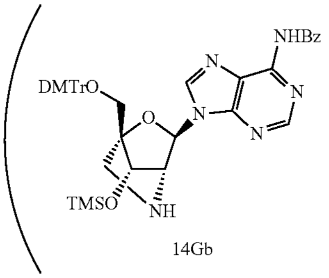

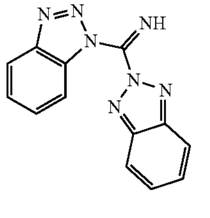

14Aa

14Gb

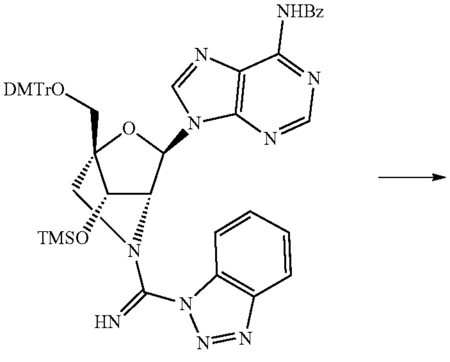

14Gc

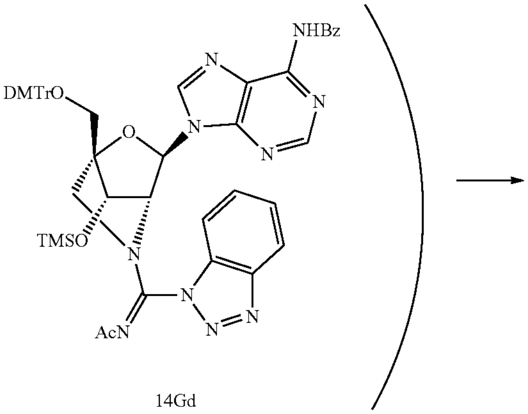

14Gd

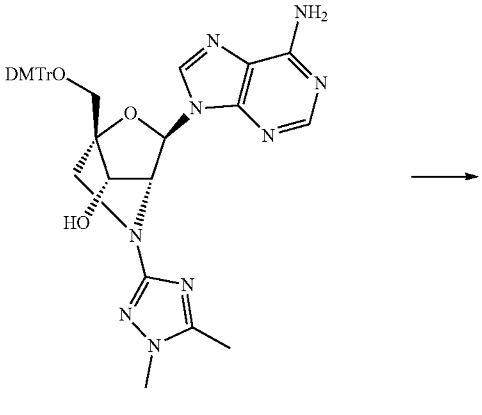

14Ae

-continued

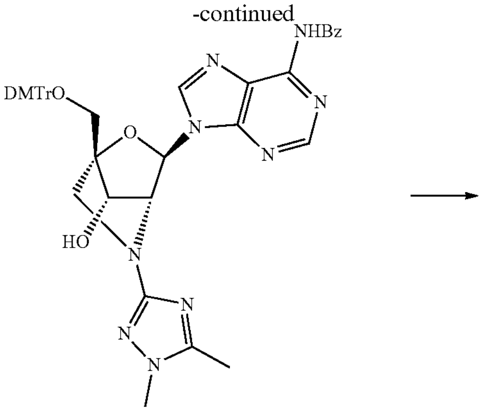

14Af

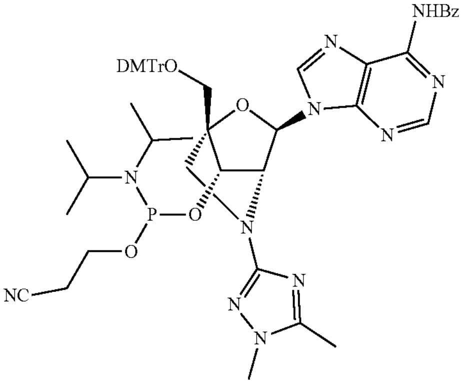

14Ag

Example 111 Synthesis of Compound 14Aa

Benzotriazol-1-yl (Benzotriazol-2-yl)methaneimine

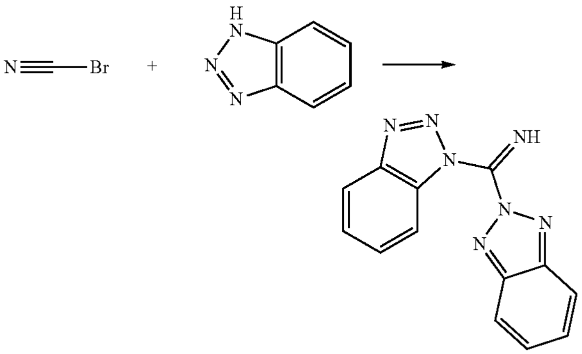

To a solution of benzotriazole (7.70 g, 64.6 mmol) in EtOH (135 mL) was added dropwise a solution of cyanogen bromide (3.41 g, 32.2 mmol) in acetone (15 mL) slowly under ice-cooling, followed by adding dropwise a solution of 2N sodium hydroxide (16.2 mL, 32.4 mmol) slowly. After the mixture was stirred for 30 minutes under ice-cooling, the precipitated materials were collected by filtration, and the filtered materials were washed with cold ethanol (80 mL). The mixture was air dried followed by drying under reduced pressure gave a compound 14Aa (5.14 g, yield 61%).

$^1H$ NMR (400 MHz, CHLOROFORM-$_d$) δ ppm 6.92-6.98 (m, 1H), 7.46-7.55 (m, 2H), 7.58-7.65 (n, 1H), 7.77 (ddd, J=8.35, 7.06, 1.03 Hz, 1H), 8.17-8.22 (m, 1H), 6.22-8.27 (m, 1H), 8-31-8.37 (m, 1H), 9.67 (s, 1H)

MS (ESI): Non-detected

Example 112 Synthesis of Compound 14Ae (1R,3R,4R,7S)-3-(6-aminopurin-9-yl)-1-[[bis(4-methoxyphenyl)-phenyl-methoxy]methyl]-5-(1,5-dimethyl-1,2,4-triazol-3-yl)-2-oxa-5-azabicyclo[2.2.1]heptane-7-cl To a suspension of N-(9K-purin-6-yl)benzamide (5.15 g, 21.5 mmol) in toluene (200 mL) was injected the compound 1a (10.3 g, 17.9 mmol) portionwise, followed by adding BSA (38 mL, 120 mmol), and the mixture was stirred vigorously at 60° C. for 30 minutes. Thereto was added TMSOTf (0.324 mL, 179 mmol) at the same temperature, and the mixture was stirred at 60° C. for 15 minutes. The reaction solutions were cooled under ice-cooling, and the reaction solutions were added vigorously while stirring to a mixed solution of IPE (100 mL), water (100 mL) and saturated sodium bicarbonate water (100 mL) that was cooled under ice-cooling. After the mixture was stirred vigorously for 20 minutes, insoluble materials were filtered off by Celite. The organic layer of the filtrates were separated with a separatory funnel, washed with saturated brine (200 mL) and then dried over anhydrous sodium sulfate, and the solvents were evaporated to obtain the residue of the crude compound 14Gb.

To the solution of the resulting crude residue in THF (200 mL) was added the compound 14Aa (4.72 g, 17.9 mmol), and the mixture was stirred at room temperature for 92 hours, and further stirred at 50° C. for 9 hours. To the reaction solution were added ethyl acetate (400 mL) and saturated sodium bicarbonate water (200 mL), and after stirring for 20 minutes, the organic layer was separated with a separatory funnel. The organic layer was washed with water (300 mL) and saturated brine (100 mL), and then dried over anhydrous sodium sulfate, and insoluble materials were filtered off, and the solvents were evaporated to obtain the residue of the crude compound 14Gc.

To a solution of the resulting residue in pyridine (65 mL) were added acetic anhydride (5.08 mL, 53.8 mmol) and DMAP (219 mg, 1.75 mmol), and the mixture was stirred at room temperature for 3 hours. To the reaction solutions were added ethyl acetate (400 mL) and saturated sodium bicarbonate water (200 mL), and after stirring for 20 minutes, the organic layer was separated with a separatory funnel. The organic layer was washed with water (300 mL) and saturated brine (100 mL) and then dried over anhydrous sodium sulfate. After insoluble materials were filtered off, the solvents were evaporated under reduced pressure, and the residue was azeotroped with toluene to obtain the residue of crude compound 14Gd.

To the solution of the resulting residue in 1,4-dioxane (100 ml) was added dropwise methyl hydrazine (9.44 mL, 179 mmol) under ice-cooling using cold water, and the mixture was stirred at room temperature for 3 hours. The mixture was warmed to 50° C., and stirred for 10 hours. Water (100 ml) was added to the reaction solutions, and the solvents were then evaporated under reduced pressure from the mixture, and the residue was extracted with chloroform (2×150 mL) using a separatory funnel. The organic layers were combined, the mixture was washed with saturated brine (100 mL), and then dried over anhydrous sodium sulfate. After insoluble materials were filtered off, the solvents were evaporated under reduced pressure, and the resulting residue was purified by silica gel chromatography (NH silica:chloroform/methanol=100/0 to 99/1) to obtain a compound 14Ae (4.91 g, yield 41%).

MS (ESI): m/Z=675 $[M-H]^-$

Example 113 Synthesis of Compound 14Af

N-[9-(1R,3R,4R,7S)-1-[[bis(4-methoxyphenyl)-phenyl-methoxy]methyl]-5-(1,5-dimethyl-1,2,4-triazol-3-yl)-7-hydroxy-2-oxa-5-azabicyclo[2.2.1]heptan-3-yl]purin-6-yl]benzamide To a mixture of the compound 14Ae (4.80 g, 7.10 mmol) and pyridine (10 mL) was added benzoyl chloride (2.48 mL, 21.3 mmol) under ice-cooling, and the mixture was stirred under ice-cooling for 3 hours. To the reaction solutions was added a solution of 2N sodium hydroxide (25 mL, 50 mmol), and the mixture was stirred at room temperature for 2 hours. The reaction solutions were washed with chloroform (50 mL) four times, and the organic layer was passed through a phase separator, and dried over anhydrous sodium sulfate. The solutions were filtered through Celite and concentrated. The residue was purified by column chromatography ($SiO_2$: chloroform/methanol=100/0 to 93/7) to obtain a compound 14Af (4.60 g, yield 83%).

MS (ESI): m/Z=781 $[M+H]^+$

Example 114 Synthesis of Compound 14Ag

N-[9-(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]purin-6-yl]benzamide (Present Compound 36)

To a mixture of the compound 14Af (4.26 g, 5.46 mmol) and dichloromethane (50 mL) were added DIPEA (3.78 mL, 21.8 mmol) and 2-cyanoethyl N,N-diisopropylchlorophosphoramidite (3.66 mL, 16.4 mmol) under ice-cooling, and the mixture was stirred at room temperature for 2 hours. The reaction solution was cooled under ice-cooling, and saturated aqueous sodium hydrogen carbonate solution (ICC mL) was added to the reaction solution, and the mixture was extracted with chloroform (100 mL). The organic layer was dried over anhydrous sodium sulfate, and insoluble materials were then flited off, and the solvents were evaporated. The residue was purified by column chromatography ($SiO_2$: ethyl acetate/methanol=100/0 to 94/6, NH silica: ethyl acetate/methanol=100/0 to 93/7) to obtain a compound 14Ag as the present compound 36 (3.68 g, yield 67%).

MS (ESI): m/Z=980 [M+H]+

$^{31}P$-NMR ($CDCl_3$) δ: 143.84, 149.04

Synthesis of ALNA[Oxz]-T

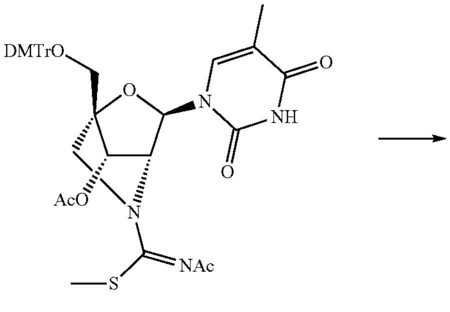

14Tc

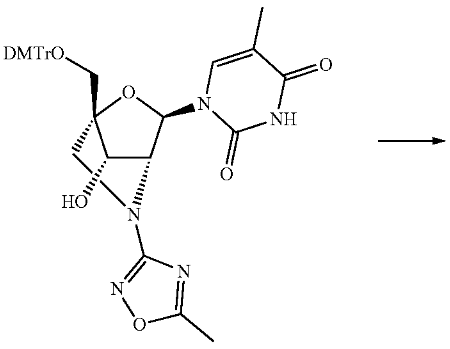

15Ta

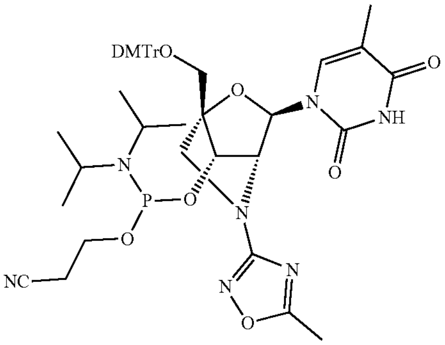

15Tb

Example 115 Synthesis of Compound 15Ta

1-[(1R,3R,4R,7S)-1-[[bis(4-methoxyphenyl)-phenyl-methoxy]methyl]-7-hydroxy-5-(5-methyl-1,2,4-oxa-diazol-3-yl)-2-oxa-5-azabicyclo[2.2.1]heptan-3-yl]-5-methylpyrimidin-2,4-dione To a mixture of the compound 14Tc (2.10 g, 2.88 mmol) and EtOH (14.4 mL) was added hydroxyl amine (50% aqueous solution, 1.90 mL, 28.8 mmol), and the mixture was stirred at room temperature for 2 days. The reaction solution was concentrated, and the residue was purified by column chromatography ($SiO_2$:chloroform/methanol=100/0 to 90/10) to obtain a compound 15Ta (1.34 g, yield 71%).

HRMS(MALDI): calculated value as $C_{35}H_{35}N_5O_8$ $[M+Na]^+$: 676.2378, measured value: 676.2363

Example 116 Synthesis of Compound 15Tb

3-[[(1R,3R,4R,7S)-1-[[bis(4-methoxyphenyl)-phe-nyl-methoxy]methyl]-3-(5-methyl-2,4-dioxopyrimi-din-1-yl)-5-(5-methyl-1,2,4-oxadiazol-3-yl)-2-oxa-5-azabicyclo[2.2.1]heptan-7-yl]oxy-(diisopropylamino)phosphanyl]oxypropanenitrile (Present Compound 37)

To a mixture of the compound 15Ta (300 mg, 0.459 mmol), dichloromethane (4.6 mL) and DIPEA (240 μL, 1.38 mmol) was added 2-cyanoethyl N,N-diisopropylchlorophos-phoramidite (205 μL, 0.918 mmol), and the mixture was stirred at room temperature under nitrogen atmosphere for 5 days. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$: hexane/ethyl acetate=60/40 to 10/90, Did: hexane/ethyl acetate=70/30 to 20/80, NH: chloroform/methanol=100/0 to 95/5) to obtain a compound 15Tb as the present compound 37 (214 mg, yield 55%).

HRMS(MALDI): calculated value as $C_{44}H_{52}N_7O_9P$ $[M+Na]^+$: 876.3456, measured value: 876.3441

$^{31}$P-NMR ($CDCl_3$) δ: 148.83, 149.09

Synthesis of ALNA[Oxz]-mC

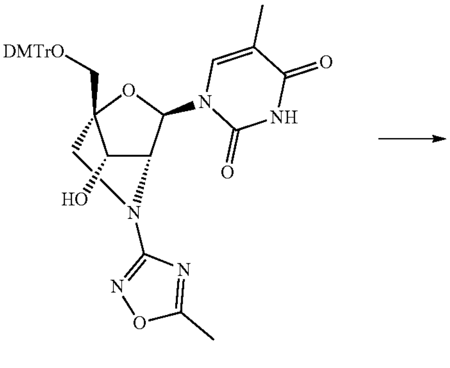

15Ta

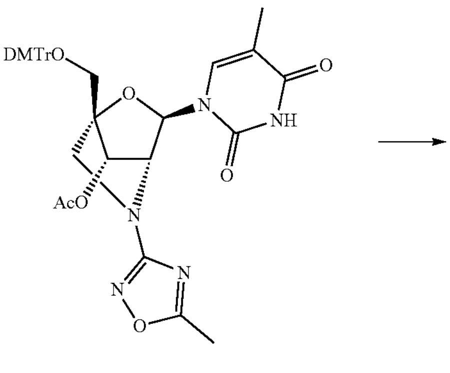

15Ca

-continued

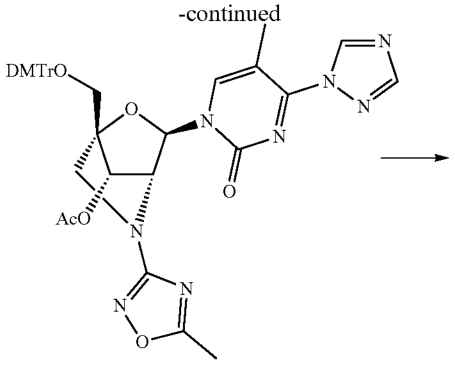

15Cb

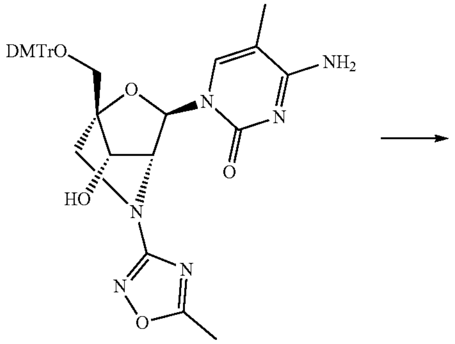

15Cc

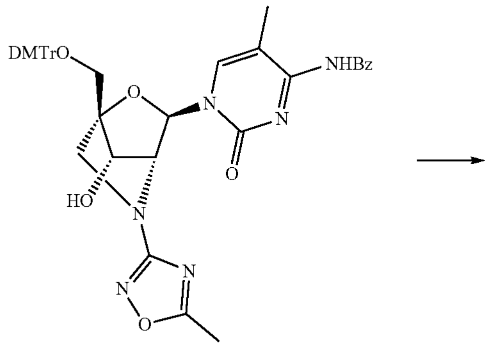

15Cd

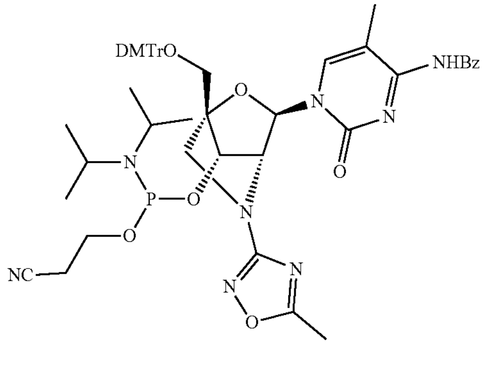

15Ce

Example 117 Synthesis of Compound 15Ca

[(1R,3R,4R,7S)-1-[[bis(4-methoxyphenyl)-phenyl-methoxy]methyl]-3-(5-methyl-2,4-dioxopyrimidin-1-yl)-5-(5-methyl-1,2,4-oxadiazol-3-yl)-2-oxa-5-azabicyclo[2.2.1]heptan-7-yl)acetate To a mixture of the compound 15Ta (999 mg, 1.53 mmol), DMAP (18.7 mg, 0.153 mmol) and pyridine (7.7 mL) was added acetic anhydride (217 μL, 2.30 mmol), and the mixture was stirred at room temperature for 2 days. Ethyl acetate was added to the reaction solution, and the mixture was washed with saturated aqueous sodium hydrogen carbonate solution, water, and saturated brine. The organic layer was dried over anhydrous magnesium sulfate, and insoluble materials were filtered off, and concentrated under reduced pressure to obtain a compound 15Ca (1.10 g, the reaction has been proceeded quantitatively).

HRMS(MALDI): calculated value as $C_{37}H_{37}N_5O_9$ $[M+Na]^+$: 718.2483, measured value: 713.2470

Example 118 Synthesis of Compound 15Cb

[(1R,3R,4R,7S)-1-[[bis(4-methoxyphenyl)-phenyl-methoxy]methyl]-5-(5-methyl-1,2,4-oxadiazol-3-yl)-3-[5-methyl-2-oxo-4-(1,2,4-triazol-1-yl)pyrimidin1-yl]-2-oxa-5-azabicyclo[2.2.1]heptan-7-yl]acetate To a mixture of the compound 15Ca (1.05 g, 1.51 mmol), 1,2,4-triazole (939 mg, 13.6 mmol), DIPEA (2.63 mL, 15.1 mmol) and acetonitrile (15 mL) was added phosphoryl chloride (239 μL, 2.57 mmol) under ice-cooling, and the mixture was stirred at room temperature under nitrogen atmosphere overnight. Ethyl acetate was added to the reaction solution, and the mixture was washed with saturated aqueous sodium hydrogen carbonate solution, and saturated brine. The organic layer was dried over anhydrous magnesium sulfate, and insoluble materials were filtered off, and the filtrates were concentrated under reduced pressure to obtain a compound 15Cb (1.32 g) as a crude product.

HRMS(MALDI): calculated value as $C_{39}H_{38}N_8O_8$ $[M+Na]^+$: 769.2705, measured value: 769.2707

Example 119 Synthesis of Compound 15Cc 4-amino-1-[(1R,3R,4R,7S)-1-[[bis(4-methoxyphenyl)-phenyl-methoxy]methyl]-7-hydroxy-5-(5-methyl-1,2,4-oxadiazol-3-yl)-2-oxa-5-azabicyclo[2.2.1]heptan-3-yl]-5-methyl-pyrimidin-2-one To a mixture of the compound 15Cb (1.30 g, 1.51 mmol, crude product) and acetonitrile (15.1 mL) was added 28% ammonia water (10.1 ml), and the mixture was stirred at room temperature overnight. Water was added to the reaction solution, and the mixture was extracted with chloroform. The organic layer was passed through a phase separator, and concentrated to obtain a compound 15Cc (0.96 g, yields over 2 steps 97%).

HRMS(MALDI): calculated value as $C_{35}H_{36}N_6O_7$ $[M+Na]^+$: 675.2538, measured value: 675.2539

Example 120 Synthesis of Compound 15Cd

N-[1-[(1R,3R,4R,7S)-1-[[bis(4-methoxyphenyl)-phenyl-methoxy]methyl]-7-hydroxy-5-(5-methyl-1,2,4-oxadiazol-3-yl)-2-oxa-5-azabicyclo[2.2.1]heptan-3-yl]-5-methyl-2-oxo-pyrimidin-4-yl]benzamide To a mixture of the compound 15Cc (0.93 g, 1.42 mmol) and pyridine (7.1 mL) was added benzoic anhydride (482 mg, 2.13 mmol), and the mixture was stirred at room temperature overnight. To the reaction solution was added 2N aqueous sodium hydroxide solution (7.1 mL), and the mixture was stirred at room temperature for 1 hour. Ethyl acetate was added to the reaction solution, and the mixture was washed with saturated aqueous sodium hydrogen carbonate solution, and saturated brine. The organic layer was dried over anhydrous magnesium sulfate, and insoluble materials were filtered off, and the filtrates were concentrated under reduced pressure. The residue was purified by column chromatography ($SiO_2$:chloroform/methanol=100/0 to 90/10; to obtain a compound 15Cd (958 mg, yield 89%).

HRMS(MALDI): calculated value as $C_{42}H_{40}N_6O_8$ $[M+Na]^+$: 779.2800, measured value: 779.2794

Example 121 Synthesis of Compound 15Ce

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(5-methyl-1,2,4-oxadiazol-3-yl)-2-oxa-5-azabicyclo[2.2.1]heptan-3-yl]-5-methyl-2-oxo-pyrimidin-4-yl]benzamide (Present Compound 38t To a mixture of the compound 15Cd (949 mg, 1.25 mmol), dichloromethane (12.5 mL) and DIPEA (0.653 mL, 3.75 mmol) was added 2-cyanoethyl N,N-diisopropylchlorophosphoramidite (0.559 mL, 2.50 mmol) under ice-cooling, and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$:hexane/ethyl acetate=80/20 to 30/70, NH:hexane/ethyl acetate=50/50 to 0/100) to obtain a compound 15Ce as the present compound 38 (834 mg, yield 70%).

HRMS(MALDI): calculated value as $C_{51}H_{57}N_8O_9P$ $[M+Na]^+$: 979.3878, measured value: 979.3676

$^{31}P$-NMR ($CDCl_3$) δ: 148.98, 149.27

Synthesis of ALNA[Tdz]-T

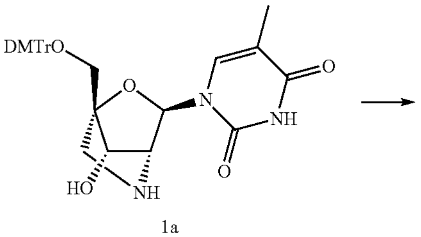

1a

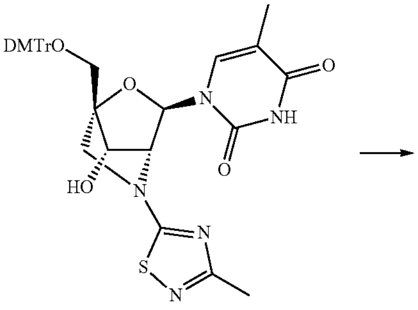

16Ta

-continued

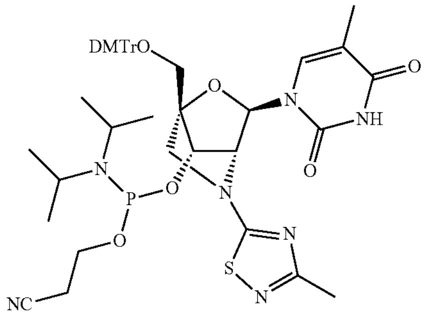

16Tb

Example 122 Synthesis of Compound 16Ta

1-[(1R,3R,4R,7S)-1-[[bis(4-methoxyphenyl)-phenyl-methoxy]methyl]-7-hydroxy-5-(3-methyl-1,2,4-thiadiazol-5-yl)-2-oxa-5-azabicyclo[2.2.1]heptan-3-yl]-5-methyl-pyrimidin-2,4-dione A mixture of the compound 1a (3.00 g, 5.25 mmol), 5-chloro-3-methyl-1,2,4-thiadiazole (848 mg, 6.30 mmol), DIPEA (2.72 mL, 15.7 mmol) and DMSO (26 mL) was stirred at 120° C. for 2 hours. Ethyl acetate was added to the reaction solution, and the mixture was washed with water and saturated brine. The organic layer was dried over anhydrous magnesium sulfate, and insoluble materials were filtered off, and the filtrates were concentrated under reduced pressure. The residue was purified by column chromatography ($SiO_2$:chloroform/methanol=100/0 to 95/5) to obtain a compound 16Ta (3.30 g, yield 94%).

MS(ESI): m/z=670 $(M+H)^+$

Example 123 Synthesis of Compound 16Tb

3-[[(1R,3R,4R,7S)-1-[[bis(4-methoxyphenyl)-phenyl-methoxy]methyl]-3-(5-methyl-2,4-dioxopyrimidin-1-yl)-5-(3-methyl-1,2,4-thiadiazol-5-yl)-2-oxa-5-azabicyclo[2.2.1]heptan-7-yl]oxy-(diisopropylamino)phosphanyl]oxopropanenitrile (Present Compound 39)

To a mixture of the compound 16Ta (2.26 g, 3.37 mmol), dichloromethane (17 mL), DIPEA (1.75 mL, 10.1 mmol) was added 2-cyanoethyl N,N-diisopropylchlorophosphoramidite (1.51 mL, 6.77 mmol), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$: hexane/ethyl acetate=70/30 to 20/30, Did: hexane/ethyl acetate=70/30 to 20/80) to obtain a compound 16Tb as the present compound 39 (2.45 g, yield 841).

MS(ESI): m/z=870 $(M+H)^+$ $^{31}P$-NMR ($CDCl_3$) δ: 149.23, 149.51

Synthesis of ALNA[Tdz]-mC

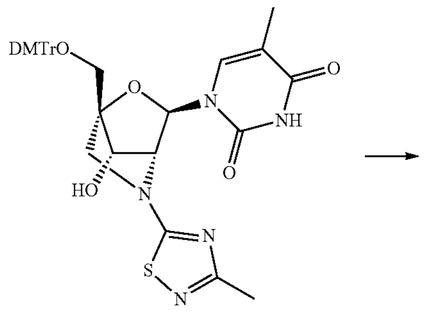

16Ta

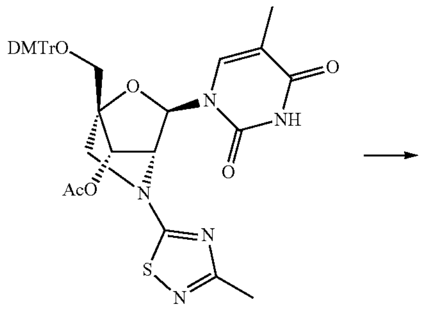

16mCa

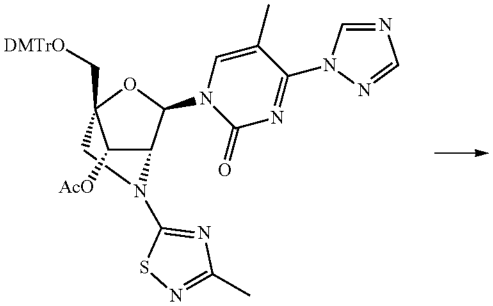

16mCb

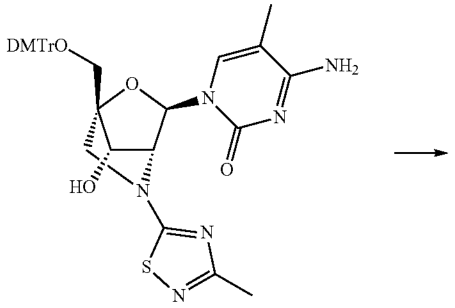

16mCc

-continued

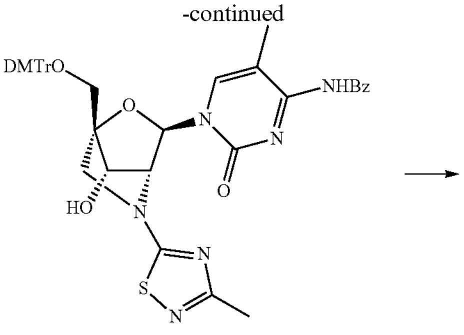

16mCd

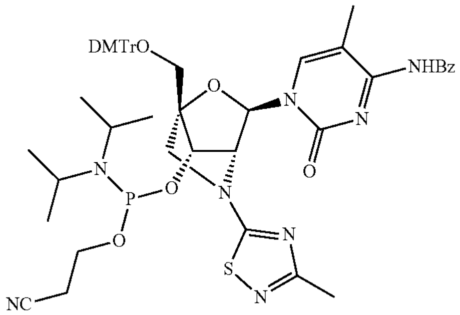

16mCe

Example 124 Synthesis of Compound 16mCa

[[(1R,3R,4R,7S)-1-[[bis(4-methoxyphenyl)-phenyl-methoxy]methyl]-3-(5-methyl-2,4-dioxopyrimidin-1-yl)-5-(3-methyl-1,2,4-thiadiazol-5-yl)-2-oxa-5-azabicyclo[2.2.1]heptan-7-yl]acetate To a mixture of the compound 16Ta (5.92 g, 8.84 mmol), DMAP (120 mg, 0.982 mmol; and pyridine (18 ml) was added acetic anhydride (1.25 mL, 13.2 mmol), and the mixture was stirred at room temperature overnight. The reaction solution was concentrated, and ethyl acetate was added to the residue, and the mixture was washed with saturated aqueous sodium hydrogen carbonate solution, and saturated brine. The organic layer was dried over anhydrous magnesium sulfate, and insoluble materials were filtered off, and the filtrates were concentrated to obtain a compound 16mCa (5.69 g, yield 90%).

MS(ESI): m/z=712 $(M+H)^+$

Example 125 Synthesis of Compound 16mCb

[[(1R,3R,4R,7S)-1-[[bis(4-methoxyphenyl)-phenyl-methoxy]methyl]-3-[5-methyl-2-oxo-4-(1,2,4-thiadiazole-1-yl)pyrimidin-1-yl]-5-(3-methyl-1,2,4-thiadiazol-5-yl)-2-oxa-5-azabicyclo[2.2.1]heptan-7-yl] acetate To a mixture of the compound 16mCa (5.52 g, 7.75 mmol), 1,2,4-triazole (4.82 g, 69.8 mmol), DIPEA (13.4 mL, 77.5 mmol) and acetonitrile (39 mL) was added phosphoryl chloride (1.23 mL, 13.2 mmol) under ice-cooling, and the mixture was ≡stirred at room temperature under nitrogen atmosphere for 2 hours. Ethyl acetate was added to the reaction solution, and the mixture was extracted with saturated aqueous sodium hydrogen carbonate solution, and saturated brine. The organic layer was dried over anhydrous magnesium sulfate, and insoluble materials were filtered off, and the filtrates were concentrated to obtain a compound 16mCb as a crude product (6.18 g, containing impurities).

Example 126 Synthesis of Compound 16mCc 4-amino-1-[[(1R,3R,4R,7S)-1-[[bis(4-methoxyphenyl)-phenyl-methoxy]methyl)-7-hydroxy-5-(3-methyl-1,2,4-thiadiazol-5-yl)-2-oxa-5-azabicyclo[2.2.1]heptan-3-yl]-5-methyl-pyrimidin-2-one To a mixture of the compound 16mCb (6.18 g, 7.75 mmol/containing impurities) and acetonitrile (39 mL) was added 28% ammonia water (39 mL), and the mixture was stirred at room temperature for 4 days. Water was added to the reaction solution, and the mixture was extracted with chloroform. The organic layer was dried over anhydrous magnesium sulfate, and insoluble materials were filtered off, and the filtrates were concentrated. The residue was purified by column chromatography ($SiO_2$:chloroform/methanol=100/0 to 90/10) to obtain a compound 16mCc (4.50 g, yields over 2 steps 87%).

MS(ESI): m/z=667 $(M-H)^-$

Example 127 Synthesis of Compound 16mCd

N-[1-[(1R,3R,4R,7S)-1-[[bis(4-methoxyphenyl)-phenyl-methoxy]methyl]-7-hydroxy-5-(3-methyl-1,2,4-thiadiazol-5-yl)-2-oxa-5-azabicyclo[2.2.1]heptan-3-yl]-5-methyl-2-oxo-pyrimidin-4-yl]benzamide A mixture of the compound 16mCc (4.37 g, 6.53 mmol), benzoic anhydride (2.22 g, 9.81 mmol) and pyridine (13 mL) was stirred at room temperature overnight. To the reaction solution was added 2N aqueous sodium hydroxide solution (13 mL, 26 mmol), and the mixture was stirred at room temperature for 1.5 hours. Ethyl acetate was added to the reaction, solution, and the mixture was washed with saturated aqueous sodium hydrogen carbonate solution, and saturated brine. The organic layer was dried over anhydrous magnesium sulfate, and insoluble materials were filtered off, and the filtrates were concentrated. The residue was purified by column chromatography ($SiO_2$:chloroform/methanol=100/0 to 90/10) to obtain a compound 16mCd (4.76 g, yield 94%).

MS (ESI): m/z=773 $(M+H)^+$

Example 128 Synthesis of Compound 16mCe

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(3-methyl-1,2,4-thiadiazol-5-yl)-2-oxa-5-azabicyclo[2.2.1]heptan-3-yl]-5-methyl-2-oxo-pyrimidin-4-yl]benzamide (Present Compound 40)

To a mixture of the compound 16mCd (4.62 g, 5.98 mmol), dichloromethane (12 mL) and DIPEA (3.10 mL, 17.9 mmol) was added 2-cyanoethyl N,N-diisopropylchlorophosphoramidite (2.67 mL, 12.0 mmol), and the mixture was stirred at room temperature under nitrogen atmosphere overnight. Saturated aqueous sodium hydrogen carbonate solution was added to the reaction solution, and the mixture was extracted with chloroform. The organic layer was passed through a phase separator, and the solvents were evaporated. The residue was purified by column chromatography ($SiO_2$:hexane/ethyl acetate=80/20 to 30/70, NK: hexane/ethyl acetate=70/30 to 20/80) to obtain a compound 16mCe as the present compound (3.57 g, yield 61%).

MS(ESI): m/z=S74 $(M+H)^+$ $^{31}$P-NMR ($CDCl_3$) δ: 149.45, 149.78

ALNA[Ms]-mC can be also synthesized by transforming a nucleic acid base moiety of ALNA[Ms]-T nucleoside as follows. Synthesis of Compound 2Cf

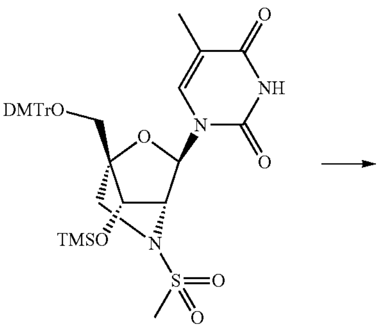

2Tb

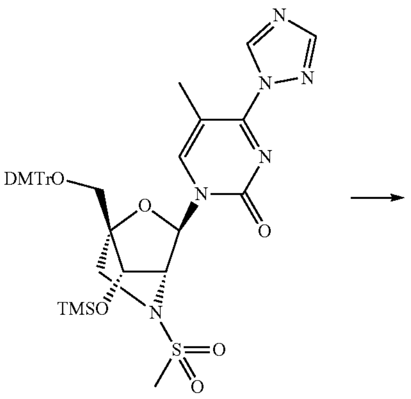

2Cd

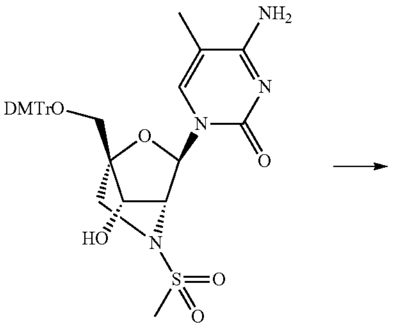

2Ce

-continued

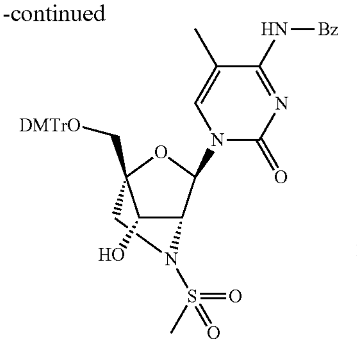

2Cf

Example 129 Synthesis of Compound 2Cd

3-[(1R,3R,4R,7S)-1-[[bis(4-methoxyphenyl)-phenyl-methoxy]methyl]-5-methylsulfonyl-7-trimethylsilyloxy-2-oxa-5-azabicyclo[2.2.1]heptan-3-yl]-5-methyl-6-(1,2,4-triazol-1-yl)-1,6-dihydropyrimidin-2-one Compound 2Tb (14.1 g, 0.019 mol) was solubilized in acetonitrile (310 mL), and thereto was added triethylamine (97.29 mL, 0.961 mol), and the mixture was stirred at 0° C. for 15 minutes. To the reaction solution was added 1,2,4-triazole (30.36 g, 0.439 mol), and the mixture was stirred at 0° C. for 15 minutes, and thereto was then added phosphoryl chloride (4.44 mL, 0.028 mol), and the mixture was stirred at 0° C. for 15 minutes, and warmed to room temperature for 2 hours. The reaction solution was concentrated under reduced pressure, and thereto were added ethyl acetate (200 mL) and water (100 ml), and the mixture was separated with a separatory funnel. The organic layer was washed with sodium carbonate (100 mL) twice, dried over sodium sulfate, and concentrated under reduced pressure to obtain a compound 2Cd as crude product (11.8 g).

Example 130 Synthesis of Compound 2Ce 6-amino-3-[(1R,3R,4R,7S)-1-([bis(4-methoxyphenyl)-phenyl-methoxy]methyl]-7-hydroxy-5-methylsulfonyl-2-oxa-5-azabicyclo[2.2.1]heptan-3-yl]-5-methyl-pyrimidin-2-one The crude compound 2Cd (11.8 g) was solubilized in 1,4-dioxane (118 mL), and 25% ammonia water (118 mL) was added thereto, and the mixture was stirred at room temperature overnight. The reaction solution was concentrated under reduced pressure, and the resulting residue was purified by silica gel chromatography (dichloromethane/methanol, 95/5 to 94/6). The resulting mixture was stirred in a mixed solution of dichloromethane/hexane (10/90), and the precipitated materials were collected by filtration to obtain a compound 2Ce (8.3 g, yields over two steps 64%).

MS(ESI): m/z=649.3 $(M+H)^+$

Example 131 Synthesis of Compound 2Cf

N-[1-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-5-methyl-2-oxo-pyrimidin-4-yl]dihydropyrimidin-2-one To a solution of the compound 2Ce (8.3 g, 0.012 mol) in DMF (63 mL) was added benzoic anhydride (2.57 g, 0.011 mol), and the mixture was stirred at room temperature for 24 hours. The reaction solution was diluted with ethyl acetate (200 mL), and the mixture was washed with water (100 mL) twice. The organic layer was washed with water (100 mL) and saturated brine (100 mL) successively, and dried over sodium sulfate. The resulting mixture was concentrated under reduced pressure, and the resulting residue was purified by silica gel chromatography (dichloromethane/methanol, 99.5/0.5 to 99/1). The resulting mixture was stirred in a mixed solution of dichloromethane/hexane (10/90), and the precipitated materials were collected by filtration to obtain the compound 2Cf (4.0 g, yield 47%).

MS(ESI): m/z=753.1 $(M+H)^+$

Also ALNA[Ms]-mC nucleoside can be also synthesized as follows.

Synthesis of Compound 2Cj

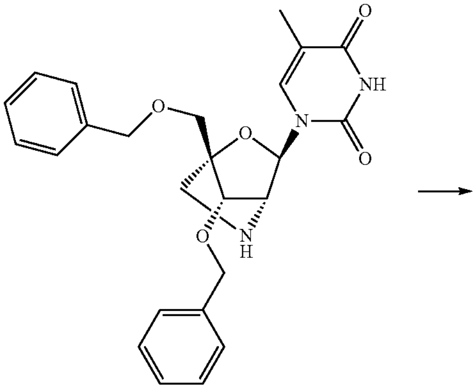

1h

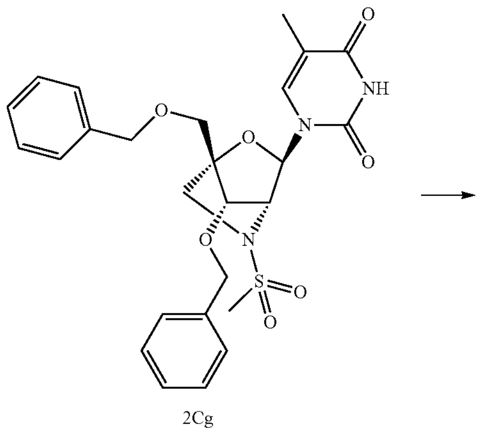

2Cg

-continued

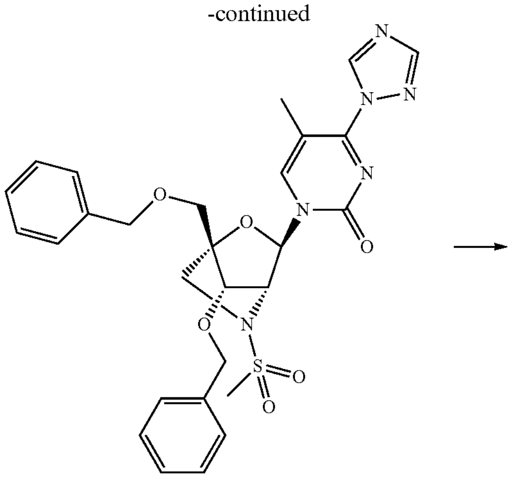

2Ch

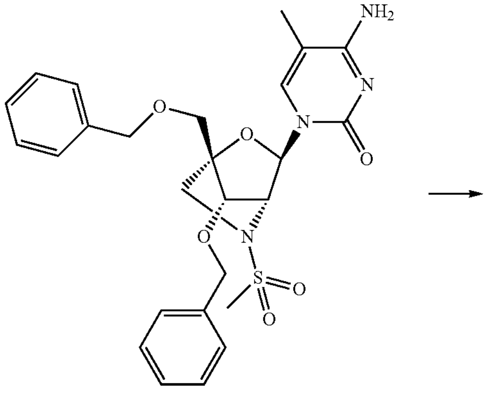

2Ci

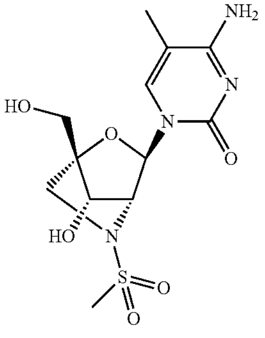

2Cj

Example 132 Synthesis of Compound 2Cg

1-[(1R,3R,4R,7S)-7-benzyloxyl-1-(benzyloxymethyl)-5-methylsulfonyl-2-oxa-5-azabicyclo[2.2.1]heptan-3-yl]-5-methylpyrimidin-2,4-dione To a mixed solution of 1-[(1R,3R,4R,7S)-7-benzyloxy-1-(benzyloxymethyl)-2-oxa-5-azabicyclo[2.2.1]heptan-3-yl]-5-methylpyrimidin-2,4-dione (1h) (20.00 g, 21.61 mmol), which was synthesized according to the method described in WO 2017/047316 A1, in dichloromethane (200 mL) was added triethylamine (15.5 mL, 111 mmol), and thereto was added mesyl chloride (4.15 mL, 53.4 mmol) in ice bath, and the mixture was stirred in ice bath for 4.5 hours. 5% Sodium bicarbonate water (60 mL) was added thereto under ice-cooling, and the mixture was stirred and separated with a separatory funnel. The aqueous layer was extracted with dichloromethane (40 mL) and the extracts were combined and mixed with the dichloromethane organic layer. The organic layer was washed with 15% brine (60 mL), and the solvents were then evaporated. The concentrated residue was washed with methanol (90 mL) as a suspension. The resulting precipitated materials were collected by filtration, dried under vacuum to obtain a compound 2Cg (21.94 g, yield 94%).

MS(ESI): m/z=526 $(M+H)^+$

Example 133 Synthesis of Compound 2Ch

1-[(1R,3R,4R,7S)-7-benzyloxy-1-(benzyloxymethyl)-5-methylsulfonyl-2-oxa-5-azabicyclo[2.2.1]heptan-3-yl]-5-methyl-4-(1,2,4-triazol-1-yl)pyrimidin-2-one Compound 2Ch (3.4 g) as a crude product was obtained from the compound 2Cg (3.0 g, 5.6 mmol) similarly to Example 129.

Example 134 Synthesis of Compound 2Ci 4-amino-1-[(1R,3R,4R,7S)-7-benzyloxyl-(benzyloxymethyl)-5-methylsulfonyl-2-oxa-5-azabicyclo[2.2.1]heptan-3-yl]-5-methyl-pyrimidin-2-one Compound 2Ci (2.6 g, yield 87%) was obtained from the compound 2Ch (3.4 g, 5.8 mmol) similarly to Example 130.

MS(ESI): m/z=527.2 $(M+H)^+$

Example 135 Synthesis of Compound 2Cj 4-amino-1-[(1R,3R,4R,7S)-7-hydroxy-1-(hydroxymethyl)-5-methylsulfonyl-2-oxa-5-azabicyclo[2.2.1]heptan-3-yl]-5-methyl-pyrimidin-2-one The compound 2Ci (2.6 g, 4.9 mmol) was solubilized in acetic acid (28.6 mL), and thereto was added 20% palladium/carbon (0.35 g), and the mixture was stirred at room temperature under hydrogen atmosphere for 16 hours. Insoluble materials were filtered off, and filtrates were concentrated under reduced pressure. To the residue were added 1-butanol and IPE, and the mixture was stirred, and the precipitated materials were collected by filtration. The resulting solids were recrystallized with methanol to obtain a compound 2Cj (1.0 g, yield 58%).

MS(ESI): m/z=346.9 $(M+H)^+$

ALNA[Ms]-G wherein a guanine moiety is protected with a dimethylamino methylene group can be synthesized as follows. Here in the case where a monomer containing such a protection, style is used in an oligomer synthesis, it is possible to control a production of by-products that may occur when oligomer synthesis is performed using Compound 2Gd wherein the 6-position of guanine is protected with DPC.

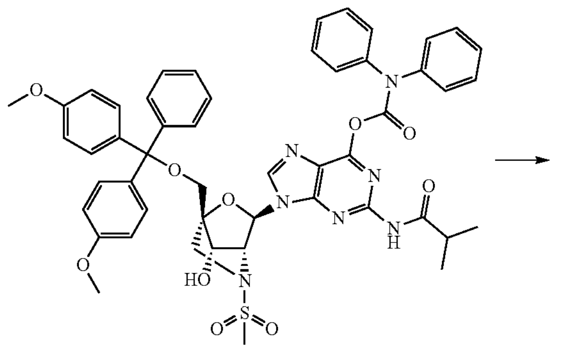

2Gc

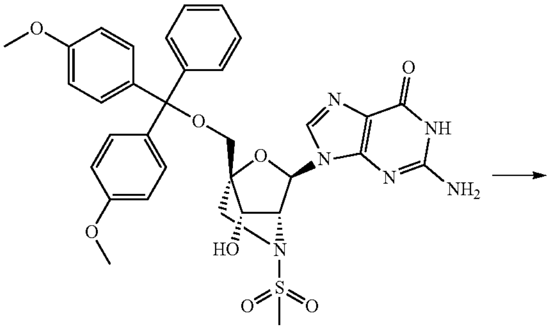

2Ge

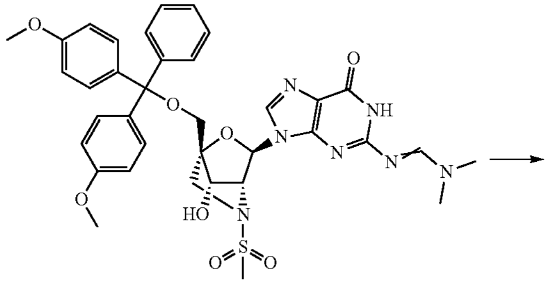

2Gf

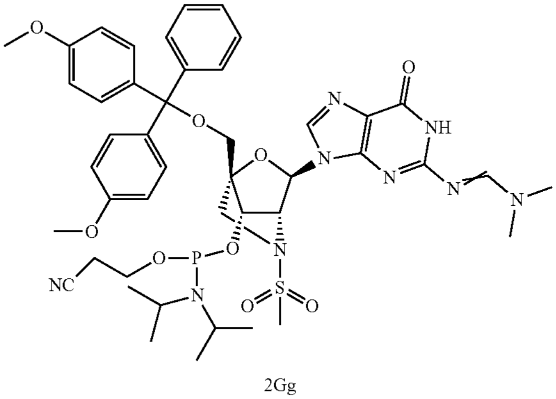

2Gg

Example 136 Synthesis of Compound 2Ge 2-amino-9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-1H-purin-6-one To a solution of the compound 2Gc (1000 mg, 1.1 mmol) in tetrahydrofuran (10 mL) was added 28% ammonia water (5 ml) at room temperature, the mixture was stirred at room temperature overnight. Thereto was further added 28% ammonia water (15 mL), and the mixture was stirred at 70° C. for 8 hours. Thereto were added water and dichloromethane at room temperature, and after stirring the mixture, the organic was recovered, and dried over sodium sulfate. The residue was filtered, and the solvents were evaporated, and the resulting mixture was purified by silica gel chromatography (chloroform/methanol, 97/3 to 92/8) to obtain a compound 2Ge (620 mg, yield 86%).

MS(ESI): m/z=675 $(M+H)^+$

Example 137 Synthesis of Compound 2Gf

N'-[9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-6-oxo-1H-purin-2-yl]-N,N-dimethylformamidine The compound 2Ge (150 mg, 0.22 mmol) was solubilized in tetrahydrofuran (2.22 ml), and thereto was added N,N-dimethyl formamide dimethylacetal (132 mg, 1.11 mmol) at room temperature, and the mixture was stirred. Ethyl acetate was added thereto at room temperature, and the mixture was extracted (2 ml) once. The resulting organic layer was washed with brine, and dried ever sodium sulfate. The residue was filtered, and the solvents were evaporated, and the residue was purified by silica gel chromatography (chloroform/methanol=99/1, chloroform/methanol=93/7) to obtain a compound 2Gf (145 mg, yield 89%).

MS(ESI): m/z=728 $(M-H)^-$

Example 133 Synthesis of Compound 2Gg

N'-[9-[(1R,3R,4R,7S)-1-[[bis(4-methoxyphenyl)-phenyl-methoxy]methyl]-7-[2-cyanoethoxy(diisopropylamino)phosphanyl]oxy-5-methylsulfonyl-2-oxa-5-azabicyclo[2.2.1]heptan-3-yl]-6-oxo-1H-purin-2-yl]-N,N-dimethylformamidine The compound 2Gf (900 mg, 1.2 mmol) was solubilized in dichloromethane (15 mL), and thereto were added N,N-diisopropyl ethylamine (747 mg, 5.8 mmol) and 2-cyanoethyl N,N-diisopropylchloro phosphoroamizide (1061 mg, 4.5 mmol) at room temperature, and the mixture was stirred overnight. Thereto were added saturated bicarbonate water and dichloromethane, and the organic layer was separated. The resulting organic layer was dried over sodium sulfate, and the residue was filtered. After the solvents were evaporated, the resulting mixture was purified by amine silica gel chromatography (chloroform/methanol, 100/0 to 97/3), followed by diol silica gel chromatography (chloroform/methanol, 100/0 to 97/3) to obtain a compound 2Gg (630 mg, yield 60%).

MS(ESI): m/z=930 $(M+H)^+$

ALNA[Ms]-G wherein a guanine moiety is protected with only an isobutyloyl group can be synthesized as follows. Here in the case where a monomer containing such a protection style is used in an oligomer synthesis, it is possible to control a production of by-products that may occur when oligomer synthesis is performed using Compound 2Gd wherein the 6-position of guanine is protected with DPC.

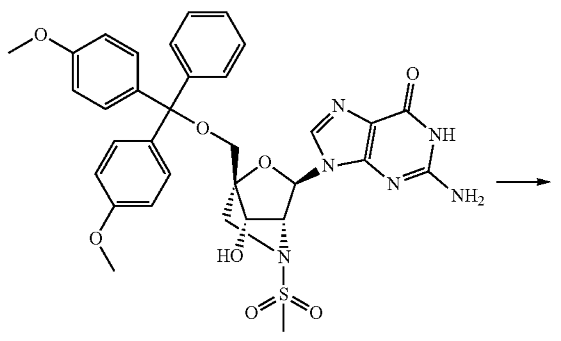

2Ge

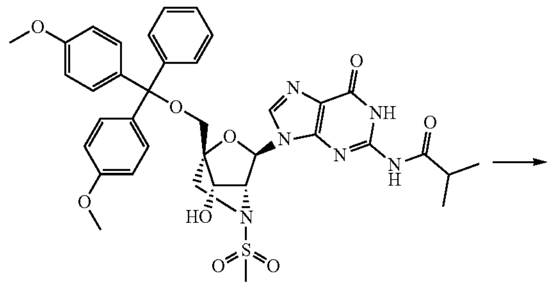

2Gh

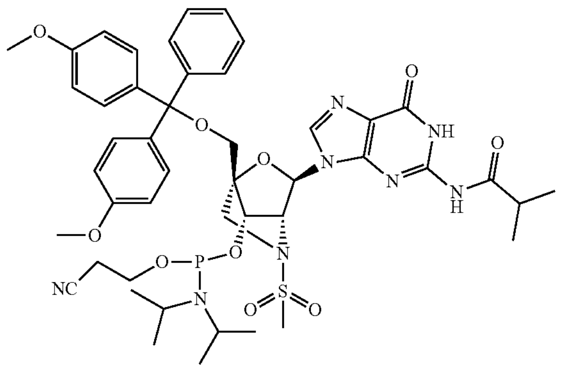

2Gi

Example 139 Synthesis of Compound 2Gh

N-[9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-6-oxo-1H-purin-2-yl]-2-methylpropane amide The compound 2Ge (100 mg, 0.15 mmol) was solubilized m pyridine (1.4 mL), and thereto were added N,N-dimethyl-4-aminopyridine (29 mg, 0.24 mmol), and 2-methyl propanoyl-2-methyl propanoate (100 μL, 0.6 mmol) at room temperature, and the mixture was stirred at 100° C. for 4 hours. Thereto was added further 2-methyl propanoyl-2-methyl propanoate (100 μL, 0.6 mmol), and the mixture was stirred at 100° C. for 2 hours. Thereto were added saturated bicarbonate water and sodium acetate at room temperature, and the organic layer was separated. The resulting organic layer was dried over sodium sulfate. The residue was filtered, and the solvents were evaporated, and purified by silica gel chromatography (hexane/ethyl acetate, 50/50 to 20/80). Further the obtained compound was solubilized in tetrahydrofuran (1 mL), and thereto was added 0.1 N aqueous sodium hydroxide solution (1 ml), and the mixture was stirred at 0° C. for 40 minutes. To the reaction solution were added water and ethyl acetate, and the organic layer was separated, and then washed with aqueous ammonium chloride solution, and the organic was separated again. After the resulting mixture was dried over sodium sulfate, the residue was filtered, and the solvents were evaporated to obtain a compound 2Gh (56 mg, yield 50%).

MS(ESI): m/z=745 $(M+H)^+$

Example 140 Synthesis of Compound 2Gi

N-[9-[(1R,3R,4R,7S)-1-[[bis(4-methoxyphenyl)-phenyl-methoxy]methyl]-7-[2-cyanoethoxy(diisopropylamino)phosphanyl]oxy-5-methylsulfonyl-2-oxa-5-azabicyclo[2.2.1]heptan-3-yl]-6-oxo-1H-purin-2-yl]-2-methylpropane amide Molecular sieve 3A was added to dichloromethane (3.6 ml) and the mixture was stirred for 1 hour, and thereto were added the compound 2Gh (500 mg, 0.67 mmol), 1-methyl imidazole (10.9 mg, 0.1 mol) and tetrazole (84 mg, 1.2 mmol), and 2-Cyanoethyl N,N,N',N'-Tetraisopropylphosphordiamidite (549 mg, 3.1 mmol) at room temperature, and the mixture was stirred for 6 hours. Thereto was added saturated bicarbonate water at room temperature, and the mixture was extracted with dichloromethane twice. The resulting organic layer was dried over sodium sulfate, and the residue was filtered. After the solvents were evaporated, the resulting residue was purified by silica gel chromatography (hexane/ethyl acetate, 50/50 to 25/75) to obtain a compound 2Gi (500 mg, yield 79%).

MS(ESI): m/z=946 $(M+H)^+$

Also ALNA[Ms]-G monomer wherein a guanine moiety is protected with only an isobutyloyl group can be also synthesized directly by a transglycosylation from the compound 1a as follows.

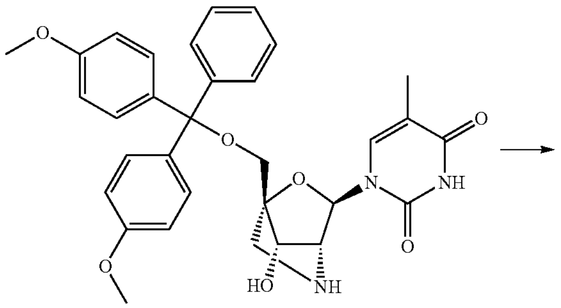

1a

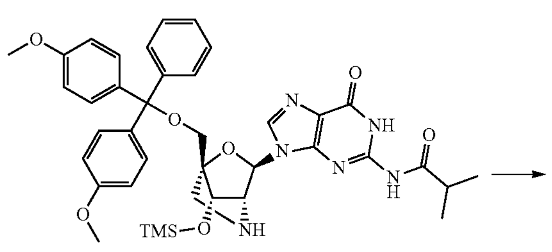

2Gj

-continued

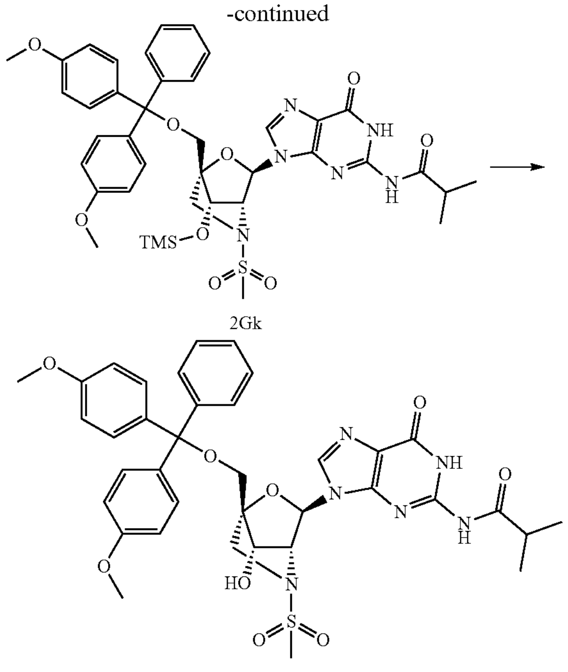

2Gk

2Gh

Example 141 Synthesis of Compound 2Gj

N-[9-[(1R,3R,4R,7S)-1-[[bis(4-methoxyphenyl)-phenyl-methoxy]methyl]-7-trimethylsilyloxy-2-oxa-5-azabicyclo[2.2.1]heptan-3-yl]-6-oxo-1H-purin-2-yl]-2-methylpropane Amide To a mixed solution of the compound 1a (5.0 g, 8.75 mmol) and 2-methyl N-(6-oxo-1,9-dihydropurin-2-yl)propane amide (3.87 g, 17.5 mmol) in 1,2-dichloroethane (30 ml) was added BSA (21.4 mL, 87.5 mmol), and the mixture was stirred at 60° C. for 30 minutes. Successively, thereto was added TMSOTf (0.254 mL, 1.31 mmol), and the mixture was stirred for 1 hour and a half. After allowed to stand to cool, to the reaction solutions were added chloroform (50 ml) and saturated aqueous sodium hydrogen carbonate solution (50 mL), and the mixture was stirred. After suction filtering an insoluble materials off, the organic layer was washed with water and saturated brine, dried over magnesium sulfate, and concentrated. The resulting residue was purified by silica gel chromatography (chloroform/methanol, 100/0 to 90/10) to obtain a compound 2Gj (3.83 g, yield 59%).

MS(ESI): m/z=739.5 $(M+H)^+$

Example 142 Synthesis of Compound 2Gk

N-[9-[(1R,3R,4R,7S)-1-[[bis(4-methoxyphenyl)-phenyl-methoxy]methyl]-5-methylsulfonyl-7-trimethylsilyloxy-2-oxa-5-azabicyclo[2.2.1]heptan-3-yl]-6-oxo-1H-purin-2-yl]-2-methylpropane Amide To a solution of the compound 2Gj (1.0 g, 1.35 mmol), pyridine (0.327 mL, 4.06 mmol) in dichloromethane (7 mL) was added methane sulfonic anhydride (284 mg, 1.63 mmol) under ice-cooling, and the mixture was stirred under ice-cooling for 45 minutes. Saturated aqueous sodium hydrogen carbonate solution was added to the reaction solution, and the mixture was extracted with chloroform. The organic layer was passed through a phase separator, and concentrated. The resulting residue was purified by silica gel chromatography (chloroform/methanol, 100/0 to 90/10) to obtain a compound 2Gk (657 mg, yield 59%).

MS(ESI): m/z=817.4 $(M+H)^+$

Example 143 Synthesis of Compound 2Gh

N-[9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-6-oxo-1H-purin-2-yl]-2-methylpropane Amide To a solution of the compound 2Gk (3.16 g, 3.87 mmol) in THE (8 mL) was added T3AF (1 mol/L THF solution, 4.6 mL, 4.6 mmol) and the mixture was stirred at room temperature for 1 hour. The reaction solution was concentrated, and thereto was added ethyl acetate, and the organic layer was washed with water and saturated brine. The organic layer was dried over magnesium sulfate, and concentrated. The resulting residue was purified by silica gel chromatography (chloroform/methanol, 100/0 to 90/10) to obtain a compound 2Gh (2.57 g, yield 89%).

MS(ESI): m/z=745.5 $(M+H)^+$

Also the compound 2Gh can be also synthesized from the compound 2Gb as follows.

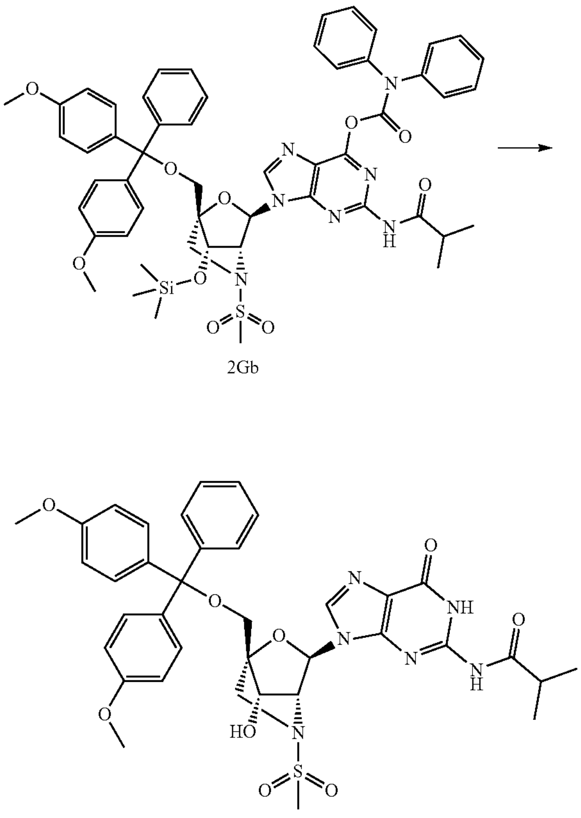

2Gb

2Gh

Example 144 Synthesis of Compound 2Gh

N-[9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-6-oxo-1H-purin-2-yl]-2-methylpropane amide The compound 2Gb (1010 mg, 1.0 mmol) was solubilized in tetrahydrofuran (10 mL), and thereto were added tetrabutyl ammonium fluoride (1 mol/L tetrahydrofuran solution, 3 mL, 3.0 mmol) at room temperature, and the mixture was stirred at 70° C. for 24 hours. Further, thereto was added tetrabutyl ammonium fluoride (1 mol/L tetrahydrofuran solution, 9 mL, 9.0 mmol) at room temperature, and the mixture was stirred at 80° C. for 8 hours. After the solvents were evaporated, the resulting mixture was purified by silica gel chromatography (chloroform/methanol, 98/2 to 93/7). The resulting mixture was further purified by silica gel chromatography (chloroform/methanol, 100/0 to 94/6) to obtain a compound 2Gh (570 mg, yield 77%).

MS(ESI): m/z=745 $(M+H)^+$

Example 145 Synthesis and Purification or Oligonucleotide Analogues (In Vitro)

Using each kind of amidite obtained in the above examples (present compounds 1 to 44), oligonucleotide analogue compounds indicated in Tables 1 to 4 below were synthesized by DNA/RNA oligonucleotide automatic synthesizer nS-8II (manufactured by GeneDesign, Inc.) using 0.2 or 1.0 μmol scale of CPG or polystyrene support. All of the amidites were adjusted to 0.1 M acetonitrile solution, and the coupling time of non-natural type of nucleoside was 10 minutes, and any steps other than the step were performed under a standard condition of ns-811. Activator 42 (Sigma-Aldrich) as an activator, Sulfurizing ReagentII (Gren Research Corporation) for thionylation were used. To the synthesized oligonucleotide was added 28% ammonia water, and the mixture was reacted at 60 to 65° C. for 8 hours to perform a cleavage from a support and a deprotection of a base moiety. Ammonia was concentrated and evaporated, and the resulting mixture was subjected to a purification by reverse phase HPLC chromatography.

Example 146 Synthesis and Purification of Oligonucleotide Analogues (In Vivo)

Using each kind of amidite obtained in the above examples (present compounds 1 to 44), oligonucleotide analogue compounds indicated m Table 5 below were synthesized by DNA/RNA oligonucleotide automatic synthesizer AKTA oligopilot plus 10 (manufactured by Gi Healthcare Inc.) using 20 μmol scale of polystyrene support. DNA amidite was adjusted to 0.1 M, and non-natural amidite was adjusted to 0.05 M acetonitrile solution, and the coupling recycle time of non-natural type of nucleoside was 20 minutes, and when the first base was introduced in a universal support, a coupling, a thiolation, a capping step was carried out twice in a row respectively. Any steps other than the step were performed under a standard condition of AKTA oligopilot plus 10. Activator 42 (Sigma-Aldrich) as an activator, Sulfurizing ReagentII (Gren Research Corporation) for thionylation were used. To the synthesized oligonucleotide was added 28% ammonia water, and the mixture was reacted at 60 to 65° C. for 8 hours to perform a cleavage from a support and a deprotection of a base moiety. Ammonia was concentrated and evaporated, and the resulting mixture was purified by an anion exchange column. Excess salts contained after anion exchange were removed by a desalting column.

The purification and confirmation of purity of the synthesized oligonucleotide analogues were carried out by reverse phase HPLC chromatography under the following conditions.

Reverse HPLC

Mobile Phase

A solution: 20 mM Cyclohexylammonium acetate aqueous solution

B solution: acetonitrile

Gradient: A:B=90:10→50:50 (40 min.) or A:B=90:10→40:60 (45 min.)

Used Column:

Analysis: Waters XBridge® Oligonucleotide BEH C18 Column, 130 Å, 2.5 μm, 4.6×50 mm Preparation: Waters XBridge® Oligonucleotide BEH C18 OBD™ Prep Column, 130 Å, 2.5 μm, 10×50 mm Flow Rate:

Analysis: 1 mL/min.

Preparation: 4 mL/min.

Column temperature: 60° C.

Detection: UV (260 nm)

Anion Exchange Purification

Mobile Phase

A solution: 20 mM Tris-HCl (pH 8.0) aqueous solution

B solution: 20 mM Tris-HCl (pH 8.0), 1 M NaBr aqueous solution

Used Column:

GE HiTrap CaptQ ImpRes (Anion exchange) 5 mL

Flow rate: 5 mL/min.

Column temperature: room temperature

Detection: UV (260 nm)

Desalting Column

Mobile Phase

A solution: $H_2O$

B solution: $K_2O$

USED column:

GE HiPrep 26/10 Desalting

Flow rate: 10 mL/min.

Column temperature: room temperature

The molecular weight of the synthesized oligonucleotide analogues was determined by a Waters ZQ under the below-mentioned conditions.

Mobile Phase

A solution: 400 mM hexafluoroisopropanol, 15 mM triethylamine aqueous solution

B solution: methanol

Gradient: A:B=60:20→70:30 (2.5 min.) or A:B=90:10→40:60 (45 min.)

Used Column:

Analysis: Waters ACQUITY UPLC® Oligonucleotide BEH C18 Column, 130 Å, 1.7 μm, 2.1×100 mm Flow rate: 0.2 mL/min.

Column temperature: 60° C.

Detection: UV (260 nm)

TABLE 1

Mass spectrum measurement results of each Tm sequence
gcgttT(X)tttgct (SEQ ID No. 1)
(wherein, small character represents each nucleic acid base, T(X) represents each artificial nucleic acid species containing thymine, and all phosphate bonds represent phosphodiester.)

| Oligonucleotide compound NO. | Artificial nucleic acid species contained in antisense strand | m/z |
|---|---|---|
| Tm-1 (SEQ ID No. 1-1) | ALNA[Me] | 1223.8 $[M-3H]^{3-}$ |
| TM-1 (SEQ ID No. 1-2) | ALNA[Ms] | 1245.3 $[M-3H]^{3-}$ |
| Tm-3 (SEQ ID No. 1-3) | ALNA[Bs] | 1266.4 $[M-3H]^{3-}$ |
| Tm-4 (SEQ ID No. 1-4) | ALNA[mU] | 1238.5 $[N-3H]^{3-}$ |
| TM-5 (SEQ ID No. 1-5) | ALNA[ipU] | 1247.7 $[M-3H]^{3-}$ |
| Tm-6 (SEQ ID No. 1-6) | ALNA[dmU] | 1243.1 $[M-3H]^{3-}$ |
| Tm-7 (SEQ ID No. 1-7) | ALNA[2Pym] | 3736.52 $[M-H]^{1-}$ |
| Tm-8 (SEQ ID No. 1-8) | ALNA[4Pym] | 3736.49 $[M-H]^{1-}$ |
| Tm-9 (SEQ ID No. 1-9) | ALNA[4CF3-2Pym] | 3804.51 $[M-H]^{1-}$ |
| Tm-10 (SEQ ID No. 1-10) | ALNA[5Cl-2Pym] | 3773.37 $[M-H]^{1-}$ |
| Tm-11 (SEQ ID No. 1-11) | ALNA[6NMe2-4Pym] | 3777.99 $[M-H]^{1-}$ |
| Tm-12 (SEQ ID No. 1-12) | ALNA[2NMe2-4Pym] | 3779.19 $[M-H]^{1-}$ |
| TM-13 (SEQ ID No. 1-13) | ALNA[Prz] | 3737.76 $[M-H]^{1-}$ |
| Tm-14 (SEQ ID No. 1-14) | ALNA[Trz] | 3752.88 $[M-H]^{1-}$ |
| TM-15 (SEQ ID No. 1-15) | ALNA[Oxz] | 3743.19 $[M-H]^{1-}$ |

TABLE 2

Mass spectrum measurement results of each SRB1 (2-10-2) sequence
T(X)C(X)agtcatgactT(X)C(X) (SEQ ID No. 2)
(wherein, small character represents each nucleic acid base of DNA, T(X) or C(X) each represents artificial nucleic acid species containing thymine, artificial nucleic acid species containing 5-methylcytosine, respectively, and all phosphate bonds represent phosphorothioate.)

| Oligonucleotide compound NO. | Artificial nucleic acid species contained in antisense strand | m/z |
|---|---|---|
| SRB1-1 (SEQ ID No. 2-1) | ALNA[Me] | 1152.9 $[M-4H]^{4-}$ |
| SRB1-2 (SEQ ID No. 2-2) | ALNA[Ms] | 1217.0 $[M-4H]^{4-}$ |
| SRB1-3 (SEQ ID No. 2-3) | ALNA[ipU] | 1224.1 $[M-4H]^{4-}$ |
| SRB1-4 (SEQ ID No. 2-4) | ALNA[2Pym] | 4869.28 $[M-H]^{1-}$ |
| SRB1-5 (SEQ ID No. 2-5) | ALNA[Prz] | 4871.85 $[M-H]^{1-}$ |
| SRB1-6 (SEQ ID No. 2-6) | ALNA[Trz] | 4937.77 $[M-H]^{1-}$ |
| SRB1-7 (SEQ ID No. 2-7) | ALNA[Oxz] | 4885.15 $[M-H]^{1-}$ |

TABLE 3

Mass spectrum measurement results of each SRB1 (3-10-3) sequence T(X)T(X)C(X)agtcatgactT(X)C(X)C(X) (SEQ ID No. 3) (wherein, small character represents each nucleic acid base of DNA, T(X) or C(X) each represents artificial nucleic acid species containing thymine, artificial nucleic acid species containing 5-methylcytosine, respectively, and all phosphate bonds represent phosphorothioate.)

| Oligonucleotide compound NO. | Artificial nucleic acid species contained in antisense strand | m/z |
|---|---|---|
| SRB1-8 (SEQ ID No. 3-1) | ALNA[Me] | 1066.4 $[M-5H]^{3-}$ |
| SRB1-9 (SEQ ID No. 3-2) | ALNA[Ms] | 1143.3 $[M-5H]^{3-}$ |
| SRB1-10 SEQ ID No. 3-3) | ALNA[ipU] | 1151.8 $[M-5H]^{3-}$ |
| SRB1-11 (SEQ ID No. 3-4) | ALNA[2Pym] | 5718.12 $[M-5H]^{1-}$ |
| SRB1-12 (SEQ ID No. 3-5) | ALNA[Prz] | 5719.86 $[M-5H]^{1-}$ |
| SRB1-13 (SEQ ID No. 3-6) | ALNA[Trz] | 5824.11 $[M-5H]^{1-}$ |
| SRB1-14 (SEQ ID No. 3-7) | ALNA[Oxz] | 5741.47 $[M-5H]^{1-}$ |

TABLE 4

Mass spectrum measurement results of each antimiR-21 sequence A(m)C(X)atC(X)agtC(X)tgaT(X)aagC(X)tA(m) (SEQ ID No. 4) (wherein, A(m) represents 2'-MOE adenosine, small character represents each nucleic acid case of DNA, T(X) or C(X) each represents artificial nucleic acid species containing thymine, artificial nucleic acid species containing 5-methylcytosine, respectively, and all phosphate bonds represent phosphorothioate.)

| Oligonucleotide compound No. | Artificial nucleic acid species contained in antisense strand | m/z |
|---|---|---|
| antrmiR21-1 (SEQ ID No. 4-1) | ALNA[Me] | 1081.4 $[M-6H]^{3-}$ |
| antimiR21-2 (SEQ ID No. 4-2) | ALNA[mU] | 1117.6 $[M-6H]^{3-}$ |
| antimiR21-3 (SEQ ID No. 4-3) | AINA[ipU] | 1140.8 $[M-6H]^{3-}$ |
| antimiR21-4 (SEQ ID No. 4-4) | ALNA[dmU] | 1129.1 $[M-6H]^{3-}$ |
| antimiR21-5 (SEQ ID No. 4-5) | ALNA[Trz] | 6897.87 $[M-6H]^{1-}$ |
| antimiR21-6 (SEQ ID No. 4-6) | ALNA[Oxz] | 6832.17 $[M-6H]^{1-}$ |

Table 5 Mass spectrum measurement results of each Malat1 sequence G(X)T(X)T(X)cactgaatG(X)C(X G(X SEQ ID No. 5)

(wherein, small character represents each nucleic acid base of DNA, T(X),C(X) or G(X) each represents artificial nucleic acid species containing thymine, artificial nucleic acid species containing 5-methylcytosine, or artificial nucleic acid species containing guanine, respectively, and all phosphate bonds represent phosphorothioate.)

TABLE 5

| Mass spectrum measurement results of each Malat1 sequence G(X)T(X)T(X)cactgaatG(X)C(X) (SEQ ID No. 5) (wherein, small character represents each nucleic acid base of DNA, T(X), C(X) or G(X) each represents artificial nucleic acid species containing thymine, artificial nucleic acid species containing 5-methylcytosine, or artificial nucleic acid species containing guanine, respectively, and all phosphate bonds represent phosphorothioate.) | | |
|---|---|---|
| Oligonucleotide compound No. | Artificial nucleic acid species contained in antisense strand | m/z |
| Malat1-1 (SEQ ID No. 5-1) | ALNA[Me] | 1089.8 $[M-4H]^{4-}$ |
| Malat1-2 (SEQ ID No. 5-2) | ALNA[Ms] | 1169.3 $[M-4H]^{4-}$ |
| Malat1-3 (SEQ ID No. 5-3) | ALNA[2Pym] | 4680.86 $[M-H]^{1-}$ |

Example 147 Evaluation of Binding Ability to Target Strand and Mismatch Selectivity Each of an antisense strand containing various artificial nucleic acid species (wherein sequence represents gcgttT (X)tttgct (the above-mentioned SEQ ID No. 1), small character represents each nucleic acid base of DNA, T(X) represents each artificial nucleic acid specie containing thymine); a sense strand, that is, DNA strand having a sequence complementary to the antisense strand (wherein sequence represents agcaaaaaacgc (SEQ ID No. 6), and small character represents each nucleic acid base of DNA); a RNA strand having a complementary sequence (wherein sequence represents AGCAAAAAACGC (SEQ ID No. 1), and large character represents each nucleic acid base.); and a RNA strand having 3 complementary sequences containing 1 base mismatch (wherein sequence represents AGCAAANAACGC (SEQ ID No. 8), and large character represents each nucleic acid base, and each N represents uracil (U), guanine (G), cytosine (C).) was annealed to form a double strand, and then Tm value that is a temperature at which 50% of the double strand is deviated, was measured, and the double strand-forming capacity of oligonucleotide was examined.

Specifically, a sample solution (150 µL) which contains aqueous sodium chloride solution 100 mmol/L, sodium phosphate buffer (pH 7.4) 10 mmol/L, antisense strand 4 µmol/L, and antisense strand 4 µmol/L was warmed to 95° C. and then cooled to room temperature over 4 hours. Nitrogen stream was passed into a cell chamber of spectrophotometer (JASCO, V-730, PAC-743R) so as to prevent a condensation phenomenon, and the sample solution was cooled to 10° C. gradually, and further kept at 10° C. for 1 minute, and the measurement was then started. The temperature was warmed to 80° C. at a rate of 0.5° C. per minute, and the ultraviolet absorption at 260 nm was measured at every timing of 0.5° C. rise. Here in order to prevent a concentration change due to a temperature rise, the cell with a lid was used. The measurement results are shewn in Table 6.

TABLE 6

| Measurement results of each Tm value | | | | | |
|---|---|---|---|---|---|
| Structure of | Tm (° C.) | | | | |
| T(X) in antisense strand | | v.s. RNA 5'-AGC AAA NAA CGC-3' | | | |
| 5'-gcgttT(X)tttgct-3' | v.s. DNA | N = A T-A match | N = U T-U mismatch | N = G T-G mismatch | N = C T-C mismatch |
| DNA | 51 | 48 | 32 | 42 | 30 |
| ALNA[Me] | 53 | 51 | 37 | 45 | 38 |
| ALNA[Ms] | 51 | 51 | 37 | 45 | 35 |
| ALNA[Bs] | 49 | 49 | 35 | 42 | 34 |
| ALNA[mU] | 51 | 51 | 38 | 44 | 36 |
| ALNA[ipU] | 52 | 51 | 38 | 42 | 35 |
| ALNA[dmU] | 50 | 50 | 39 | 42 | 35 |
| ALNA[2Pym] | 48 | 48 | 34 | 42 | 33 |

TABLE 6-continued

| Measurement results of each Tm value | | | | | |
|---|---|---|---|---|---|
| Structure of | Tm (° C.) | | | | |
| T(X) in antisense strand | | v.s. RNA 5'-AGC AAA NAA CGC-3' | | | |
| 5'-gcgttT(X)tttgct-3' | v.s. DNA | N = A T-A match | N = U T-U mismatch | N = G T-G mismatch | N = C T-C mismatch |
| ALNA[4Pym] | 52 | 52 | 39 | 43 | 36 |
| ALNA[4CF3-2Pym] | 47 | 49 | 35 | 42 | 32 |
| ALNA[5C1-2Pym] | 47 | 48 | 34 | 42 | 32 |
| ALNA[6NMe2-4Pym] | 54 | 52 | 38 | 39 | 34 |
| ALNA[2MNe2-4Pym] | 52 | 50 | 38 | 40 | 35 |
| ALNA[Prz] | 50 | 51 | 38 | 43 | 34 |
| ALNA[Trz] | 48 | 50 | 36 | 42 | 34 |
| ALNA[Oxz ] | 49 | 50 | 36 | 44 | 35 |

As clearly shown in Table 6, the antisense strand containing various artificial nucleic acids has the same or higher sense strand binding ability and mismatch selectivity as compared with antisense strand containing natural DNA and ALNA[Me] as known ALNA.

Example 147 In Vitro SR-B1 Knockdown Activity Test

Hepa 1c1c7 cells were seeded at $2.5\times10^3$ cells per well and cultured for 24 hours, and then various modified antisense oligonucleic acids having a complementary sequence to SRB1 were added at a final concentration of 100, 20, 4 mmol/L, and after 48 hours, a quantitative PCR was performed. The same conditions were carried out in 3 wells each. Regarding antisense activity, the inhibition rate of SRB1 expression when the antisense compound was added was set as 100% based on the amount ratio of SRB1 to GAPDH in a negative control. The results are shown in Table 7.

TABLE 7

| In vitro SRB1 knockdown activity test | | |
|---|---|---|
| Artificial nucleic | Knockdown activity (%) | |
| acid species | 3-10-3 | 2-10-2 |
| ALNA[Me] | 36 | 27 |
| ALNA[Ms] | 48 | 38 |
| ALNA[ipU] | 43 | 29 |
| ALNA[2Pym] | 57 | 19 |
| ALNA[Prz] | 40 | 44 |
| ALNA[Trz] | 60 | 39 |
| ALNA[Oxz] | 67 | 50 |

The target gene (SRB1) knockdown activity of the antisense oligonucleotide containing each artificial nucleic acid in the two sequence patterns of 3-10-3, and 2-10-2 at Gymnosis 100 nM was shown.

The two array patterns are as follows.

3-10-3: T(X)T(X)C(X)agtcatgactT(X)C(X)C(X) (as the same as SEQ ID No. 3 in the above Table 3)

2-10-2: T(X)C(X)agtcatgactT(X)C(X) (as the same as SEQ ID No. 2 in the above Table 2)

Here small character represents each nucleic acid base, each of T(X) or C(X) represents artificial nucleic acid specie containing thymine, or artificial nucleic acid specie containing 5-methylcytosine, and all phosphate bonds represent phosphorothioate.

As clearly shown in Table 7, ALNA[Ms], ALNA[ipU], ALNA[2Pym], ALNA[Trz], ALNA[Trz], and ALNA[Oxz] had a strong in vitro target gene knockdown activity as compared to ALNA[Me] as a known ALNA.

Example 148 In Vitro miRNA-21 Inhibitory Activity Rest $3.0\times10^6$ ceils/ml of HEK293 cells were seeded in a 10 cm dish, and the cells were cultured overnight in a $CO_2$ incubator. Next day, using FuGENE HD Transfection Reagent, and cells were transfected with 10 μg of reporter plasmid in which the complementary sequence of miR-21 was cloned into the multicloning site of psiCHECK-2 vector (Promega), and were cultured in a $CO_2$ incubator for about 24 hours. These cells were recovered, and $2.0\times10^4$ cells/well of cells were reseeded in a 96-well plate, and a miR-21 inhibitor into which each artificial nucleic acid was introduced was added. After cells were cultured in a $CO_2$ incubator for 96 hours. Using the Dual-Glo Luciferase Assay System, luminescence values of intracellular firefly luciferase and Renilla luciferase were detected with a plate reader. To correct the effects of transfection efficiency or cell number from the luminescence value due to Renilla luciferase activity, the ratio to the luminescence value due to firefly luciferase activity was calculated. Further, from the calculated ratio, the ratio in the ceils into which the psiCHECK-2 vector was introduced was set as 100% inhibition rate, and the ratio of cells into which the psiCHECK-2 vector into which the miR-21 complementary sequence was cloned was set as 0%, and each inhibition rate was calculated and the inhibitory activity was determined. The results are shown in Table 8.

TABLE 8

| In vitro miRNA-21 inhibitory activity | | |
|---|---|---|
| Artificial nucleic | miR-21 inhibition rate (%) | |
| acid species | Gymnosis, 1 μM | Gymnosis, 3 μM |
| ALNA[Me] | 6 | 19 |
| ALNA[MU] | 69 | 85 |
| ALNA[ipU] | 45 | 61 |
| ALNA[dmU] | 42 | 63 |
| ALNA[Trz] | 61 | 105 |
| ALNA[Oxz] | 31 | 63 |

Sequence of used antisense oligo is shown below.

A(m)C(X)atC(X)agtC(X)tgaT(X)aagC(X)tA(m) (the same as SEQ ID No. 4 in the above Table 4)

(wherein, A(m) represents 2'-MOE adenosine, small character represents each nucleic acid base of DNA, T(X) or C(X) each represents artificial nucleic acid species containing thymine, artificial nucleic acid species containing 5-methylcytosine, respectively, and all phosphate bends represent phosphorothioate.)

As clearly shewn in Table 8, ALNA[mU], ALNA[ipU], ALNA[dmU], ALNA[Trz], and ALNA[Oxz] had a strong in vitro micro RNA inhibitory activity as compared to ALNA [Me] as a known ALNA.

Example 149 In Vivo MALAT1 Knockdown Test

Antisense oligonucleotides (10 mg/kg and 50 mg/kg) targeting MALAT1 were prepared with PBS to make a concentration of 10 mg/mL and then diluted with FBS to make a 5 mL/kg, which was administered intravenously to 6 week-old C57BL/6J mice (male, Charles River Japan). After 72 hours, blood was collected from the abdominal vena cava of the mouse under anesthesia of isoflurane (Japan Pharmacopoeia, manufactured by Pfizer, Inc.) and euthanized by exsanguination. Blood was coagulated and then centrifuged to prepare serum, which was then stored frozen (set at −80° C.) until the time of measurement. After euthanizing by exsanguination, liver, kidney, fat, skeletal muscle (quadriceps femoris, gastrocnemius muscle), lung, heart, stomach, jejunum, testis, skin, spleen, and brain were collected and frozen in liquid nitrogen. A homogenization buffer of Maxwell RSC simply RNA Tissue Kit was added to frozen tissue, and the tissue was disrupted using a multi-bead shocker, RNA was purified according to the protocol described in the kit. RT reaction and the subsequent reactions were performed duplicately, and the amount of RNA per reaction was used in 50 to 500 ng. Regarding knockdown activity, the inhibition rate of Malat1 expression was set as 100% based on the amount ratio of Malat1 to GAPDH in vehicle group. The results are shown in Tables S and 10.

TABLE 9

| Malat1 knockdown rate (%) in each organ when 50 mg/kg was administered | | | | | | | | | | | | |
|---|---|---|---|---|---|---|---|---|---|---|---|---|
| Artificial nucleic acid | liver | kidney | quadriceps femoris | gastrocnemius muscle | brain | lung | heart | stomach | jejunum | testis | spleen | fat |
| ALNA[Me] | 88 | 56 | 55 | 49 | 4 | 64 | 9 | 37 | 9 | 30 | 51 | 43 |
| ALNA[Ms] | 97 | 80 | 67 | 63 | 0 | 80 | 48 | 54 | 56 | 69 | 46 | 82 |
| ALNA[2Pym] | 83 | 46 | 28 | 20 | 0 | 51 | 34 | 0 | 49 | 28 | 26 | 47 |
| ALNA[ipU] | 89 | 62 | 0 | 24 | 0 | 82 | 39 | 63 | 60 | 49 | 84 | 57 |

TABLE 10

| Malat1 knockdown rate (%) in each organ when 10 mg/kg was administered | | | | | | | | | | | | |
|---|---|---|---|---|---|---|---|---|---|---|---|---|
| Artificial nucleic acid | liver | kidney | quadriceps femoris | gastrocnemius muscle | brain | lung | heart | stomach | jejunum | testis | spleen | fat |
| ALNA[Me] | 47 | 41 | 0 | 21 | 10 | 50 | 12 | 1 | 0 | 0 | 43 | 3 |
| ALNA[Ms] | 90 | 66 | 22 | 47 | 0 | 49 | 17 | 32 | 10 | 39 | 19 | 70 |
| ALNA[2Pym] | 53 | 4 | 0 | 0 | 0 | 1 | 37 | 0 | 27 | 15 | 0 | 18 |
| ALNA[ipU] | 56 | 66 | 0 | 11 | 24 | 75 | 29 | 50 | 33 | 22 | 73 | 47 |

Sequence of used antisense oligonucleotide is shown below. G(X)T(X)T(X)cactgaatG(X)C(X) (the same as SEQ ID No. 5 in the above Table 5) (wherein, small character represents each nucleic acid base of DNA, T(X), C(X) or G(X) each represents artificial nucleic acid species containing thymine, artificial nucleic acid species containing 5-methylcytosine, or artificial nucleic acid species containing guanosine, respectively, and all phosphate bonds represent phosphorothioate.)

As clearly shown in Tables 9 and 10, ALNA[Ms] had a strong target gene knockdown m many organs (liver, kidney, skeletal muscle, lung, heart, stomach, jejunum, testis, fat) as compared to ALNA[Me] as a known ALNA. Also ALNA [2Pym] had a strong target gene knockdown in particular organs (heart, jejunum, testis, fat) as compared to ALNA [Me] as a known ALNA. Also ALNA[ipU] had a similar degree of target gene knockdown effect in liver as compared to ALNA[Me], whilst, had a remarkably stronger target gene knockdown effect in lung and spleen than ALNA[Me]. Since various immune cells are accumulated in spleen, antisense oligos including ALNA[ipU] can be expected to act on immune cells, which are considered to have low migration with ordinary nucleic acid drugs. In addition, ALNA[ipU] can be expected to have a strong drug effect on lung or immune system while reducing toxicity in liver.

Example 150 MALAT1 Knockdown Activity Test in Each Central Tissue, Liver, and Kidney by Intraventricular Administration 7 week-old C57BL/6J (male, Japan Charles River) was fixed to a brain stereotaxic device under anesthesia by Isoflurane (manufactured by Pfizer Inc.). An incision was made in the scalp while lying on a heat insulating mat to expose the skull. After confirming the position of the bregma, a hole was drilled in the skull 1 to 2 mm around the upper left ventricle (1.0 mm to the left and 0.4 mm behind the bregma) with a dental electric drill. A 27 gauge needle was inserted into the left ventricle (1.0 mm to the left of Bregma, 0.4 mm behind, 2.3 mm deep), and a single dose of antisense oligo (5 μg/10 μL/head) targeting MALAT1 that was prepared to 5 μg/10 μL in saline using a needle-mounted microinfusion pump was administered at a flow rate of 2 μL/min for 5 minutes. Thereafter, the hole in skull was closed with the medical cement Belfast (manufactured by Mutsukagaku Kogyo), the incision was sutured, and gentamicin ointment 0.1% (manufactured by Takata Seiyaku) was applied to prevent infectious diseases. Seventy-two (72, hours after administration, blood was collected from the abdominal vena cava of mice under isoflurane anesthesia and euthanized by exsanguination. Blood was coagulated and then centrifuged to prepare serum, which was then stored frozen (set at −30° C.) until the time of measurement. After euthanizing by exsanguination, brain, spinal cord, kidney, and liver were collected. For the brain, after euthanasia, skull and spine were separated, and then brain was taken out, and using Brain Matrices (RBM-2030S, manufactured by Bio Research Center Co., Ltd.), which is a slicer for making sagittal sections, and a brain is sliced from the median to the left brain side to a thickness of about 2 mm, and then an olfactory bulb, cerebral cortex, hippocampus, striatum, and cerebellum were taken out from the section. The rest of the section from which the 5 sites were removed was also collected as a complex site such as the brain stem. The spinal cord was separated at the boundary of T13, and two sites were collected as a part in the brain side from T13 (hereinafter, proximal spinal cord), and another part from T13 to L5 (hereinafter, distal spinal cord). The collected organs were immersed in RNA later (Invitrogen) and stored at −30° C. The organs and QIAzol Lysis Reagent (QIAGEN) were added to the tube, and the tissue was disrupted using a multi-bead shocker, and chloroform (manufactured by jyunsei chemical) and mixed. The aqueous layer was recovered from this mixture by centrifuge separation. RNA was purified according to the protocol described in RNeasy 96 Universal Tissue Kit (QIAGEN). RT reaction and the subsequent reactions were performed by using the amount of RNA per reaction in 2 to 7 ng. Regarding knockdown activity, the inhibition rate of Malat1 expression was set as 100% based on the amount ratio of Malat1 to GAPDH in vehicle group. Standard error was calculated based on individual values.

TABLE 11

MALAT1 knockdown rate (%) in each central tissue, liver, and kidney when 5 μg/head was administered

| Modified nucleic acid | olfactory bulb | cerebral cortex | hippocampus | striatum | cerebellum | complex site including brain stem | proximal spinal cord | distal spinal cord | kidney | liver |
|---|---|---|---|---|---|---|---|---|---|---|
| ALNA[Me] | −5.0 | 26.2 | 11.2 | 37.1 | −27.6 | 31.8 | 25.0 | 2.9 | 14.0 | 36.3 |
| ALNA[Ms] | 4.7 | 37.4 | 35.2 | 49.5 | 12.9 | 46.5 | 25.0 | 18.2 | 34.3 | 21.1 |
| ALNA[mU] | 8.5 | 29.8 | 13.3 | 24.0 | −42.6 | 40.6 | 23.4 | 1.1 | 4.7 | 17.8 |
| ALNA[Oxz] | 8.0 | 28.2 | 18.7 | 33.1 | −5.3 | 44.3 | 44.9 | 18.5 | 11.1 | 31.5 |

Sequence of used antisense oligonucleotide is shown below.
G(X)T(X)T(X)cactgaatG(X)C(X) (the same as SEQ ID No. 5 in the above Table 5)
(wherein, small character represents each nucleic acid base of ON A, T(X), C(X) or G(X) each represents artificial nucleic acid species containing thymine, artificial nucleic acid species containing 5-methylcytosine, or artificial nucleic acid species containing guanosine, respectively, and ail phosphate bonds represent phosphorothioate.)

As clearly shown in Table 11, ALNA[Ms], ALNA[mU], and ALNA[Oxz] had stronger target gene knockdown activity in each central tissue as compared to ALNA[Me] as a known ALNA.

INDUSTRIAL APPLICABILITY

An amino bridged artificial nucleic acid (ALNA) of the present invention can be used in a preparation of novel artificial nucleic acid oligomer. Also an oligomer containing the amino bridged artificial nucleic acid of the present invention has a strong target gene knockdown activity in particular organs and can be used as nucleic acid drugs.

SEQUENCE LISTING FREE TEXT

SEQ ID Nos. 1 to 6 show DNA oligonucleotides.
SEQ ID Nos. 7 to 8 show RNA oligonucleotides.

The invention claimed is:

1. A compound represented by general formula I:

(I)

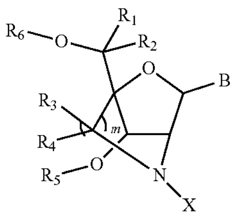

wherein

B represents a base moiety of nucleic acid wherein the base moiety may be optionally substituted with one or more substituents;

$R_1$, $R_2$, $R_3$ and $R_4$ represent independently of each other a hydrogen atom, or a $C_{1-6}$ alkyl group which may be optionally substituted with one or more substituents;

$R_5$ and $R_6$ represent independently of each other a hydrogen atom, a protecting group for hydroxy group, or a phosphate group which may be optionally substituted with substituents;

m is an integer of 1 or 2;

X represents a group represented by the following formula (II-1), (II-2) or (II-3):

(II-1)

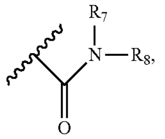

(II-2)

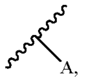

(II-3)

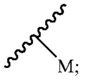

the symbols:

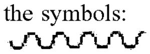

which are described in the formula (II-1), (II-2) or (II-3) represent a binding point to 2'-amino group;

$R_7$ and $R_8$ represent independently of each other a hydrogen atom, a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, or an aromatic group which may be optionally substituted with one or more substituents;

A represents an aromatic group that is directly bonded to an aromatic ring in said aromatic group to the 2' amino group;

M represents a sulfonyl group which is substituted with one substituent selected from the group consisting of a $C_{1-6}$ alkyl group which may be optionally substituted with one or more substituents and an aromatic group which may be optionally substituted with one or more substituents, or salts thereof.

2. The compound according to claim 1 or salt thereof wherein B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents, or an uracilyl group which may be optionally substituted with one or more substituents.

3. The compound according to claim 1 or salts thereof wherein $R_1$, $R_2$, $R_3$ and $R_4$ represent independently of each other a hydrogen atom; and m is an integer of 1.

4. The compound according to claim 1 or salts thereof wherein

X represents a group represented by formula (II-1); and $R_7$ and $R_8$ represent independently of each other a hydrogen atom, a $C_{1-6}$ alkyl group which may be optionally substituted with one or more substituents, or an aromatic group which may be optionally substituted with one or more substituents.

5. The compound according to claim 4 or salts thereof wherein $R_7$ and $R_8$ represent independently of each other a hydrogen atom, or a $C_{1-3}$ alkyl group which may be optionally substituted with one or more substituents.

6. The compound according to claim 5 or salts thereof wherein one of $R_7$ and $R_8$ represents a hydrogen atom, and the other thereof represents a methyl group.

7. The compound according to claim 5 or salts thereof wherein one of $R_7$ and $R_8$ represents a hydrogen atom, and the other thereof represents an isopropyl group.

8. The compound according to claim 1 or salts thereof wherein

X represents a group represented by formula (II-2);

A represents a five or six membered heteroaryl group containing one or more heteroatoms selected from the group consisting of nitrogen atom, oxygen atom and sulfur atom, which may be optionally substituted with one or more substituents.

9. The compound according to claim 8 or salts thereof wherein A represents a five or six membered heteroaryl group containing two or three heteroatoms selected from the group consisting of nitrogen atom, oxygen atom and sulfur atom, provided that at least two nitrogen atoms are included, which may be optionally substituted with one or more substituents, and the substituent is selected independently of each other from a group consisting of a $C_{1-3}$ alkyl group which may be optionally substituted with one or more halogen atoms, a halogen atom, and an amino group which may be optionally substituted with one or more $C_{1-3}$ alkyl group.

10. The compound according to claim 9 or salts thereof wherein the five or six membered heteroaryl group represents a group consisting of a triazolyl group, an oxadiazolyl group, a thiadiazolyl group, a pyrimidinyl group, and a pyrazinyl group, each may be optionally substituted with one or more substituents.

11. The compound according to claim 10 or salts thereof wherein the triazolyl group which may be optionally substituted with one or more substituents represents 1,5-dimethyl-1,2,4-triazol-3-yl group.

12. The compound according to claim 10 or salts thereof wherein the oxadiazolyl group which may be optionally substituted with one or more substituents represents 5-methyl-1,2,4-oxadiazol-3-yl group.

13. The compound according to claim 10 or salts thereof wherein the thiadiazol group which may be optionally substituted with one or more substituents represents 3-methyl-1,2,4-thiadiazol-5-yl group.

14. The compound according to claim 1 or salts thereof wherein

X represents a group represented by formula (II-3); and

M represents a sulfonyl group which is substituted with one or more substituents selected from the group consisting of a $C_{1-6}$ alkyl group which may be optionally substituted with one or more substituents, and an aryl group which may be optionally substituted with one or more substituents.

15. The compound according to claim 14 or salts thereof wherein M represents a sulfonyl group which is substituted with one or more substituents selected from the group consisting of a methyl group and a phenyl group.

16. The compound according to according to claim 1 or salts thereof wherein $R_6$ represents a hydrogen atom or DMTr group, and $R_5$ represents a hydrogen atom or —P(O$(CH_2)_2$CN)(N(ipr)$_2$).

17. A compound selected from the group consisting of

3-[[(1R,4R,6R,7S)-4-[[bis(4-methoxyphenyl)-phenyl-methoxy]methyl]-6-(5-methyl-2,4-dioxo-pyrimidin-1-yl)-2-methylsulfonyl-5-oxa-2-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-5-methyl-2-oxo-pyrimidin-4-yl]benzamide;

[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-2-(2-methylpropanoylamino)purin-6-yl]N,N-diphenylcarbamate;

N-[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-purin-6-yl]benzamide;

3-[[(1R,3R,4R,7S)-5-(benzenesulfonyl)-1-[[bis(4-methoxyphenyl)-phenylmethoxy]methyl]-3-(5-methyl-2,4-dioxopyrimidin-1-yl)-2-oxa-5-azabicyclo[2.2.1]heptan-7-yl]oxy-(diisopropylamino)phosphanyl]oxypropanenitrile;

N-[1-[(1R,3R,4R,7S)-5-(benzenesulfonyl)-1-[[bis(4-methoxyphenyl)-phenyl-methoxy]methyl]-7-[2-cyanoethoxy-(diisopropylamino)phosphanyl)oxy-2-oxa-5-azabicyclo[2.2.1]heptan-3-yl]-5-methyl-2-oxo-pyrimidin-4-yl]benzamide;

(1R,3R,4R,7S)-1-[[bis(4-methoxyphenyl)-phenyl-methoxy]methyl]-7-[2-cyanoethoxy-(diisopropylamino)phosphanyl]oxy-N-methyl-3-(5-methyl-2,4-dioxo-pyrimidin-1-yl)-2-oxa-5-azabicyclo[2.2.1]heptane-5-carboxamide;

(1R,3R,4R,7S)-3-(4-benzamide-5-methyl-2-oxo-pyrimidin-1-yl)-1-[[bis(4-methoxyphenyl)-phenyl-methoxy]methyl]-7-[2-cyanoethoxy-(diisopropylamino)phosphanyl]oxy-N-methyl-2-oxa-5-azabicyclo[2.2.1]heptane-5-carboxamide;

[9-[(1R,3R,4R,7S)-1-[[bis(4-methoxyphenyl)-phenyl-methoxy]methyl]-7-[2-cyanoethoxy-(diisopropylamino)phosphanyl]oxy-5-(methylcarbamoyl)-2-oxa-5-azabicyclo[2.2.1]heptan-3-yl]-2-(2-methylpropanoylamino)purin-6-yl]N,N-diphenylcarbamate;

(1R,3R,4R,7S)-3-(6-benzamidepurin-9-yl)-1-[[bis(4-methoxyphenyl)phenylmethoxy]methyl]-7-[2-cyanoethoxy-(diisopropylamino)phosphanyl]oxy-N-methyl-2-oxa-5-azabicyclo[2.2.1]heptane-5-carboxamide;

(1R,3R,4R,7S)-1-[[bis(4-methoxyphenyl)phenyl-methoxy]methyl]-7-[2-cyanoethoxy-(diisopropylamino)phosphanyl]oxy-N-isopropyl-3-(5-methyl-2,4-dioxopyrimidin-1-yl)-2-oxa-5-azabicyclo[2.2.1]heptane-5-carboxamide;

(1R,3R,4R,7S)-3-(4-benzamide-5-methyl-2-oxopyrimidin-1-yl)-1-[[bis(4-methoxyphenyl)phenyl-methoxy]methyl]-7-[2-cyanoethoxy-(diisopropylamino)phosphanyl]oxy-N-isopropyl-2-oxa-5-azabicyclo[2.2.1]heptane-5-carboxamide;

[9-[(1R,3R,4R,7S)-1-[[bis(4-methoxyphenyl)-phenyl-methoxy]methyl]-7-[2-cyanoethoxy-(diisopropylamino)phosphanyl]oxy-5-(isopropylcarbamoyl)-2-oxa-5-azabicyclo[2.2.1]heptan-3-yl]-2-(2-methylpropanoylamino)purin-6-yl]N,N-diphenylcarbamate;

(1R,3R,4R,7S)-3-(6-benzamidepurin-9-yl)-1-[[bis(4-methoxyphenyl)-phenyl-methoxy]methyl]-7-[2-cyanoethoxy-(diisopropylamino)phosphanyl]oxy-N-isopropyl-2-oxa-5-azabicyclo[2.2.1]heptane-5-carboxamide;

(1R,3R,4R,7S)-1-[[bis(4-methoxyphenyl)-phenyl-methoxy]methyl]-7-[2-cyanoethoxy-(diisopropylamino)phosphanyl]oxy-N,N-dimethyl-3-(5-methyl-2,4-dioxopyrimidin-1-yl)-2-oxa-5-azabicyclo[2.2.1]heptane-5-carboxamide;

(1R,3R,4R,7S)-3-(4-benzamide-5-methyl-2-oxo-pyrimidin-1-yl)-1-[[bis(4-methoxyphenyl)-phenylmethoxy]methyl]-7-[2-cyanoethoxy-(diisopropylamino)phosphanyl]oxy-N,N-dimethyl-2-oxa-5-azabicyclo[2.2.1]heptane-5-carboxamide;

3-[(1R,3R,4R,7S)-1-[[bis(4-methoxyphenyl)-phenyl-methoxy]methyl]-3-(5-methyl-2,4-dioxo-pyrimidin-1-yl)-5-pyrimidin-2-yl-2-oxa-5-azabicyclo[2.2.1]heptan-7-yl]oxy-(diisopropylamino)phosphanyl]oxypropanenitrile;

1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]-5-methyl-2-oxo-pyrimidin-4-yl]benzamide;

N'-[9-(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]-6-oxo-1H-purin-2-yl]-N,N-dimethyl-6-formamidine;

N'-[9-(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-2-yl-2-oxa-5-azabicyclo[2.2.1]heptan-3-yl]purin-6-yl]benzamide;

3-[(1R,3R,4R,7S)-1-[[bis(4-methoxyphenyl)-phenyl-methoxy]methyl]-3-(5-methyl-2,4-dioxopyrimidin-1-yl)-5-pyrimidin-4-yl-2-oxa-5-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrimidin-4-yl-2-oxa-5-azabicyclo[2.2.1]heptan-3-yl]-5-methyl-2-oxo-pyrimidin-4-yl]benzamide;

3-[[(1R,3R,4R,7S)-1-[[bis(4-methoxyphenyl)-phenyl-methoxy]methyl]-3-(5-methyl-2,4-dioxo-pyrimidin-1-yl)-5-[4-(trifluoromethyl)pyrimidin-2-yl]-2-oxa-5-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-[4-(trifluoromethyl)pyrimidin-2-yl]-2-oxa-5-azabicyclo[2.2.1]heptan-3-yl]-5-methyl-2-oxo-pyrimidin-4-yl]benzamide;

3-[[(1R,3R,4R,7S)-1-[[bis(4-methoxyphenyl)-phenyl-methoxy]methyl]-5-(5-chloropyrimidin-2-yl)-3-(5-methyl-2,4-dioxo-pyrimidin-1-yl)-2-oxa-5-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-5-(5-chloropyrimidin-2-yl)-7-[2-cyanoethoxy-(diisopropylamino)phosphanyl]oxy-2-oxa-5-azabicyclo[2.2.1]heptan-3-yl]-5-methylpyrimidin-4-yl]benzamide;

3-[[(1R,3R,4R,7S)-1-[[bis(4-methoxyphenyl)-phenyl-methoxy]methyl]-5-[6-(dimethylamino)pyrimidin-4-yl]-3-(5-methyl-2,4-dioxo-pyrimidin-1-yl)-2-oxa-5-azabicyclo[2.2.1]heptan-7-yl]oxy-(diisopropylamine)phosphanyl]oxypropanenitrile;

N-[1-[(1R,3R,4R,7S)-1-[[bis(4-methoxyphenyl)-phenyl-methoxy]methyl]-7-[2-cyanoethoxy(diisopropylamino)phosphanyl]oxy-5-[(6-dimethylamino)pyrimidin-4-yl]-2-oxa-5-azabicyclo[2.2.1]heptan-3-yl]-5-methyl-2-oxo-pyrimidin-4-yl]benzamide;

3-[[(1R,3R,4R,7S)-1-[[bis(4-methoxyphenyl)-phenyl-methoxy]methyl]-5-[2-(dimethylamino)pyrimidin-4-yl]-3-(5-methyl-2,4-dioxo-pyrimidin-1-yl)-2-oxa-5-azabicyclo[2.2.1]heptan-7-yl]oxy-(diisopropylamino)oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-[2-(dimethylamino)pyrimidin-4-yl]-7-hydroxy-2-oxa-5-azabicyclo[2.2.1]heptan-3-yl]-5-methyl-2-oxo-pyrimidin-4-yl]benzamide;

3-[1-[(1R,3R,4R,7S)-1-[[bis(4-methoxyphenyl)-phenyl-methoxy]methyl]-3-(5-methyl-2,4-dioxopyrimidin-1-yl)-5-pyrazin-2-yl-2-oxa-5-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-pyrazine-2-yl-2-oxa-5-azabicyclo[2.2.1]heptan-3-yl]-5-methyl-2-oxo-pyrimidin-4-yl]benzamide;

3-[[(1R,3R,4R,7S)-1-[[bis(4-methoxyphenyl)-phenyl-methoxy]methyl]-5-(1,5-dimethyl-1,2,4-triazol-3-yl)-3-(5-methyl-2,4-dioxopyrimidin-1-yl)-2-oxa-5-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-5-methyl-2-oxo-pyrimidin-4-yl]benzamide;

N'-[9-[(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]-6-oxo-1H-purin-2-yl]-N,N-dimethylformamidine N-[9-(1R,3R,4R,7S)-1-[[bis(4-methoxyphenyl)-phenyl-methoxy]methyl]-7-[2-cyanoethoxy-(diisopropylamino)phosphanyl]oxy-5-(1,5-dimethyl-1,2,4-triazol-3-yl)-2-oxa-5-azabicyclo[2.2.1]heptan-3-yl]purin-6-yl]benzamide;

3-[[(1R,3R,4R,7S)-1-[[bis(4-methoxyphenyl)-phenyl-methoxy]methyl]-3-(5-methyl-2,4-dioxopyrimidin-1-yl)-5-(5-methyl-1,2,4-oxadiazol-3-yl)-2-oxa-5-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(5-methyl-1,2,4-oxadiazol-3-yl)-2-oxa-5-azabicyclo[2.2.1]heptan-3-yl]-5-methyl-2-oxo-pyrimidin-4-yl]benzamide;

3-[[(1R,3R,4R,7S)-1-[[bis(4-methoxyphenyl)-phenyl-methoxy]methyl]-3-(5-methyl-2,4-dioxopyrimidin-1-yl)-5-(3-methyl-1,2,4-thiadiazol-5-yl)-2-oxa-5-azabicyclo[2.2.1]heptan-7-yl]oxy-(diisopropylamino)phosphanyl]oxypropanenitrile;

N-[1-[(1R,3R,4R,7S)-1-[[bis(4-methoxyphenyl)-phenyl-methoxy]methyl]-7-[2-cyanoethoxy-(diisopropylamino)phosphanyl]oxy-5-(3-methyl-1,2,4-thiadiazol-5-yl)-2-oxa-5-azabicyclo[2.2.1]heptan-3-yl]-5-methyl-2-oxo-pyrimidin-4-yl]benzamide;

N-[1-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-5-methyl-2-oxo-pyrimidin-4-yl]dihydropyrimidin-2-one;

N'-[9-[(1R,3R,4R,7S)-1-[[bis(4-methoxyphenyl)-phenyl-methoxy]methyl]-7-[2-cyanoethoxy(diisopropylamino)phosphanyl]oxy-5-methylsulfonyl-2-oxa-5-azabicyclo[2.2.1]heptan-3-yl]-6-oxo-1H-purin-2-yl]-N,N-dimethylformamidine;

N-[9-[(1R,3R,4R,7S)-1-[[bis(4-methoxyphenyl)-phenyl-methoxy]methyl]-7-[2-cyanoethoxy-(diisopropylamino)phosphanyl]oxy-5-methylsulfonyl-2-oxa-5-azabicyclo[2.2.1]heptan-3-yl]-6-oxo-1H-purin-2-yl]-2-methylpropane amide; and N-[9-[(1R,3R,4R,7S)-1-[[bis(4-methoxyphenyl)-phenyl-methoxy]methyl]-7-hydroxy-5-methylsulfonyl-2-oxa-5-azabicyclo[2.2.1]heptan-3-yl]-6-oxo-1H-purin-2-yl]-2-methylpropane amide.

18. An oligonucleotide compound comprising one or more nucleosides represented by general formula (I'):

(I')

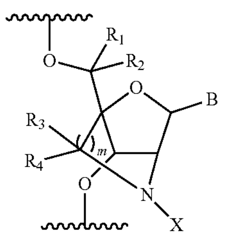

wherein, the symbols

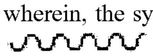

which are described in the formula (I') represent a phosphate bond between 5' carbon atom of a ribose in one nucleoside and 3' carbon atom of a ribose in the adjacent nucleoside;

B represents a base moiety of nucleic acid wherein the base moiety may be optionally substituted with one or more substituents;

R1, R2, R3 and R4 represent independently of each other a hydrogen atom, or a C1-6 alkyl group which may be optionally substituted with one or more substituents;

m is an integer of 1 or 2;

X represents a group represented by the following formula (II'-1), (II'-2), or (II'-3):

(II'-1)

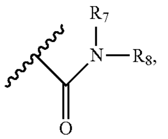

(II'-2)

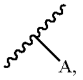

(II'-3)

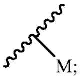

the symbols:

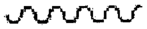

which are described in the formula (II'-1), (II'-2) or (II'-3) represent a binding point to 2'-amino group;

R7 and R8 represent independently of each other a hydrogen atom, a C1-6 alkyl group which may be optionally substituted with one or more substituents, a C2-6 alkenyl group which may be optionally substituted with one or more substituents, a C2-6 alkynyl group which may be optionally substituted with one or more substituents, or an aromatic group which may be optionally substituted with one or more substituents;

A represents an aromatic group containing one or more heteroatoms selected from the group consisting of nitrogen atom, oxygen atom and sulfur atom, which may be optionally substituted with one or more substituents;

M represents a sulfonyl group which is substituted with one or more substituents selected from the group consisting of a C1-6 alkyl group which may be optionally substituted with one or more substituents, and an aromatic group which may be optionally substituted with one or more substituents, or salts thereof.

19. The compound according to claim 18 or salts thereof wherein B represents an adeninyl group which may be optionally substituted with one or more substituents, a guaninyl group which may be optionally substituted with one or more substituents, a cytosinyl group which may be optionally substituted with one or more substituents, a 5-methylcytosinyl group which may be optionally substituted with one or more substituents or an uracilyl group which may be optionally substituted with one or more substituents.

20. The oligonucleotide compound according to claim 18 or salts thereof wherein $R_1$, $R_2$, $R_3$ and $R_4$ represent independently of each other a hydrogen atom; and m is an integer of 1.

21. The oligonucleotide compound according to claim 18 or salts thereof, wherein X represents a group represented by formula (II'-1); and $R_7$ and $R_8$ represent independently of each other a hydrogen atom, a C1-6 alkyl group which may be optionally substituted with one or more substituents, or an aromatic group which may be optionally substituted with one or more substituents.

22. The oligonucleotide compound according to claim 21 or salts thereof wherein $R_7$ and $R_8$ represent independently of each other a hydrogen atom, a C1-3 alkyl group which may be optionally substituted with one or more substituents.

23. The oligonucleotide compound according to claim 22 or salts thereof wherein one of $R_7$ and $R_8$ represents a hydrogen atom, and the other thereof represents a methyl group.

24. The oligonucleotide compound according to claim 23 or salts thereof wherein one of $R_7$ and $R_8$ represents a hydrogen atom, and the other thereof represents an isopropyl group.

25. The oligonucleotide compound according to claim 18 or salts thereof wherein X represents a group represented by formula (II'-2); and A represents a five or six membered heteroaryl group containing one or more heteroatoms selected from the group consisting of nitrogen atom, oxygen atom and sulfur atom, which may be optionally substituted with one or more substituents.

26. The oligonucleotide compound according to claim 25 or salts thereof wherein A represents a five or six membered heteroaryl group containing two or three heteroatoms selected from nitrogen atom, oxygen atom, and sulfur atom, provided that at least two nitrogen atoms are included, which may be optionally substituted with one or more substituents, and the substituent is selected independently of each other from a group consisting of a C1-3 alkyl group which may be optionally substituted with one or more halogen atoms, a halogen atom, and an amino group which may be optionally substituted with one or more C1-3 alkyl groups.

27. The oligonucleotide compound according to claim 26 or salts thereof wherein the five or six membered heteroaryl group is selected from the group consisting of a triazolyl group, an oxadiazolyl group, a thiadiazolyl group, a pyrimidinyl group, and a pyrazinyl group, each may be optionally substituted with one or more substituents.

28. The oligonucleotide compound according to claim 27 or salts thereof wherein the triazolyl group which may be optionally substituted with one or more substituents represents 1,5-dimethyl-1,2,4-triazol-3-yl group.

29. The oligonucleotide compound according to claim 27 or salts thereof wherein the oxadiazolyl group which may be optionally substituted with one or more substituents represents 5-methyl-1,2,4-oxadiazol-3-yl group.

30. The oligonucleotide compound according to claim 27 or salts thereof wherein the thiadiazolyl group which may be optionally substituted with one or more substituents represents 3-methyl-1,2,4-thiadiazol-5-yl group.

31. The oligonucleotide compound according to claim 18 or salts thereof, wherein X represents a group represented by formula (II'-3); and M represents a sulfonyl group which is substituted with one or more substituents selected from the group consisting of a C1-6 alkyl group which may be optionally substituted with one or more substituents, and an aryl group which may be optionally substituted with one or more substituents.

32. The compound according to claim 18 or salts thereof wherein M represents a sulfonyl group which is substituted with one or more substituents selected from the group consisting of a methyl group and a phenyl group.

33. The oligonucleotide compound according to claim 18 or salts thereof wherein individual nucleosides in said oligonucleotide are connected by phosphate bonds and one or more of said phosphate bonds between nucleosides represent a phosphorothioate bond.

34. The oligonucleotide compound according to claim 18 or salts thereof wherein said oligonucleotide compound comprises at least 5 nucleosides connected by phosphate bonds and wherein one or more phosphate bonds between said at least 5 nucleosides represent a phosphorothioate bond.

35. A compound represented by general formula I:

(I)

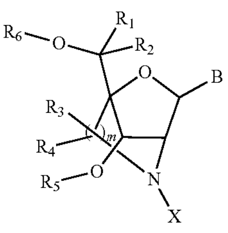

wherein

B represents a base moiety of nucleic acid wherein the base moiety may be optionally substituted with one or more substituents;

$R_1$, $R_2$, $R_3$ and $R_4$ represent independently of each other a hydrogen atom, or a $C_{1-6}$ alkyl group which may be optionally substituted with one or more substituents;

$R_5$ and $R_6$ represent independently of each other a hydrogen atom, a protecting group for hydroxy group, or a phosphate group which may be optionally substituted with substituents;

m is an integer of 1 or 2;

X represents a group represented by the following formula (II-1) or (II-3):

(II-1)

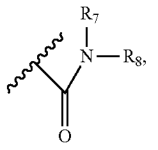

(II-3)

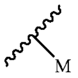

the symbols:

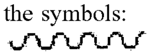

which are described in the formula (II-1) or (II-3) represent a binding point to 2'-amino group;

$R_7$ and $R_8$ represent independently of each other a hydrogen atom, a $C_{1-6}$ alkyl group which may be optionally substituted with one or more substituents, a $C_{2-6}$ alkenyl group which may be optionally substituted with one or more substituents, a $C_{2-6}$ alkynyl group which may be optionally substituted with one or more substituents, or an aromatic group which may be optionally substituted with one or more substituents;

M represents a sulfonyl group which is substituted with one substituent selected from the group consisting of a $C_{1-6}$ alkyl group which may be optionally substituted with one or more substituents and an aromatic group which may be optionally substituted with one or more substituents, or salts thereof.

36. An oligonucleotide compound comprising one or more nucleosides represented by general formula (I'):

(I')

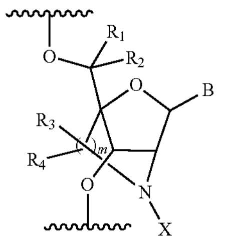

wherein, the symbols:

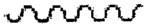

which are described in the formula (I') represent a phosphate bond between 5' carbon atom of a ribose in one nucleoside and 3' carbon atom of a ribose in the adjacent nucleoside;

B represents a base moiety of nucleic acid wherein the base moiety may be optionally substituted with one or more substituents;

R1, R2, R3 and R4 represent independently of each other a hydrogen atom, or a C1-6 alkyl group which may be optionally substituted with one or more substituents;

m is an integer of 1 or 2;

X represents a group represented by the following formula (II'-1) or (II'-3):

(II'-1)

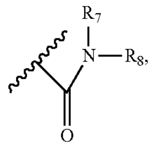

(II'-3)

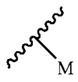

the symbols:

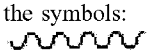

which are described in the formula (II'-1) or (II'-3) represent a binding point to 2'-amino group;

R7 and R8 represent independently of each other a hydrogen atom, a C1-6 alkyl group which may be optionally substituted with one or more substituents, a C2-6 alkenyl group which may be optionally substituted with one or more substituents, a C2-6 alkynyl group which may be optionally substituted with one or more substituents, or an aromatic group which may be optionally substituted with one or more substituents;

M represents a sulfonyl group which is substituted with one or more substituents selected from the group consisting of a C1-6 alkyl group which may be optionally substituted with one or more substituents, and an aromatic group which may be optionally substituted with one or more substituents, or salts thereof.

* * * * *

SEQUENCE LISTING

```
<160> NUMBER OF SEQ ID NOS: 8

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (6)..(6)
<223> OTHER INFORMATION: n is any one of bridged artificial nucleric
      acid ALNA containing thymine

<400> SEQUENCE: 1

gcgttntttg ct                                                      12


<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (1)..(1)
<223> OTHER INFORMATION: n is any one of bridged artificial nucleric
      acid ALNA containing thymine
<220> FEATURE:
<221> NAME/KEY: modified_base
<222> LOCATION: (2)..(2)
<223> OTHER INFORMATION: n is any one of bridged artificial nucleric
      acid ALNA containing 5-methylcytosine
<220> FEATURE:
<221> NAME/KEY: modified_base
<222> LOCATION: (13)..(13)
<223> OTHER INFORMATION: n is any one of bridged artificial nucleric
      acid ALNA containing thymine
<220> FEATURE:
<221> NAME/KEY: modified_base
<222> LOCATION: (14)..(14)
<223> OTHER INFORMATION: n is any one of bridged artificial nucleric
      acid ALNA containing 5-methylcytosine

<400> SEQUENCE: 2

nnagtcatga ctnn                                                    14


<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (1)..(1)
<223> OTHER INFORMATION: n is any one of bridged artificial nucleric
      acid ALNA containing thymine
<220> FEATURE:
<221> NAME/KEY: modified_base
<222> LOCATION: (2)..(2)
<223> OTHER INFORMATION: n is any one of bridged artificial nucleric
      acid ALNA containing thymine
<220> FEATURE:
<221> NAME/KEY: modified_base
```

<222> LOCATION: (3)..(3)
<223> OTHER INFORMATION: n is any one of bridged artificial nucleric
      acid ALNA containing 5-methylcytosine
<220> FEATURE:
<221> NAME/KEY: modified_base
<222> LOCATION: (14)..(14)
<223> OTHER INFORMATION: n is any one of bridged artificial nucleric
      acid ALNA containing thymine
<220> FEATURE:
<221> NAME/KEY: modified_base
<222> LOCATION: (15)..(15)
<223> OTHER INFORMATION: n is any one of bridged artificial nucleric
      acid ALNA containing 5-methylcytosine
<220> FEATURE:
<221> NAME/KEY: modified_base
<222> LOCATION: (16)..(16)
<223> OTHER INFORMATION: n is any one of bridged artificial nucleric
      acid ALNA containing 5-methylcytosine

<400> SEQUENCE: 3
nnnagtcatg actnnn                                                    16

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (1)..(1)
<223> OTHER INFORMATION: n is 2'-MOE adenosine
<220> FEATURE:
<221> NAME/KEY: modified_base
<222> LOCATION: (2)..(2)
<223> OTHER INFORMATION: n is any one of bridged artificial nucleric
      acid ALNA containing 5-methylcytosine
<220> FEATURE:
<221> NAME/KEY: modified_base
<222> LOCATION: (5)..(5)
<223> OTHER INFORMATION: n is any one of bridged artificial nucleric
      acid ALNA containing 5-methylcytosine
<220> FEATURE:
<221> NAME/KEY: modified_base
<222> LOCATION: (9)..(9)
<223> OTHER INFORMATION: n is any one of bridged artificial nucleric
      acid ALNA containing 5-methylcytosine
<220> FEATURE:
<221> NAME/KEY: modified_base
<222> LOCATION: (13)..(13)
<223> OTHER INFORMATION: n is any one of bridged artificial nucleric
      acid ALNA containing thymine
<220> FEATURE:
<221> NAME/KEY: modified_base
<222> LOCATION: (17)..(17)
<223> OTHER INFORMATION: n is any one of bridged artificial nucleric
      acid ALNA containing 5-methylcytosine
<220> FEATURE:
<221> NAME/KEY: modified_base
<222> LOCATION: (19)..(19)
<223> OTHER INFORMATION: n is 2'-MOE adenosine

<400> SEQUENCE: 4
nnatnagtnt ganaagntn                                                 19

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base

```
<222> LOCATION: (1)..(1)
<223> OTHER INFORMATION: n is any one of bridged artificial nucleric
      acid ALNA containing guanine
<220> FEATURE:
<221> NAME/KEY: modified_base
<222> LOCATION: (2)..(2)
<223> OTHER INFORMATION: n is any one of bridged artificial nucleric
      acid ALNA containing 5-methylcytosine
<220> FEATURE:
<221> NAME/KEY: modified_base
<222> LOCATION: (3)..(3)
<223> OTHER INFORMATION: n is any one of bridged artificial nucleric
      acid ALNA containing 5-methylcytosine
<220> FEATURE:
<221> NAME/KEY: modified_base
<222> LOCATION: (12)..(12)
<223> OTHER INFORMATION: n is any one of bridged artificial nucleric
      acid ALNA containing guanine
<220> FEATURE:
<221> NAME/KEY: modified_base
<222> LOCATION: (13)..(13)
<223> OTHER INFORMATION: n is any one of bridged artificial nucleric
      acid ALNA containing 5-methylcytosine
<220> FEATURE:
<221> NAME/KEY: modified_base
<222> LOCATION: (14)..(14)
<223> OTHER INFORMATION: n is any one of bridged artificial nucleric
      acid ALNA containing guanine

<400> SEQUENCE: 5

nnncactgaa tnnn                                                        14

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6

agcaaaaaac gc                                                          12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7

agcaaaaaac gc                                                          12

<210> SEQ ID NO 8
<211> LENGTH: 12
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: modified_base
<222> LOCATION: (7)..(7)
<223> OTHER INFORMATION: n is any one of uracil, guanine or cytosine

<400> SEQUENCE: 8

agcaaanaac gc                                                          12
```